(12) United States Patent
Hughes et al.

(10) Patent No.: US 9,561,209 B2
(45) Date of Patent: Feb. 7, 2017

(54) METHODS OF TREATING LIVER DISEASES

(71) Applicant: Zafgen, Inc., Boston, MA (US)

(72) Inventors: Thomas E. Hughes, Boston, MA (US); James E. Vath, Lynnfield, MA (US)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 14/440,724

(22) PCT Filed: Nov. 5, 2013

(86) PCT No.: PCT/US2013/068483
§ 371 (c)(1),
(2) Date: May 5, 2015

(87) PCT Pub. No.: WO2014/071368
PCT Pub. Date: May 8, 2014

(65) Prior Publication Data
US 2016/0058731 A1    Mar. 3, 2016

Related U.S. Application Data

(60) Provisional application No. 61/779,396, filed on Mar. 13, 2013, provisional application No. 61/722,529, filed on Nov. 5, 2012.

(51) Int. Cl.
*A61K 31/352* (2006.01)
*A61P 31/06* (2006.01)

(52) U.S. Cl.
CPC .................................. *A61K 31/352* (2013.01)

(58) Field of Classification Search
CPC .................................................... A61K 31/352
See application file for complete search history.

(56) References Cited

U.S. PATENT DOCUMENTS

| | | |
|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,238,950 A | 8/1993 | Clader et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,242,494 B1 | 6/2001 | Craig et al. |
| 6,268,387 B1 | 7/2001 | Connor et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Tarnus et al. |
| 6,887,863 B2 | 5/2005 | Craig et al. |
| 6,989,392 B2 | 1/2006 | Collins et al. |
| 7,005,440 B1 | 2/2006 | Jayyosi et al. |
| 7,030,262 B2 | 4/2006 | BaMaung et al. |
| 7,084,108 B2 | 8/2006 | Olson et al. |
| 7,115,632 B1 | 10/2006 | Bedell et al. |
| 7,268,111 B2 | 9/2007 | Olson et al. |
| 7,282,588 B2 | 10/2007 | Dhanak et al. |
| 7,288,651 B2 | 10/2007 | Deng et al. |
| 7,297,816 B2 | 11/2007 | Allison et al. |
| 7,396,833 B2 | 7/2008 | Xie et al. |
| 7,491,718 B2 | 2/2009 | Comess et al. |
| 7,718,695 B2 | 5/2010 | Kim et al. |
| 8,119,663 B2 | 2/2012 | Heimbach et al. |
| 9,067,905 B2 | 6/2015 | Dyke et al. |
| 9,187,494 B2 | 11/2015 | Cramp et al. |
| 9,221,787 B2 | 12/2015 | Zahler et al. |
| 9,242,997 B2 | 1/2016 | Cramp et al. |
| 9,266,896 B2 | 2/2016 | Clark et al. |
| 9,321,740 B2 | 4/2016 | Dyke et al. |
| 9,359,369 B2 | 6/2016 | Pallin et al. |
| 2002/0002152 A1 | 1/2002 | Craig et al. |
| 2004/0019113 A1 | 1/2004 | Jozefiak et al. |

(Continued)

FOREIGN PATENT DOCUMENTS

| | | |
|---|---|---|
| EP | 0682020 A1 | 11/1995 |
| WO | WO-98/38859 A1 | 9/1998 |

(Continued)

OTHER PUBLICATIONS

Anderson, "The Use of Fumagillin in Amoebiasis" Ann N Y Acad Sci. Dec. 30, 1952;55(6):1118-24.
Benny et al., "An Orally Delivered Small-Molecule Formulation with Antiangiogenic and Anticancer Activity" Nat Biotechnol. (Jul. 26, 2008).
Bernier et al., "Fumagillin class inhibitors of methionine aminopeptidase-2" Drugs of the Future 30(5):497-500 (2005).
Brakenhielm et al., "Angiogenesis Inhibitor, TNP-470, Prevents Diet-Induced and Genetic Obesity in Mice" Circulation Research, http://circres.ahajournals.org (accessed on Feb. 8, 2007), 2004.
Braunwald et al., "Obesity" in Harrison's Principles of Internal Medicine, 15th Ed., McGraw Hill (new York) pp. 479-86, 2001.
Chan et al.,"Discovery of thiophene-2-carboxylic acids as potent inhibitors of HCV NS5B polymerase and HCV subgenomic RNA replication. Part 1: Sulfonamides", Bioorg Med Chem Lett. Feb. 9, 2004;14(3):793-6.

(Continued)

*Primary Examiner* — Sahar Javanmard
(74) *Attorney, Agent, or Firm* — Goodwin Procter LLP

(57) ABSTRACT

The invention provides tricyclic compounds and their use in treating liver disorders, such as non-alcoholic steatohepatitis and related disorders (e.g., fibrosis). The compounds are contemplated to have activity against methionyl aminopeptidase 2.

13 Claims, 11 Drawing Sheets

(56) References Cited

U.S. PATENT DOCUMENTS

| | | |
|---|---|---|
| 2004/0067266 A1 | 4/2004 | Toppo |
| 2004/0068012 A1 | 4/2004 | Comess et al. |
| 2004/0116495 A1 | 6/2004 | Marino, Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2008/0312231 A1 | 12/2008 | Merla et al. |
| 2009/0088437 A1 | 4/2009 | Xie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2010/0158855 A1 | 6/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2013/0123235 A1 | 5/2013 | Clark et al. |
| 2013/0217759 A1 | 8/2013 | Zahler et al. |
| 2013/0331420 A1 | 12/2013 | Dyke et al. |
| 2014/0073623 A1 | 3/2014 | Cramp et al. |
| 2014/0080822 A1 | 3/2014 | Cramp et al. |
| 2014/0088078 A1 | 3/2014 | Cramp et al. |
| 2015/0119456 A1 | 4/2015 | Pallin et al. |
| 2015/0284369 A1 | 10/2015 | Pallin et al. |
| 2016/0051531 A1 | 2/2016 | Dyke et al. |
| 2016/0083362 A1 | 3/2016 | Pallin et al. |

FOREIGN PATENT DOCUMENTS

| | | |
|---|---|---|
| WO | WO-99/57097 A2 | 11/1999 |
| WO | WO-99/59986 A1 | 11/1999 |
| WO | WO-99/59987 A1 | 11/1999 |
| WO | WO-00/64876 A1 | 11/2000 |
| WO | WO-01/24796 A1 | 4/2001 |
| WO | WO-02/26782 A2 | 4/2002 |
| WO | WO-02/059124 A2 | 8/2002 |
| WO | WO-02/083065 A2 | 10/2002 |
| WO | WO-03/027104 A1 | 4/2003 |
| WO | WO-2004/033419 A1 | 4/2004 |
| WO | WO-2005/025554 A2 | 3/2005 |
| WO | WO-2005/082349 A1 | 9/2005 |
| WO | WO-2005/113513 A2 | 12/2005 |
| WO | WO-2006/080591 A1 | 8/2006 |
| WO | WO-2008/008374 A2 | 1/2008 |
| WO | WO-2008/131947 A1 | 11/2008 |
| WO | WO-2009/009501 A2 | 1/2009 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/088055 A2 | 7/2011 |
| WO | WO-2011/150338 A1 | 12/2011 |
| WO | WO-2012/012642 A1 | 1/2012 |
| WO | WO-2012/012645 A1 | 1/2012 |
| WO | WO-2012/036789 A1 | 3/2012 |
| WO | WO-2012/064838 A1 | 3/2012 |
| WO | WO-2012/051318 A1 | 4/2012 |
| WO | WO-2012/064928 A1 | 5/2012 |
| WO | WO-2012/074968 A1 | 6/2012 |
| WO | WO-2012/103333 A1 | 8/2012 |
| WO | WO-2012/154678 A1 | 11/2012 |
| WO | WO-2012/154679 A1 | 11/2012 |
| WO | WO-2013/033430 A1 | 3/2013 |

OTHER PUBLICATIONS

Chun et al., "Novel inhibitors targeted to methionine aminopeptidase 2 (MetAP2) strongly inhibit the growth of cancers in xenografted nude model" Int J Cancer. Mar. 10, 2005;114(1):124-30.

Database Registry [Online] (Apr. 18, 2001), Chemical Abstracts Service, XP002664465.

Database Registry [Online] (Apr. 10, 2004), Chemical Abstracts Service, XP002664464.

Database Registry [Online] (Apr. 13, 2007), Chemical Abstracts Service, XP002664462.

Database Registry [Online] (Aug. 24, 2008), Chemical Abstracts Service, XP002664461.

Database Registry [Online] (Jan. 20, 2009), Chemical Abstracts Service, XP002664460.

Database Registry [Online] (Jan. 23, 2009), Chemical Abstracts Service, XP002664459.

Database Registry [Online] (Jan. 27, 2009), Chemical Abstracts Service, XP002664458.

Database Registry [Online] (Jan. 28, 2009), Chemical Abstracts Service, XP002664457.

Database Registry [Online] (Sep. 15, 2009), Chemical Abstracts Service, XP002664454.

Database Registry [Online], (Sep. 11, 2009) Chemical Abstracts Service, XP002664455.

Database Registry [Online], (Oct. 4, 2010) Chemical Abstracts Service, XP002664453.

Database Registry [Online} (Jun. 7, 2009), Chemical Abstracts Service, XP002664456.

Database Regsitry [Online] (Mar. 13, 2007), Chemical Abstracts Service, XP002664463.

Didier et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo et al., "Studies on the Carcinolytic Activity of Fumagillin and Some of its Derivatives," Antibiot Annu. 1958-1959;6:541-6.

Drevs et al., "Antiangiogenic Potency of FK866/K22.175, a New Inhibitor of Intracellular NAD Biosynthesis, in Murine Renal Cell Carcinoma" Anticancer Res. Nov.-Dec. 2003;23(6C):4853-8.

Dumas et al., "Synthesis and Structure Activity Relationships of Novel Small Molecule Cathepsin D Inhibitors" Bioorg Med Chem Lett. Sep. 6, 1999;9(17):2531-6.

Eder et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics.") 2006.

European Search Report for EP 09798793 dated Oct. 11, 2011, 9 pages.

Everhart, "Contributions of Obesity and Weight Loss to Gallstone Disease" Ann Intern Med. Nov. 15, 1993;119(10):1029-35.

Garrabrant et al., "Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

Han et al.,"Design and Synthesis of Highly Potent Fumagillin Analogues from Homology Modeling for a Human MetAP-2" Bioorg Med Chem Lett. Jan. 3, 2000;10(1):39-43.

Hughes et al., "Ascending dose-controlled trial of beloranib, a novel obesity treatment for safety, tolerability, and weight loss in obese women" Obesity (Silver Spring). Sep. 2013;21(9):1782-8. doi: 10.1002/oby.20356. Epub May 25, 2013.

Ingber et al.,"Synthetic analogues of fumagillin that inhibit angiogenesis and suppress tumour growth" Nature. Dec. 6, 1990;348(6301):555-7.

International Search Report and Written Opinion for International Application No. PCT/US2011/044864, mailed on Oct. 7, 2011, 7 pages.

International Search Report and Written Opinion for International Application No. PCT/US2011/055987, mailed Jan. 16, 2012, 24 pages.

(56) References Cited

OTHER PUBLICATIONS

International Search Report and Written Opinion for International Application No. PCT/US2013/021914, mailed Apr. 18, 2013, 12 pages.
International Search Report and Written Opinion for International Application No. PCT/US2013/021919, mailed Mar. 25, 2013, 14 pages.
International Search Report and Written opinion for International Application No. PCT/US2010/052050, mailed Mar. 25, 2011, 11 pages.
International Search Report and Written Opinion for International Application No. PCT/US2012/022721, mailed on Mar. 29, 2012, 3 pages.
International Search Report for International Application No. PCT/US2012/036789, mailed Jul. 17, 2012, 4 pages.
International Search Report for International Application No. PCT/US2012/036792, mailed on Jun. 27, 2012, 3 pages.
International Search Report for International Application No. PCT/US2012/036793, mailed on Jun. 21, 2012, 4 pages.
Jeong et al, "Total synthesis and antiangiogenic activity of cyclopentane analogues of fumagillol" Bioorg Med Chem Lett. Aug. 1, 2005;15(15):3580-3.
Kawai et al., "Development of sulfonamide compounds as potent methionine aminopeptidase type II inhibiotrs with antiproliferative properties", Bioorg Med Chem Lett. Jul. 1, 2006;16(13):3574-7. Epub May 2, 2006.
Kim et al., "Assessment of the Anti-Obesity Effects of the TNP-470 Analog, CKD-732" J Mol Endocrinol. Apr. 2007;38(4):455-65.
Kim et al.,"Development of parenteral formulation for a novel angiogenesis inhibitor, CKD-732 through complexation with hydroxypropyl-beta-cyclodextrin" Int J Pharm. Mar. 19, 2004;272(12):79-89.
Kim et al., "General pharmacology of CKD-732, a new anticancer agent: effects on central nervous, cardiovascular, and respiratory system" Biol Pharm Bull. Feb. 2005;28(2):217-23.
Kruger, "TNP-470: An Angiogenesis Inhibitor in Clinical Development for Cancer" Expert Opin Investig Drugs. Jun. 2000;9(6):1383-1396.
Lee et al.,"Absorption, distribution, metabolism, and excretion of CKD-732, a novel antiangiogenic fumagillin derivative, in rats, mice, and dogs" Arch Pharm Res. Feb. 2004;27(2):265-72.
Lee et al., "Design, Synthesis, and Antiangiogenic Effects of a Series of Potent Novel Fumagillin Analogues" Chem Pharm Bull (Tokyo). Jul. 2007;55(7):1024-9.
Lee et al. "Selective N-demethylation of tertiary aminofumagillols with selenium dioxide via a non-classical Polonovski type reaction" Heterocycles 68(5):915-932, 2006.
Lijnen et al.,"Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.
Makosza et al. "Reaction of organic anions. 131. Vicarious nucleophilic substitution of hydrogen in nitrobenzoic acids" Makosza, M.; Ludwiczak, S. Dep. Chem.,Tech. Univ. Warsaw, Warsaw, Pol. Synthesis (1986), (1), 50-2. CODEN: SYNTBF ISSN: 0039-7881. Journal written in English. CAN 105:171971 AN 1986:571971 CAPLUS (Copyright (C) 2009 ACS on SciFinder (R)).
Masiero et al.,"New Anti-angiogenesis Agents: Review of the Clinical Experience with Carboxyamido-Triazole (CAI), Thalidomide, TNP-470 and Interleukin-12" Angiogenesis. 1997;1(1):23-35.
McCowen et al., "Fumagillin (H-3), a New Antibiotic with Amebicidal Properties" Science. Feb. 23, 1951;113(2930):202-3.
Milkowski et al., Antiangiogenic Agents in Cancer Therapy, Chapter 22 "TNP-470," pp. 385-398, 2012.
Molina et al., "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.
Molina et al., "Fumagillin Treatment of Intestinal Microsporidiosis" N Engl J Med. Jun. 20, 2002;346(25)1963-9.
Molina et al.,"Trial of Oral Fumagillin for the Treatment of Intestinal Microsporidiosis in Patients with HIV Infection" AIDS. Jul. 7, 2000;14(10):1341-8.
Myung et al., "The identification of in vitro metabolites of CKD-732 by liquid chromatography/tandem mass spectrometry" Rapid Commun Mass Spectrom. 2002;16(21):204853.
Naganuma et al., "Metronomic doxifluridine chemotherapy combined with the anti-angiogenic agent TNP-470 inhibits the growth of human uterine carcinosarcoma xenografts" Cancer Sci. Aug. 2011;102(8):1545-52. doi: 10.1111/j.1349-7006.2011.01998.x. Epub Jul. 3, 2011.
National Task Force on the Prevention and Treatment of Obesity "Very low-calorie diets. National Task Force on the Prevention and Treatment of Obesity, National Institutes of Health" JAMA. Aug. 25, 1993;270(8):967-74.
Noel et al., "Increased Risk of Acute Pancreatitis and Biliary Disease Observed in Patients with Type 2 Diabetes "Diabetes Care. May 2009;32(5):834-8. doi: 10.2337/dc08-1755. Epub Feb. 10, 2009.
Pagliarulo et al.,"Gallstone disease and related risk factors in a large cohort of diabetic patients" Dig. Liver Dis. Feb. 2004;36(2):130-4.
Patra et al., "Regiospecific Synthesis of Benzo[b]fluorenones via Ring Contraction by Benzil-Benzilic Acid Rearrangement of Benz[a]anthracene-5,6-diones" Synthesis 2006, (15), 2556-2562.
Picoul et al. "Progress in fumagillin synthesis" Pure Appl. Chem. 75(2-3): 235-249, 2003.
Rhee et al. "Angiogenesis inhibitor attenuates parathyroid hormone-induced anabolic effect" Biomed Pharmacother. Jan. 2009;63(1):63-8. doi: 10.1016/j.biopha.2007.10.013. Epub Nov. 20, 2007.
Rupnick "Adipose Tissue Mass Can be Regulated Through the Vasculature" Proc Natl Acad Sci U S A. Aug. 6, 2002;99(16)1 0730-5. Epub Jul. 29, 2002.
Sankar et al., "2[1-(Phenylsulfonyl)ethyl]benzoic acid and 2-[1-(phenylsulfonyl)propyl]benzoic acid" Acta Crystallogr C. May 2002;58(Pt 5):o257-9. Epub Apr. 11, 2002.
Seneca et al. "Amebiasis: a review. II. Laboratory diagnosis, differential diagnosis and therapy" Am J Dig Dis. Jul. 1956;1(7):310-22.
Sheppard et al., "3-Amino-2-hydroxyamides and related compounds as inhibitors of methionine aminopeptidase-2" Bioorg Med Chem Lett. Feb. 23, 2004;14(4):865-8.
Sheppard et al., "Discovery and Optimization of Anthranilic Acid Sulfonamides as Inhibitors of Methionine Aminopeptidase-2: A Structural Basis for the Reduction of Albumin Binding" J Med Chem. Jun. 29, 2006;49(13):3832-49.
Shin et al. "A Phase lb pharmacokinetic study of the anti-angiogenic agent CKD-732 used in combination with capecitabine and oxaliplatin (XELOX) in metastatic colorectal cancer patients who progressed on irinotecan-based chemotherapy" Invest New Drugs. Apr. 2012;30(2):672-80.
Shin, "A Phase I Pharmacokinetic and Pharmacodynamic Stdy of CKD-732, an Antiangiogenic Agent, in Patients with Refractory Solid Cancer" Invest New Drugs. Oct. 2010;28(5):650-8.
Shvedov et al., "Functional Derivatives of Thiophene" Chemistry of Heterocyclic Compounds Feb. 1977, vol. 13, Issue 2, pp. 163-165.
Siddiqui et al., "The Presence of Substituents on the Aryl Moiety of the Aryl Phosphoramidate Derivative of d4T Enhances Anti-HIV Efficacy in Cell Culture: A Structure-Activity Relationship" J Med Chem. <http://www.ncbi.nlm.nih.gov/pubmed/9986709> Feb. 11, 1999;42(3):393-9.
Srikumar et al. "Structural insights on Brugia malayi transglutaminase with cinnamoyl derivatives—a molecular docking approach," International Journal of Pharma and Bio Sciences 3(3):998-1006 2012.
Teicher et al.,"Antiangiogenic Agents in Cancer Therapy" pp. 385-398 (1999).
Thirumamagal et al., "Formation of 2-arylindane-1,3-diones and 3-alkylphthalides from methyl o-[?-phenylsulfonyl]toluate" Tetrahedron Letters 49(3) 512-515 (2008).
Wang et al., "Correlation of tumor growth suppression and methionine aminopetidase-2 activity blockade using an orally active

(56) References Cited

OTHER PUBLICATIONS inhibitor" Proc Natl Acad Sci U S A. <http://www.ncbi.nlm.nih.gov/pubmed/?term=Wang+et+al.+Correlation+of+Tumor+Growth+Suppressionand+Methionine+Aminopetidase-2> Feb. 12, 2008;105(6):1838-43. doi: 10.1073/pnas.0708766105. Epub Feb. 5, 2008.

Wang et al., "Lead optimization of methionine aminopeptidase-2 (MetAP2) inhibitors containing sulfonamides of 5, 6-disubstituted anthranilic acids," Bioorg Med Chem Lett. May 15, 2007;17(10):2817-22. Epub Feb. 25, 2007.

Wang et al., "Tumor Suppression by a Rationally Designed Reversible Inhibitor of Methionine Aminopeptidase-2" Cancer Res. Nov. 15, 2003;63(22):7861-7869.

Weinsier et al., "Gallstone Formation and Weight Loss," Obes Res. Jan. 1993;1(1):51-6.

Weinsier et al., "Medically Safe Rate of Weight Loss for the Treatment of Obesity: A Guideline Based on Risk of Gallstone Formation," Am J Med. Feb. 1995;98(2):115-117.

Winter et al., "Endothelial anb3 Integrin-Targeted Fumagillin Nanoparticles Inhibit Angiogenesis in Atherosclerosis," Arterioscler Thromb Vasc Biol. Sep. 2006;26(9):2103-2109. Epub Jul. 6, 2006.

Written Opinion of the International Searching Authority for International Application No. PCT/US2009/066811, mailed on Sep. 1, 2010, 3 pages.

Yanai et al., "Antitumor Effect of Arterial Administration of a Medium-Chain Triglyceride Solutionof an Angiogenesis Inhibitor, TNP-470, in Rabbits Bearing VX-2 Carcinoma" Pharm Res. May 1995;12(5):653-657.

Yanai et al., "Antitumor activity of a medium-chain triglyceride solution of the angiogenesis inhibitor TNP-470 (AGM-1470) when administered via the hepatic artery to rats bearing Walker 256 carcinosarcoma in the liver" J Pharmacol Exp Ther. Dec. 1994;271(3):1267-73.

Whole Blood HbA$_{1c}$

Plasma Total Cholesterol

METHODS OF TREATING LIVER DISEASES

CROSS REFERENCE TO RELATED APPLICATIONS

This application claims priority to U.S. Provisional Patent Application No. 61/722,529 filed Nov. 5, 2012 and U.S. Provisional Patent Application No. 61/779,396 filed Mar. 13, 2013, both of which are incorporated by reference in their entireties.

BACKGROUND

Fatty liver disease and liver fibrosis can be chronic liver diseases and represent a common and difficult clinical challenge of worldwide importance. Liver fibrosis is the excessive accumulation of extracellular matrix proteins including collagen that occurs in most types of chronic liver diseases. Advanced liver fibrosis results in cirrhosis, liver failure, and portal hypertension and often requires liver transplantation.

Non-alcoholic steatohepatitis (NASH) is a severe form of fatty liver disease that affects 2 to 5 percent of Americans. It resembles alcoholic liver disease but occurs in people who drink little or no alcohol. The major feature of NASH is excess fat content in the liver, along with inflammation and liver damage. NASH can lead to liver cirrhosis, fibrosis, hepatocellular carcinoma, liver failure, liver-related death, and liver transplantation. NASH can also lead to an increased risk of cardiovascular disease.

Although NASH affects only 2-5% of Americans, it is becoming prevalent, likely because of the greater number of Americans with obesity. Many people with NASH are middle-aged, obese, diabetic and/or have elevated blood cholesterol levels. However, NASH can occur in people without any apparent risk factor and can even occur in children. Currently, there are no specific therapies for treating NASH, although some studies suggest that diet, exercise and reducing alcohol intake may be useful in altering the course of the disease.

At present, the only curative treatment for end stage cirrhosis is transplantation, but limited availability of donor organs and the clinical condition of the potential recipient limit the applicability of this technique.

MetAP2 encodes a protein that functions at least in part by enzymatically removing the amino terminal methionine residue from certain newly translated proteins such as glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res. 63:7861) and infectious diseases such as microsporidiosis, leishmaniasis, and malaria (Zhang et al. (2002) J. Biomed. Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc. Natl. Acad. Sci. USA 99:10730).

SUMMARY

This disclosure is directed in part to, for example, methods of treating non-alcoholic steatohepatitis NASH and associated disorders (e.g., fibrosis) by administering compounds which may be modulators of MetAP2, such as disclosed compounds. In an embodiment, the disclosure is directed to methods of reducing cholesterol (e.g., total cholesterol in plasma) in a patient in need thereof.

DETAILED DESCRIPTION

Figure 1:
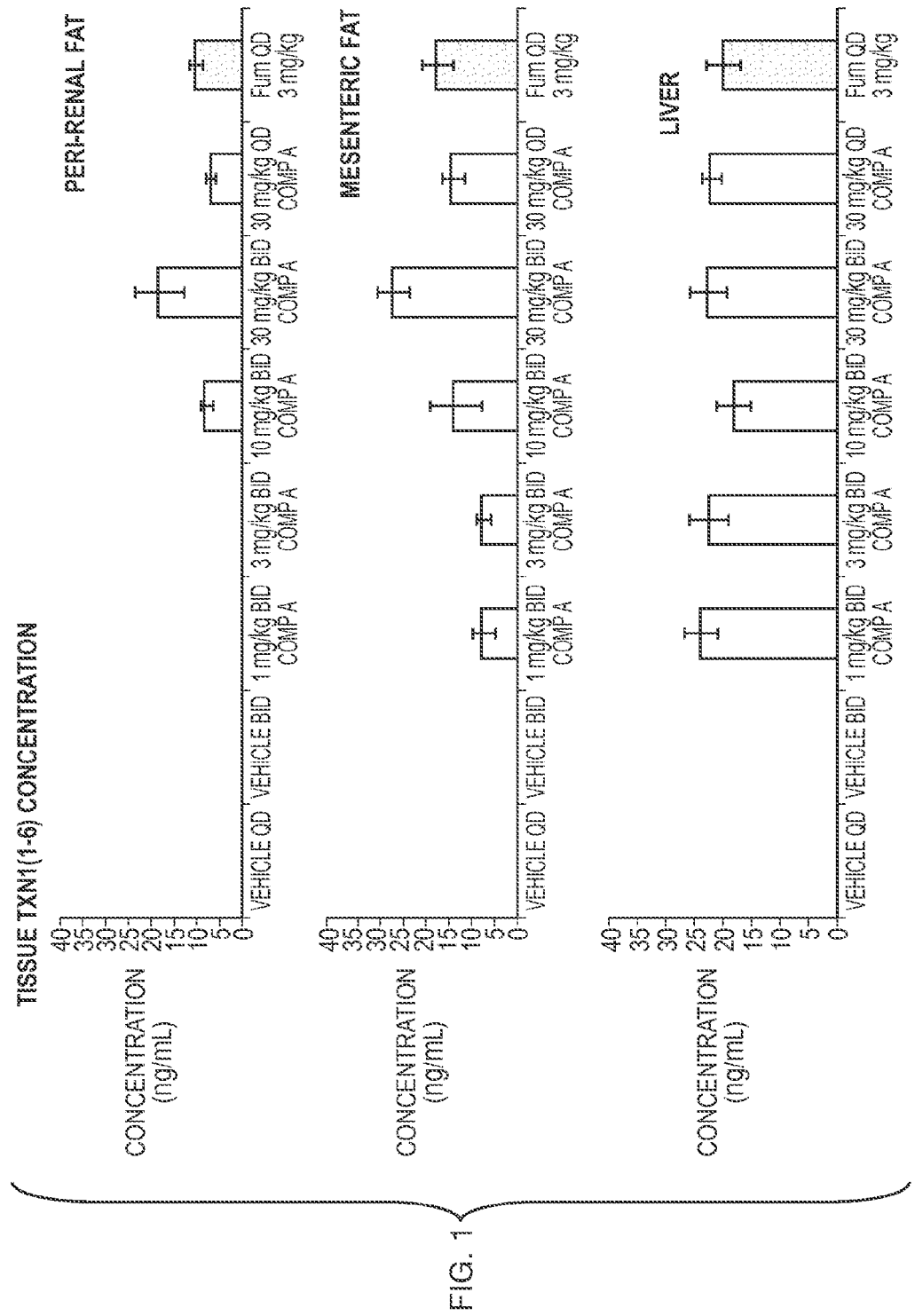
FIG. 1 indicates a disclosed compound targets the liver based on the presence of tissue biomarkers.

The features and other details of the disclosure will now be more particularly described. Before further description of the present invention, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

DEFINITIONS

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkoxyalkyl" as used herein refers to a straight or branched alkyl group attached to oxygen, attached to a second straight or branched alkyl group (alkyl-O-alkyl-). Exemplary alkoxyalkyl groups include, but are not limited to, alkoxyalkyl groups in which each of the alkyl groups independently contains 1-6 carbon atoms, referred to herein as $C_{1-6}$alkoxy-$C_{1-6}$alkyl. Exemplary alkoxyalkyl groups include, but are not limited to methoxymethyl, 2-methoxyethyl, 1-methoxyethyl, 2-methoxypropyl, ethoxymethyl, 2-isopropoxyethyl etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to oxygen (alkenyl-O—). Exemplary alkenyloxy groups include, but are not limited to, groups with an alkenyl group of 3-6 carbon atoms, referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to oxygen (alkynyl-O). Exemplary alkynyloxy groups include, but are not limited to, groups with an alkynyl group of 3-6 carbon atoms, referred to herein as $C_{3-6}$alkynyloxy. Exemplary alkynyloxy groups include, but are not limited to, propynyloxy, butynyloxy, etc.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The term "cycloalkoxy" as used herein refers to a cycloalkyl group attached to oxygen (cycloalkyl-O—). Exemplary cycloalkoxy groups include, but are not limited to, cycloalkoxy groups of 3-6 carbon atoms, referred to herein as $C_{3-6}$cycloalkoxy groups. Exemplary cycloalkoxy groups include, but are not limited to, cyclopropoxy, cyclobutoxy, cyclohexyloxy, etc The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated, 4-10 membered ring structures, including bridged or fused rings, and whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The term "heterocyclyloxy" as used herein refers to a heterocyclyl group attached to oxygen (heterocyclyl-O—).

The term "heteroaryloxy" as used herein refers to a heteroaryl group attached to oxygen (heteroaryl-O—).

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of obesity or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system or animal, (e.g. mammal or human) that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount that results in weight loss.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1, F-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts, particularly calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol ═══ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diasteriomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, Classics in Stereoselective Synthesis, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{31}P$, $^{32}P$, 35S, 18F, and 36Cl, respectively. For example, a compound of the invention may have one or more H atom replaced with deuterium.

Certain isotopically-labeled disclosed compounds (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as $(C_{1-8})$alkyl, $(C_{2-12})$alkylcarbonyloxymethyl, 1-(alkylcarbonyloxy)ethyl having from 4 to 9 carbon atoms, 1-methyl-1-(alkylcarbonyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound of the invention contains an alcohol functional group, a prodrug can be formed by the replacement of the hydrogen atom of the alcohol group with a group such as $(C_{1-6})$alkylcarbonyloxymethyl, 1-$((C_{1-6})$alkylcarbonyloxy)ethyl, 1-methyl-1-$((C_{1-6})$alkylcarbonyloxy)ethyl $(C_{1-6})$alkoxycarbonyloxymethyl, N—$(C_{1-6})$alkoxycarbonylaminomethyl, succinoyl, $(C_{1-6})$alkylcarbonyl, α-amino$(C_{1-4})$alkylcarbonyl, arylalkylcarbonyl and α-aminoalkylcarbonyl, or α-aminoalkylcarbonyl-α-aminoalkylcarbonyl, where each α-aminoalkylcarbonyl group is independently selected from the naturally occurring L-amino acids, P(O)(OH)$_2$, —P(O)(O(C$_{1-6}$)alkyl)$_2$ or glycosyl (the radical resulting from the removal of a hydroxyl group of the hemiacetal form of a carbohydrate).

If a compound of the invention incorporates an amine functional group, a prodrug can be formed, for example, by creation of an amide or carbamate, an N-alkylcarbonyloxyalkyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

I. Tricyclic Compounds

In certain embodiments, the present disclosure provides for methods of treating disclosed disease and indications using compounds of Formula I or Formula II:

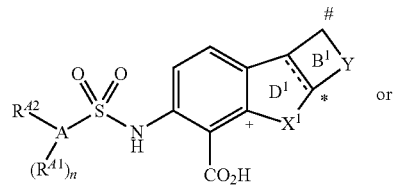

Formula I

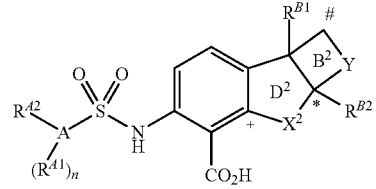

Formula II wherein $B^1$ may be a 3-6 membered saturated or partially unsaturated heterocyclic or carbocyclic ring;

$B^2$ may be a 3-6 membered saturated heterocyclic or carbocyclic ring;

wherein the ring $B^1$ or $B^2$ may optionally be substituted by one or more fluorine atoms on any of the available carbon atoms $D^1$ may be a 5-7 membered heterocyclic, carbocyclic, heteroaromatic or aromatic ring;

$D^2$ may be a 5-7 membered heterocyclic or carbocyclic ring;

wherein $B^1$ is fused to $D^1$ such that the two atoms shared by $B^1$ and $D^1$ are both carbon and $B^2$ is fused to $D^2$ such that the two atoms shared by $B^2$ and $D^2$ are both carbon; and wherein for Formula I the bond common to both the $B^1$ and $D^1$ rings may be a single or double bond;

$X^1$ may be selected from the group consisting of: $^+$—C(R$^{D1}$R$^{D2}$)—*, $^+$—W$^1$—*, $^+$—C(R$^{D1}$R$^{D2}$)—C(R$^{D5}$R$^{D6}$)—*, $^+$—C(R$^{C1}$)=C(R$^{C2}$)—*, $^+$—W$^2$—C(R$^{D5}$R$^{D6}$)—*, $^+$—W$^2$—C(O)—*, $^+$—C(R$^{D1}$R$^{D2}$)—W$^4$—*, $^+$—N=C(R$^{C2}$)—*, $^+$—C(R$^{C1}$)=N—*, $^+$—C(R$^{D1}$R$^{D2}$)—C(R$^{D3}$R$^{D4}$)—C(R$^{D5}$R$^{D6}$)—*, $^+$—W$^2$—C(R$^{D3}$R$^{D4}$)—C(R$^{D5}$R$^{D6}$)—*, $^+$—W$^2$—C(O)—C(R$^{D5}$R$^{D6}$)—*, $^+$—C(R$^{D1}$R$^{D2}$)—*, $^+$—W$^3$—C(R$^{D5}$R$^{D6}$)—*, $^+$—C(R$^{D1}$R$^{D2}$)—W$^3$—C(O)—*, $^+$—C(R$^{D1}$R$^{D2}$)—C(R$^{D3}$R$^{D4}$)—W$^4$—* and $^+$—C(R$^{D1}$R$^{D2}$)—C(O)—W$^4$—*; wherein the $^+$ and * indicate the attachment points of $X^1$ as indicated in Formula I;

$X^2$ may be selected from the group consisting of: $^+$—C(R$^{D1}$R$^{D2}$)—*, $^+$—W$^1$—*, $^+$—C(R$^{D1}$R$^{D2}$)—C(R$^{D5}$R$^{D6}$)—*, $^+$—W$^2$—C(R$^{D5}$R$^{D6}$)—*, $^+$—W$^2$—C(O)—*, $^+$—C(R$^{D1}$R$^{D2}$)—W$^4$—*, $^+$—C(R$^{D1}$R$^{D2}$)—C(R$^{D3}$R$^{D4}$)—C(R$^{D5}$R$^{D6}$)—*, $^+$—W$^2$—C(R$^{D3}$R$^{D4}$)—C(R$^{D5}$R$^{D6}$)—*, $^+$—W$^2$—C(O)—C(R$^{D5}$R$^{D6}$)—*, $^+$—C(R$^{D1}$R$^{D2}$)—W$^3$—C(R$^{D5}$R$^{D6}$)—*, $^+$—C(R$^{D1}$R$^{D2}$)—W$^3$—C(O)—*, $^+$—C(R$^{D1}$R$^{D2}$)—C(R$^{D3}$R$^{D4}$)—W$^4$—* and $^+$—C(R$^{D1}$R$^{D2}$)—C(O)—W$^4$—*; wherein the $^+$ and * indicate the attachment points of $X^2$ as indicated in Formula II;

Y may be selected from the group consisting of: a bond, *—CH$_2$—#, *—O—#, *—CH$_2$—CH$_2$—#, *—O—CH$_2$—#, *—CH$_2$—O—#, *—CH$_2$—CH$_2$—CH$_2$—#, *—O—CH$_2$—CH$_2$—# and *—CH$_2$—O—CH$_2$—#; wherein the * and # indicate the attachment points of Y as indicated in Formula I or Formula II;

W$^1$ may be selected from the group consisting of O, S, or N(R$^{N1}$);

W$^2$ may be selected from the group consisting of O or N(R$^{N2}$);

W$^3$ may be selected from the group consisting of O or N(R$^{N3}$);

W$^4$ may be selected from the group consisting of O or N(R$^{N4}$);

A may be a ring selected from the group consisting of phenyl, a 5-6 membered heteroaryl having 1, 2 or 3 heteroatoms each selected from S, N or O, and a 4-7 membered heterocycle having 1, 2 or 3 heteroatoms each selected from N or O;

R$^{B1}$ and R$^{B2}$ are independently selected from the group consisting of H, F, OH, CN, C$_{1-2}$alkoxy or C$_{1-3}$alkyl; wherein C$_{1-3}$alkyl and C$_{1-2}$alkoxy are optionally substituted by a group selected from OH, C$_{1-2}$alkoxy, CN or one or more fluorine atoms;

R$^{A1}$ may be selected, independently for each occurrence, from the group consisting of hydrogen, hydroxyl, cyano, halogen, C$_{1-4}$alkyl or C$_{1-3}$alkoxy; wherein C$_{1-4}$alkyl, or C$_{1-3}$alkoxy may be optionally substituted by one or more fluorines;

n may be 1 or 2;

R$^{A2}$ may be selected from the group consisting of hydrogen, R$^i$R$^j$N—, heterocyclyl, heterocyclyloxy and heterocyclyl-(NR$^a$)—; wherein said heterocyclyl may optionally be substituted by one or more substituents selected from R$^g$ and wherein if said heterocyclyl contains a —NH moiety that nitrogen may optionally be substituted by one or more groups R$^h$; or R$^{A2}$ may be selected from the group consisting of: C$_{1-6}$alkyl, C$_{2-6}$alkenyl, C$_{2-6}$alkynyl, C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-S(O)$_w$— (wherein w is 0, 1 or 2), C$_{1-6}$alkyl-N(R$^a$)—, C$_{1-6}$alkyl-N(R$^a$)-carbonyl-, C$_{1-6}$alkyl-carbonyl-N(R$^a$)—, C$_{1-6}$alkyl-N(R$^a$)-carbonyl-N(R$^a$)—, C$_{1-6}$alkyl-N(R$^a$)—SO$_2$—, C$_{1-6}$alkyl-SO$_2$—N(R$^a$)—, C$_{1-6}$alkoxycarbonyl-N(R$^a$)—, C$_{1-6}$alkylcarbonyl-N(R$^a$)—C$_{1-6}$alkyl-, C$_{1-6}$alkyl-N(R$^a$)-carbonyl-C$_{1-6}$alkyl-, C$_{1-6}$alkoxyC$_{1-6}$alkyl-; wherein C$_{1-6}$alkyl, C$_{2-6}$alkenyl, C$_{2-6}$alkynyl, C$_{3-6}$cycloalkyl, C$_{1-6}$alkoxy, C$_{3-6}$alkenyloxy, C$_{3-6}$alkynyloxy, C$_{3-6}$cycloalkoxy, C$_{1-6}$alkyl-S(O)$_w$—, C$_{1-6}$alkyl-N(R$^a$)—, C$_{1-6}$alkyl-N(R$^a$)-carbonyl-, C$_{1-6}$alkyl-carbonyl-N(R$^a$)—, C$_{1-6}$alkyl-N(R$^a$)-carbonyl-N(R$^a$)—, C$_{1-6}$alkyl-N(R$^a$)—SO$_2$—, C$_{1-6}$alkyl-SO$_2$—N(R$^a$)—, C$_{1-6}$alkoxycarbonyl-N(R$^a$)—, C$_{1-6}$alkylcarbonyl-N(R$^a$)C$_{1-6}$alkyl-, C$_{1-6}$alkyl-N(R$^a$)-carbonyl-C$_{1-6}$alkyl-, C$_{1-6}$alkoxy-C$_{1-6}$alkyl may optionally be substituted by R$^P$, phenyl, phenoxy, heteroaryl, heteroaryloxy, heteroaryl-(NR$^a$)—, heterocyclyl, heterocyclyloxy or heterocyclyl-N(R$^a$)—; and wherein said heteroaryl or phenyl may optionally be substituted with one or more substituents selected from R$^f$; and wherein said heterocyclyl may optionally be substituted by one or more substituents selected from R$^g$; and wherein if said heterocyclyl contains a —NH moiety that nitrogen may optionally be substituted by one or more groups R$^h$;

R$^{D1}$ and R$^{D2}$ may be each independently selected from the group consisting of hydrogen, fluorine, hydroxyl, C$_{1-2}$alkyl or C$_{1-2}$alkoxy; wherein the C$_{1-2}$alkyl and C$_{1-2}$alkoxy may optionally be substituted by one or more fluorine atoms or a group selected from cyano or hydroxyl;

R$^{D3}$ and R$^{D4}$ may be each independently selected from the group consisting of hydrogen, fluorine, hydroxyl, cyano, C$_{1-3}$alkyl or C$_{1-3}$alkoxy; wherein the C$_{1-3}$ alkyl and C$_{1-3}$ alkoxy may optionally be substituted by one or more fluorine atoms or a group selected from cyano, hydroxyl or N(R$^a$R$^b$);

R$^{D5}$ and R$^{D6}$ may be each independently selected from the group consisting of hydrogen, fluorine, hydroxyl, cyano, C$_{1-2}$alkyl or C$_{1-2}$alkoxy; wherein the C$_{1-2}$alkyl and C$_{1-2}$alkoxy may optionally be substituted by one or more fluorine atoms or a group selected from cyano, hydroxyl or N(R$^a$R$^b$);

R$^{C1}$ may be selected from the group consisting of hydrogen, halogen, C$_{1-2}$alkyl or C$_{1-2}$alkoxy; wherein the C$_{1-2}$alkyl or C$_{1-2}$alkoxy may optionally be substituted by one or more fluorine atoms;

R$^{C2}$ may be selected from the group consisting of hydrogen, halogen, hydroxyl, cyano, C$_{1-2}$alkyl or C$_{1-2}$alkoxy; wherein the C$_{1-2}$alkyl and C$_{1-2}$alkoxy may optionally be substituted by one or more fluorine atoms or a group selected from cyano, hydroxyl or N(R$^a$R$^b$);

R$^{N1}$ may be selected from the group consisting of hydrogen or C$_{1-2}$alkyl;

R$^{N2}$ may be selected from the group consisting of hydrogen or C$_{1-2}$alkyl;

R$^{N3}$ may be selected from the group consisting of hydrogen, C$_{1-3}$alkyl or C$_{1-2}$alkylcarbonyl; wherein the C$_{1-3}$alkyl and C$_{1-2}$alkylcarbonyl may optionally be substituted by one or more fluorine atoms or a group selected from cyano, hydroxyl or N(R$^a$R$^b$);

R$^{N4}$ may be selected from the group consisting of hydrogen, C$_{1-3}$alkyl or C$_{1-2}$alkylcarbonyl; wherein the C$_{1-3}$alkyl and C$_{1-2}$alkylcarbonyl may optionally be substituted by one or more fluorine atoms or a group selected from cyano, hydroxyl or N(R$^a$R$^b$);

R$^a$ and R$^b$ may be independently selected, for each occurrence, from the group consisting of hydrogen and C$_{1-3}$alkyl; wherein C$_{1-3}$alkyl may optionally be substituted by one or more substituents selected from fluorine, cyano, oxo and hydroxyl;

or R$^a$ and R$^b$, together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

R$^f$ may be independently selected, for each occurrence, from the group consisting of R$^P$, hydrogen, C$_{1-6}$alkyl, C$_{3-6}$cycloalkyl, C$_{2-6}$alkenyl, C$_{2-6}$alkynyl, C$_{1-6}$alkoxy, C$_{1-6}$alkyl-S(O)$_w$—, (wherein w is 0, 1 or 2), C$_{1-6}$alkylcarbonyl-N(R$^a$)— and C$_{1-6}$alkoxycarbonyl-N(R$^a$)—; wherein C$_{1-6}$alkyl, C$_{3-6}$cycloalkyl, C$_{2-6}$alkenyl, C$_{2-6}$alkynyl, C$_{1-6}$alkoxy, C$_{1-6}$alkyl-S(O)$_w$—, C$_{1-6}$alkylcarbonyl-N(R$^a$)—, C$_{1-6}$alkoxycarbonyl-N(R$^a$)— may be optionally substituted by one or more substituents selected from R$^P$;

R$^g$ may be independently selected for each occurrence from the group consisting of R$^P$, hydrogen, oxo, C$_{1-6}$alkyl, C$_{2-6}$alkenyl, C$_{2-6}$alkynyl, C$_{3-6}$cycloalkyl, C$_{1-6}$alkoxy, C$_{1-6}$alkyl-S(O)$_w$—, (wherein w is 0, 1 or 2), C$_{1-6}$alkylcarbonyl-N(R$^a$)— and C$_{1-6}$alkoxycarbonyl-N(R$^a$)—; wherein C$_{1-6}$alkyl, C$_{2-6}$alkenyl, C$_{2-6}$alkynyl, C$_{3-6}$cycloalkyl, C$_{1-6}$alkoxy, C$_{1-6}$alkyl-S(O)$_w$—, C$_{1-6}$alkylcarbonyl-N(R$^a$)—, C$_{1-6}$alkoxycarbonyl-N(R$^a$)— may be optionally substituted by one or more substituents selected from R$^P$;

$R^h$ may be independently selected for each occurrence from the group consisting of hydrogen, $C_{1-6}$alkyl, $C_{3-6}$alkenyl, $C_{3-6}$alkynyl, $C_{3-6}$cycloalkyl, $C_{1-6}$alkyl-S(O)$_2$—, $C_{1-6}$alkoxycarbonyl-, $R^iR^jN$-carbonyl- and $R^iR^jN$—SO$_2$—; wherein $C_{1-6}$alkyl, $C_{3-6}$alkenyl, $C_{3-6}$alkynyl $C_{3-6}$cycloalkyl and $C_{1-6}$alkyl-S(O)$_2$—, $C_{1-6}$alkylcarbonyl- may optionally be substituted by one or more substituents selected from $R^P$;

$R^i$ and $R^j$ may be selected independently for each occurrence from the group consisting of hydrogen, $C_{1-4}$alkyl $C_{3-6}$cycloalkyl, heterocyclyl and heterocyclylcarbonyl; wherein $C_{1-4}$alkyl and $C_{3-6}$cycloalkyl may be optionally substituted by one or more substituents selected from fluorine, hydroxyl, cyano, $R^aR^bN$—, $R^aR^bN$-carbonyl- and $C_{1-3}$alkoxy and wherein heterocyclyl and heterocyclylcarbonyl may be optionally substituted by one or more substituents selected from $C_{1-6}$alkyl, $C_{2-6}$alkenyl, $C_{2-6}$alkynyl, $C_{3-6}$cycloalkyl, $C_{1-6}$alkoxy, halo-$C_{1-6}$-alkyl, hydroxyl-$C_{1-6}$-alkyl, $R^aR^bN$—$C_{1-6}$alkyl- and $C_{1-6}$-alkoxy-$C_{1-6}$-alkyl group; and wherein if said heterocyclyl or heterocyclylcarbonyl contains a —NH moiety that nitrogen may optionally be substituted by one or more groups $C_{1-6}$alkyl, $C_{3-6}$alkenyl, $C_{3-6}$alkynyl, $C_{3-6}$cycloalkyl, $C_{1-6}$alkyl-S(O)$_2$— and $C_{1-6}$-alkylcarbonyl;

or $R^i$ and $R^j$ taken together with the nitrogen to which they are attached may form a 4-7 membered heterocyclic ring, which may have an additional heteroatom selected from O, S, or N; wherein the 4-7 membered heterocyclic ring may be optionally substituted on carbon by one or more substituents selected from the group consisting of fluorine, hydroxyl, oxo, cyano, $C_{1-6}$alkyl, $C_{1-6}$alkoxy, $R^aR^bN$—, $R^aR^bN$—SO$_2$— and $R^aR^bN$-carbonyl-; wherein said $C_{1-6}$alkyl or $C_{1-6}$alkoxy may optionally be substituted by fluorine, hydroxyl or cyano; and wherein the 4-7 membered heterocyclic ring may be optionally substituted on nitrogen by one or more substituents selected from the group consisting of $C_{1-6}$alkyl and $R^aR^bN$-carbonyl-; and wherein said $C_{1-6}$alkyl may be optionally substituted by fluorine, hydroxyl, cyano;

$R^P$ may be independently selected, for each occurrence, from the group consisting of halogen, hydroxyl, cyano, $C_{1-6}$alkoxy, $R^iR^jN$-carbonyl-, $R^iR^jN$—SO$_2$— and $R^iR^jN$-carbonyl-N(R$^a$)—;

and pharmaceutically acceptable salts, stereoisomers, esters and prodrugs thereof.

In some embodiments, $X^1$ may be selected from the group consisting of: $^+$—O—*, $^+$—N(R$^{N1}$)—*, $^+$—C(R$^{D1}$R$^{D2}$)—C(R$^{D5}$R$^{D6}$)—*, $^+$—(R$^{C1}$)=C(R$^{C2}$)—*, $^+$—O—C(R$^{D5}$R$^{D6}$)—*, $^+$—O—C(R$^{D3}$R$^{D4}$)—C(R$^{D5}$R$^{D6}$)—*; wherein the $^+$ and * indicate the attachment points of $X^1$ as indicated in Formula I. Exemplary $X^1$ moieties may be selected from the group consisting of: $^+$—NH—*, $^+$—O—CH$_2$—*, $^+$—NH—CH$_2$—*, $^+$—N=CH—* and $^+$—CH=CH—*; wherein the $^+$ and * indicate the attachment points of $X^1$ as indicated in Formula I.

In some embodiments $X^2$ may be selected from the group consisting of $^+$—O—*, $^+$—N(R$^{N1}$)—*, $^+$—C(R$^{D1}$R$^{D2}$)—C(R$^{D5}$R$^{D6}$)—*, $^+$—O—C(R$^{D5}$R$^{D6}$)—*, $^+$—N(R$^{N2}$)—C(R$^{D5}$R$^{D6}$)—*, $^+$—O—C(O)—*, $^+$—N(R$^{N2}$)—C(O)—*, and $^+$—O—C(R$^{D3}$R$^{D4}$)$^C$(R$^{D5}$R$^{D6}$)—*; wherein the $^+$ and * indicate the attachment points of $X^2$ as indicated in Formula II. Exemplary $X^2$ moieties may be selected from the group consisting of: $^+$—O—CH$_2$—* and $^+$—NH—CH$_2$—*; wherein the $^+$ and * indicate the attachment points of $X^2$ as indicated in Formula II.

In one embodiment, $R^{D1}$, $R^{D2}$, $R^{C1}$, $R^{N1}$ and $R^{N2}$ may be independently selected for each occurrence from the group consisting of hydrogen and methyl. For example, $R^{D1}$, $R^{D2}$, $R^{C1}$, $R^{N1}$ and $R^{N2}$ may be hydrogen.

In certain embodiments, $R^{D3}$, $R^{D4}$, $R^{D5}$ and $R^{D6}$ may be independently selected for each occurrence from the group consisting of hydrogen, fluorine, cyano and $C_{1-2}$alkyl. For example, $R^{D3}$, $R^{D4}$, $R^{D5}$ and $R^{D6}$ may be hydrogen.

In an embodiment, $R^{C2}$ may be selected from the group consisting of hydrogen, halogen, cyano and $C_{1-2}$alkyl. For example, $R^{C2}$ may be hydrogen.

In certain embodiments, $R^{B1}$ of the tricyclic compound of Formula II may be selected from the group consisting of H, F or $C_{1-2}$alkyl. For example, $R^{B1}$ may be H or methyl.

In another embodiment, $R^{B2}$ of the tricyclic compound of Formula II may be hydrogen.

In certain embodiments, ring $D^1$ may be selected from the group consisting of:

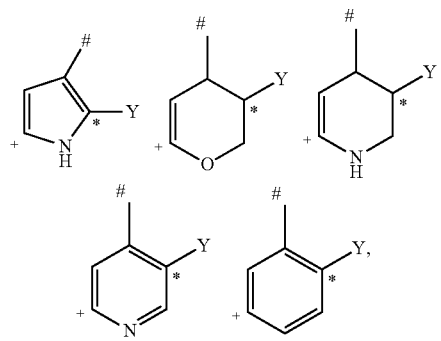

wherein the *, # and + indicate the points of attachment to the phenyl ring and the $B^1$ ring as indicated in Formula I. Exemplary $D^1$ rings that may form part of the contemplated tricyclic core may include those selected from the group consisting of:

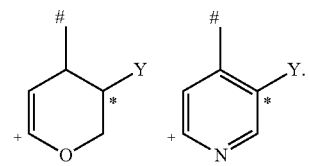

In certain embodiments, ring $D^2$ may be selected from the group consisting of:

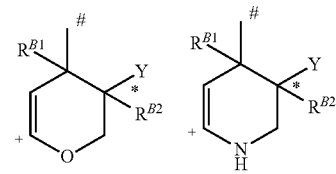

wherein the *, # and + indicate the points of attachment to the phenyl ring and the $B^2$ ring as indicated in Formula II.

In some embodiments, Y may be selected from the group consisting of a bond, *—O—CH$_2$—$^\#$ and *—CH$_2$—O—CH$_2$—$^\#$; wherein the * and $^\#$ indicate the points of attachment to Y as indicated in Formula I or Formula II. For example, Y may be a bond or *—O—CH$_2$—$^\#$; wherein the * and $^\#$ indicate the points of attachment to Y as indicated in Formula I or Formula II.

For example, ring $B^1$ or $B^2$ may, in certain embodiments, be selected from the group consisting of:

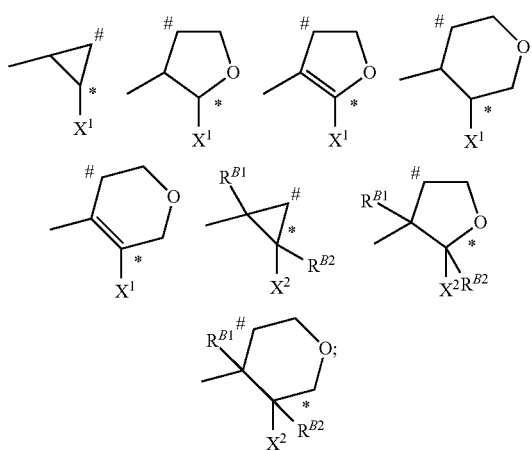

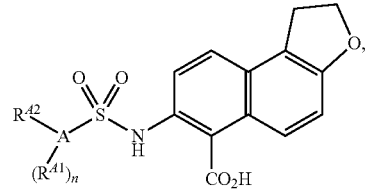
Id

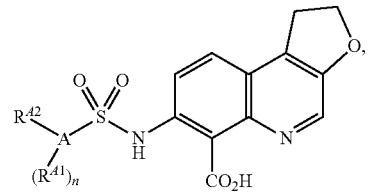
Ie

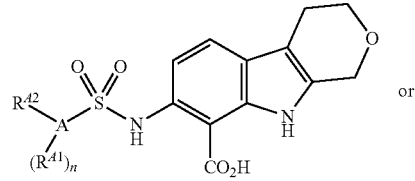
If or

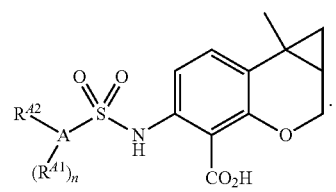
Ig wherein the * and # indicate the points of attachment to Y as indicated in Formula I and II. Exemplary $B^1$ and $B^2$ rings that may form part of the contemplated tricyclic core may include those selected from the group consisting of:

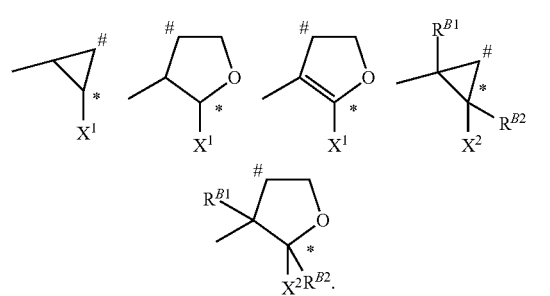

Provided herein, for example, are tricyclic compounds represented by formulas Ia, Ib, Ic, Id, Ie, If and Ig:

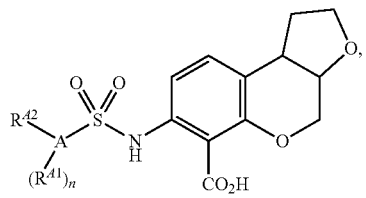
Ia

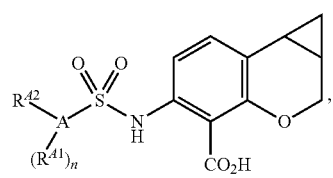
Ib

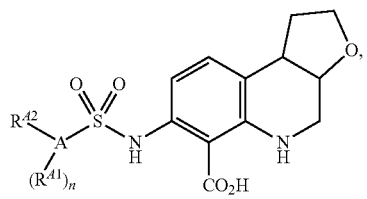
Ic

In certain embodiments, A may be phenyl.

Also provided herein is are methods of treating disclosed disease and indications using compounds represented by Formula III:

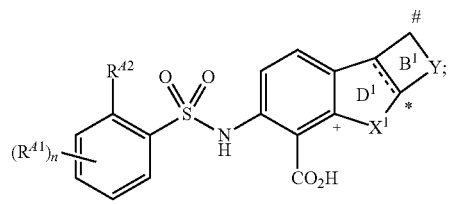
Formula III wherein:

$B^1$ may be a 3-6 membered saturated or partially unsaturated heterocyclic or carbocyclic ring; wherein the ring $B^1$ may optionally be substituted by one or more fluorine atoms on any of the available carbon atoms;

$D^1$ may be a 5-7 membered heterocyclic, carbocyclic, heteroaromatic or aromatic ring; wherein $B^1$ is fused to $D^1$ such that the two atoms shared by $B^1$ and $D^1$ are both carbon; and wherein the bond common to both the $B^1$ and $D^1$ rings may be a single or double bond;

$X^1$ may be selected from the group consisting of: $^+$—C$(R^{D1}R^{D2})$—*, $^+$—$W^1$—*, $^+$—C$(R^{D1}R^{D2})$—C$(R^{D5}R^{D6})$—*, $^+$—C$(R^{C1})$=C$(R^{C2})$—*, $^+$—$W^2$—C$(R^{D5}R^{D6})$—*, $^+$—$W^2$—C(O)—*, $^+$—C$(R^{D1}R^{D2})$—$W^4$—*, $^+$—N=C$(R^{C2})$—*, $^+$—C$(R^{C1})$=N—*, $^+$—C$(R^{D1}R^{D2})$—C$(R^{D3}R^{D4})$—C$(R^{D5}R^{D6})$—*, $^+$—$W^2$—C$(R^{D3}R^{D4})$—C$(R^{D5}R^{D6})$—*, $^+$—$W^2$—C(O)—C$(R^{D5}R^{D6})$—*, $^+$—C $(R^{D1}R^{D2})$—$W^3$—$C(R^{D5}R^{D6})$—*, $^+$—$C(R^{D1}R^{D2})$—$W^3$—$C(O)$—*, $^+$—$C(R^{D1}R^{D2})$—$C(R^{D3}R^{D4})$—$W^4$—* and $^+$—$C(R^{D1}R^{D2})$—$C(O)$—$W^4$—*; wherein the $^+$ and * indicate the attachment points of $X^1$ as indicated in Formula III;

Y may be selected from the group consisting of: a bond, *—$CH_2$—$^\#$, *—$CH_2$—$CH_2$—$^\#$, *—O—$CH_2$—$^\#$, *—$CH_2$—O—$^\#$, *—$CH_2$—$CH_2$—$CH_2$—$^\#$, *—O—$CH_2$—$CH_2$—$^\#$ and *—$CH_2$—O—$CH_2$—$^\#$; wherein the * and $^\#$ indicate the attachment points of Y as indicated in Formula III;

$W^1$ may be selected from the group consisting of O, S or $N(R^{N1})$;

$W^2$ may be selected from the group consisting of O or $N(R^{N2})$;

$W^3$ may be selected from the group consisting of O or $N(R^{N3})$;

$W^4$ may be selected from the group consisting of O or $N(R^{N4})$;

$R^{A1}$ may be selected, independently for each occurrence, from the group consisting of hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n may be 0, 1, or 2;

$R^{A2}$ may be selected from the group consisting of hydrogen, $R^iR^jN$—, heterocyclyl, heterocyclyloxy and heterocyclyl-$(NR^a)$—; wherein said heterocyclyl may optionally be substituted by one or more substituents selected from $R^g$ and wherein if said heterocyclyl contains a —NH moiety that nitrogen may optionally be substituted by one or more groups $R^h$; or $R^{A2}$ may be selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$— (wherein w is 0, 1 or 2), $C_{1-6}$alkyl-$N(R^a)$—, $C_{1-6}$alkyl-$N(R^a)$-carbonyl-, $C_{1-6}$alkyl-carbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-$N(R^a)$—, $C_{1-6}$alkylcarbonyl-$N(R^a)$—$C_{1-6}$alkyl-, $C_{1-6}$alkyl-$N(R^a)$-carbonyl-$C_{1-6}$alkyl-, $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$—, $C_{1-6}$alkyl-$N(R^a)$—, $C_{1-6}$alkyl-$N(R^a)$-carbonyl-, $C_{1-6}$alkyl-carbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-$N(R^a)$—, $C_{1-6}$alkylcarbonyl-$N(R^a)C_{1-6}$alkyl-, $C_{1-6}$alkyl-$N(R^a)$-carbonyl-$C_{1-6}$alkyl-, $C_{1-6}$alkoxy-$C_{1-6}$alkyl may optionally be substituted by $R^P$, phenyl, phenoxy, heteroaryl, heteroaryloxy, heteroaryl-$(NR^a)$—, heterocyclyl, heterocyclyloxy or heterocyclyl-$N(R^a)$—; and wherein said heteroaryl or phenyl may optionally be substituted with one or more substituents selected from $R^f$; and wherein said heterocyclyl may optionally be substituted by one or more substituents selected from $R^g$; and wherein if said heterocyclyl contains a —NH moiety that nitrogen may optionally be substituted by one or more groups $R^h$;

$R^{D1}$ and $R^{D2}$ may be each independently selected from the group consisting of hydrogen, fluorine, hydroxyl, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano or hydroxyl;

$R^{D3}$ and $R^{D4}$ may be each independently selected from the group consisting of hydrogen, fluorine, hydroxyl, cyano, $C_{1-3}$alkyl or $C_{1-3}$alkoxy; wherein the $C_{1-3}$ alkyl and $C_{1-3}$ alkoxy may optionally be substituted by one or more fluorine atoms or a group selected from cyano, hydroxyl or $N(R^aR^b)$;

$R^{D5}$ and $R^{D6}$ may be each independently selected from the group consisting of hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or $N(R^aR^b)$;

$R^{C1}$ may be selected from the group consisting of hydrogen, halogen, $C_{1-2}$alkyl or $C_{1-2}$alkoxy; wherein the $C_{1-2}$alkyl or $C_{1-2}$alkoxy may optionally be substituted by one or more fluorine atoms;

$R^{C2}$ may be selected from the group consisting of hydrogen, halogen, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or $N(R^aR^b)$;

$R^{N1}$ may be selected from the group consisting of hydrogen or $C_{1-2}$alkyl;

$R^{N2}$ may be selected from the group consisting of hydrogen or $C_{1-2}$alkyl;

$R^{N3}$ may be selected from the group consisting of hydrogen, $C_{1-3}$alkyl or $C_{1-2}$alkylcarbonyl; wherein the $C_{1-3}$alkyl and $C_{1-2}$alkylcarbonyl may optionally be substituted by one or more fluorine atoms or a group selected from cyano, hydroxyl or $N(R^aR^b)$;

$R^{N4}$ may be selected from the group consisting of hydrogen, $C_{1-3}$alkyl or $C_{1-2}$alkylcarbonyl; wherein the $C_{1-3}$alkyl and $C_{1-2}$alkylcarbonyl may optionally be substituted by one or more fluorine atoms or a group selected from cyano, hydroxyl or $N(R^aR^b)$;

$R^a$ and $R^b$ may be independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;

or $R^a$ and $R^b$, together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

$R^f$ may be independently selected, for each occurrence, from the group consisting of $R^P$, hydrogen, $C_{1-6}$alkyl, $C_{3-6}$cycloalkyl, $C_{2-6}$alkenyl, $C_{2-6}$alkynyl, $C_{1-6}$alkoxy, (wherein w is 0, 1 or 2), $C_{1-6}$alkylcarbonyl-$N(R^a)$— and $C_{1-6}$alkoxycarbonyl-$N(R^a)$—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkylcarbonyl-$N(R^a)$—, $C_{1-6}$alkoxycarbonyl-$N(R^a)$— may be optionally substituted by one or more substituents selected from $R^P$;

$R^g$ may be independently selected for each occurrence from the group consisting of $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-$S(O)_w$—, (wherein w is 0, 1 or 2), $C_{1-6}$alkylcarbonyl-$N(R^a)$— and $C_{1-6}$alkoxycarbonyl-$N(R^a)$—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkylcarbonyl-$N(R^a)$—, $C_{1-6}$alkoxycarbonyl-$N(R^a)$— may be optionally substituted by one or more substituents selected from $R^P$;

$R^h$ may be independently selected for each occurrence from the group consisting of hydrogen, $C_{1-6}$alkyl, $C_{3-6}$alkenyl, $C_{3-6}$alkynyl, $C_{3-6}$cycloalkyl, $C_{1-6}$alkyl-$S(O)_2$—, $C_{1-6}$alkoxycarbonyl-, $R^iR^jN$-carbonyl- and $R^iR^jN$—$SO_2$—; wherein $C_{1-6}$alkyl, $C_{3-6}$alkenyl, $C_{3-6}$alkynyl $C_{3-6}$cycloalkyl and $C_{1-6}$alkyl-S(O)$_2$—, $C_{1-6}$alkylcarbonyl- may optionally be substituted by one or more substituents selected from $R^P$;

$R^i$ and $R^j$ may be selected independently for each occurrence from the group consisting of hydrogen, $C_{1-4}$alkyl $C_{3-6}$cycloalkyl, heterocyclyl and heterocyclylcarbonyl; wherein $C_{1-4}$alkyl and $C_{3-6}$cycloalkyl may be optionally substituted by one or more substituents selected from fluorine, hydroxyl, cyano, $R^aR^bN$—, $R^aR^bN$-carbonyl- and $C_{1-3}$alkoxy and wherein heterocyclyl and heterocyclylcarbonyl may be optionally substituted by one or more substituents selected from $C_{1-6}$alkyl, $C_{2-6}$alkenyl, $C_{2-6}$alkynyl, $C_{3-6}$cycloalkyl, $C_{1-6}$alkoxy, halo-$C_{1-6}$-alkyl, hydroxyl-$C_{1-6}$-alkyl, $R^aR^bN$—$C_{1-6}$alkyl- and $C_{1-6}$-alkoxy-$C_{1-6}$-alkyl group; and wherein if said heterocyclyl or heterocyclylcarbonyl contains a —NH moiety that nitrogen may optionally be substituted by one or more groups $C_{1-6}$alkyl, $C_{3-6}$alkenyl, $C_{3-6}$alkynyl, $C_{3-6}$cycloalkyl, $C_{1-6}$alkyl-S(O)$_2$— and $C_{1-6}$-alkylcarbonyl;

or $R^i$ and $R^j$ taken together with the nitrogen to which they are attached may form a 4-7 membered heterocyclic ring, which may have an additional heteroatom selected from O, S, or N; wherein the 4-7 membered heterocyclic ring may be optionally substituted on carbon by one or more substituents selected from the group consisting of fluorine, hydroxyl, oxo, cyano, $C_{1-6}$alkyl, $C_{1-6}$alkoxy, $R^aR^bN$—, $R^aR^bN$—SO$_2$— and $R^aR^bN$-carbonyl-; wherein said $C_{1-6}$alkyl or $C_{1-6}$alkoxy may optionally be substituted by fluorine, hydroxyl or cyano; and wherein the 4-7 membered heterocyclic ring may be optionally substituted on nitrogen by one or more substituents selected from the group consisting of $C_{1-6}$alkyl and $R^aR^bN$-carbonyl-; and wherein said $C_{1-6}$alkyl may be optionally substituted by fluorine, hydroxyl, cyano;

$R^P$ may be independently selected, for each occurrence, from the group consisting of halogen, hydroxyl, cyano, $C_{1-6}$alkoxy, $R^iR^jN$-carbonyl-, $R^iR^jN$—SO$_2$— and $R^iR^jN$-carbonyl-N(R$^a$)—;

and pharmaceutically acceptable salts, stereoisomers, esters and prodrugs thereof.

In certain embodiments, $R^{41}$ of the tricyclic compound of Formula III may be selected from the group consisting of hydrogen, halogen, $C_{1-2}$alkyl and $C_{1-2}$alkoxy; wherein $C_{1-2}$alkyl may optionally be substituted by one or more fluorines. For example, $R^{41}$ may be hydrogen or fluorine.

In another embodiment, $R^{42}$ of the tricyclic compound of Formula III may be selected from the group consisting of hydrogen, $R^iR^jN$, heterocyclyl, $C_{1-6}$alkyl, $C_{3-6}$alkenyl, $C_{3-6}$cycloalkyl, $C_{1-6}$alkoxy; wherein said heterocyclyl may optionally be substituted by one or more groups $R^g$; and wherein if said heterocyclyl contains a —NH moiety, that nitrogen may optionally be substituted by one or more groups $R^h$; and wherein said $C_{1-6}$alkyl, $C_{3-6}$alkenyl, $C_{3-6}$cycloalkyl and $C_{1-6}$alkoxy may optionally be substituted by one or more groups $R^P$. For example, $R^{42}$ may be selected from the group consisting of 3-(N,N-diethylamino)propyl, 3-(pyrrolidin-1-yl)propyl, (Z)-3-(N,N-diethylamino)prop-1-enyl, (Z)-3-(azetidin-1-yl)prop-1-enyl and (Z)-3-(pyrrolidin-1-yl)prop-1-enyl.

Also provided herein are methods of treating disclosed disease and indications using compounds represented by Formula IV:

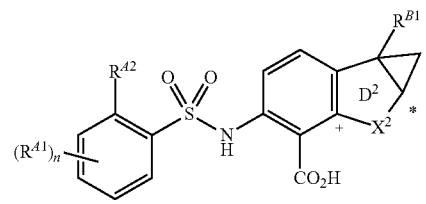

Formula IV $D^2$ may be a 5-7 membered partially unsaturated heterocyclic or carbocyclic ring;

$X^2$ may be selected from the group consisting of: $^+$—C(R$^{D1}$R$^{D2}$)—*, $^+$—W$^1$—*, $^+$—C(R$^{D1}$R$^{D2}$)—C(R$^{D5}$R$^{D6}$)—*, $^+$—W$^2$—C(R$^{D5}$R$^{D6}$)—*, $^+$—W$^2$—C(O)—*, $^+$—C(R$^{D1}$R$^{D2}$)—W$^4$—*, $^+$—C(R$^{D1}$R$^{D2}$)—C(R$^{D3}$R$^{D4}$)—C(R$^{D5}$R$^{D6}$)—*, $^+$—W$^2$—C(R$^{D3}$R$^{D4}$)—C(R$^{D5}$R$^{D6}$)—*, $^+$—W$^2$—C(O)—C(R$^{D5}$R$^{D6}$)—*, $^+$—C(R$^{D1}$R$^{D2}$)—W$^3$—C(R$^{D5}$R$^{D6}$)—*, $^+$—C(R$^{D1}$R$^{D2}$)—W$^3$—C(O)—*, $^+$—C(R$^{D1}$R$^{D2}$)—C(R$^{D3}$R$^{D4}$)—W$^4$—* and $^+$—C(R$^{D1}$R$^{D2}$)—C(O)—W$^4$—*; wherein the $^+$ and * indicate the attachment points of $X^2$ as indicated in Formula IV;

$W^1$ may be selected from the group consisting of O, S or N(R$^{N1}$);

$W^2$ may be selected from the group consisting of O or N(R$^{N2}$);

$W^3$ may be selected from the group consisting of O or N(R$^{N3}$);

$W^4$ may be selected from the group consisting of O or N(R$^{N4}$);

$R^{B1}$ may be selected from the group consisting of H, F, OH, CN, $C_{1-2}$alkoxy or $C_{1-3}$alkyl; wherein $C_{1-3}$alkyl and $C_{1-2}$alkoxy are optionally substituted by a group selected from OH, $C_{1-2}$alkoxy, CN or one or more fluorine atoms;

$R^{41}$ may be selected, independently for each occurrence, from the group consisting of hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n may be 0, 1, or 2;

$R^{42}$ may be selected from the group consisting of hydrogen, $R^iR^jN$—, heterocyclyl, heterocyclyloxy and heterocyclyl-(NR$^a$)—; wherein said heterocyclyl may optionally be substituted by one or more substituents selected from R$^g$ and wherein if said heterocyclyl contains a —NH moiety that nitrogen may optionally be substituted by one or more groups $R^h$; or $R^{42}$ may be selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— (wherein w is 0, 1 or 2), $C_{1-6}$alkyl-N(R$^a$)—, $C_{1-6}$alkyl-N(R$^a$)-carbonyl-, $C_{1-6}$alkyl-carbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^a$)—, $C_{1-6}$alkylcarbonyl-N(R$^a$)—, $C_{1-6}$alkyl-, $C_{1-6}$alkyl-N(R$^a$)-carbonyl-$C_{1-6}$alkyl-, $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$—, $C_{1-6}$alkyl-N(R$^a$)—, $C_{1-6}$alkyl-N(R$^a$)-carbonyl-, $C_{1-6}$alkyl-carbonyl-N(R$^a$)—, $C_{1-6}$alkyl-N(R$^a$)-carbonyl-N(R$^a$)—, $C_{1-6}$alkyl-N(R$^a$)—SO$_2$—, $C_{1-6}$alkyl-SO$_2$—N(R$^a$)—, $C_{1-6}$alkoxycarbonyl-N(R$^a$)—, $C_{1-6}$alkylcarbonyl-N(R$^a$)$C_{1-6}$alkyl-, $C_{1-6}$alkyl-N(R$^a$)-carbonyl-$C_{1-6}$alkyl-, $C_{1-6}$alkoxy-$C_{1-6}$alkyl may optionally be substituted by R$^P$, phenyl, phenoxy, heteroaryl, heteroaryloxy, heteroaryl-(NR$^a$)—, heterocyclyl, heterocyclyloxy or heterocyclyl-N($R^a$)—; and wherein said heteroaryl or phenyl may optionally be substituted with one or more substituents selected from $R^f$; and wherein said heterocyclyl may optionally be substituted by one or more substituents selected from $R^g$; and wherein if said heterocyclyl contains a —NH moiety that nitrogen may optionally be substituted by one or more groups $R^h$;

$R^{D1}$ and $R^{D2}$ may be each independently selected from the group consisting of hydrogen, fluorine, hydroxyl, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano or hydroxyl;

$R^{D3}$ and $R^{D4}$ may be each independently selected from the group consisting of hydrogen, fluorine, hydroxyl, cyano, $C_{1-3}$alkyl or $C_{1-3}$alkoxy; wherein the $C_{1-3}$ alkyl and $C_{1-3}$ alkoxy may optionally be substituted by one or more fluorine atoms or a group selected from cyano, hydroxyl or N($R^a R^b$);

$R^{D5}$ and $R^{D6}$ may be each independently selected from the group consisting of hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by a substituent or substituents selected from the group consisting of: one or more fluorine atoms, cyano, hydroxyl or N($R^a R^b$);

$R^{C1}$ may be selected from the group consisting of hydrogen, halogen, $C_{1-2}$alkyl or $C_{1-2}$alkoxy; wherein the $C_{1-2}$alkyl or $C_{1-2}$alkoxy may optionally be substituted by one or more fluorine atoms;

$R^{C2}$ may be selected from the group consisting of hydrogen, halogen, hydroxyl, cyano, $C_{1-2}$alkyl or $C_{1-2}$alkoxy; wherein the $C_{1-2}$alkyl and $C_{1-2}$alkoxy may optionally be substituted by one or more fluorine atoms or a group selected from cyano, hydroxyl or N($R^a R^b$);

$R^{N1}$ may be selected from the group consisting of hydrogen or $C_{1-2}$alkyl;

$R^{N2}$ may be selected from the group consisting of hydrogen or $C_{1-2}$alkyl;

$R^{N3}$ may be selected from the group consisting of hydrogen, $C_{1-3}$alkyl or $C_{1-2}$alkylcarbonyl; wherein the $C_{1-3}$alkyl and $C_{1-2}$alkylcarbonyl may optionally be substituted by a substituent or substituents selected from the group consisting of: one or more fluorines, cyano, hydroxyl or N($R^a R^b$);

$R^{N4}$ may be selected from the group consisting of hydrogen, $C_{1-3}$alkyl or $C_{1-2}$alkylcarbonyl; wherein the $C_{1-3}$alkyl and $C_{1-2}$alkylcarbonyl may optionally be substituted by a substituent or substituents selected from the group consisting of: one or more fluorines, cyano, hydroxyl or N($R^a R^b$);

$R^a$ and $R^b$ may be independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;

or $R^a$ and $R^b$, together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

$R^f$ may be independently selected, for each occurrence, from the group consisting of $R^P$, hydrogen, $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-S(O)$_w$—, (wherein w is 0, 1 or 2), $C_{1-6}$alkylcarbonyl-N($R^a$)— and $C_{1-6}$alkoxycarbonyl-N($R^a$)—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-S(O)$_w$—, $C_{1-6}$alkylcarbonyl-N($R^a$)—, $C_{1-6}$alkoxycarbonyl-N($R^a$)— may be optionally substituted by one or more substituents selected from $R^P$;

$R^g$ may be independently selected for each occurrence from the group consisting of $R^P$, hydrogen, oxo, $C_{2-6}$alkenyl, $C_{2-6}$alkynyl, $C_{3-6}$cycloalkyl, $C_{1-6}$alkoxy, (wherein w is 0, 1 or 2), $C_{1-6}$alkylcarbonyl-N($R^a$)— and $C_{1-6}$alkoxycarbonyl-N($R^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkylcarbonyl-N($R^a$)—, $C_{1-6}$alkoxycarbonyl-N($R^a$)— may be optionally substituted by one or more substituents selected from $R^P$;

$R^h$ may be independently selected for each occurrence from the group consisting of hydrogen, $C_{1-6}$alkyl, $C_{3-6}$alkenyl, $C_{3-6}$alkynyl, $C_{3-6}$cycloalkyl, $C_{1-6}$alkoxycarbonyl-, $R^i R^j$N-carbonyl- and $R^i R^j$N—SO$_2$—; wherein $C_{1-6}$alkyl, $C_{3-6}$alkenyl, $C_{3-6}$alkynyl $C_{3-6}$cycloalkyl and $C_{1-6}$alkyl-S(O)$_2$—, $C_{1-6}$alkylcarbonyl- may optionally be substituted by one or more substituents selected from $R^P$;

$R^i$ and $R^j$ may be selected independently for each occurrence from the group consisting of hydrogen, $C_{1-4}$alkyl $C_{3-6}$cycloalkyl, heterocyclyl and heterocyclylcarbonyl; wherein $C_{1-4}$alkyl and $C_{3-6}$cycloalkyl may be optionally substituted by one or more substituents selected from fluorine, hydroxyl, cyano, $R^a R^b$N—, $R^a R^b$N-carbonyl- and $C_{1-3}$alkoxy and wherein heterocyclyl and heterocyclylcarbonyl may be optionally substituted by one or more substituents selected from $C_{1-6}$alkyl, $C_{2-6}$alkenyl, $C_{2-6}$alkynyl, $C_{3-6}$cycloalkyl, $C_{1-6}$alkoxy, halo-$C_{1-6}$-alkyl, hydroxyl-$C_{1-6}$ alkyl and $C_{1-6}$-alkoxy-$C_{1-6}$-alkyl group; and wherein if said heterocyclyl or heterocyclylcarbonyl contains a —NH moiety that nitrogen may optionally be substituted by one or more groups $C_{1-6}$alkyl, $C_{3-6}$alkenyl, $C_{3-6}$alkynyl, $C_{3-6}$cycloalkyl, $C_{1-6}$alkyl-S(O)$_2$— and $C_{1-6}$-alkylcarbonyl;

or $R^i$ and $R^j$ taken together with the nitrogen to which they are attached may form a 4-7 membered heterocyclic ring, which may have an additional heteroatom selected from O, S, or N; wherein the 4-7 membered heterocyclic ring may be optionally substituted on carbon by one or more substituents selected from the group consisting of fluorine, hydroxyl, oxo, cyano, $C_{1-6}$alkyl, $C_{1-6}$alkoxy, $R^a R^b$N—, $R^a R^b$N—SO$_2$— and $R^a R^b$N-carbonyl-; wherein said $C_{1-6}$alkyl or $C_{1-6}$alkoxy may optionally be substituted by fluorine, hydroxyl or cyano; and wherein the 4-7 membered heterocyclic ring may be optionally substituted on nitrogen by one or more substituents selected from the group consisting of $C_{1-6}$alkyl and $R^a R^b$N-carbonyl-; and wherein said $C_{1-6}$alkyl may be optionally substituted by one or more substituents selected from the group consisting of fluorine, hydroxyl, cyano;

$R^P$ may be independently selected, for each occurrence, from the group consisting of halogen, hydroxyl, cyano, $C_{1-6}$alkoxy, $R^i R^j$N-carbonyl-, $R^i R^j$N—SO$_2$— and $R^i R^j$N-carbonyl-N($R^a$)—;

and pharmaceutically acceptable salts, stereoisomers, esters and prodrugs thereof.

In certain embodiments, $R^{A1}$ of the tricyclic compound of Formula IV may be hydrogen or fluorine.

In another embodiment, $R^{A2}$ of the tricyclic compound of Formula IV may be selected from the group consisting of hydrogen, $R^i R^j$N, heterocyclyl, $C_{1-6}$alkyl, $C_{3-6}$alkenyl, $C_{3-6}$cycloalkyl, $C_{1-6}$alkoxy, heterocyclyl-NR$^a$-carbonyl-$C_{1-6}$alkyl and heterocyclyl-carbonyl-NR$^a$—$C_{1-6}$alkyl; wherein said heterocyclyl may optionally be substituted by one or more groups $R^g$; and wherein if said heterocyclyl contains a —NH moiety, that nitrogen may optionally be substituted by one or more groups $R^h$; and wherein said $C_{1-6}$alkyl, $C_{3-6}$alkenyl, $C_{3-6}$cycloalkyl and $C_{1-6}$alkoxy may optionally be substituted by one or more groups $R^P$.

Also provided herein are methods of treating disclosed disease and indications using compounds that may be selected from the group consisting of: cis-(3aRS,9bRS)-7-(benzenesulfonylamino)-1,3a,4,9b-tetrahydro-2H-furo[2,3-c]chromene-6-carboxylic acid; cis-(3aRS,9bRS)-7-[2-(3-diethylaminopropyl)-4-fluorobenzenesulfonyl-amino]-1,3a,4, 9b-tetrahydro-2H-furo[2,3-c]chromene-6-carboxylic acid; cis-(3aRS,9bRS)-7-[2-(3-{pyrrolidin-1-yl}propyl)-4-fluorobenzenesulfonylamino]-1,3a,4,9b-tetrahydro-2H-furo[2, 3-c]chromene-6-carboxylic acid; cis-(3aRS,9bRS)-7-[2-((Z)-3-diethylaminoprop-1-enyl)-4-fluorobenzenesulfonylamino]-1,3a,4,9b-tetrahydro-2H-furo [2,3-c]chromene-6-carboxylic acid; cis-(3aR,9bR)-7-[2-((Z)-3-diethylaminoprop-1-enyl)-4-fluoro-benzenesulfonylamino]-1,3a,4,9b-tetrahydro-2H-furo[2,3-c]chromene-6-carboxylic acid; cis-(3aS,9bS)-7-[2-((Z)-3-diethylaminoprop-1-enyl)-4-fluorobenzenesulfonylamino]-1,3a,4,9b-tetrahydro-2H-furo[2,3-c]chromene-6-carboxylic acid; 7-[2-((Z)-3-diethylaminoprop-1-enyl)-4-fluorobenzenesulfonylamino]-1,2-dihydrofuro[2,3-c]quinoline-6-carboxylic acid formate salt; 7-(benzenesulfonylamino))-1,2-dihydrofuro[2,3-c]quinoline-6-carboxylic acid formate salt; cis-(3aRS,9bRS)-7-[2-((Z)-3-diethylaminoprop-1-enyl)-4-fluorobenzenesulfonylamino]-1,2,3a,4,5,9b-hexahydrofuro [2,3-c]quinoline-6-carboxylic acid; (1aRS,7bSR)-5-[2-((Z)-3-diethylaminoprop-1-enyl)-4-fluorobenzenesulfonylamino]-1,1a,2,7b-tetrahydrocyclopropa[c]chromene-4-carboxylic acid; (1aR, 7bS)-5-[2-((Z)-3-diethylaminoprop-1-enyl)-4-fluorobenzenesulfonylamino]-1,1a,2,7b-tetrahydrocyclopropa[c]chromene-4-carboxylic acid; (1aS, 7bR)-5-[2-((Z)-3-diethylaminoprop-1-enyl)-4-fluorobenzenesulfonylamino]-1,1a,2,7b-tetrahydrocyclopropa[c]chromene-4-carboxylic acid; (1aRS,7bSR)-5-[2-((Z)-3-diethylaminoprop-1-enyl)-4-fluorobenzenesulfonylamino]-7b-methyl-1,1a,2,7b-tetrahydrocyclopropa[c]chromene-4-carboxylic acid; (1aRS,7bSR)-5-[2-((E)-3-diethylaminoprop-1-enyl)-4-fluorobenzenesulfonylamino]-7b-methyl-1,1a,2,7b-tetrahydrocyclopropa[c]chromene-4-carboxylic acid; cis-(3aRS,9bRS)-7-[2-(4-dimethylamino-butylamino)-benzenesulfonylamino]-1,3a,4,9b-tetrahydro-2H-furo[2,3-c]chromene-6-carboxylic acid; (1aR,7bS)-5-[2-(3-diethylaminopropyl)-4-fluorobenzenesulfonyl-amino]-1,1a, 2,7b-tetrahydrocyclopropa[c]chromene-4-carboxylic acid; (1aRS,7bSR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1aR,7bS)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1aS, 7bR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid; (1aRS,7bSR)-5-[2((Z)-3-ethylaminoprop-1-enyl)-4-fluorobenzenesulfonylamino]-1,1a,2,7b-tetrahydrocyclopropa-[c]chromene-4-carboxylic acid; (1aR,7bS)-5-[2((Z)-3-ethylaminoprop-1-enyl)-4-fluorobenzenesulfonylamino]-1,1a, 2,7b-tetrahydrocyclopropa[c]chromene-4-carboxylic acid; (1aS,7bR)-5-[2((Z)-3-ethylaminoprop-1-enyl)-4-fluorobenzene-sulfonylamino]-1,1a,2,7b-tetrahydro-cyclopropa[c]chromene-4-carboxylic acid; (1aRS,7bSR)-5-{2[(Z)-3-(pyrrolidin-1-yl)prop-1-enyl]-4-fluorobenzenesulfonylamino}-1,1a,2,7b-tetrahydrocyclopropa[c]chromene-4-carboxylic acid; (1aR,7bS)-5-{2[(Z)-3-(pyrrolidin-1-yl)prop-1-enyl]-4-fluorobenzenesulfonyl-amino}-1,1a,2,7b-tetrahydro-cyclopropa[c]chromene-4-carboxylic acid; (1 aS,7bR)-5-{2[(Z)-3-(pyrrolidin-1-yl)prop-1-enyl]-4-fluorobenzenesulfonylamino}-1,1a,2,7b-tetrahydrocyclopropa[c]chromene-4-carboxylic acid; (1aRS,7bSR)-5-[2-(3-dimethylaminopropylamino)-benzenesulfonylamino]-1,1a,2,7b-tetrahydrocyclopropa[c]chromene-4-carboxylic acid; (1aR,7bS)-5-[2-(3-dimethylaminopropylamino)benzene-sulfonylamino]-1,1a,2,7b-tetrahydrocyclopropa[c]chromene-4-carboxylic acid; (1aS,7bR)-5-[2-(3-dimethylaminopropyl-amino)benzenesulfonylamino]-1,1a,2,7b-tetrahydrocyclopropa[c]chromene-4-carboxylic acid; (1aRS,7bSR)-5-[2-(4-dimethylaminobutylamino)benzenesulfonylamino]-1,1a,2,7b-tetrahydrocyclopropa[c]chromene-4-carboxylic acid; (1aR,7bS)-5-[2-(4-dimethylamino-butylamino)benzenesulfonylamino]-1,1a,2,7b-tetrahydrocyclopropa[c]chromene-4-carboxylic acid; (1aS, 7bR)-5-[2-(4-dimethylaminobutylamino)benzenesulfonylamino]-1,1a,2,7b-tetrahydrocyclopropa[c]chromene-4-carboxylic acid; (1aRS,7bSR)-5-[2-(5-dimethylamino-pentylamino)benzene-sulfonylamino]-1,1a, 2,7b-tetrahydrocyclopropa[c]chromene-4-carboxylic acid; (1aRS,7bSR)-5-{2[(Z)-3-(propan-2-yl)aminoprop-1-enyl]-4-fluorobenzenesulfonyl-amino}-1,1a,2,7b-tetrahydrocyclopropa[c]chromene-4-carboxylic acid; (1aRS,7bSR)-5-{2 [(Z)-3-((S)-3-hydroxypyrrolidin-1-yl)aminoprop-1-enyl]-4-fluorobenzenesulfonylamino}-1,1a,2,7b-tetrahydrocyclopropa[c]chromene-4-carboxylic acid; (1aRS,7bSR)-5-{2[(Z)-3-((R)-3-hydroxypyrrolidin-1-yl) aminoprop-1-enyl]-4-fluorobenzene-sulfonylamino}-1,1a, 2,7b-tetrahydro-cyclopropa[c]chromene-4-carboxylic acid; (1aRS,7bSR)-5-[2((Z)-4-diethylaminobut-1-enyl)-4-fluorobenzenesulfonyl-amino]-1,1a,2,7b-tetrahydrocyclopropa [c]chromene-4-carboxylic acid; (1aR,7bS)-5-[2((Z)-4-diethylaminobut-1-enyl)-4-fluorobenzenesulfonyl-amino]-1,1a, 2,7b-tetrahydrocyclopropa[c]chromene-4-carboxylic acid; (1aS,7bR)-5-[2((Z)-4-diethylaminobut-1-enyl)-4-fluorobenzenesulfonyl-amino]-1,1a,2,7b-tetrahydro-cyclopropa [c]chromene-4-carboxylic acid; (1aRS,7bSR)-5-{2-[2-(4-ethylpiperazin-1-yl)-ethyl]-4-fluorobenzenesulfonylamino}-1,1a,2,7b-tetrahydrocyclopropa[c]chromene-4-carboxylic acid; (1aRS,7bSR)-5-{2[(Z)-3-(azetidin-1-yl)prop-1-enyl]-4-fluorobenzene-sulfonylamino}-1,1a,2,7b-tetrahydro-cyclopropa[c]chromene-4-carboxylic acid; (1aRS,7bSR)-5-{2 [(Z)-3-(3-hydroxy-azetidin-1-yl)prop-1-enyl]-4-fluorobenzene-sulfonylamino}-1,1a,2,7b-tetrahydrocyclopropa-[c]chromene-4-carboxylic acid; (1aRS,7bSR)-5-{2[(Z)-3-(azetidin-1-yl)propyl]-4-fluorobenzenesulfonylamino}-1,1a,2,7b-tetrahydrocyclopropa[c]chromene-4-carboxylic acid; (1aRS,7bSR)-5-[2((Z)-4-diethylaminobutyl)-4-fluorobenzenesulfonylamino]-1,1a,2, 7b-tetrahydrocyclopropa[c]chromene-4-carboxylic acid; (1aRS,7bSR)-5-{2-[N-(4-dimethylaminobutyl))-N-methyl-amino]-benzenesulfonyl-amino}-1,1a,2,7b-tetrahydrocyclopropa-[c]chromene-4-carboxylic acid; (1aRS,7bSR)-5-{2-[((S)-1-ethylpyrrolidin-3-ylcarbamoyl)-methyl]-4-fluorobenzenesulfonyl-amino}-1,1a,2,7b-tetrahydrocyclopropa-[c]chromene-4-carboxylic acid; (1aRS,7bSR)-5-[2-(1-ethylazetidin-3-yl)-4-fluorobenzenesulfonylamino]-1,1a,2, 7b-tetrahydro-cyclopropa[c]chromene-4-carboxylic acid; (1aRS,7bSR)-5-{2-[((R)-1-ethylpyrrolidin-3-ylcarbamoyl) methyl]-4-fluorobenzenesulfonyl-amino}-1,1a,2,7b-tetrahydro-cyclopropa[c]chromene-4-carboxylic acid; (1aRS, 7bSR)-5-{2-[2-(pyrrolidin-1-yl)-ethyl]-4-fluorobenzenesulfonylamino}-1,1a,2,7b-tetrahydrocyclopropa[c]chromene-4-carboxylic acid; (1aRS,7bSR)-5-[2-((R)-1-ethylpyrrolidin-3-ylmethyl)-4-fluorobenzenesulfonyl-amino]- 1,1a,2,7b-tetrahydro-cyclopropa[c]chromene-4-carboxylic acid; (1aS,7bR)-5-[2-((R)-1-ethylpyaolidin-3-ylmethyl)-4-fluorobenzenesulfonyl-amino]-1,1a,2,7b-tetrahydro-cyclopropa[c]chromene-4-carboxylic acid; (1aR,7bS)-5-[2-((R)-1-ethylpyrrolidin-3-ylmethyl)-4-fluorobenzenesulfonyl-amino]-1,1a,2,7b-tetrahydro-cyclopropa[c]chromene-4-carboxylic acid; (1aRS,7bSR)-5-{2-[((S)-1-ethylpyrrolidin-2-yl)cabonyl-aminomethyl]-4-fluorobenzene-sulfonylamino}-1,1a,2,7b-tetrahydrocyclopropa[c]chromene-4-carboxylic acid; (1aRS,7bSR)-5-[2-(4-dimethylaminobutyrylamino)-4-fluorobenzenesulfonyl-amino]-1,1a,2,7b-tetrahydrocyclopropa-[c]chromene-4-carboxylic acid; (1aRS,7bSR)-5-[2-((S)-1-ethyl-pyrrolidin-3-ylmethyl)-4-fluorobenzenesulfonyl-amino]-1,1a,2,7b-tetrahydrocyclopropa[c]chromene-4-carboxylic acid; (1aRS,7bSR)-5-[2-(3-dimethylaminopropylcarbamoyl)benzene-sulfonylamino]-1,1a,2,7b-tetrahydrocyclopropa[c]chromene-4-carboxylic acid; (1aRS,7bSR)-5-(2-{[N—((S)-1-ethyl-pyrrolidin-3-yl)-N-methylcarbamoyl]methyl}-4-fluoro-benzenesulfonylamino)-1,1a,2,7b-tetrahydrocyclopropa-[c]chromene-4-carboxylic acid; (1aRS,7bSR)-5-(2-{[N—((R)-1-ethyl-pyrrolidin-3-yl)-N-methylcarbamoyl]methyl}-4-fluoro-benzenesulfonylamino)-1,1a,2,7b-tetrahydrocyclopropa-[c]chromene-4-carboxylic acid; (1aRS,7bSR)-5-{2-[2-((S)-1-ethylpyrrolidin-2-yl)ethylamino]-benzenesulfonyl-amino}-1,1a,2,7b-tetrahydrocyclopropa-[c]chromene-4-carboxylic acid; (1aRS,7bSR)-5-{2-[2-((R)-1-ethylpyrrolidin-2-yl)ethylamino]-benzenesulfonyl-amino}-1,1a,2,7b-tetrahydrocyclopropa-[c]chromene-4-carboxylic acid; (1aRS,7bSR)-5-[2-(3-N,N,-diethylaminopropylamino)benzene-sulfonylamino]-1,1a,2,7b-tetrahydrocyclopropa[c]chromene-4-carboxylic acid; (1aRS,7bSR)-5-(2-{[((R)-1-ethylpyrrolidine-2-yl)carbonyl-amino]methyl}-4-fluorobenzenesulfonylamino)-1,1a,2,7b-tetrahydrocyclopropa[c]chromene-4-carboxylic acid; (1aRS,7bSR)-5-{2-[(1-ethylazetidin-3-ylmethyl)amino]benzene-sulfonylamino}-1,1a,2,7b-tetrahydrocyclopropa[c]chromene-4-carboxylic acid; (1aS,7bR)-5-[2-((Z)-3-diethyl-aminoprop-1-enyl)benzenesulfonylamino]-1,1a,2,7b-tetrahydrocyclopropa[c]chromene-4-carboxylic acid; (1aR,7bS)-5-[2-((Z)-3-diethylaminoprop-1-enyl)benzenesulfonylamino]-1,1a,2,7b-tetrahydrocyclopropa[c]chromene-4-carboxylic acid; (1aRS,7bSR)-5-(2-{N—[((R)-1-ethylpyrrolidine-2-yl)carbonyl]-N-methyl-aminomethyl}-4-fluorobenzenesulfonylamino)-1,1a,2,7b-tetrahydrocyclopropa[c]chromene-4-carboxylic acid; (1aRS,7bSR)-5-(2-{N—[((S)-1-ethylpyrrolidine-2-yl)carbonyl]-N-methylamino-methyl}-4-fluorobenzenesulfonylamino)-1,1a,2,7b-tetrahydrocyclopropa[c]chromene-4-carboxylic acid; (1aRS,7bSR)-5-[2-(4-dimethylaminobutylamino)-4-fluorobenzenesulfonyl-amino]-1,1a,2,7b-tetrahydrocyclopropa[c]chromene-4-carboxylic acid; (1aRS,7bSR)-5-{2-[((R)-1-ethylpyrrolidin-3-ylmethyl)amino]-benzenesulfonylamino}-1,1a,2,7b-tetrahydrocyclopropa-[c]chromene-4-carboxylic acid; (1aRS,7bSR)-5-{2-[((S)-1-ethylpyrrolidin-3-ylmethyl)amino]-benzenesulfonylamino}-1,1a,2,7b-tetrahydrocyclopropa-[c]chromene-4-carboxylic acid; (1aRS,7bSR)-5-[2-(4-ethyl-2-oxopiperazin-1-ylmethyl)-4-fluorobenzene-sulfonylamino]-1,1a,2,7b-tetrahydrocyclopropa[c]chromene-4-carboxylic acid; (1aRS,7bSR)-5-(2-(1-ethylpiperidin-4-ylmethyl)-4-fluoro-benzenesulfonylamino]-1,1a,2,7b-tetrahydrocyclopropa-[c]chromene-4-carboxylic acid; (1aRS,7bSR)-5-{2-[2-(1-ethylazetidin-3-yl)ethyl]-4-fluoro-benzenesulfonyl-amino}-1,1a,2,7b-tetrahydrocyclopropa[c]chromene-4-carboxylic acid; (1aRS,7bSR)-5-{2-[((S)-1-azabicyclo[2.2.2]oct-3-yl)amino]benzenesulfonyl-amino}-1,1a,2,7b-tetrahydrocyclopropa[c]chromene-4-carboxylic acid; (1aRS,7bSR)-5-{2-[((R)-1-azabicyclo-[2.2.2]oct-3-yl)amino]benzenesulfonyl-amino}-1,1a,2,7b-tetrahydrocyclopropa[c]chromene-4-carboxylic acid; (1aRS,7bSR)-5-(2-{[((S)-1-ethylpyrrolidine-3-carbonyl)amino]methyl}-4-fluoro-benzenesulfonylamino)-1,1a,2,7b-tetrahydrocyclopropa[c]chromene-4-carboxylic acid; (1aRS,7bSR)-5-{2-[2-((R)-1-ethylpyrrolidin-3-ylamino)ethyl]-4-fluoro-benzenesulfonylamino}-1,1a,2,7b-tetrahydrocyclopropa-[c]chromene-4-carboxylic acid; (1aRS,7bSR)-5-{2-[((R)-1-ethylpyrrolidin-3-yl)amino]-benzenesulfonylamino}-1,1a,2,7b-tetrahydrocyclopropa-[c]chromene-4-carboxylic acid; (1aRS,7bSR)-5-{2-[((S)-1-ethylpyrrolidin-3-yl)amino]-benzenesulfonylamino}-1,1a,2,7b-tetrahydrocyclopropa-[c]chromene-4-carboxylic acid; (1aRS,7bSR)-5-(2-{[((R)-1-ethylpyrrolidine-3-carbonyl)amino]-methyl}-4-fluoro-benzenesulfonylamino)-1,1a,2,7b-tetrahydro-cyclopropa[c]chromene-4-carboxylic acid; (1aRS,7bSR)-5-[2-((Z)-3-diethylamino-2-methylprop-1-enyl)-4-fluorobenzene-sulfonylamino]-1,1a,2,7b-tetrahydrocyclopropa[c]chromene-4-carboxylic acid; (1aRS,7bSR)-5-{2-[2-((R)-1-ethylpyrrolidin-3-yl)ethylamino]-benzenesulfonylamino}-1,1a,2,7b-tetrahydrocyclopropa-[c]chromene-4-carboxylic acid; (1aRS,7bSR)-5-{2-[2-((S)-1-ethylpyrrolidin-3-yl)ethylamino]-benzenesulfonyl-amino}-1,1a,2,7b-tetrahydrocyclopropa-[c]chromene-4-carboxylic acid; (1aR,7bS)-5-[2-((S)-1-ethylpyrrolidin-3-yloxymethyl)-4-fluoro-benzenesulfonylamino]-1,1a,2,7b-tetrahydrocyclopropa-[c]chromene-4-carboxylic acid; (1aR,7bS)-5-[2-((R)-1-ethylpyrrolidin-3-yloxymethyl)-4-fluoro-benzenesulfonylamino]-1,1a,2,7b-tetrahydrocyclopropa-[c]chromene-4-carboxylic acid; (1aR,7bS)-5-[2-(1-ethylpiperidin-3-ylmethyl)-4-fluorobenzene-sulfonylamino]-1,1a,2,7b-tetrahydrocyclopropa[c]chromene-4-carboxylic acid; (1aR,7bS)-5-{2-[2-((R)-1-ethylpyrrolidin-2-yl)ethyl]-4-fluorobenzenesulfonyl-amino}-1,1a,2,7b-tetrahydrocyclopropa-[c]chromene-4-carboxylic acid; and pharmaceutically acceptable salts, stereoisomers, esters and prodrugs thereof.

Other contemplated compounds that may be used in the disclosed methods may be selected from the group consisting of:

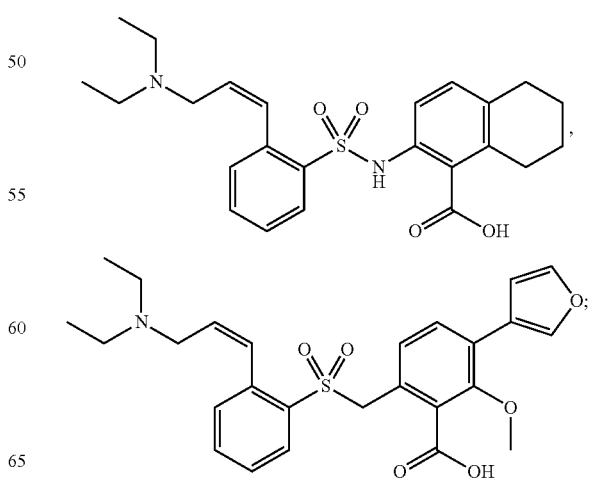

-continued

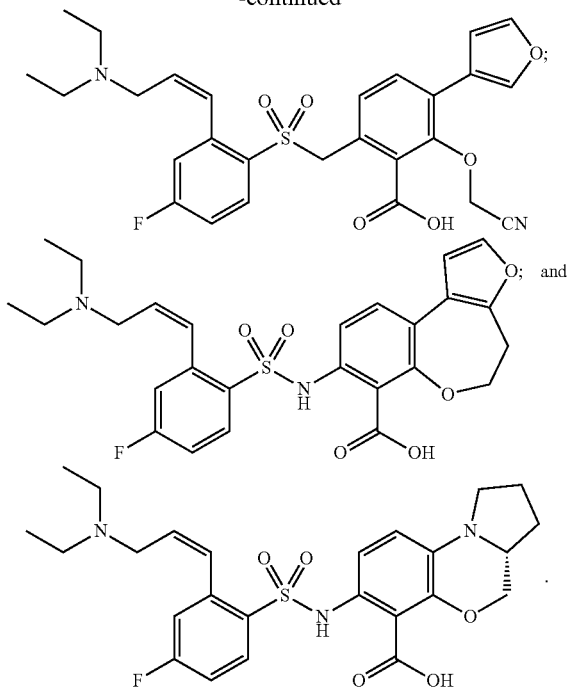

Compounds in PCT/US12/036792, hereby incorporated by reference, are also contemplated for use in the disclosed methods.

II. Methods

In certain embodiments, the disclosure provides a method of treating and/or substantially preventing fatty liver disease and/or liver fibrosis, for example, treating non-alcoholic steatohepatitis and/or associated hepatic fibrosis, hepatocellular carcinoma, cirrhosis, liver failure, liver-related death and liver transplantation in a patent by administering to a patient in need thereof a therapeutically effective amount of a disclosed compound. Contemplated patients include not only humans, but other animals such as companion animals (e.g., dogs, cats).

Methods of reducing hepatic fat in a patient in need thereof are also contemplated herein, comprising administering an effective amount of a disclosed compound. For example, contemplated methods include treating a patient suffering from inflammation of the liver that accompanies fatty liver, e.g., non-alcoholic steatohepatitis (NASH). Other contemplated disorders that may be treated using the disclosed methods include liver fibrosis or scarring, and focal fatty liver. Contemplated herein is a method of treating a patient in need of a liver transplant and/or having a liver transplant, comprising administering a disclosed compound.

For example, provided herein are methods of treating or substantially preventing non-alcoholic liver disease or NASH in a patient in need thereof, wherein the patient had been administered or is currently being administered, or wherein the NASH was caused by amiodarone, antiviral drugs such as nucleoside analogues, aspirin, NSAIDS, corticosteroids, methotrexate, tamoxifen, or tetracycline.

Also provided herein are methods of reducing cholesterol levels (e.g. reducing total plasma cholesterol) in a patient in need thereof. In another embodiment, provided herein are methods of lowering plasma HbA1c levels in a patient in need thereof.

The compounds of the invention may be administered to patients (animals and/or humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound of this invention may be administered orally, subcutaneously, topically, parenterally, by inhalation spray or rectally in dosage unit formulations containing conventional non-toxic pharmaceutically acceptable carriers, adjuvants and vehicles. Parenteral administration may include subcutaneous injections, intravenous or intramuscular injections or infusion techniques.

In certain embodiments, disclosed methods of treatment may include oral administration to a patient. For example, a disclosed method may comprise administering a dose to a patient (e.g. orally administering) of about 0.001 to about 10 mg/kg (or about 0.001 to about 50 mg/kg, or e.g. less than or about 10 mg/kg) twice or once daily.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, and/or a targeted percentage reduction in liver fat or abdominal fat content is achieved. A treatment regimen can include a corrective phase, during which dose sufficient to provide reduction of weight is administered, and can be followed by a maintenance phase, during which a e.g. a lower dose sufficient to prevent weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

In some embodiments, disclosed methods are directed to treatment of patients having a diabetic (e.g. type 2 diabetes) or pre-diabetic condition. Contemplated herein is treatment of patients that are not obese, or alternatively, are suffering from obesity.

III. Pharmaceutical Compositions and Kits

Another aspect of the invention provides pharmaceutical compositions comprising compounds as disclosed herein formulated together with a pharmaceutically acceptable carrier. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous)

rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, the invention provides enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HP-MCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that would meet the objectives of the present invention.

Also contemplated herein are methods and compositions that include a second active agent, or administering a second active agent. For example, a patient with NASH may also have other conditions, such as diabetes, high blood pressure or high cholesterol levels. Thus, contemplated herein are disclosed compounds in combination with at least one other agent that may be used to treat one or more of these conditions. For example, the second active agent can be, for example, an antidiabetic medication (e.g., metformin, and/or a thiazolidinedione such as rosiglitazone, pioglitazone, troglitazone, and/or netoglitazone), an antioxidant (e.g., vitamin E, selenium or betaine), a blood pressure lowering medication (e.g., lisinopril, losartan, metoprolol, amlodipine, aliskiren), or a cholesterol lowering medication (e.g., atorvastatin, rosuvastatin, or nicotinic acid), or another agent such as vitamin E. In other embodiments, contemplated methods further include administering to the patient an active agent such as one or more of: amiodarone, antiviral drugs such as nucleoside analogues, aspirin, NSAIDS, corticosteroids, methotrexate, tamoxifen, or tetracycline.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as compounds of the invention.

$^1$H NMR spectra were recorded at ambient temperature using a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts are expressed in ppm relative to tetramethylsilane. The following abbreviations have been used: br=broad signal, s=singlet, d=doublet, dd=double doublet, ddd=double double doublet, dt=double triplet, t=triplet, td=triple doublet, q=quartet, m=multiplet.

Mass Spectrometry (LCMS) experiments to determine retention times and associated mass ions were performed using the following methods:

Method A: Experiments were performed on a Waters ZMD LC quadrapole mass spectrometer linked to a Waters 1525 LC system with a diode array detector. The spectrometer has an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. The final solvent system was held constant for a further 1 minute.

Method B: Experiments were performed on a Waters V G Platform quadrupole spectrometer linked to a Hewlett Packard 1050 LC system with a diode array detector. The spectrometer has an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 minutes. The final solvent system was held constant for a further 1 minute.

Method C: Experiments were performed on a Waters Micromass ZQ2000 quadrapole mass spectrometer linked to a Waters Acquity UPLC system with a PDA UV detector. The spectrometer has an electrospray source operating in positive and negative ion mode. LC was carried out using an Acquity BEH 1.7 micron C18 column, an Acquity BEH Shield 1.7 micron RP18 column or an Acquity HSST 1.8 micron column. Each column has dimensions of 100×2.1 mm and was maintained at 40° C. with a flow rate of 0.4 mL/minute. The initial solvent system was 95% water containing 0.1% formic acid (solvent A) and 5% acetonitrile containing 0.1% formic acid (solvent B) for the first 0.4 minute followed by a gradient up to 5% solvent A and 95% solvent B over the next 6 minutes. The final solvent system was held constant for a further 0.8 minutes.

Method D: Experiments were performed on a Shimadzu LCMS-2020 spectrometer with an electrospray source operating in positive ion mode. LC was carried out using a Shimadzu Shim-pack XR-ODS 2.2 micron 50×3.0 mm column. The initial solvent system was 95% water containing 0.05% trifluoroacetic acid (solvent A) and 5% acetonitrile (solvent B) for the first 0.01 minute then a gradient up to 100% solvent B over the next 1.3 minutes. The final solvent system was held constant for a further 1 minute.

Method E: Experiments were performed on a Waters ZMD LC quadrapole mass spectrometer linked to a Hewlett Packard HD 1100 system with a diode array detector. The spectrometer has an electrospray source operating in positive and negative ion mode. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.5 minute followed by a gradient up to 5% solvent A and 95% solvent B over the next 4 minutes. The final solvent system was held constant for a further 1 minute.

Method F: Experiments were performed on a Waters V G Platform quadrupole spectrometer linked to a Hewlett Packard 1050 LC system with a diode array detector. The spectrometer has an electrospray source operating in positive and negative ion mode. Additional detection was achieved using a Sedex 85 evaporative light scattering detector. LC was carried out using a Luna 3 micron 30×4.6 mm C18 column and a 2 mL/minute flow rate. The initial solvent system was 95% water containing 0.1% formic acid (solvent A) and 5% acetonitrile containing 0.1% formic acid (solvent B) for the first 0.3 minute followed by a gradient up to 5% solvent A and 95% solvent B over the next 4 minutes. The final solvent system was held constant for a further 1 minute. Microwave experiments were carried out using a Biotage Initiator™, which uses a single-mode resonator and dynamic field tuning. Temperatures from 40-250° C. can be achieved, and pressures of up to 20 bars can be reached. A facility exists to apply air cooling during the irradiation.

Preparative HPLC purification was carried out using either a C18-reverse-phase column from Genesis (C18) or a C6-phenyl column from Phenomenex (C6-phenyl) (100× 22.5 mm i.d. with 7 micron particle size, UV detection at 230 or 254 nm, flow 5-15 mL/min), eluting with gradients from 100-0 to 0-100% water/acetonitrile or water/methanol containing 0.1% formic acid. Fractions containing the required product (identified by LCMS analysis) were pooled, the organic fraction removed by evaporation, and the remaining aqueous fraction lyophilised, to give the product.

Compounds which required column chromatography were purified manually or fully automatically using either a Biotage SP1™ Flash Purification system with Touch Logic Control™ or a Combiflash Companion® with pre-packed silica gel Isolute® SPE cartridge, Biotage SNAP cartridge or Redisep® Rf cartridge respectively.

Compounds have been named using Autonom2000 within ISISDraw.

ABBREVIATIONS

DCM Dichloromethane
IMS Industrial methylated spirits
DMF N,N-Dimethylformamide
DMAP 4-Dimethylaminopyridine
THF Tetrahydrofuran
DMSO Dimethylsulfoxide
NMP N-methylpyrrolidinone
DCE 1,2-Dichloroethane
HATU 7-Azabenzotriazol-1-yl-N,N,N',N',tetramethyluronium hexafluorophosphate
EDAC N-(3-Dimethylaminopropyl)-N'ethylcarbodiimide hydrochloride
IMS Industrial methylated spirit
NMM N-methylmorpholine
DBU 1,8-Diazabicyclo[5.4.0]undec-7-ene

Example 1

Cis-(3aRS,9bRS)-7-(Benzenesulfonylamino)-1,3a,4,9b-tetrahydro-2H-furo[2,3-c]chromene-6-carboxylic acid

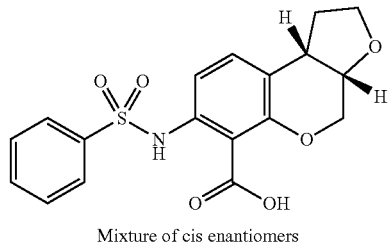 [SMILES: O=C(O)c1c(NS(=O)(=O)c2ccccc2)ccc2c1OC[C@H]1OCC[C@@H]21]

Mixture of cis enantiomers

Lithium hydroxide (0.048 g) was added to a solution of methyl cis-(3aRS,9bRS)-7-(benzenesulfonylamino)-1,3a,4,9b-tetrahydro-2H-furo[2,3-c]chromene-6-carboxylate (Intermediate 1, 0.08 g) in a mixture of dioxane (10 mL) and water (5 mL) and the resultant mixture was irradiated in the microwave at 110° C. with air cooling for 20 minutes. Further lithium hydroxide (0.2 g) was added and the mixture was irradiated in the microwave at 110° C. with air cooling for a total of 80 minutes. After cooling, the solution was acidified by addition of aqueous formic acid solution (10%) and the resultant mixture was extracted with ethyl acetate, dried (MgSO₄) and filtered. The filtrate was evaporated to dryness. The residue was dissolved in a mixture of methanol (10 mL) and water (5 mL) and treated with lithium hydroxide (0.2 g) then irradiated in the microwave at 110° C. with air cooling for 40 minutes. After cooling, the solution was acidified by addition of formic acid (10%) and the resultant mixture was extracted with ethyl acetate, dried (MgSO₄) and filtered. The filtrate was evaporated to dryness and the residue was purified by preparative HPLC (C18) eluting with a mixture of acetonitrile and water, containing 0.1% formic acid, with a gradient of 30-50% to give cis-(3aRS, 9bRS)-7-(benzenesulfonylamino)-1,3a,4,9b-tetrahydro-2H-furo[2,3-c]chromene-6-carboxylic acid (0.019 g) as a white solid.

¹H NMR (CD₃OD) δ: 7.71 (2H, d), 7.54 (1H, t), 7.44 (2H, t), 7.24 (1H, d), 7.12 (1H, d), 4.24 (1H, m), 4.09 (1H, dd), 3.92 (1H, dd), 3.8-3.65 (2H, m), 3.47 (1H, m), 2.45 (1H, m), 1.83 (1H, m).

LCMS (Method C) r/t 3.79 (M−H) 374.

Example 2

Cis-(3aRS,9bRS)-7-[2-(3-Diethylaminopropyl)-4-fluorobenzenesulfonyl-amino]-1,3a,4,9b-tetrahydro-2H-furo[2,3-c]chromene-6-carboxylic acid

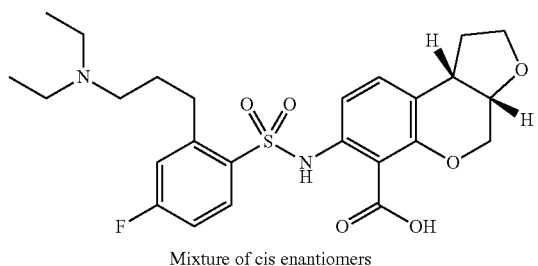 [SMILES: CCN(CC)CCCc1cc(F)ccc1S(=O)(=O)Nc1ccc2c(c1C(=O)O)OC[C@H]1OCC[C@@H]21]

Mixture of cis enantiomers

A solution of 7-[2-((Z)-3-diethylaminoprop-1-enyl)-4-fluorobenzenesulfonylamino]-4H-furo[2,3-c]chromene-6-carboxylic acid (Intermediate 8, 0.1 g) in a mixture of IMS (2 mL) and glacial acetic acid (3 mL) was treated, under an atmosphere of nitrogen, with palladium hydroxide on carbon (10%, 0.02 g). The nitrogen was replaced by hydrogen and the mixture was stirred under an atmosphere of hydrogen for 100 minutes. The mixture was filtered through Celite and the filtrate was evaporated to dryness. The residue was dissolved in toluene and the solution was re-evaporated. The residue was triturated with ether and the solid was collected by filtration and purified by preparative HPLC (C6-phenyl) eluting with a mixture of acetonitrile and water, containing 0.1% formic acid, with a gradient of 20-40% to give cis-(3aRS,9bRS)-7-[2-(3-diethylaminopropyl-4-fluorobenzenesulfonyl-amino]-1,3a,4,9b-tetrahydro-2H-furo[2,3-c]chromene-6-carboxylic acid (0.1 g) as a white solid.

¹H NMR (CD₃OD) δ: 7.94 (1H, dd), 7.18 (1H, d), 7.17 (1H, m), 7.06 (1H, d), 6.99 (1H, dt), 4.21 (1H, m), 3.98 (1H, dd), 3.88 (1H, dd), 3.72 (2H, m), 3.42 (1H, m), 3.23 (6H, m), 3.10 (2H, m), 2.42 (1H, m), 1.98 (2H, m), 1.81 (1H, m), 1.31 (6H, t).

LCMS (Method C) r/t 3.10 (M+H) 507.

Example 3

Cis-(3aRS,9bRS)-7-[2-(3-{Pyrrolidin-1-yl}propyl)-4-fluorobenzene-sulfonylamino]-1,3a,4,9b-tetrahydro-2H-furo[2,3-c]chromene-6-carboxylic acid

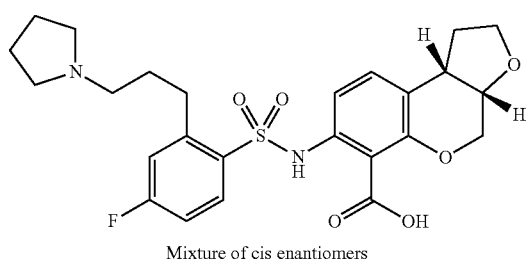 [SMILES: O=C(O)c1c(NS(=O)(=O)c2ccc(F)cc2CCCN2CCCC2)ccc2c1OC[C@H]1OCC[C@@H]21]

Mixture of cis enantiomers

Lithium hydroxide (0.028 g) was added to a solution of methyl cis-(3aRS,9bRS)-7-[2-(3-{pyrrolidin-1-yl}propyl)-4-fluorobenzenesulfonylamino]-1,3a,4,9b-tetrahydro-2H-furo[2,3-c]chromene-6-carboxylate (Intermediate 14, 0.06 g) in dioxane (2 mL) and water (1 mL) and the mixture was stirred and heated at 80° C. for 8 hours. After cooling, the mixture was acidified by addition of aqueous formic acid solution (10%) and extracted with DCM. The organic layer was dried (MgSO₄) and filtered. The filtrate was evaporated to dryness and the residue was purified by chromatography on silica eluting with a mixture of ammonia in methanol (2M) and DCM with a gradient of 1-10%. The isolated solid was triturated with a mixture of ether and cyclohexane (50%) and the solid was collected by filtration. The solid was purified by preparative HPLC (C18) eluting with a mixture of acetonitrile and water, containing 0.1% formic acid, with a gradient of 10-95%. The isolated product was triturated with ether and the solid was collected by filtration to give cis-(3aRS,9bRS)-7-[2-(3-{pyrrolidin-1-yl}propyl)-4-fluorobenzenesulfonylamino]-1,3a,4,9b-tetrahydro-2H-furo[2,3-c]chromene-6-carboxylic acid (0.006 g) as a white solid.

¹H NMR (CD₃OD) δ: 7.93 (1H, dd), 7.21 (1H, d), 7.14 (1H, dd), 7.08 (1H, d), 6.99 (1H, dt), 4.21 (1H, m), 3.98 (1H, dd), 3.88 (1H, dd), 3.72 (2H, m), 3.43 (2H, m), 3.30 (4H, m), 3.13 (3H, m), 2.42 (1H, m), 2.07 (4H, m), 2.0 (2H, m), 1.81 (1H, m).

LCMS (Method C) r/t 3.11 (M+H) 505.

Example 4

Cis-(3aRS,9bRS)-7-[2-((Z)-3-Diethylaminoprop-1-enyl)-4-fluoro-benzenesulfonylamino]-1,3a,4,9b-tetrahydro-2H-furo[2,3-c]chromene-6-carboxylic acid

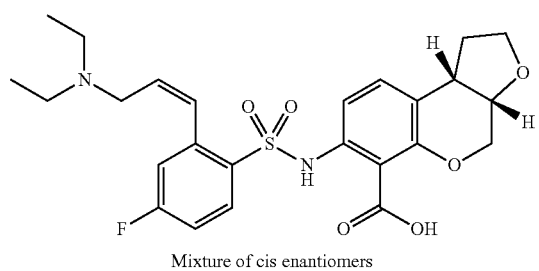 [SMILES: CCN(CC)C/C=C\c1cc(F)ccc1S(=O)(=O)Nc1ccc2c(c1C(=O)O)OC[C@H]1OCC[C@@H]21]

Mixture of cis enantiomers

Prepared by proceeding in a similar manner to Example 3, starting from methyl cis-(3aRS,9bRS)-7-[2-((Z)-3-diethylaminoprop-1-enyl)-4-fluorobenzenesulfonylamino]-1,3a,4,9b-tetrahydro-2H-furo[2,3-c]chromene-6-carboxylate (Intermediate 17) and heating at 80° C. overnight.

$^1$H NMR (DMSO-d$_6$) δ: 7.65 (1H, dd), 7.30 (1H, d), 7.19 (2H, m), 7.02 (1H, d), 6.92 (1H, d), 6.10 (1H, m), 4.09 (1H, m), 3.82-3.64 (4H, m), 3.63-3.30 (3H, m), 3.03 (4H, q), 2.35 (1H, m), 1.68 (1H, m), 1.07 (6H, t).

LCMS (Method C) r/t 3.05 (M+H) 505.

Examples 5 and 6

Separation of Enantiomers from Example 4

Sample from Example 4 was subjected to chiral separation using a ChiralPak IC column, 4.6 mm×250 mm, particle size 5 micron. Injection solvent DCE: absolute ethanol 1:1, injection concentration 1 mg/100 μL, injection volume 120 μL. Eluting solvent absolute ethanol, flow rate 0.55 mL/minute, temperature 21° C.

Example 5

First eluting enantiomer: retention time on above column: 34.96 minutes, 93% de.

$^1$H NMR (DMSO-d$_6$) δ: 7.64 (1H, dd), 7.29 (1H, d), 7.18 (2H, m), 7.01 (1H, d), 6.92 (1H, d), 6.08 (1H, m), 4.09 (1H, m), 3.75 (2H, m), 3.59 (2H, m), 3.33 (3H, m), 3.03 (4H, br), 2.34 (1H, m), 1.68 (1H, m), 1.06 (6H, t).

LCMS (Method C) r/t 3.07 (M+H) 505.

Example 6

Second eluting enantiomer: retention time on above column 40.97 minutes, 65% de.

$^1$H NMR (DMSO-d$_6$) δ: 7.64 (1H, dd), 7.29 (1H, d), 7.18 (2H, m), 7.01 (1H, d), 6.92 (1H, d), 6.08 (1H, m), 4.09 (1H, m), 3.75 (2H, m), 3.59 (2H, m), 3.33 (3H, m), 3.03 (4H, br), 2.34 (1H, m), 1.68 (1H, m), 1.06 (6H, t).

LCMS (Method C) r/t 3.06 (M+H) 505.

Example 7

7-[2-((Z)-3-Diethylaminoprop-1-enyl)-4-fluorobenzenesulfonylamino]-1,2-dihydrofuro[2,3-c]quinoline-6-carboxylic acid formate salt

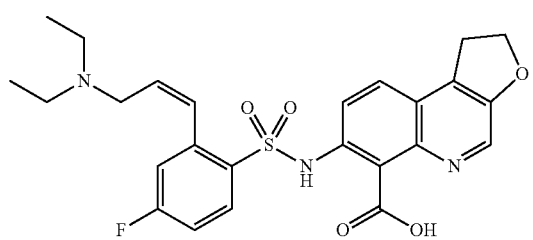 [SMILES: CCN(CC)C/C=C\c1cc(F)ccc1S(=O)(=O)Nc1ccc2c3c(cnc2c1C(=O)O)OCC3]

Prepared by proceeding in a similar manner to Example 1, starting from methyl 7-[N-{2-((Z)-3-diethylaminoprop-1-enyl)-4-fluorobenzenesulfonyl}-N-(methoxy-carbonyl)amino]-1,2-dihydrofuro[2,3-c]quinoline-6-carboxylate (Intermediate 20) as a yellow solid.

$^1$H NMR (CD$_3$OD) δ: 8.50 (1H, s), 8.47 (2H, s), 7.96 (1H, m), 7.91 (1H, d), 7.79 (1H, d), 7.45 (1H, d), 7.11 (2H, m), 6.13 (1H, m), 3.79 (2H, d), 3.59 (2H, t), 3.10 (6H, m), 1.16 (6H, m).

LCMS (Method C) r/t 2.84 (M+H) 500.

Example 8

7-(Benzenesulfonylamino)-1,2-dihydrofuro[2,3-c]quinoline-6-carboxylic acid formate salt

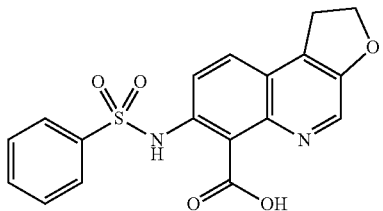 [SMILES: O=C(O)c1c(NS(=O)(=O)c2ccccc2)ccc2c3c(cnc12)OCC3]

Prepared by proceeding in a similar manner to Example 1, starting from methyl 7-(benzenesulfonylamino)-1,2-dihydrofuro[2,3-c]quinoline-6-carboxylate (Intermediate 26).

$^1$H NMR (DMSO-d$_6$) δ: 8.54 (1H, s), 8.25 (1H, s), 7.78 (3H, m), 7.66 (1H, d), 7.44 (3H, m), 4.69 (2H, t), 3.46 (2H, t).

LCMS (Method C) r/t 3.66 (M+H) 371.

Example 9

Cis-(3aRS,9bRS)-7-[2-((Z)-3-Diethylaminoprop-1-enyl)-4-fluorobenzenesulfonylamino]-1,2,3a,4,5,9b-hexahydrofuro[2,3-c]quinoline-6-carboxylic acid

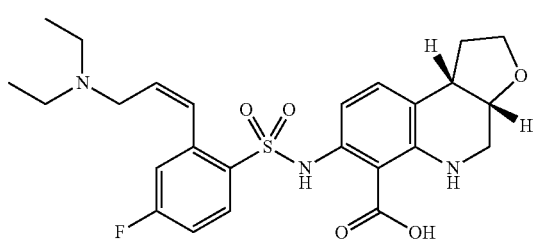

Mixture of cis enantiomers

Lithium hydroxide (0.09 g) was added to a solution of methyl cis-(3aRS,9bRS)-5-acetyl-7-[2-((Z)-3-diethylaminoprop-1-enyl)-4-fluorobenzenesulfonylamino]-1,2,3a,4,5,9b-hexahydrofuro[2,3-c]quinoline-6-carboxylate (Intermediate 27, 0.06 g) in a mixture of dioxane (5 mL) and water (1 mL) and the mixture was stirred and heated at 80° C. overnight. The mixture was then irradiated in the microwave at 150° C. for 30 minutes and then at 180° C. for 30 minutes. After cooling, the mixture was filtered and the filtrate was acidified by addition of formic acid (1 mL) and then evaporated to dryness. The residue was purified by preparative HPLC (C18) eluting with a mixture of acetonitrile and water, containing 0.1% formic acid, with a gradient of 10-98%. The isolated product was dissolved in DCM and evaporated to dryness then dissolved in ether and evaporated to dryness to give cis-(3aRS,9bRS)-7-[2-((Z)-3-diethylaminoprop-1- enyl)-4-fluorobenzenesulfonylamino]-1,2,3a,4,5,9b-hexahydrofuro[2,3-c]quinoline-6-carboxylic acid (0.005 g) as a white solid.

¹H NMR (CDCl₃) δ: 8.54 (1H, br s), 7.99 (1H, br s), 7.48 (1H, d), 7.04 (1H, m), 6.90 (1H, d), 6.76 (1H, d), 6.62 (1H, m), 6.11 (1H, m), 4.17 (1H, m), 3.82 (1H, m), 3.78-3.59 (2H, m), 3.32-3.10 (4H, m), 3.04-2.86 (3H, m), 2.35 (1H, m), 1.79 (1H, m), 1.15 (6H, t).

LCMS (Method C) r/t 3.31 (M+H) 504

Example 10

(1aRS,7bSR)-5-[2-((Z)-3-Diethylaminoprop-1-enyl)-4-fluorobenzenesulfonylamino]-1,1a,2,7b-tetrahydrocyclopropa[c]chromene-4-carboxylic acid

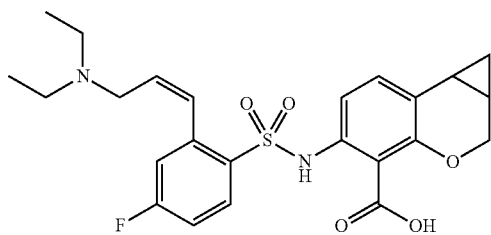 [SMILES: CCN(CC)C/C=C\c1cc(F)ccc1S(=O)(=O)Nc1ccc2c(c1C(=O)O)OCC1CC21]

Methyl (1aRS,7bSR)-5-[2-((Z)-3-diethylaminoprop-1-enyl)-4-fluorobenzenesulfonylamino]-1,1a,2,7b-tetrahydrocyclopropa[c]chromene-4-carboxylate (Intermediate 40, 0.185 g) and lithium hydroxide monohydrate (0.159 g) were suspended in dioxane (4 mL) and water (1 mL). The reaction mixture was irradiated in the microwave at 135° C. for 30 minutes. After cooling, the mixture was acidified to pH4 with formic acid, then ethanol and toluene were added and the mixture concentrated in vacuo. The residue was triturated with a mixture of methanol and DCM (10%) and the solid was filtered off and washed with a mixture of methanol and DCM. The filtrate was concentrated in vacuo and the residue was purified by chromatography on silica, eluting with a mixture of methanol and DCM with a gradient of 0-8%. The resultant product was triturated with ethyl acetate and dried in vacuo at 50° C. to give (1aRS,7bSR)-5-[2-((Z)-3-diethylaminoprop-1-enyl)-4-fluorobenzenesulfonylamino]-1,1a,2,7b-tetrahydrocyclopropa[c]chromene-4-carboxylic acid (0.066 g) as a white solid.

¹H NMR (DMSO-d₆) δ: 7.64 (1H, dd), 7.35 (1H, d), 7.27-7.19 (2H, m), 7.10 (1H, d), 6.93 (1H, d), 6.20-6.10 (1H, m), 4.17 (1H, d), 3.76 (2H, br, s), 3.57 (1H, d), 3.10 (4H, br, q), 1.92 (1H, td), 1.75-1.69 (1H, m), 1.13 (6H, t), 0.94 (1H, td), 0.74 (1H, m).

LCMS (Method C) r/t 3.32 (M+H) 475

Examples 11 and 12

Separation of Enantiomers from Example 10

Sample from Example 10 was subjected to chiral separation using a ChiralPak IC column, 10 mm×250 mm, particle size 5 micron. Eluting solvent tert-butyl methyl ether: isopropanol: DCM (16:20:64).

Example 11

First eluting enantiomer: r/t on analytical column (4.6 mm×250 mm): 21.8 minutes >99% ee: (1aS,7bR)-5-[2-((Z)-3-Diethylaminoprop-1-enyl)-4-fluorobenzenesulfonylamino]-1,1a,2,7b-tetrahydrocyclopropa[c]chromene-4-carboxylic acid

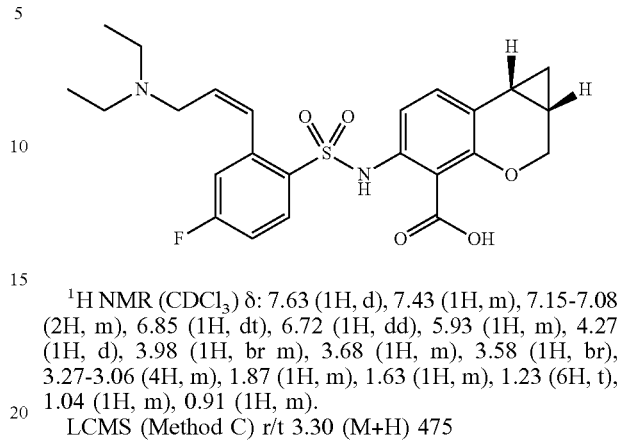

¹H NMR (CDCl₃) δ: 7.63 (1H, d), 7.43 (1H, m), 7.15-7.08 (2H, m), 6.85 (1H, dt), 6.72 (1H, dd), 5.93 (1H, m), 4.27 (1H, d), 3.98 (1H, br m), 3.68 (1H, m), 3.58 (1H, br), 3.27-3.06 (4H, m), 1.87 (1H, m), 1.63 (1H, m), 1.23 (6H, t), 1.04 (1H, m), 0.91 (1H, m).

LCMS (Method C) r/t 3.30 (M+H) 475

Example 12

Second eluting enantiomer: r/t on analytical column (4.6 mm×250 mm): 27.5 minutes, >99% ee: (1aR,7bS)-5-[2-((Z)-3-Diethylaminoprop-1-enyl)-4-fluorobenzenesulfonylamino]-1,1a,2,7b-tetrahydrocyclopropa[c]chromene-4-carboxylic acid (Compound A)

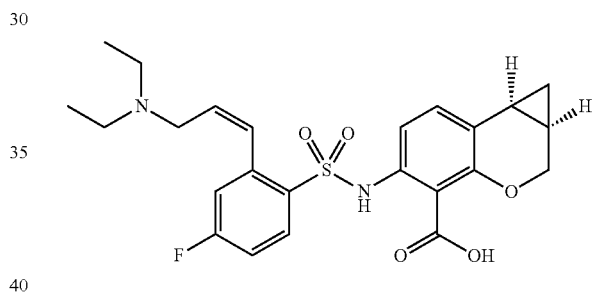

¹H NMR (CDCl₃) δ: 7.63 (1H, d), 7.43 (1H, m), 7.15-7.08 (2H, m), 6.85 (1H, dt), 6.72 (1H, dd), 5.93 (1H, m), 4.27 (1H, d), 3.98 (1H, br m), 3.68 (1H, m), 3.58 (1H, br), 3.27-3.06 (4H, m), 1.87 (1H, m), 1.63 (1H, m), 1.23 (6H, t), 1.04 (1H, m), 0.91 (1H, m).

LCMS (Method C) r/t 3.32 (M+H) 475.

Solubility ~0.1 mg/ml (at pH 7.4). Absolute configuration of Examples 11 and 12 determined by X-ray crystal analysis of Example 12 with MetAP2.

Example 13

(1aRS,7bSR)-5-[2-((Z)-3-Diethylaminoprop-1-enyl)-4-fluorobenzenesulfonylamino]-7b-methyl-1,1a,2,7b-tetrahydrocyclopropa[c]chromene-4-carboxylic acid

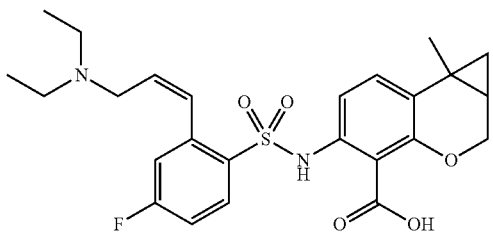 [SMILES: CCN(CC)C/C=C\c1cc(F)ccc1S(=O)(=O)Nc1ccc2c(c1C(=O)O)OCC1CC21C]

Prepared by proceeding in a similar manner to Example 3, starting from methyl (1aRS,7bSR)-5-[2-((Z)-3-diethylaminoprop-1-enyl)-4-fluorobenzenesulfonylamino]-7b-methyl-1,1a,2,7b-tetrahydrocyclopropa[c]chromene-4-carboxylate (Intermediate 48).

$^1$H NMR (CDCl$_3$) δ: 9.8-9.2 (1H, br s), 7.65 (1H, d), 7.39 (1H, m), 7.24 (1H, d), 7.18 (1H, d), 6.83 (1H, dt), 6.72 (1H, dd), 5.91 (1H, m), 4.21 (1H, d), 3.98 (1H, br t), 3.71 (1H, d), 3.61 (1H, br s), 3.28-3.06 (4H, m), 1.41 (3H, s), 1.37 (1H, m), 1.24 (6H, t), 1.14 (1H, t), 0.74 (1H, dd).

LCMS (Method C) r/t 3.55 (M+H) 489.

Example 14

(1aRS,7bSR)-5-[2-((E)-3-Diethylaminoprop-1-enyl)-4-fluorobenzenesulfonylamino]-7b-methyl-1,1a,2,7b-tetrahydrocyclopropa[c]chromene-4-carboxylic acid

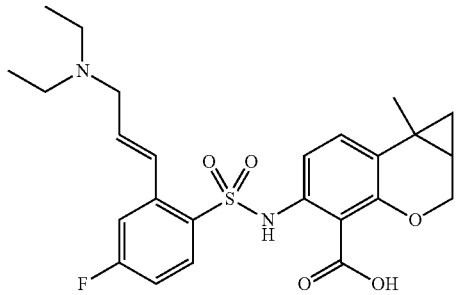 [SMILES: CCN(CC)C/C=C/c1cc(F)ccc1S(=O)(=O)Nc1ccc2c(c1C(=O)O)OCC1CC21C]

Isolated as a minor by-product by preparative HPLC from the preparation of Example 13.

$^1$H NMR (CDCl$_3$) δ: 11.9 (1H, br s), 7.93 (1H, dd), 7.70 (1H, d), 7.25 (1H, d), 7.10 (1H, d), 7.06 (1H, dd), 6.90 (1H, dt), 6.19 (1H, m), 4.23 (1H, d), 3.76 (1H, d), 3.68 (2H, m), 3.29 (4H, q), 1.36 (6H, t), 1.35 (3H, s), 1.31 (1H, m), 1.10 (1H, t), 1.67 (1H, dd).

LCMS (Method C) r/t 3.66 (M+H) 489.

Example 15

Cis-(3aRS,9bRS)-7-[2-(4-dimethylaminobutylamino)benzenesulfonylamino]-1,3a,4,9b-tetrahydro-2H-furo[2,3-c]chromene-6-carboxylic acid

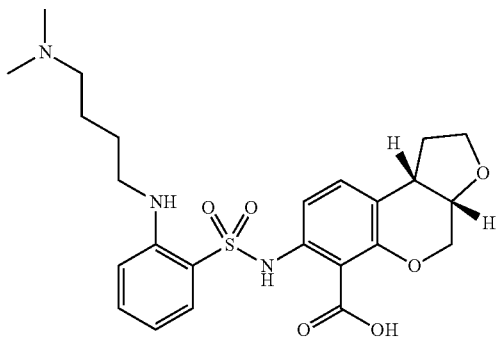

Mixture of cis enantiomers

4-Dimethylaminobutylamine (0.348 g) and triethylamine (0.2 ml) were added to a suspension of cis-(3aRS,9bRS)-7-(2-fluorobenzenesulfonylamino)-1,3a,4,9b-tetrahydro-2H-furo[2,3-c]chromene-6-carboxylic acid (Intermediate 57, 0.15 g) in acetonitrile (1.5 mL) and the mixture was heated at 130° C. in a sealed tube for 36 hours. The mixture was then diluted with water (2 mL) and the solution was purified by preparative HPLC (C6-phenyl) eluting with a mixture of methanol and water, containing 0.1% formic acid, with a gradient of 5-98%. The isolated product was further purified by chromatography on silica eluting with a mixture of methanol and DCM with a gradient of 0-15% to give cis-(3aRS,9bRS)-7-[2-(4-dimethylaminobutylamino)-benzenesulfonylamino]-1,3a,4,9b-tetrahydro-2H-furo[2,3-c]chromene-6-carboxylic acid (0.062 g) as a glass foam.

$^1$H NMR (CDCl$_3$) δ: 11.21 (1H, br s), 7.72 (1H, dd), 7.37 (1H, d), 7.26 (1H, m), 7.02 (1H, d), 6.59 (1H, d), 6.56 (1H, t), 5.85 (1H, t), 4.29 (1H, dt), 4.05 (1H, dd), 3.85 (1H, m), 3.77 (2H, m), 3.34 (1H, q), 3.21 (2H, m), 2.98 (2H, t), 2.80 (6H, s), 2.41 (1H, m), 2.05 (1H, m), 1.83 (1H, m), 1.71 (2H, m).

LCMS (Method C) r/t 3.18 (M+H) 490

Example 16

(1aR,7bS)-5-[2-(3-Diethylaminopropyl)-4-fluorobenzenesulfonyl-amino]-1,1a,2,7b-tetrahydrocyclopropa[c]chromene-4-carboxylic acid

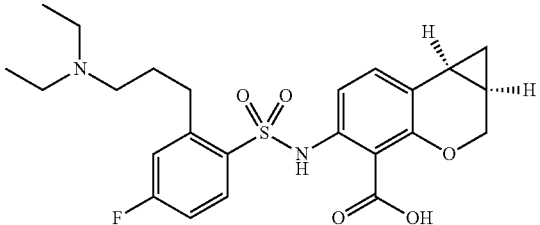 [SMILES: CCN(CC)CCCc1cc(F)ccc1S(=O)(=O)Nc1ccc2c(c1C(=O)O)OC[C@@H]1C[C@H]21]

Prepared by proceeding in a similar manner to Example 2, starting from (1aR,7bS)-5-[2-((Z)-3-diethylaminoprop-1-enyl)-4-fluorobenzenesulfonylamino]-1,1a,2,7b-tetrahydrocyclopropa[c]-chromene-4-carboxylic acid (Example 12)

$^1$H NMR (CDCl$_3$) δ: 7.81 (1H, dd), 7.31 (1H, d), 7.07 (1H, d), 6.82 (2H, m), 4.32 (1H, d), 3.74 (1H, d), 3.42-3.32 (1H, m), 3.18 (4H, m), 3.14-2.94 (3H, m), 2.00 (2H, m), 1.84 (1H, m), 1.62 (1H, m), 1.31 (6H, t), 1.04 (1H, m), 0.88 (1H, m).

LCMS (Method C) r/t 3.36 (M+H) 477.

Example 17

(1aRS,7bSR)-5-[2-((Z)-3-Diethylaminoprop-1-enyl)-4-fluorobenzene-sulfonylamino]-1,1-difluoro-1,1a,2,7b-tetrahydrocyclopropa[c]chromene-4-carboxylic acid

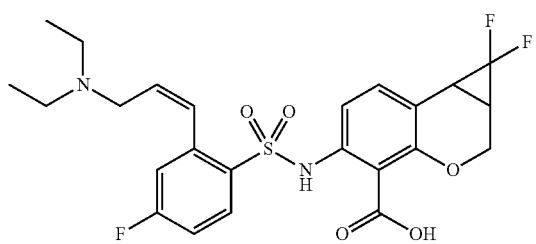 [SMILES: CCN(CC)C/C=C\c1cc(F)ccc1S(=O)(=O)Nc1ccc2c(c1C(=O)O)OCC1C2C1(F)F]

Prepared by proceeding in a similar manner to Example 10, starting from methyl (1aRS,7bSR)-5-[2-((Z)-3-diethylaminoprop-1-enyl)-4-fluorobenzenesulfonylamino]-1,1-difluoro-1,1a,2,7b-tetrahydrocyclopropa[c]chromene-4-carboxylate (Intermediate 59) as a white solid.

$^1$H NMR (CDCl$_3$) δ: 10.0-9.6 (1H, br s), 7.64 (1H, d), 7.47 (1H, dd), 7.21 (1H, d), 7.13 (1H, d), 6.87 (1H, dt), 6.73 (1H, dd), 5.95 (1H, m), 4.28 (1H, d), 3.96 (1H, m), 3.92-3.79 (1H, br s), 3.78-3.67 (1H, br s), 3.17 (4H, q), 2.64 (1H, t), 2.23 (1H, m), 1.24 (6H, t).

LCMS (Method C) r/t 3.38 (M+H) 511.

Examples 18 and 19

Separation of Enantiomers from Example 17

Sample from Example 17 was subjected to chiral separation using a ChiralPak IA column, 20 mm×250 mm, particle size 5 micron. Eluting solvent methanol:ethanol:heptane (12.5:12.5:75).

Example 18

First eluting enantiomer: r/t on analytical column (4.6 mm×250 mm): 14.7 minutes >95% ee.

$^1$H NMR (DMSO-d$_6$) δ: 7.83 (1H, t), 7.27-7.17 (3H, m), 7.09 (1H, d), 6.85 (1H, d), 5.98 (1H, m), 4.27 (1H, d), 3.76 (1H, m), 3.56 (1H, t), 2.90 (1H, t), 2.85 (1H, t), 2.77 (4H, br s), 2.55 (1H, s), 0.97 (6H, br t).

LCMS (Method C) r/t 3.39 (M+H) 511

Example 19

Second eluting enantiomer: r/t on analytical column 19.0 minutes, >95% ee.

$^1$H NMR (DMSO-d$_6$) δ: 7.72 (1H, dd), 7.36 (1H, d), 7.26 (1H, dt), 7.21 (1H, dd), 7.18 (1H, d), 6.99 (1H, d), 6.13 (1H, m), 4.29 (1H, d), 3.87-3.70 (3H, m), 3.10 (4H, m), 2.96 (1H, t), 2.56 (1H, m), 1.11 (6H, t).

LCMS (Method C) r/t 3.39 (M+H) 511.

Example 20

(1aRS,7bSR)-5-[2((Z)-3-Ethylaminoprop-1-enyl)-4-fluorobenzenesulfonyl-amino]-1,1a,2,7b-tetrahydrocyclopropa[c]chromene-4-carboxylic acid

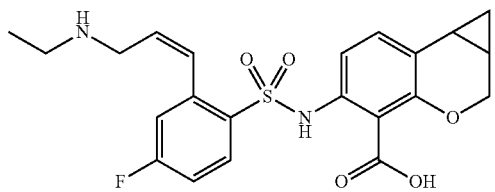 [SMILES: CCNC/C=C\c1cc(F)ccc1S(=O)(=O)Nc1ccc2c(c1C(=O)O)OCC1CC21]

A mixture of methyl (1aRS,7bSR)-5-[2((Z)-3-ethylaminoprop-1-enyl)-4-fluorobenzenesulfonylamino]-1,1a,2,7b-tetrahydrocyclopropa[c]chromene-4-carboxylate (Intermediate 63, 0.09 g) and lithium hydroxide monohydrate (0.047 g) in a mixture of dioxane (10 mL) and water (5 mL) was stirred and heated at 120° C. for 32 hours. After cooling, the mixture was concentrated under vacuum and the residue was acidified to pH4 with formic acid.

The resultant solid was collected by filtration and washed with water to give (1aRS,7bSR)-5-[2((Z)-3-ethylaminoprop-1-enyl)-4-fluorobenzene-sulfonylamino]-1,1a,2,7b-tetrahydrocyclopropa-[c]chromene-4-carboxylic acid (0.029 g) as a grey solid.

$^1$H NMR (DMSO-d$_6$) δ: 10.4-9.95 (1H, br s), 7.51 (1H, dd), 7.21 (1H, d), 7.17 (1H, dt), 7.11 (1H, dd), 7.07 (1H, d), 6.99 (1H, d), 5.93 (1H, m), 4.11 (1H, d), 3.60 (2H, m), 3.51 (1H, d), 2.92 (2H, q), 1.87 (1H, m), 1.67 (1H, m), 1.12 (3H, t), 0.89 (1H, m), 0.69 (1H, m).

LCMS (Method C) r/t 3.32 (M+H) 447.

Examples 21 and 22

Separation of Enantiomers from Example 20

Sample from Example 20 was subjected to chiral separation using a ChiralPak IC column, 10 mm×250 mm, particle size 5 micron. Eluting solvent tert-butyl methyl ether:isopropanol:DCM (15:20:65).

Example 21

First eluting enantiomer: r/t on analytical column (4.6 mm×250 mm): 14.3 minutes >99% ee.

$^1$H NMR (DMSO-d$_6$) δ: 10.16 (2H, br s), 7.56 (1H, dd), 7.26 (1H, d), 7.22 (1H, dt), 7.17 (1H, dd), 7.12 (1H, d), 7.05 (1H, d), 5.99 (1H, m), 4.16 (1H, d), 3.65 (2H, m), 3.57 (1H, d), 2.98 (2H, q), 1.93 (1H, m), 1.73 (1H, m), 1.17 (3H, t), 0.94 (1H, m), 0.78 (1H, q).

LCMS (Method C) r/t 3.27 (M+H) 447.

Example 22

Second eluting enantiomer: r/t on analytical column 20.6 minutes, >99% ee.

$^1$H NMR (DMSO-d$_6$) δ: 10.16 (2H, br s), 7.56 (1H, dd), 7.26 (1H, d), 7.22 (1H, dt), 7.17 (1H, dd), 7.12 (1H, d), 7.05 (1H, d), 5.99 (1H, m), 4.16 (1H, d), 3.65 (2H, m), 3.57 (1H, d), 2.98 (2H, q), 1.93 (1H, dt), 1.73 (1H, m), 1.17 (3H, t), 0.94 (1H, dt), 0.75 (1H, q).

LCMS (Method C) r/t 3.26 (M+H) 447.

Example 23

(1aRS,7bSR)-5-{2[(Z)-3-(Pyrrolidin-1-yl)prop-1-enyl]-4-fluorobenzene-sulfonylamino}-1,1a,2,7b-tetrahydrocyclopropa[c]chromene-4-carboxylic acid

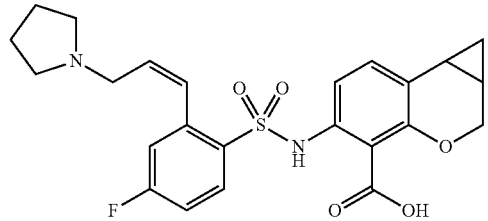 [SMILES: O=C(O)c1c(NS(=O)(=O)c2ccc(F)cc2/C=C\CN2CCCC2)ccc2c1OCC1CC21]

Prepared by proceeding in a similar manner to Example 20, starting from methyl (1aRS,7bSR)-5-{2[(Z)-3-(pyrrolidin-1-yl)prop-1-enyl]-4-fluorobenzene-sulfonylamino}-1,1a,2,7b-tetrahydrocyclopropa[c]chromene-4-carboxylate (Intermediate 66) as a white solid.

$^1$H NMR (DMSO-d$_6$) δ: 12.2-11.6 (1H, br s), 7.49 (1H, dd), 7.30 (1H, d), 7.21-7.12 (2H, m), 7.09 (1H, m), 6.97 (1H, d), 6.10 (1H, m), 4.12 (1H, d), 3.80 (2H, d), 3.51 (1H, d), 3.28 (4H, m), 1.89 (1H, m), 1.85 (4H, m), 1.68 (1H, m), 0.90 (1H, m), 0.69 (1H, m).

LCMS (Method C) r/t 3.39 (M+H) 473

Examples 24 and 25

Separation of Enantiomers from Example 23

Sample from Example 23 was subjected to chiral separation using a ChiralPak IC column, 10 mm×250 mm, particle size 5 micron. Eluting solvent tert-butyl methyl ether:ethanol (75:25).

Example 24

First eluting enantiomer: r/t on analytical column (4.6 mm×250 mm): 17.5 minutes >99% ee $^1$H NMR (DMSO-$d_6$) δ: 7.55 (1H, dd), 7.35 (1H, d), 7.22 (2H, m), 7.14 (1H, d), 7.02 (1H, d), 6.14 (1H, m), 4.17 (1H, d), 3.84 (2H, br d), 3.57 (1H, d), 3.30 (4H, br), 1.97-1.85 (5H, br m), 1.73 (1H, m), 0.95 (1H, dt), 0.74 (1H, q).

LCMS (Method C) r/t 3.33 (M+H) 473

Example 25

Second eluting enantiomer: r/t on analytical column 21.4 minutes, >98% ee.

$^1$H NMR (DMSO-$d_6$) δ: 7.55 (1H, dd), 7.34 (1H, d), 7.24 (1H, dd), 7.19 (1H, dd), 7.14 (1H, d), 7.02 (1H, d), 6.14 (1H, dt), 4.17 (1H, d), 3.84 (2H, br d), 3.57 (1H, d), 3.29 (4H, br), 1.97-1.85 (5H, br m), 1.73 (1H, m), 0.95 (1H, dt), 0.74 (1H, q).

LCMS (Method C) r/t 3.34 (M+H) 473.

Example 26

(1aRS,7bSR)-5-[2-(3-Dimethylaminopropylamino)benzenesulfonyl-amino]-1,1a,2,7b-tetrahydrocyclopropa[c]chromene-4-carboxylic acid

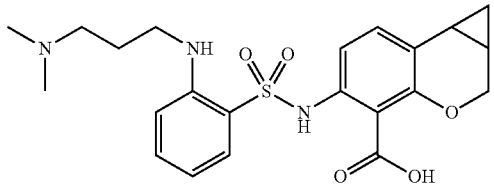 [SMILES: CN(C)CCCNc1ccccc1S(=O)(=O)Nc1ccc2c(c1C(=O)O)OCC1CC21]

A mixture of (1aRS,7bSR)-5-(2-fluorobenzenesulfonylamino)-1,1a,2,7b-tetrahydrocyclopropa-[c]chromene-4-carboxylic acid (Intermediate 67, 0.15 g), 3-dimethylaminopropylamine (1.26 g) and triethylamine (0.62 g) in NMP (6 mL) was stirred and heated at 140° C. for 48 hours. After cooling, the mixture was concentrated under vacuum and the residue was purified by chromatography on silica, eluting with a mixture of methanol and DCM with a gradient of 5-10%. The resultant product was repurified by preparative TLC, eluting with a mixture of methanol and DCM (10%) to give (1aRS,7bSR)-5-[2-(3-dimethylaminopropylamino)-benzenesulfonylamino]-1,1a,2,7b-tetrahydrocyclopropa[c] chromene-4-carboxylic acid (0.08 g) as an off white solid.

$^1$H NMR (DMSO-$d_6$) δ: 7.36 (1H, dd), 7.22 (1H, dt), 7.02 (2H, s), 6.68 (1H, d), 6.44 (1H, t), 6.24 (1H, br s), 4.11 (1H, d), 3.51 (1H, d), 3.30-3.10 (4H, m), 2.68 (6H, s), 1.83 (1H, m), 1.72-1.52 (3H, m), 0.85 (1H, m), 0.65 (1H, m).

LCMS (Method C) r/t 3.31 (M+H) 446.

Examples 27 and 28

Separation of Enantiomers from Example 26

Sample from Example 26 was subjected to chiral separation using a ChiralPak IB column 20 mm×250 mm, particle size 5 micron. Eluting solvent hexane:ethanol:diethylamine (49.8:50:0.2).

Example 27

First eluting enantiomer: r/t on analytical column (4.6 mm×250 mm) 14.61 minutes (>98% ee).

$^1$H NMR (DMSO-$d_6$) δ: 7.37 (1H, dd), 7.23 (1H, dt),7.02 (2H, s), 6.68 (1H, d), 6.45 (1H, t), 6.24 (1H, br s), 4.11 (1H, d), 3.52 (1H, d), 3.35-3.02 (4H, m), 2.67 (6H, s), 1.84 (1H, m), 1.74-1.52 (3H, m), 0.85 (1H, m), 0.66 (1H, m).

LCMS (Method C) r/t 3.21 (M+H) 446.

Example 28

Second eluting enantiomer: r/t on analytical column (4.6 mm×250 mm) 18.16 minutes (>98% ee).

$^1$H NMR (DMSO-$d_6$) δ: 7.37 (1H, dd), 7.23 (1H, dt),7.02 (2H, s), 6.68 (1H, d), 6.44 (1H, t), 6.25 (1H, br s), 4.11 (1H, d), 3.51 (1H, d), 3.41-3.05 (4H, m), 2.69 (6H, s), 1.84 (1H, m), 1.74-1.52 (3H, m), 0.85 (1H, m), 0.66 (1H, m).

LCMS (Method C) r/t 3.20 (M+H) 446.

Example 29

(1aRS,7bSR)-5-[2-(4-Dimethylaminobutylamino)benzenesulfonyl-amino]-1,1a,2,7b-tetrahydrocyclopropa[c]chromene-4-carboxylic acid

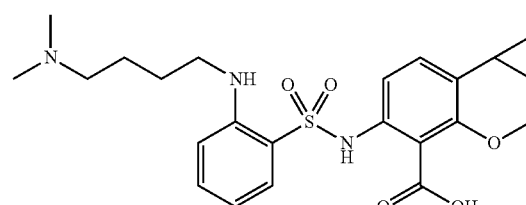

Prepared by proceeding in a similar manner to Example 26, starting from (1aRS,7bSR)-5-(2-fluorobenzenesulfonylamino)-1,1a,2,7b-tetrahydrocyclopropa[c]chromene-4-carboxylic acid (Intermediate 67) and 4-dimethylaminobutylamine.

$^1$H NMR (DMSO-$d_6$) ε: 13.0-12.0 (1H, br s), 7.58 (1H, dd), 7.28 (1H, dt), 7.02 (2H, s), 6.69 (1H, d), 6.55 (1H, t), 5.70 (1H, m), 4.14 (1H, d), 3.53 (1H, d), 3.15 (2H, m), 2.91 (2H, m), 2.67 (6H, s), 1.83 (1H, m), 1.76 (2H, m), 1.66 (1H, m), 1.53 (2H, m), 0.84 (1H, m), 0.67 (1H, m).

LCMS (Method C) r/t 3.43 (M+H) 460.

Examples 30 and 31

Separation of Enantiomers from Example 29

Sample from Example 29 was subjected to chiral separation using a ChiralPak IB column 20 mm×250 mm, particle size 5 micron. Eluting solvent hexane: ethanol: diethylamine (49.8:50:0.2).

Example 30

First eluting enantiomer: r/t on analytical column (4.6 mm×250 mm) 12.69 minutes (>98% ee).

$^1$H NMR (DMSO-d$_6$) ε: 13.0-12.2 (1H, br s), 7.58 (1H, dd), 7.28 (1H, dt), 7.02 (2H, m), 6.69 (1H, d), 6.55 (1H, t), 5.71 (1H, m), 4.14 (1H, d), 3.53 (1H, d), 3.15 (2H, m), 2.89 (2H, m), 2.67 (6H, s), 1.83 (1H, m), 1.76 (2H, m), 1.66 (1H, m), 1.54 (2H, m), 0.85 (1H, m), 0.68 (1H, m).

LCMS (Method C) r/t 3.33 (M+H) 460.

Example 31

Second eluting enantiomer: r/t on analytical column (4.6 mm×250 mm) 16.82 minutes (>98% ee).

$^1$H NMR (DMSO-d$_6$) δ: 12.9-12.1 (1H, br s), 7.58 (1H, dd), 7.28 (1H, dt), 7.02 (2H, s), 6.70 (1H, d), 6.55 (1H, t), 5.71 (1H, m), 4.14 (1H, d), 3.53 (1H, d), 3.15 (2H, m), 2.91 (2H, m), 2.68 (6H, s), 1.83 (1H, m), 1.77 (2H, m), 1.66 (1H, m), 1.54 (2H, m), 0.85 (1H, m), 0.68 (1H, m).

LCMS (Method C) r/t 3.33 (M+H) 460.

Example 32

(1aRS,7bSR)-5-[2-(5-Dimethylaminopentylamino) benzenesulfonylamino]-1,1a,2,7b-tetrahydrocyclopropa[c]chromene-4-carboxylic acid

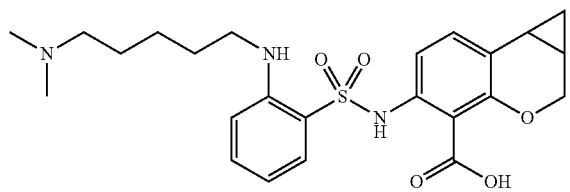 [SMILES: CN(C)CCCCCNc1ccccc1S(=O)(=O)Nc1ccc2c(c1C(=O)O)OCC1CC21]

Prepared by proceeding in a similar manner to Example 26, starting from (1aRS,7bSR)-5-(2-fluorobenzenesulfonylamino)-1,1a,2,7b-tetrahydrocyclopropa[c]chromene-4-carboxylic acid (Intermediate 67) and 5-dimethylaminopentylamine.

$^1$H NMR (DMSO-d$_6$) δ: 12.8-12.2 (1H, br s), 7.67 (1H, dd), 7.30 (1H, dt), 6.98 (1H, d), 6.85 (1H, d), 6.68 (1H, d), 6.60 (1H, t), 5.54 (1H, m), 4.14 (1H, d), 3.54 (1H, d), 3.05 (4H, m), 2.66 (6H, s), 1.81 (1H, m), 1.63 (5H, m), 1.51 (2H, m), 0.83 (1H, m), 0.67 (1H, m).

LCMS (Method C) r/t 3.55 (M+H) 474.

Example 33

(1aRS,7bSR)-5-{2[(Z)-3-(Propan-2-yl)aminoprop-1-enyl]-4-fluorobenzene-sulfonylamino}-1,1a,2,7b-tetrahydrocyclopropa[c]chromene-4-carboxylic acid

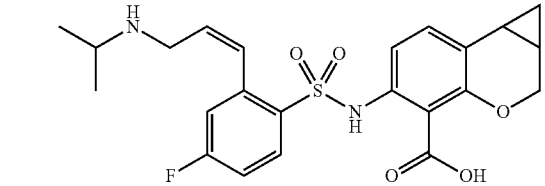 [SMILES: CC(C)NC/C=C\c1cc(F)ccc1S(=O)(=O)Nc1ccc2c(c1C(=O)O)OCC1CC21]

A mixture of methyl (1aRS,7bSR)-5-{2[(Z)-3-(propan-2-yl)aminoprop-1-enyl]-4-fluorobenzenesulfonylamino}-1,1a,2,7b-tetrahydrocyclopropa[c]chromene-4-carboxylate (Intermediate 69, 0.12 g) and lithium hydroxide monohydrate (0.1 g) in a mixture of dioxane (10 mL) and water (5 mL) was stirred and heated at 100° C. overnight. After cooling, the mixture was concentrated under vacuum and the residue was acidified to pH4 with formic acid then extracted with a mixture of ethyl acetate and THF (1:1). The organic phase was dried (Na$_2$SO$_4$) and filtered. The filtrate was evaporated to dryness and the residue was dissolved in ethyl acetate (2 mL) and hexane was added (10 mL). The solid was collected by filtration and washed with ether to give (1aRS,7bSR)-5-{2[(Z)-3-(propan-2-yl)aminoprop-1-enyl]-4-fluorobenzene-sulfonylamino}-1,1a,2,7b-tetrahydrocyclopropa[c]chromene-4-carboxylic acid (0.04 g) as an off white solid.

$^1$H NMR (DMSO-d$_6$) δ: 10.5-9.8 (1H, br s), 7.54 (1H, dd), 7.23-7.08 (3H, m), 7.04 (1H, d), 6.96 (1H, d), 5.91 (1H, m), 4.09 (1H, d), 3.63 (2H, m), 3.53 (1H, m), 3.49 (1H, d), 1.85 (1H, m), 1.67 (1H, m), 1.16 (6H, d), 0.86 (1H, m), 0.67 (1H, m).

LCMS (Method C) r/t 3.37 (M+H) 461.

Example 34

(1aRS,7bSR)-5-{2[(Z)-3-((S)-3-Hydroxypyrrolidin-1-yl)aminoprop-1-enyl]-4-fluorobenzenesulfonylamino}-1,1a,2,7b-tetrahydrocyclopropa[c]chromene-4-carboxylic acid

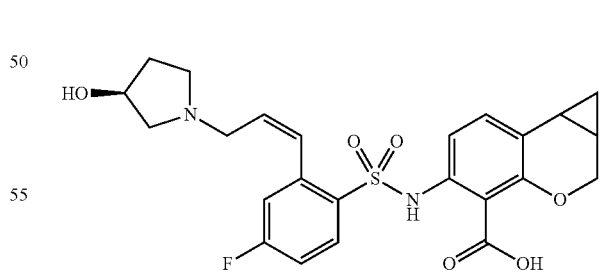

Prepared by proceeding in a similar manner to Example 33, starting from methyl (1aRS,7bSR)-5-{2[(Z)-3-((S)-3-hydroxypyrrolidin-1-yl)aminoprop-1-enyl]-4-fluorobenzenesulfonylamino}-1,1a,2,7b-tetrahydrocyclopropa[c]chromene-4-carboxylate (Intermediate 70).

$^1$H NMR (DMSO-d$_6$) δ: 12.5-11.3 (1H, br s), 7.62 (1H, m), 7.32 (1H, d), 7.22 (2H, m), 7.13 (1H, d), 6.98 (1H, d), 6.12 (1H, m), 5.26 (1H, m), 4.37 (1H, m), 4.19 (1H, d), 3.79

(2H, m), 3.59 (1H, dd), 3.20-3.00 (3H, br s), 2.05 (1H, m), 1.94 (1H, m), 1.77 (2H, m), 0.96 (1H, m), 0.76 (1H, m).
LCMS (Method C) r/t 3.15 (M+H) 489.

Example 35

(1aRS,7bSR)-5-{2[(Z)-3-((R)-3-Hydroxypyrrolidin-1-yl)aminoprop-1-enyl]-4-fluorobenzenesulfonylamino}-1,1a,2,7b-tetrahydro-cyclopropa[c]chromene-4-carboxylic acid

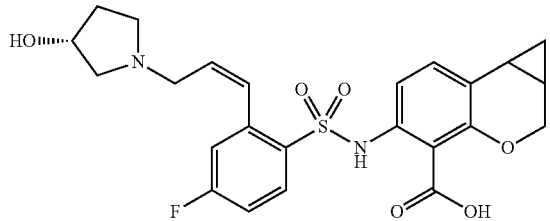 [SMILES: O=C(O)c1c(NS(=O)(=O)c2ccc(F)cc2/C=C\CN2CC[C@@H](O)C2)ccc2c1OCC1CC21]

Prepared by proceeding in a similar manner to Example 33, starting from methyl (1aRS,7bSR)-5-{2[(Z)-3-((R)-3-hydroxypyrrolidin-1-yl)aminoprop-1-enyl]-4-fluorobenzene-sulfonylamino}-1,1a,2,7b-tetrahydrocyclopropa[c]chromene-4-carboxylate (Intermediate 71).

$^1$H NMR (DMSO-$d_6$) δ: 12.5-11.4 (1H, br s), 7.62 (1H, m), 7.33 (1H, d), 7.22 (2H, m), 7.13 (1H, d), 6.98 (1H, d), 6.14 (1H, m), 5.26 (1H, m), 4.37 (1H, m), 4.19 (1H, d), 3.79 (2H, m), 3.59 (1H, dd), 3.20-3.00 (3H, br s), 2.05 (1H, m), 1.94 (1H, m), 1.77 (2H, m), 0.96 (1H, m), 0.76 (1H, m).
LCMS (Method C) r/t 3.14 (M+H) 489.

Example 36

(1aRS,7bSR)-5-[2((Z)-4-Diethylaminobut-1-enyl)-4-fluorobenzenesulfonyl-amino]-1,1a,2,7b-tetrahydro-cyclopropa[c]chromene-4-carboxylic acid

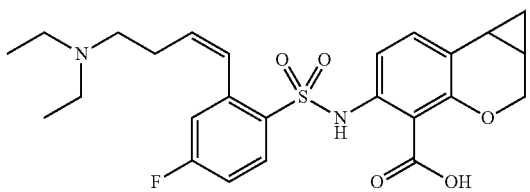 [SMILES: CCN(CC)CC/C=C\c1cc(F)ccc1S(=O)(=O)Nc1ccc2c(c1C(=O)O)OCC1CC21]

Prepared by proceeding in a manner similar to Example 33, starting from methyl (1aRS,7bSR)-5-{N-(methoxycarbonyl)-N-[2((Z)-4-diethylaminobut-1-enyl)-4-fluorobenzenesulfonyl]amino}-1,1a,2,7b-tetrahydrocyclopropa[c]chromene-4-carboxylate (Intermediate 72).

$^1$H NMR (DMSO-$d_6$) δ: 12.8-11.4 (1H, br s), 7.54 (1H, dd), 7.14-7.02 (4H, m), 6.83 (1H, d), 5.66 (1H, m), 4.09 (1H, d), 3.51 (1H, d), 3.13 (2H, m), 2.92 (4H, m), 2.34 (2H, m), 1.84 (1H, m), 1.66 (1H, m), 1.06 (6H, t), 0.86 (1H, m), 0.67 (1H, m).
LCMS (Method C) r/t 3.35 (M+H) 489.

Examples 37 and 38

Separation of Enantiomers from Example 36

Sample from Example 37 was subjected to chiral separation using a ChiralPak IC column, 10 mm×250 mm, particle size 5 micron. Eluting solvent tert-butyl methyl ether:isopropanol:DCM (16:20:64).

Example 37

First eluting enantiomer: r/t on analytical column (4.6 mm×250 mm): 25.8 minutes >98% ee $^1$H NMR (DMSO-$d_6$) δ: 7.61 (1H, dd), 7.20-7.09 (4H, m), 6.90 (1H, d), 5.74 (1H, m), 4.16 (1H, d), 3.58 (1H, d), 3.22-3.11 (2H, m), 2.99 (4H, m), 2.50 (2H, m), 1.92 (1H, dt), 1.72 (1H, m), 1.15 (6H, t), 0.93 (1H, m), 0.75 (1H, m).
LCMS (Method C) r/t 3.36 (M+H) 489

Example 38

Second eluting enantiomer: r/t on analytical column 44.0 minutes, >98% ee.

$^1$H NMR (DMSO-$d_6$) δ: 7.61 (1H, dd), 7.20-7.10 (4H, m), 6.90 (1H, d), 5.74 (1H, m), 4.16 (1H, d), 3.58 (1H, d), 3.23-3.10 (2H, m), 2.99 (4H, q), 2.51 (2H, m), 1.92 (1H, dt), 1.72 (1H, m), 1.15 (6H, t), 0.93 (1H, m), 0.75 (1H, m).
LCMS (Method C) r/t 3.36 (M+H) 489

Example 39

(1aRS,7bSR)-5-{2-[2-(4-Ethylpiperazin-1-yl)-ethyl]-4-fluorobenzenesulfonyl-amino}-1,1a,2,7b-tetrahydrocyclopropa[c]chromene-4-carboxylic acid

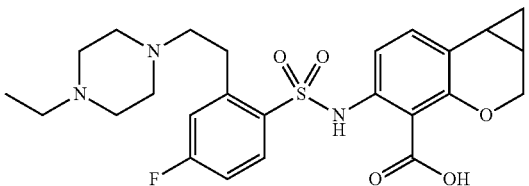 [SMILES: CCN1CCN(CCc2cc(F)ccc2S(=O)(=O)Nc2ccc3c(c2C(=O)O)OCC2CC32)CC1]

A solution of (1aRS,7bSR)-5-(4-Fluoro-2-vinylbenzenesulfonylamino)-1,1a,2,7b-tetrahydro-cyclopropa[c]chromene-4-carboxylic acid (Intermediate 74, 0.035 g) and 3 drops of N-ethyl piperazine in isopropanol (0.5 mL) was irradiated in the microwave at 160° C. for 15 minutes then again at 170° C. for 15 minutes. After cooling, the mixture was purified by preparative HPLC (C18) eluting with a mixture of methanol and water, containing 0.1% formic acid, with a gradient of 20-60%. The isolated product was further purified by chromatography on silica eluting with a mixture of methanol and DCM with a gradient of 0-10% to give (1 aS,7bR)-5-{2-[2-(4-ethylpiperazin-1-yl)-ethyl]-4-fluorobenzenesulfonylamino}-1,1a,2,7b-tetrahydrocyclopropa[c]chromene-4-carboxylic acid (0.018 g) as an off white solid.

$^1$H NMR (CDCl$_3$) δ: 7.95 (1H, dd), 7.07 (2H, s), 6.95 (1H, dd), 6.91 (1H, dt), 4.38 (1H, d), 3.79 (1H, d), 3.42 (2H, q), 3.35 (2H, q), 3.21-3.05 (4H, m), 3.04-2.88 (4H, m), 2.79 (2H, m), 1.86 (1H, dt), 1.66 (1H, m), 1.22 (3H, t), 1.06 (1H, q), 0.93 (1H, m).
LCMS (Method C) r/t 2.95 (M+H) 504

Example 40

(1aRS,7bSR)-5-{2[(Z)-3-(Azetidin-1-yl)prop-1-enyl]-4-fluorobenzenesulfonyl-amino}-1,1a,2,7b-tetrahydrocyclopropa[c]chromene-4-carboxylic acid

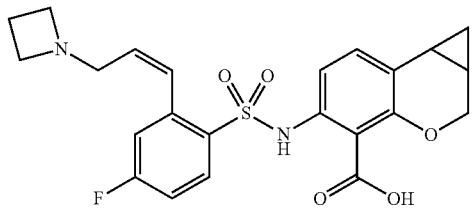 [SMILES: O=C(O)c1c(NS(=O)(=O)c2ccc(F)cc2/C=C\CN2CCC2)ccc2c1OCC1CC21]

Prepared by proceeding in a manner similar to Example 33, starting from methyl (1aRS,7bSR)-5-{2-[(Z)-3-(azetidin-1-yl)prop-1-enyl]-4-fluorobenzenesulfonyl-amino}-1,1a,2,7b-tetrahydro-cyclopropa[c]chromene-4-carboxylate (Intermediate 76).

$^1$H NMR (DMSO-d$_6$) δ: 12.8-11.1 (1H, br s), 7.51 (1H, dd), 7.26 (1H, d), 7.17 (1H, dt), 7.10 (2H, m), 7.00 (1H, d), 5.90 (1H, m), 4.12 (1H, d), 3.96 (4H, m), 3.74 (2H, m), 3.52 (1H, d), 2.27 (2H, m), 1.89 (1H, m), 1.69 (1H, m), 0.90 (1H, m), 0.69 (1H, m).

LCMS (Method C) r/t 3.26 (M+H) 459.

Example 41

(1aRS,7bSR)-5-{2[(Z)-3-(3-Hydroxyazetidin-1-yl)prop-1-enyl]-4-fluorobenzene-sulfonylamino}-1,1a,2,7b-tetrahydrocyclopropa[c]chromene-4-carboxylic acid

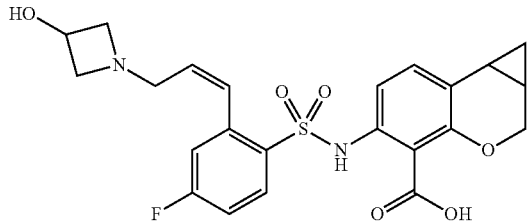 [SMILES: O=C(O)c1c(NS(=O)(=O)c2ccc(F)cc2/C=C\CN2CC(O)C2)ccc2c1OCC1CC21]

Prepared by proceeding in a manner similar to Example 33, starting from methyl (1aRS,7bSR)-5-{2-[(Z)-3-(3-hydroxyazetidin-1-yl)prop-1-enyl]-4-fluorobenzene-sulfonylamino}-1,1a,2,7b-tetrahydrocyclopropa[c]chromene-4-carboxylate (Intermediate 77).

$^1$H NMR (DMSO-d$_6$) δ: 12.8-11.2 (1H, br s), 7.53 (1H, m), 7.22 (1H, d), 7.17 (1H, dt), 7.09 (2H, m), 6.97 (1H, d), 5.90 (1H, m), 4.40 (1H, m), 4.18 (2H, m), 4.12 (1H, d), 3.69 (4H, m), 3.52 (1H, d), 1.87 (1H, m), 1.69 (1H, m), 0.89 (1H, m), 0.70 (1H, m).

LCMS (Method C) r/t 3.18 (M+H) 475.

Example 42

(1aRS,7bSR)-5-{2[(Z)-3-(Azetidin-1-yl)propyl]-4-fluorobenzenesulfonylamino}-1,1a,2,7b-tetrahydrocyclopropa[c]chromene-4-carboxylic acid

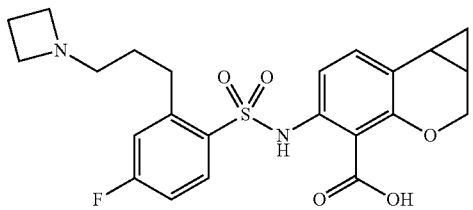 [SMILES: O=C(O)c1c(NS(=O)(=O)c2ccc(F)cc2CCCN2CCC2)ccc2c1OCC1CC21]

A solution of (1aRS,7bSR)-5-{2[(Z)-3-(azetidin-1-yl)prop-1-enyl]-4-fluorobenzene-sulfonylamino}-1,1a,2,7b-tetrahydrocyclopropa[c]chromene-4-carboxylic acid (Example 40, 0.03 g) in methanol was treated, under an atmosphere of nitrogen with palladium on carbon (10%, 0.01 g). The nitrogen was replaced by hydrogen and the mixture was stirred under an atmosphere of hydrogen overnight. The mixture was filtered and the filtrate was evaporated to dryness. The residue was purified by HPLC (C18) to give (1aRS,7bSR)-5-{2 [(Z)-3-(azetidin-1-yl)propyl]-4-fluorobenzenesulfonylamino}-1,1a,2,7b-tetrahydrocyclopropa[c]chromene-4-carboxylic acid (0.019 g) as a white solid.

$^1$H NMR (DMSO-d$_6$) δ: 7.76 (1H, dd), 7.20 (1H, dd), 7.09 (1H, dt), 7.05 (1H, d), 6.99 (1H, d) 4.15 (1H, d), 3.97 (2H, m) 3.56 (1H, d), 3.14 (2H, m), 2.99 (4H, m), 2.29 (2H, m), 1.86 (1H, m), 1.81-1.64 (3H, m), 0.88 (1H, m), 0.69 (1H, m).

$^1$H LCMS (Method C) r/t 3.20 (M+H) 461.

Example 43

(1aRS,7bSR)-5-[2((Z)-4-Diethylaminobutyl)-4-fluorobenzenesulfonylamino]-1,1a,2,7b-tetrahydrocyclopropa[c]chromene-4-carboxylic acid

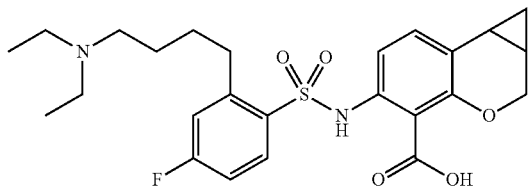 [SMILES: CCN(CC)CCCCc1cc(F)ccc1S(=O)(=O)Nc1ccc2c(c1C(=O)O)OCC1CC21]

Prepared by proceeding in a similar manner to Example 42, starting from (1aRS,7bSR)-5-[2((Z)-4-diethylaminobut-1-enyl)-4-fluorobenzene-sulfonylamino]-1,1a,2,7b-tetrahydrocyclopropa-[c]chromene-4-carboxylic acid (Example 36) as a white solid.

$^1$H NMR (DMSO-d$_6$) δ: 13.0-11.6 (1H, br s), 7.82 (1H, dd), 7.21 (1H, dd), 7.08 (1H, dt), 7.02 (1H, d), 6.96 (1H, d), 4.14 (1H, d), 3.55 (1H, d), 2.99 (8H, m), 1.83 (1H, m), 1.65 (5H, m), 1.14 (6H, t), 0.85 (1H, m), 0.69 (1H, m).

LCMS (Method C) r/t 3.45 (M+H) 491.

Example 44

(1aRS,7bSR)-5-{2-[N-(4-Dimethylaminobutyl)-N-methylamino]-benzenesulfonyl-amino}-1,1a,2,7b-tetrahydrocyclopropa[c]chromene-4-carboxylic acid

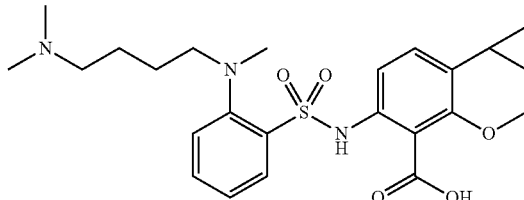

A mixture of (1aRS,7bSR)-5-(2-fluorobenzenesulfonylamino)-1,1a,2,7b-tetrahydrocyclopropa-[c]chromene-4-carboxylic acid (Intermediate 67, 0.1 g), N-(4-dimethylaminobutyl)-N-methylamine (Intermediate 78, 1.07 g) and triethylamine (0.42 g) in NMP (6 mL) was stirred and heated in a sealed tube at 150° C. for 3 days. After cooling, the mixture was concentrated under vacuum and the residue was purified by chromatography on silica, eluting with a mixture of methanol and DCM (10%) followed by repurification by HPLC (C18) to give (1aRS,7bSR)-5-{2-[N-(4-dimethylaminobutyl)-N-methylamino]-benzenesulfonylamino}-1,1a,2,7b-tetrahydrocyclopropa[c]chromene-4-carboxylic acid (0.03 g) as a white solid.

$^1$H NMR (DMSO-$d_6$) δ: 7.81 (1H, dd), 7.54 (1H, dt), 7.41 (1H, dd), 7.21 (1H, dt), 6.94 (1H, d), 6.85 (1H, d), 4.12 (1H, d), 3.55 (1H, d), 2.96 (2H, t), 2.85 (2H, t), 2.64 (6H, s), 2.49 (3H, s), 1.83 (1H, m), 1.74 (2H, m), 1.63 (3H, m), 0.87 (1H, m), 0.68 (1H, m).

LCMS (Method C) r/t 3.37 (M+H) 474.

Example 45

(1aRS,7bSR)-5-{2-[((S)-1-Ethylpyrrolidin-3-ylcarbamoyl)methyl]-4-fluoro-benzenesulfonylamino}-1,1a,2,7b-tetrahydrocyclopropa[c]chromene-4-carboxylic acid

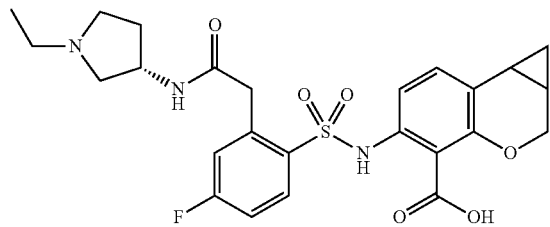 [SMILES: CCN1CC[C@H](NC(=O)Cc2cc(F)ccc2S(=O)(=O)Nc2ccc3c(c2C(=O)O)OCC2CC32)C1]

A mixture of methyl (1aRS,7bSR)-5-{2-[((S)-1-ethylpyrrolidin-3-ylcarbamoyl)methyl]-4-fluorobenzenesulfonylamino}-1,1a,2,7b-tetrahydrocyclopropa[c]chromene-4-carboxylate (Intermediate 80, 0.148 g) and lithium hydroxide monohydrate (0.168 g) in dioxane (3 mL) and water (1 mL) was irradiated in the microwave at 130° C. for 40 minutes. After cooling, the mixture was diluted with methanol, acidified with formic acid and evaporated in vacuo. The residue was triturated with 10% methanol in DCM and filtered. The filtrate was evaporated in vacuo and the residue was purified by chromatography on silica, eluting with a mixture of methanol and DCM with a gradient of 0-20%. The resultant solid was triturated with ether and filtered off to give (1aRS,7bSR)-5-{2-[((S)-1-ethylpyrrolidin-3-ylcarbamoyl)methyl]-4-fluorobenzenesulfonylamino}-1,1a,2,7b-tetrahydrocyclopropa[c]chromene-4-carboxylic acid (0.091 g) as a white solid.

$^1$H NMR (DMSO-$d_6$) δ: 9.56 (0.5H, br, d), 9.48 (0.5H, br, d), 7.59 (1H, m), 7.34 (1H, m), 7.16 (2H, m), 7.06 (1H, t), 4.46 (1H, br, q), 4.13 (1H, d), 3.92 (1H, dd), 3.70 (1H, m), 3.65 (1H, d), 3.58 (1H, br, m), 2.95-3.25 (6H, m), 2.40 (1H, m), 1.95 (2H, m), 1.76 (1H, m), 1.20 (3H, t), 0.97 (1H, m), 0.78 (1H, m).

LCMS (Method C) r/t 3.04 (M+H) 518.

Example 46

(1aRS,7bSR)-5-[2-(1-Ethylazetidin-3-yl)-4-fluorobenzenesulfonylamino]-1,1a,2,7b-tetrahydrocyclopropa[c]chromene-4-carboxylic acid

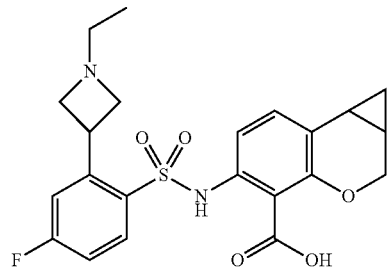 [SMILES: CCN1CC(c2cc(F)ccc2S(=O)(=O)Nc2ccc3c(c2C(=O)O)OCC2CC32)C1]

Prepared by proceeding in a similar manner to Example 45, starting from methyl (1aRS,7bSR)-5-[2-(1-ethylazetidin-3-yl)-4-fluorobenzenesulfonylamino]-1,1a,2,7b-tetrahydrocyclopropa-[c]chromene-4-carboxylate (Intermediate 86) as a white solid.

$^1$H NMR (DMSO-$d_6$) δ: 7.91 (1H, dd), 7.64 (1H, dd), 7.24 (1H, dt), 6.96 (1H, d), 6.66 (1H, d), 4.79 (1H, m), 4.21 (1H, d), 4.15 (2H, br, t), 3.89 (2H, br, m), 3.62 (1H, d), 3.06 (2H, q), 1.83 (1H, m), 1.70 (1H, m), 1.05 (3H, t), 0.88 (1H, m), 0.72 (1H, m).

LCMS (Method C) r/t 2.99 (M+H) 447.

Example 47

(1aRS,7bSR)-5-{2-[((R)-1-Ethylpyrrolidin-3-ylcarbamoyl)methyl]-4-fluoro-benzenesulfonylamino}-1,1a,2,7b-tetrahydrocyclopropa[c]chromene-4-carboxylic acid

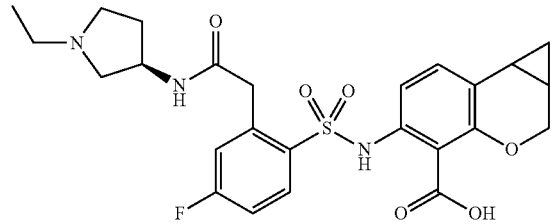 [SMILES: CCN1CC[C@@H](NC(=O)Cc2cc(F)ccc2S(=O)(=O)Nc2ccc3c(c2C(=O)O)OCC2CC32)C1]

Prepared by proceeding in a similar manner to Example 45, starting from methyl (1aRS,7bSR)-5-{2-[((R)-1-ethylpyrrolidin-3-ylcarbamoyl)methyl]-4-fluorobenzenesulfonylamino}-1,1a,2,7b-tetrahydrocyclopropa[c]chromene-4-carboxylate (Intermediate 92) as a white solid.

¹H NMR (CDCl₃) δ: 10.30 (0.5H, br, s), 10.25 (0.5H, br, s), 9.88 (1H, br, s), 7.52 (1H, m), 7.18-7.41 (3H, m), 6.75 (1H, m), 4.83 (0.5H, m), 4.70 (0.5H, m), 4.17 (1.5H, m), 3.84-4.10 (1.5H, m), 3.60-3.86 (3H, m), 3.45 (0.5H, d), 3.31 (0.5H, m), 3.13 (0.5H, m), 2.98 (0.5H, m), 2.83 (2H, m), 2.46 (1H, m), 2.29 (1H, m), 1.93 (1H, m), 1.67 (1H, q), 1.40 (3H, t), 1.13 (0.5H, m), 1.07 (0.5H, m), 0.97 (1H, m).

LCMS (Method C) r/t 3.03 (M+H) 518.

Example 48

(1aRS,7bSR)-5-{2-[2-(Pyrrolidin-1-yl)-ethyl]-4-fluorobenzenesulfonylamino}-1,1a,2,7b-tetrahydro-cyclopropa[c]chromene-4-carboxylic acid

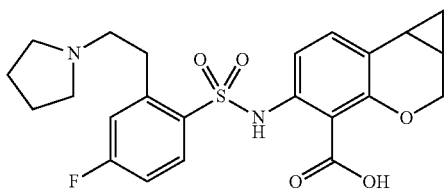 [SMILES: O=C(O)c1c(NS(=O)(=O)c2ccc(F)cc2CCN2CCCC2)ccc2c1OCC1CC21]

Prepared by proceeding in a similar manner to Example 39, starting from (1aRS,7bSR)-5-(4-fluoro-2-vinylbenzenesulfonylamino)-1,1a,2,7b-tetrahydrocyclopropa[c]chromene-4-carboxylic acid (Intermediate 74) and pyrrolidine as a white solid.

¹H NMR (DMSO-d₆) δ: 7.84 (1H, dd), 7.26 (1H, dd), 7.17 (1H, dt), 7.02 (1H, d), 6.74 (1H, d), 4.16 (1H, d), 3.59 (1H, d), 3.36-3.20 (8H, m), 1.91 (4H, m), 1.85 (1H, m), 1.69 (1H, m), 0.89 (1H, m), 0.70 (1H, m).

LCMS (Method C) r/t 3.12 (M+H) 461.

Example 49

(1aRS,7bSR)-5-[2-((R)-1-Ethylpyrrolidin-3-ylmethyl)-4-fluorobenzenesulfonyl-amino]-1,1a,2,7b-tetrahydrocyclopropa[c]chromene-4-carboxylic acid

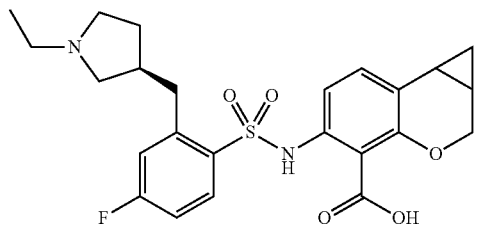 [SMILES: CCN1CC[C@@H](Cc2cc(F)ccc2S(=O)(=O)Nc2ccc3c(c2C(=O)O)OCC2CC32)C1]

Lithium hydroxide (0.111 g) was added to a solution of methyl (1aRS,7bSR)-5-[2-((R)-1-ethyl-pyrrolidin-3-ylmethyl)-4-fluorobenzenesulfonylamino]-1,1a,2,7b-tetrahydrocyclopropa-[c]chromene-4-carboxylate (Intermediate 95, 0.13 g) in a mixture of dioxane (4 mL) and water (1 mL) and the mixture was stirred and heated at 85° C. overnight. After cooling, the mixture was filtered and the filtrate was acidified by addition of 10% aqueous citric acid (1 mL) and then extracted with DCM. The organic extract was dried (MgSO₄) and filtered. The filtrate was evaporated to dryness and the residue was triturated with diethyl ether and the solid was collected by filtration to give (1aRS,7bSR)-5-[2-((R)-1-ethylpyrrolidin-3-ylmethyl)-4-fluorobenzenesulfonylamino]-1,1a,2,7b-tetrahydrocyclopropa[c]chromene-4-carboxylic acid (0.085 g) as a white solid.

¹H NMR (DMSO-d₆) δ: 7.81 (1H, dd), 7.28 (1H, dd), 7.16 (1H, dt), 7.11 (1H, dd), 6.99 (1H, dd), 4.20 (1H, dd), 3.60 (1H, t), 3.48-2.98 (9H, br m), 2.25 (1H, m), 1.91 (1H, dt), 1.73 (2H, m), 1.23 (3H, t), 0.93 (1H, dt), 0.75 (1H, m).

LCMS (Method C) r/t 3.21 (M+H) 475.

Examples 50 and 51

Separation of Enantiomers from Example 49

Sample from Example 49 was subjected to chiral separation using a ChiralPak IC column, 10 mm×250 mm, particle size 5 micron. Eluting solvent tert-butyl methyl ether:isopropanol:DCM (10:15:75).

Example 50

First eluting enantiomer: r/t on analytical column (4.6 mm×250 mm): 30.0 minutes >99% ee.

¹H NMR (DMSO-d₆) δ: 7.81 (1H, dd), 7.27 (1H, dd), 7.15 (1H, dt), 7.10 (1H, d), 7.01 (1H, d), 4.20 (1H, d), 3.58 (1H, d), 3.23-3.11 (6H, m), 3.11-3.06 (3H, m), 2.25 (1H, m), 1.91 (1H, dt), 1.73 (2H, m), 1.22 (3H, t), 0.92 (1H, dt), 0.73 (1H, m).

LCMS (Method C) r/t 3.25 (M+H) 475.

Example 51

Second eluting enantiomer: r/t on analytical column 40.0 minutes, >99% ee.

¹H NMR (DMSO-d₆) δ: 7.80 (1H, dd), 7.27 (1H, dd), 7.15 (1H, dt), 7.10 (1H, d), 7.03 (1H, d), 4.18 (1H, d), 3.61 (1H, d), 3.48-2.97 (9H, br m), 2.27 (1H, m), 1.91 (1H, dt), 1.71 (2H, m), 1.23 (3H, t), 0.93 (1H, dt), 0.74 (1H, m).

LCMS (Method C) r/t 3.23 (M+H) 475.

Example 52

(1aRS,7bSR)-5-{2-[((S)-1-Ethylpyrrolidin-2-yl)cabonylaminomethyl]-4-fluorobenzenesulfonylamino}-1,1a,2,7b-tetrahydrocyclopropa[c]chromene-4-carboxylic acid

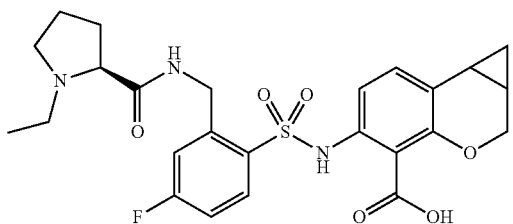 [SMILES: CCN1CCC[C@H]1C(=O)NCc1cc(F)ccc1S(=O)(=O)Nc1ccc2c(c1C(=O)O)OCC1CC21]

A mixture of methyl (1aRS,7bSR)-5-{2-[((S)-1-ethylpyrrolidin-2-yl)cabonylaminomethyl]-4-fluorobenzenesulfonylamino}-1,1a,2,7b-tetrahydrocyclopropa-[c]chromene-4-carboxylate (Intermediate 101, 0.212 g) and lithium hydroxide (0.05 g) in dioxane (5.5 mL) and water (2.5 mL) was irradiated in the microwave at 150° C. for 30 minutes. After cooling, the mixture was diluted with water, acidifed with formic acid to pH5 and extracted with ethyl acetate.

The organic layer was washed with water, dried (MgSO₄) and filtered. The filtrate was evaporate to dryness and the residue was purifed by HPLC (C18) eluting with a mixture of methanol and water, containing 0.1% formic acid, with a gradient of 35-75% to give (1aRS,7bSR)-5-{2-[((S)-1-ethylpyrrolidin-2-yl)cabonylaminomethyl]-4-fluorobenzenesulfonylamino}-1,1a,2,7b-tetrahydrocyclopropa-[c]chromene-4-carboxylic acid (0.064 g) as a white solid.

¹H NMR (CDCl₃) δ: 10.8-9.6 (1H, br s), 8.90 (1H, br t), 7.71 (1H, m), 7.20 (3H, m), 6.86 (1H, m), 4.88 (2H, m), 4.37 (1H, dd), 3.85 (1H, dt), 3.61 (1H, m), 3.43 (1H, m), 2.97 (1H, m), 2.77 (2H, m), 2.23 (2H, m), 2.03 (1H, m), 1.91 (2H, m), 1.69 (1H, m), 1.18 (3H, q), 1.01 (2H, m).

LCMS (Method C) r/t 3.09 (M+H) 518.

Example 53

(1aRS,7bSR)-5-[2-(4-Dimethylaminobutyrylamino)-4-fluorobenzenesulfonyl-amino]-1,1a,2,7b-tetrahydrocyclopropa[c]chromene-4-carboxylic acid

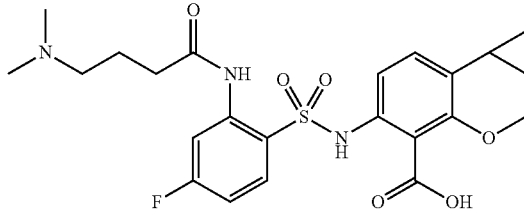 [SMILES: CN(C)CCCC(=O)Nc1cc(F)ccc1S(=O)(=O)Nc1ccc2c(c1C(=O)O)OCC1CC21]

A mixture of methyl (1aRS,7bSR)-5-[2-(4-dimethylaminobutyryl)-4-fluorobenzenesulfonyl-amino]-1,1a,2,7b-tetrahydrocyclopropa[c]chromene-4-carboxylate (Intermediate 108, 0.2 g), potassium carbonate (0.22 g), 1H-pyrazole-3-amine (0.34 g) and lithium iodide (1.07 g) in DMF (10 mL) was irradiated in the microwave at 150° C. for 1 hour. After cooling, the mixture was diluted with methanol and acidified to pH 3 with formic acid then concentrated under vacuum. The residue was purified by chromatography on silica, eluting with a mixture of methanol and DCM (5%). The resultant product was purified by HPLC (C18) to give (1aRS,7bSR)-5-[2-(3-dimethylaminobutyryl)-4-fluorobenzenesulfonyl-amino]-1,1a,2,7b-tetrahydrocyclopropa-[c]chromene-4-carboxylic acid (0.03 g) as a white solid.

¹H NMR (DMSO-d₆) δ: 7.95 (1H, dd), 7.80 (1H, dd), 6.96 (1H, d), 6.95 (1H, dt), 6.79 (1H, d), 4.13 (1H, d), 3.56 (1H, d), 3.04 (2H, t), 2.68 (6H, s), 2.56 (2H, t), 1.94 (2H, m), 1.81 (1H, m), 1.64 (1H, m), 0.84 (1H, m), 0.66 (1H, m).

LCMS (Method C) r/t 3.12 (M+H) 492.

Example 54

(1aRS,7bSR)-5-[2-((S)-1-Ethylpyrrolidin-3-ylmethyl)-4-fluorobenzenesulfonyl-amino]-1,1a,2,7b-tetrahydrocyclopromene-4-carboxylic acid

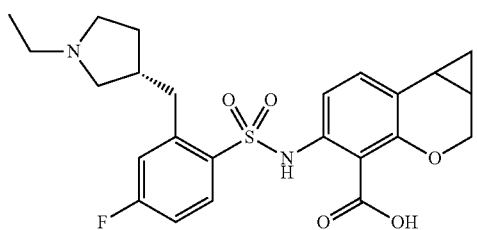 [SMILES: CCN1CC[C@H](Cc2cc(F)ccc2S(=O)(=O)Nc2ccc3c(c2C(=O)O)OCC2CC32)C1]

Prepared by proceeding in a similar manner to Example 49, starting from methyl (1aRS,7bSR)-5-[2-((S)-1-ethylpyrrolidin-3-ylmethyl)-4-fluorobenzenesulfonylamino]-1,1a,2,7b-tetrahydro-cyclopropa[c]chromene-4-carboxylate (Intermediate 113).

¹H NMR (DMSO-d₆) δ: 7.81 (1H, dd), 7.27 (1H, dd), 7.15 (1H, dt), 7.10 (1H, d), 7.02 (1H, dd), 4.19 (1H, dd), 3.56 (1H, t), 3.23-3.11 (6H, m), 3.11-3.06 (3H, m), 2.25 (1H, m), 1.91 (1H, dt), 173 (2H, m), 1.22 (3H, t), 0.92 (1H, dt), 0.73 (1H, m).

LCMS (Method C) r/t 3.21 (M+H) 475.

Example 55

(1aRS,7bSR)-5-[2-(3-Dimethylaminopropylcarbamoyl)benzenesulfonylamino]-1,1a,2,7b-tetrahydrocyclopropa-[c]chromene-4-carboxylic acid

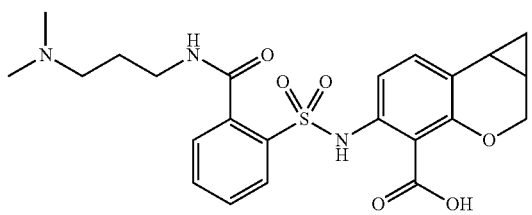 [SMILES: CN(C)CCCNC(=O)c1ccccc1S(=O)(=O)Nc1ccc2c(c1C(=O)O)OCC1CC21]

A solution of tert-butyl (1aRS,7bSR)-5-{2-[N-(2,4-dimethoxybenzyl)-N-(3-dimethylamino-propyl)carbamoyl]benzenesulfonylamino}-1,1a,2,7b-tetrahydro-cyclopropa[c]chromene-4-carboxylate (Intermediate 119, 0.03 g) in trifluoroacetic acid (5 mL) was stirred and heated at 30° C. overnight. The mixture was evaporated to dryness and the residue was purified by HPLC (C18) to give (1aRS,7bSR)-5-[2-(3-dimethylaminopropylcarbamoyl)benzenesulfonylamino]-1,1a,2,7b-tetrahydrocyclopropa[c]chromene-4-carboxylic acid (0.013 g) as a white solid.

¹H NMR (DMSO-d₆) δ: 8.61 (1H, br t), 7.73 (1H, d), 7.52 (1H, t), 7.43 (2H, m), 6.97 (1H, d), 6.82 (1H, d), 4.14 (1H, d), 3.58 (1H, d), 3.26 (2H, m), 3.04 (2H, t), 2.60 (6H, s), 1.85 (3H, m), 1.67 (1H, m), 0.87 (1H, m), 0.68 (1H, m).

LCMS (Method C) r/t 2.79 (M+H) 473.

Example 56

(1aRS,7bSR)-5-(2-{[N—((S)-1-Ethylpyrrolidin-3-yl)-N-methylcarbamoyl]methyl}-4-fluorobenzenesulfonylamino)-1,1a,2,7b-tetrahydrocyclopropa[c]chromene-4-carboxylic acid

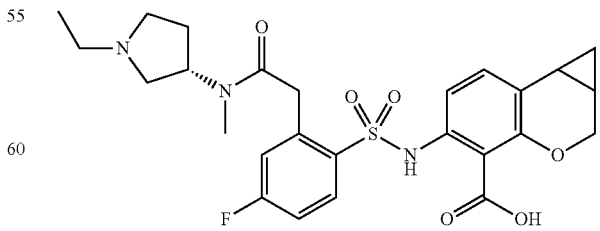

A mixture of methyl (1aRS,7bSR)-5-(2-{[N—((S)-1-ethylpyrrolidin-3-yl)-N-methylcarbamoyl]-methyl}-4-fluorobenzenesulfonylamino)- 1,1a,2,7b-tetrahydrocyclopropa

[c]chromene-4-carboxylate (Intermediate 126, 0.047 g) and lithium hydroxide monohydrate (0.168 g) in dioxane (3 mL) and water (1 mL) was irradiated in the microwave at 130° C. for 40 minutes. After cooling, the mixture was diluted with methanol, acidified with formic acid and evaporated in vacuo. The residue was triturated with 10% methanol in DCM, filtered and the filtrate was evaporated in vacuo. The residue was purified by chromatography on silica, eluting with a mixture of methanol and DCM with a gradient of 0-40%. The resultant solid was triturated with ethyl acetate and filtered off to give (1aRS,7bSR)-5-(2-{[N—((S)-1-ethylpyrrolidin-3-yl)-N-methylcarbamoyl]-methyl}-4-fluorobenzenesulfonylamino)-1,1a,2,7b-tetrahydrocyclopropa[c]chromene-4-carboxylic acid (0.022 g) as a white solid.

$^1$H NMR (DMSO-d$_6$ at 80° C.) ϵ: 7.83 (1H, t), 7.12 (1H, dt), 7.08 (1H, d), 7.01 (1H, d), 6.84 (1H, m), 4.61 (1H, br, s), 4.19 (1H, d), 4.12 (2H, s), 3.73 (1H, d), 2.71-3.18 (7H, br, m), 2.94 (3H, s), 1.85-2.15 (3H, m), 1.72 (1H, m), 1.17 (3H, t), 0.95 (1H, m), 0.78 (1H, m).

LCMS (Method C) r/t 3.08 (M+H) 532.

Example 57

(1aRS,7bSR)-5-(2-{[N—((R)-1-Ethylpyrrolidin-3-yl)-N-methylcarbamoyl]methyl}-4-fluorobenzenesulfonylamino)-1,1a,2,7b-tetrahydrocyclopropa[c]chromene-4-carboxylic acid

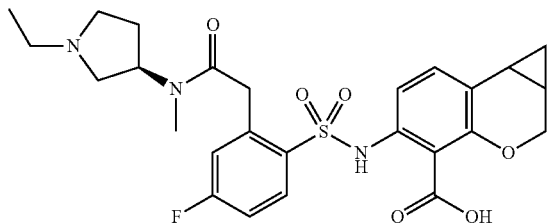 [SMILES: CCN1CC[C@@H](N(C)C(=O)Cc2cc(F)ccc2S(=O)(=O)Nc2ccc3c(c2C(=O)O)OCC2CC32)C1]

A mixture of methyl (1aRS,7bSR)-5-(2-{[N—((R)-1-ethylpyrrolidin-3-yl)methylcarbamoyl]-N-methyl}-4-fluorobenzenesulfonylamino)-1,1a,2,7b-tetrahydrocyclopropa[c]chromene-4-carboxylate (Intermediate 131, 0.076 g) and lithium hydroxide monohydrate (0.168 g) in dioxane (3 mL) and water (1 mL) was irradiated in the microwave at 130° C. for 40 minutes. After cooling the mixture was diluted with methanol, acidified with formic acid and evaporated in vacuo. The residue was triturated with 10% methanol in DCM, filtered and the filtrate was evaporated in vacuo. The residue was purified by chromatography on silica, eluting with a mixture of methanol and DCM with a gradient of 0-40%. The resultant solid was triturated with ethyl acetate and filtered off to give (1 aRS,7bSR)-5-(2-{[N—((R)-1-ethylpyrrolidin-3-yl)-N-methylcarbamoyl]-methyl}-4-fluoro-benzenesulfonylamino)-1,1a,2,7b-tetrahydrocyclopropa[c]chromene-4-carboxylic acid (0.028 g) as a white solid.

$^1$H NMR (DMSO-d$_6$ at 80° C.) δ: 7.83 (1H, t), 7.12 (1H, dt), 7.08 (1H, d), 7.01 (1H, d), 6.84 (1H, m), 4.61 (1H, br, s), 4.19 (1H, d), 4.12 (2H, s), 3.73 (1H, d), 2.71-3.18 (7H, br, m), 2.94 (3H, s), 1.85-2.15 (3H, m), 1.72 (1H, m), 1.17 (3H, t), 0.95 (1H, m), 0.78 (1H, m).

LCMS (Method C) r/t 3.08 (M+H) 532.

Example 58

(1aRS,7bSR)-5-{2-[2-((S)-1-Ethylpyrrolidin-2-yl)ethylamino]benzenesulfonyl-amino}-1,1a,2,7b-tetrahydrocyclopropa[c]chromene-4-carboxylic acid

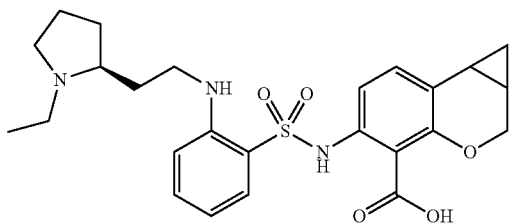 [SMILES: CCN1CCC[C@H]1CCNc1ccccc1S(=O)(=O)Nc1ccc2c(c1C(=O)O)OCC1CC21]

A mixture of (1aRS,7bSR)-5-(2-fluorobenzenesulfonylamino)-1,1a,2,7b-tetrahydrocyclopropa-[c]chromene-4-carboxylic acid (Intermediate 67, 0.1 g), 2-((S)-1-ethylpyrrolidin-2-yl)ethylamine (Intermediate 136, 0.5 g) and triethylamine (0.5 mL) was stirred and heated in a sealed tube at 140° C. overnight. After cooling, the mixture was concentrated under vacuum and the residue was purified by chromatography on silica, eluting with a mixture of methanol and DCM (10%). The product was repurified by HPLC (C18) to give (1aRS,7bSR)-5-{2-[2-((S)-1-ethylpyrrolidin-2-yl)ethylamino]benzenesulfonylamino}-1,1a,2,7b-tetrahydrocyclopropa[c]chromene-4-carboxylic acid (0.022 g) as a white solid.

NMR (DMSO-d$_6$) δ: 7.47 (1H, m), 7.25 (1H, t), 6.92 (1H, d), 6.89 (1H, m), 6.72 (1H, d), 6.53 (1H, dt),6.0-5.3 (1H, br s), 4.11 (1H, dd), 3.53 (1H, t), 3.33-2.80 (7H, m), 2.19 (2H, m), 1.92 (2H, m), 1.82 (2H, m), 1.64 (2H, m), 1.17 (3H, t), 0.84 (1H, m), 0.67 (1H, m).

LCMS (Method C) r/t 3.34 (M+H) 486.

Example 59

(1aRS,7bSR)-5-{2-[2-((R)-1-Ethylpyrrolidin-2-yl)ethylamino]benzenesulfonyl-amino}-1,1a,2,7b-tetrahydrocyclopropa[c]chromene-4-carboxylic acid

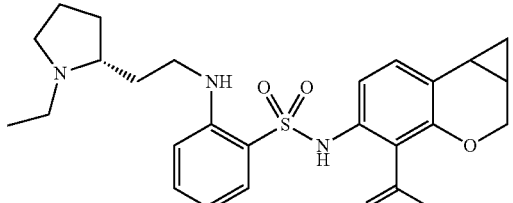

Prepared by proceeding in a similar manner to Example 58, starting from (1aRS,7bSR)-5-(2-fluorobenzenesulfonylamino)-1,1a,2,7b-tetrahydrocyclopropa-[c]chromene-4-carboxylic acid (Intermediate 67) and 2-((R)-1-ethylpyrrolidin-2-yl)ethylamine (Intermediate 141).

$^1$H NMR (DMSO-d$_6$) δ: 7.47 (1H, m), 7.25 (1H, t), 6.97 (1H, d), 6.90 (1H, m), 6.72 (1H, d), 6.53 (1H, dt), 6.0-5.4 (1H, br s), 4.12 (1H, dd), 3.53 (1H, t), 3.35-2.85 (7H, m), 2.20 (2H, m), 1.93 (2H, m), 1.81 (2H, m), 1.65 (2H, m), 1.18 (3H, t), 0.84 (1H, m), 0.67 (1H, m).
LCMS (Method C) r/t 3.32 (M+H) 486.

Example 60

(1aRS,7bSR)-5-[2-(3-N,N,-Diethylaminopropylamino)benzenesulfonylamino]-1,1a,2,7b-tetrahydrocyclopropa[c]chromene-4-carboxylic acid

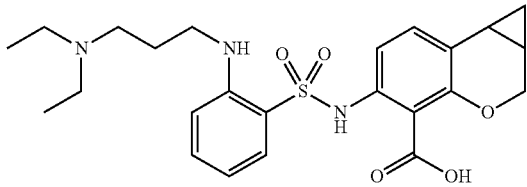 [SMILES: CCN(CC)CCCNc1ccccc1S(=O)(=O)Nc1ccc2c(c1C(=O)O)OCC1CC21]

3-Diethylaminopropyl amine (0.975 g) was added to a solution of (1aRS,7bSR)-5-(2-fluorobenzenesulfonylamino)-1,1a,2,7b-tetrahydrocyclopropa[c]chromene-4-carboxylic acid (Intermediate 67, 0.091 g) in NMP (3 mL) and the mixture was heated at 140° C. in a sealed tube for 36 hours. After cooling, the mixture was diluted with water (2 mL) and the solution was purified by preparative HPLC (C18) eluting with a mixture of methanol and water, containing 0.1% formic acid, with a gradient of 10-98% to give (1aRS,7bSR)-5-[2-(3-diethylaminopropylamino)benzenesulfonylamino]-1,1a,2,7b-tetrahydrocyclopropa[c]chromene-4-carboxylic acid (0.039 g) as a white solid.

$^1$H NMR (DMSO-d$_6$) δ: 7.45 (1H, dd), 7.28 (1H, dt), 7.04 (2H, m), 6.74 (1H, d), 6.51 (1H, t), 6.17 (1H, br s), 4.16 (1H, d), 3.57 (1H, d), 3.54-2.97 (8H, br m), 1.87 (1H, dt), 1.81-1.63 (3H, m), 1.15 (6H, t), 0.89 (1H, m), 0.72 (1H, m).
LCMS (Method C) r/t 3.31 (M+H) 474.

Example 61

(1aRS,7bSR)-5-(2-{[((R)-1-Ethylpyrrolidine-2-yl)carbonylamino]methyl}-4-fluorobenzenesulfonylamino)-1,1a,2,7b-tetrahydrocyclopropa[c]chromene-4-carboxylic acid

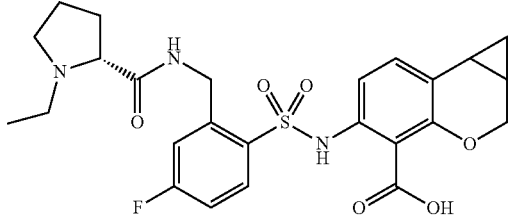 [SMILES: CCN1CCC[C@@H]1C(=O)NCc1cc(F)ccc1S(=O)(=O)Nc1ccc2c(c1C(=O)O)OCC1CC21]

A mixture of methyl (1aRS,7bSR)-5-(2-{[((R)-1-ethylpyrrolidine-2-yl)carbonylamino]methyl}-4-fluorobenzenesulfonylamino)-1,1a,2,7b-tetrahydrocyclopropa[c]chromene-4-carboxylate (Intermediate 146, 0.120 g) and lithium hydroxide monohydrate (0.095 g) was suspended in dioxane (5 mL) and water (1 mL) and the mixture was stirred and heated at 110° C. for 22.5 hours. After cooling, the volatiles were removed in vacuo and the residue was acidified by addition of aqueous citric acid solution (10%) and extracted with DCM. The organic layer was dried (Na$_2$SO$_4$) and filtered and the filtrate was evaporated to dryness. The residue was purified by preparative HPLC (C18) eluting with a mixture of methanol and water, containing 0.1% formic acid, with a gradient of 10-98% to give (1aRS,7bSR)-5-(2-{[((R)-1-ethylpyrrolidine-2-yl)carbonylamino]methyl}-4-fluorobenzenesulfonylamino)-1,1a,2,7b-tetrahydrocyclopropa-[c]chromene-4-carboxylic acid (0.043 g) as a white solid.

$^1$H NMR (DMSO-d$_6$) δ: 8.77 (1H, d), 7.83 (1H, dd), 7.22 (1H, td), 7.12 (1H, dd), 7.08 (1H, d), 6.16 (1H, dd), 4.73 (2H, d), 4.24 (1H, d), 3.67 (1H, d), 3.54 (1H, br s), 3.37-3.28 (1H, m), 2.93-2.80 (1H, m), 2.80-2.61 (2H, m), 2.30-2.20 (1H, m), 1.95-1.70 (5H, m), 1.08 (3H, t), 0.95 (1H, dt), 0.76 (1H, q).
LCMS (Method C) r/t 3.09 (M+H) 518.

Example 62

(1aRS,7bSR)-5-{2-[(1-Ethylazetidin-3-ylmethyl)amino]benzene-sulfonylamino}-1,1a,2,7b-tetrahydrocyclopropa[c]chromene-4-carboxylic acid

A mixture of (1aRS,7bSR)-5-(2-fluorobenzenesulfonylamino)-1,1a,2,7b-tetrahydrocyclopropa-[c]chromene-4-carboxylic (Intermediate 67, 0.07 g) and (1-ethylazetidin-3-yl)methylamine (Intermediate 149, 0.7 g) in DMSO (1.4 mL) was divided evenly between 7 microwave vials and each was irradiated in the microwave at 130° C. for 4 hours. After cooling, the combined mixture was concentrated under vacuum and the residue was purified by chromatography on silica, eluting with a mixture of methanol and DCM (10%). The product was repurified by HPLC (C18) to give (1aRS,7bSR)-5-{2-[(1-ethylazetidin-3-ylmethyl)amino]benzenesulfonylamino}-1,1a,2,7b-tetrahydrocyclopropa[c]chromene-4-carboxylic acid (0.012 g) as an off-white solid.

$^1$H NMR (DMSO-d$_6$) δ: 7.34 (1H, d), 7.22 (1H, t), 7.04 (1H, d), 6.97 (1H, d), 6.74 (1H, d), 6.49 (1H, t), 6.34 (1H, br s), 4.10 (1H, d), 3.75-3.55 (4H, m), 3.18 (1H, br m), 3.03 (1H, br m), 2.88 (2H, m), 2.32 (1H, m), 1.85 (1H, m), 1.67 (1H, m), 1.19 (1H, m), 0.98 (3H, t), 0.86 (1H, m), 0.69 (1H, m)
LCMS (Method C) r/t 3.21 (M+H) 457.

Examples 63 and 64

(1aR,7bS)-5-[2-((Z)-3-Diethylaminoprop-1-enyl)benzenesulfonyl-amino]-1,1a,2,7b-tetrahydrocyclopropa[c]chromene-4-carboxylic acid and (1aS,7bR)-5-[2-((Z)-3-diethylaminoprop-1-enyl)benzenesulfonylamino]-1,1a,2,7b-tetrahydrocyclopropa-[c]chromene-4-carboxylic acid

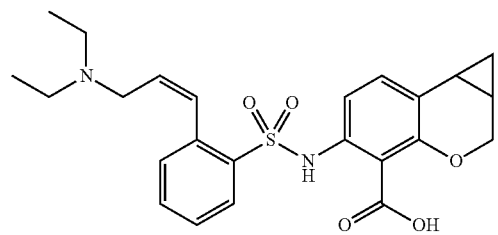 [SMILES: CCN(CC)C/C=C\c1ccccc1S(=O)(=O)Nc1ccc2c(c1C(=O)O)OCC1CC21]

A mixture of methyl (1aRS,7bSR)-5-[2-((Z)-3-diethylaminoprop-1-enyl)benzenesulfonylamino]-1,1a,2,7b-tetrahydrocyclopropa[c]chromene-4-carboxylate (Intermediate 153, 0.495 g) and lithium hydroxide monohydrate (0.442 g) was suspended in dioxane (20 mL) and water (5 mL) and the mixture was stirred and heated at 80° C. for 12.5 hours. After cooling, the volatiles were removed in vacuo and the residue was acidified by addition of aqueous citric acid solution (10%) and extracted with DCM. The organic layer was dried ($Na_2SO_4$) and filtered. The filtrate was evaporated to dryness and the residue was purified by preparative HPLC (C18) eluting with a mixture of acetonitrile and water, containing 0.1% formic acid, with a gradient of 35-70% to give (1aRS,7bSR)-5-[2-((Z)-3-diethylaminoprop-1-enyl)benzenesulfonylamino]-1,1a,2,7b-tetrahydrocyclopropa[c]chromene-4-carboxylic acid (0.147 g) as a white solid.

This material was subjected to chiral separation using a ChiralPak IC column, 4.6 mm×250 mm, particle size 5 micron. Eluting solvent absolute ethanol,

Example 63

First eluting enantiomer: retention time on above column: 25.71 minutes, >99% ee.

$^1$H NMR (DMSO-$d_6$) δ: 7.65 (1H, dd), 7.60 (1H, td), 7.44-7.37 (2H, m), 7.28 (1H, d), 7.08 (1H, d), 6.95 (1H, d), 6.15-6.05 (1H, m), 4.16 (1H, d), 3.77-3.67 (2H, m), 3.56 (1H, d), 3.13-3.03 (4H, m), 1.90 (1H, dt), 1.71 (1H, q), 1.12 (6H, t), 0.92 (1H, dt), 0.72 (1H, q).

LCMS (Method C) r/t 3.20 (M+H) 457.

Example 64

Second eluting enantiomer: retention time on above column 35.51 minutes, >99% ee.

$^1$H NMR (DMSO-$d_6$) δ: 7.65 (1H, dd), 7.60 (1H, td), 7.43-7.38 (2H, m), 7.28 (1H, d), 7.08 (1H, d), 6.95 (1H, d), 6.16-6.07 (1H, m), 4.16 (1H, d), 3.77-3.67 (2H, m), 3.56 (1H, d), 3.09 (4H, q), 1.91 (1H, dt), 1.71 (1H, q), 1.12 (6H, t), 0.93 (1H, dt), 0.72 (1H, q).

LCMS (Method C) r/t 3.20 (M+H) 457.

Example 65

(1aRS,7bSR)-5-(2-{N—[((R)-1-Ethylpyrrolidine-2-yl)carbonyl]-N-methylamino-methyl}-4-fluorobenzenesulfonylamino)-1,1a,2,7b-tetrahydrocyclopropa[c]chromene-4-carboxylic acid

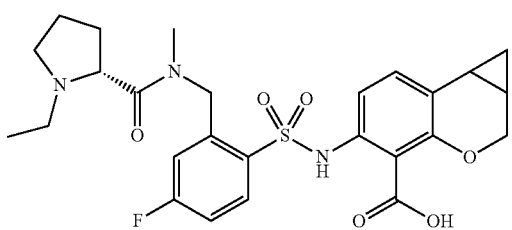 [SMILES: CCN1CCC[C@@H]1C(=O)N(C)Cc1cc(F)ccc1S(=O)(=O)Nc1ccc2c(c1C(=O)O)OCC1CC21]

A mixture of methyl (1aRS,7bSR)-5-(2-{N—[((R)-1-ethylpyrrolidine-2-yl)carbonyl]-N-methyl-aminomethyl}-4-fluorobenzenesulfonylamino)-1,1a,2,7b-tetrahydrocyclopropa[c]chromene-4-carboxylate (Intermediate 155, 0.177 g) and lithium hydroxide monohydrate (0.136 g) in dioxane (5 mL) and water (2 mL) was stirred and heated at 100° C. for 19.5 hours. After cooling, the mixture was evaporated to dryness and the residue was acidified by addition of aqueous citric acid solution (10%). The resultant solid was collected by filtration, washed with water and dried under vacuum at 40° C. The solid was purified by preparative HPLC (C18) eluting with a mixture of methanol and water, containing 0.1% formic acid, with a gradient of 10-98% to give (1aRS,7bSR)-5-(2-{N—[((R)-1-ethylpyrrolidine-2-yl)carbonyl]-N-methylaminomethyl}-4-fluoro-benzenesulfonylamino)-1,1a,2,7b-tetrahydrocyclopropa[c]chromene-4-carboxylic acid (0.053 g) as a white solid.

$^1$H NMR (DMSO-$d_6$) δ: 7.93-7.78 (1H, m), 7.17 (1H, m), 6.99 (0.5H, m), 6.95 (0.5H, d), 6.90-6.76 (1.5H, m), 6.69 (0.5H, dd), 5.02 (1.5H, m), 4.86 (0.5H, dd), 4.61-4.44 (1H, br s), 4.15 (1H, dd), 3.55 (3H, m), 3.11 (2H, m), 2.90 (3H, 2s), 2.06-1.54 (6H, m), 1.18-1.05 (4H, m), 0.84 (1H, m), 0.68 (1H, m).

LCMS (Method C) r/t 3.14 (M+H) 532.

Example 66

(1aRS,7bSR)-5-(2-{N—[((S)-1-Ethylpyrrolidine-2-yl)carbonyl]-N-methylamino-methyl}-4-fluorobenzenesulfonylamino)-1,1a,2,7b-tetrahydrocyclopropa[c]chromene-4-carboxylic acid

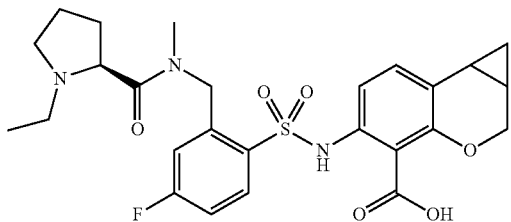 [SMILES: CCN1CCC[C@H]1C(=O)N(C)Cc1cc(F)ccc1S(=O)(=O)Nc1ccc2c(c1C(=O)O)OCC1CC21]

Prepared by proceeding in a similar manner to Example 65, starting from methyl (1aRS,7bSR)-5-(2-{N—[((S)-1-ethylpyrrolidine-2-yl)carbonyl]-N-methylaminomethyl}-4-fluorobenzene-sulfonylamino)-1,1a,2,7b-tetrahydrocyclopropa[c]chromene-4-carboxylate (Intermediate 160) as a white solid.

$^1$H NMR (DMSO-$d_6$) 7.94-7.76 (1H, m), 7.18 (1H, m), 7.02-6.92 (1H, m), 6.92-6.76 (1.5H, m), 6.68 (0.5H, m), 5.02 (1.5H, m), 4.86 (0.5H, dd), 4.65-4.49 (1H, br s), 4.15 (1H, dd), 3.55 (3H, m), 3.14 (2H, m), 2.91 (3H, 2s), 2.07-1.59 (6H, m), 1.13 (4H, m), 0.85 (1H, m), 0.68 (1H, m).

LCMS (Method C) r/t 3.15 (M+H) 532.

Example 67

(1aRS,7bSR)-5-[2-(4-Dimethylaminobutylamino)-4-fluorobenzenesulfonylamino]-1,1a,2,7b-tetrahydrocyclopropa[c]chromene-4-carboxylic acid

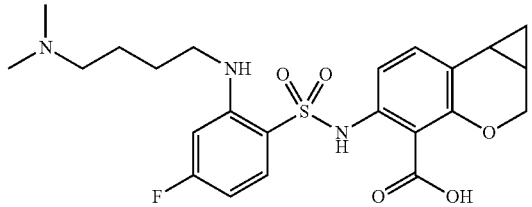 [SMILES: CN(C)CCCCNc1cc(F)ccc1S(=O)(=O)Nc1ccc2c(c1C(=O)O)OCC1CC21]

A mixture of methyl (1aRS,7bSR)-5-[2-(4-dimethylaminobutylamino)-4-fluorobenzene-sulfonylamino]-1,1a,2,7b-tetrahydrocyclopropa[c]chromene-4-carboxylate (Intermediate 161, 0.485 g) and lithium hydroxide monohydrate (0.505 g) in dioxane (9 mL) and water (3 mL) was irradiated in the microwave at 130° C. for 45 minutes. After cooling, the mixture was diluted with methanol, acidified with formic acid and evaporated in vacuo. The residue was triturated with 20% methanol in DCM, filtered and the filtrate was evaporated in vacuo. The residue was purified by chromatography on silica, eluting with a mixture of methanol and DCM with a gradient of 0-20%. The resultant solid was triturated with ethyl acetate and filtered off to give (1aRS,7bSR)-5-[2-(4-dimethylaminobutylamino)-4-fluorobenzenesulfonylamino]-1,1a,2,7b-tetrahydrocyclopropa-[c]chromene-4-carboxylic acid (0.215 g) as a white solid.

$^1$H NMR (DMSO-$d_6$) δ: 12.52 (2H, br, s), 7.65 (1H, dd), 7.08 (2H, q), 6.56 (1H, dd), 6.39 (1H, dt), 5.98 (1H, m), 4.20 (1H, d), 3.59 (1H, d), 3.22 (2H, q), 2.98 (2H, m), 2.75 (6H, s), 1.91 (1H, m), 1.81 (2H, m), 1.72 (1H, m), 1.58 (2H, m), 0.92 (1H, m), 0.76 (1H, m).

LCMS (Method C) r/t 3.43 (M+H) 478.

Example 68

(1aRS,7bSR)-5-{2-[((R)-1-Ethylpyrrolidin-3-ylmethyl)amino]benzene-sulfonylamino}-1,1a,2,7b-tetrahydrocyclopropa[c]chromene-4-carboxylic acid

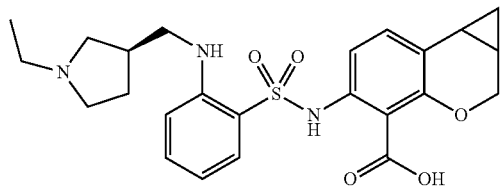 [SMILES: CCN1CC[C@H](CNc2ccccc2S(=O)(=O)Nc2ccc3c(c2C(=O)O)OCC2CC32)C1]

A solution of (1aRS,7bSR)-5-(2-fluorobenzenesulfonylamino)-1,1a,2,7b-tetrahydrocyclopropa-[c]chromene-4-carboxylic acid (Intermediate 67, 0.105 g), ((R)-1-ethylpyrrolidin-3-yl)methyl-amine (Intermediate 163, 0.5 g) and triethylamine (0.5 g) in DMSO (1 mL) was stirred and heated at 140° C. overnight. After cooling, the mixture was concentrated under vacuum and the residue was purified by chromatography on silica, eluting with a mixture of methanol and DCM (5%). The product was purified by HPLC (C18) to give (1aRS,7bSR)-5-{2-[((R)-1-ethylpyrrolidin-3-ylmethyl)amino]benzene-sulfonylamino}-1,1a,2,7b-tetrahydrocyclopropa[c]-chromene-4-carboxylic acid (0.03 g) as a white solid, $^1$H NMR (DMSO-$d_6$) δ: 7.38 (1H, dd), 7.24 (1H, t), 7.06 (2H, s), 6.81 (1H, d), 6.49 (1H, t), 6.14 (1H, br s), 4.13 (1H, dd), 3.54 (2H, m), 3.25 (2H, m) 3.07 (4H, m), 2.82 (1H, m), 2.63 (1H, m), 1.96 (1H, m), 1.86 (1H, m), 1.71-1.46 (2H, m), 1.19 (3H, m), 0.87 (1H, m), 0.70 (1H, m).

LCMS (Method C) r/t 3.31 (M+H) 472.

Example 69

(1aRS,7bSR)-5-{2-[((S)-1-Ethylpyrrolidin-3-ylmethyl)amino]benzene-sulfonylamino}-1,1a,2,7b-tetrahydrocyclopropa[c]chromene-4-carboxylic acid

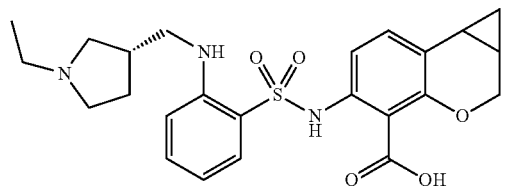 [SMILES: CCN1CC[C@@H](CNc2ccccc2S(=O)(=O)Nc2ccc3c(c2C(=O)O)OCC2CC32)C1]

A solution of (1aRS,7bSR)-5-(2-fluorobenzenesulfonylamino)-1,1a,2,7b-tetrahydrocyclopropa-[c]chromene-4-carboxylic (Intermediate 67, 0.08 g), and ((S)-1-ethylpyrrolidin-3-yl)methylamine (Intermediate 169, 0.8 g) in DMSO (0.2 mL) was stirred and heated at 120° C. for 24 hours. After cooling, the mixture was diluted with methanol and concentrated under vacuum. The residue was purified by HPLC (C18) to give (1aRS,7bSR)-5-{2-[((S)-1-ethylpyrrolidin-3-ylmethyl)amino]benzene-sulfonylamino}-1,1a,2,7b-tetrahydrocyclopropa[c]-chromene-4-carboxylic acid (0.03 g) as a white solid.

$^1$H NMR (DMSO-$d_6$) δ: 7.37 (1H, dd), 7.24 (1H, t), 7.05 (2H, s), 6.80 (1H, d), 6.48 (1H, t), 6.13 (1H, br s), 4.13 (1H, dd), 3.54 (2H, m), 3.24 (2H, m), 3.05 (4H, m), 2.82 (1H, m), 2.62 (1H, m), 1.95 (1H, m), 1.85 (1H, m), 1.71-1.46 (2H, m), 1.18 (3H, m), 0.86 (1H, m), 0.69 (1H, m).

LCMS (Method C) r/t 3.25 (M+H) 472.

Example 70

(1aRS,7bSR)-5-[2-(4-Ethyl-2-oxopiperazin-1-ylmethyl)-4-fluorobenzene-sulfonylamino]-1,1a,2,7b-tetrahydrocyclopropa[c]chromene-4-carboxylic acid

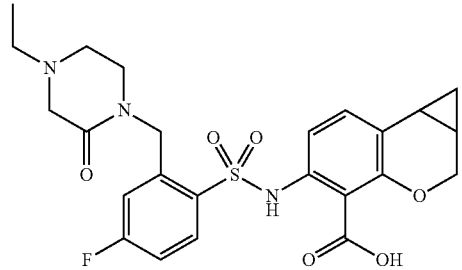 [SMILES: CCN1CCN(Cc2cc(F)ccc2S(=O)(=O)Nc2ccc3c(c2C(=O)O)OCC2CC32)C(=O)C1]

A mixture of methyl (1aRS,7bSR)-5-[2-(4-ethyl-2-oxopiperazin-1-ylmethyl)-4-fluorobenzenesulfonylamino]-1,1a,2,7b-tetrahydrocyclopropa[c]chromene-4-carboxylate (Intermediate 173, 0.28 g) and lithium hydroxide monohydrate (0.126 g) in dioxane (9 mL) and water (3 mL) was irradiated in the microwave at 130° C. for 30 minutes. After cooling, the mixture was diluted with methanol, acidified with formic acid and evaporated in vacuo. The residue was triturated with 20% methanol in DCM, filtered and the filtrate was evaporated in vacuo. The residue was purified by chromatography on silica, eluting with a mixture of methanol and DCM with a gradient of 0-20%. The resultant solid was triturated with ether and filtered to give (1aRS,7bSR)-5-[2-(4-ethyl-2-oxo-piperazin-1-ylmethyl)-4-fluorobenzenesulfonylamino]-1,1a,2,7b-tetrahydrocyclopropa-[c]chromene-4-carboxylic acid (0.176 g) as a white solid.

¹H NMR (CDCl₃) δ: 11.28 (1H, br, s), 8.02 (1H, dd), 7.31 (1H, d), 7.23 (1H, d), 6.98 (2H, m), 4.98 (2H, q), 4.57 (1H, d), 4.04 (1H, d), 3.36 (2H, t), 3.30 (2H, s), 2.72 (2H, t), 2.51 (2H, q), 1.96 (1H, m), 1.80 (1H, m), 1.11 (4H, m), 1.03 (1H, m).

LCMS (Method C) r/t 2.96 (M+H) 504.

Example 71

(1aRS,7bSR)-5-[2-(1-Ethylpiperidin-4-ylmethyl)-4-fluorobenzenesulfonylamino]-1,1a,2,7b-tetrahydrocyclopropa[c]chromene-4-carboxylic acid

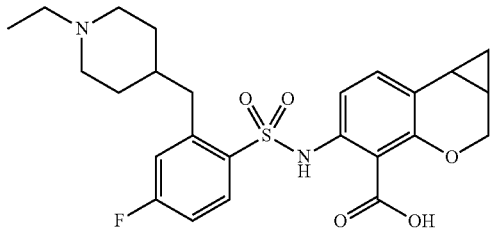 [SMILES: CCN1CCC(Cc2cc(F)ccc2S(=O)(=O)Nc2ccc3c(c2C(=O)O)OCC2CC32)CC1]

Methyl (1aRS,7bSR)-5-[2-(1-ethylpiperidin-4-ylmethyl)-4-fluorobenzenesulfonylamino]-1,1a,2,7b-tetrahydrocyclopropa[c]chromene-4-carboxylate (Intermediate 177, 0.279 g) and lithium hydroxide monohydrate (0.233 g) were suspended in dioxane (7 mL) and water (3 mL) and the mixture was stirred and heated at 80° C. for 25 hours. Further lithium hydroxide monohydrate (0.116 g) was added and the mixture heating was continued for 18 hours. After cooling, the volatiles were removed in vacuo, the residue was acidified by addition of aqueous citric acid solution (10%) and saturated with sodium chloride. The mixture was extracted with DCM and the organic layer was dried (Na₂SO₄) and filtered. The filtrate was evaporated to dryness and the residue was purified by preparative HPLC (C18), eluting with a mixture of methanol and water, containing 0.1% formic acid, with a gradient of 10-98% to give (1aRS,7bSR)-5-[2-(1-ethylpiperidin-4-ylmethyl)-4-fluorobenzenesulfonylamino]-1,1a,2,7b-tetrahydrocyclopropa[c]chromene-4-carboxylic acid (0.117 g) as a white solid.

¹H NMR (DMSO-d₆) δ: 7.99 (1H, dd), 7.22-7.14 (2H, m), 6.99 (1H, d), 6.76 (1H, d), 4.20 (1H, d), 3.60 (1H, d), 3.34 (2H, d), 3.02-2.88 (4H, m), 2.71 (2H, br s), 1.99 (1H, br s), 1.84 (1H, dt), 1.74-1.62 (3H, m), 1.56-1.40 (2H, m), 1.18 (3H, t), 0.89 (1H, dt), 0.73 (1H, q).

LCMS (Method C) r/t 3.22 (M+H) 489.

Example 72

(1aRS,7bSR)-5-{2-[2-(1-Ethylazetidin-3-yl)ethyl]-4-fluorobenzene-sulfonylamino}-1,1a,2,7b-tetrahydrocyclopropa[c]chromene-4-carboxylic acid

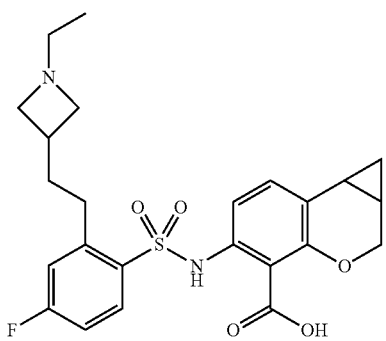 [SMILES: CCN1CC(CCc2cc(F)ccc2S(=O)(=O)Nc2ccc3c(c2C(=O)O)OCC2CC32)C1]

A mixture of methyl (1aRS,7bSR)-5-{2-[2-(1-ethylazetidin-3-yl)ethyl]-4-fluorobenzene-sulfonylamino}-1,1a,2,7b-tetrahydrocyclopropa[c]chromene-4-carboxylate (intermediate 183, 0.306 g) and lithium hydroxide monohydrate (0.421 g) in dioxane (7.5 mL) and water (2.5 mL) was irradiated in the microwave at 130° C. for 45 minutes. After cooling, the mixture was diluted with methanol, acidified with formic acid and evaporated in vacuo. The residue was triturated with 20% methanol in DCM, filtered and the filtrate was evaporated in vacuo. The residue was purified by chromatography on silica, eluting with a mixture of methanol and DCM with a gradient of 0-30%. The resultant solid was triturated with ether and filtered to give (1aRS,7bSR)-5-{2-[2-(1-ethyl-azetidin-3-yl)ethyl]-4-fluorbenzenesulfonylamino}1,1a,2,7b-tetrahydrocyclopropa[c]chromene-4-carboxylic acid (0.241 g) as a white solid.

¹H NMR (DMSO-d₆) δ: 7.92 (1H, br, s), 7.35 (1H, dd), 7.22 (1H, dt), 7.17 (1H, d), 6.78 (1H, br, s), 4.27 (1H, d), 4.05 (2H, m), 3.78 (2H, br, s), 3.70 (1H, d), 3.17 (2H, q), 2.86 (2H, br, s), 2.70 (1H, br, s), 1.95 (1H, m), 1.84 (2H, m), 1.75 (1H, m), 1.11 (3H, t), 0.98 (1H, m), 0.76 (1H, m).

LCMS (Method C) r/t 3.36 (M+H) 475.

Example 73

(1aRS,7bSR)-5-{2-[((S)-1-Azabicyclo[2.2.2]oct-3-yl)amino]benzenesulfonyl-amino}-1,1a,2,7b-tetrahydrocyclopropa[c]chromene-4-carboxylic acid

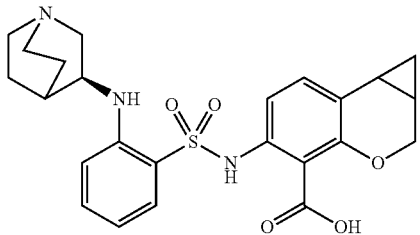 [SMILES: O=C(O)c1c(NS(=O)(=O)c2ccccc2N[C@@H]2CN3CCC2CC3)ccc2c1OCC1CC21]

A solution of (1aRS,7bSR)-5-(2-fluorobenzenesulfonylamino)-1,1a,2,7b-tetrahydrocyclopropa-[c]chromene-4-carboxylic acid (Intermediate 67, 0.6 g) and (S)-1-azabicyclo[2.2.2]oct-3-ylamine (6.0 g) in DMSO (6 mL) was stirred and heated in a sealed vessel at 140° C. for 22 hours. After cooling, the mixture was diluted with methanol and concentrated under vacuum. The residue was purified by HPLC (C18) to give (1aRS,7bSR)-5-{2-[((S)-1-azabicyclo[2.2.2]oct-3-yl)amino]benzenesulfonylamino}-1,1a,2,7b-tetrahydrocyclopropa[c]chromene-4-carboxylic acid (0.107 g) as a white solid.

¹H NMR (DMSO-d₆) δ: 7.58 (1H, ddd), 7.25 (1H, t), 6.94 (1H, dd), 6.76 (2H, t), 6.62 (2H, m), 6.06 (1H, d), 4.14 (1H, t), 3.86 (1H, br s), 3.57 (3H, m), 3.16-2.87 (4H, m), 2.12 (1H, m), 2.01 (1H, m), 1.82 (3H, m), 1.65 (2H, m), 0.83 (1H, m), 0.67 (1H, m).

LCMS (Method C) r/t 3.16 (M+H) 470).

Example 74

(1aRS,7bSR)-5-{2-[((R)-1-Azibicyclo[2.2.2]oct-3-yl)amino]benzenesulfonyl-amino}-1,1a,2,7b-tetrahydrocyclopropa[c]chromene-4-carboxylic acid

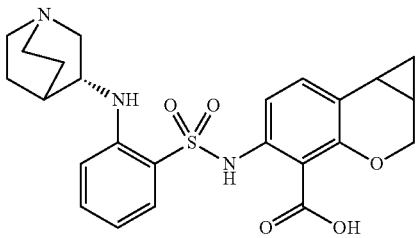 [SMILES: O=C(O)c1c(NS(=O)(=O)c2ccccc2N[C@H]2CN3CCC2CC3)ccc2c1OCC1CC21]

Prepared by proceeding in a similar manner to Example 73, starting from (1aRS,7bSR)-5-(2-fluorobenzenesulfonylamino)-1,1a,2,7b-tetrahydrocyclopropa-[c]chromene-4-carboxylic acid (Intermediate 67) and (R)-1-azabicyclo[2.2.2]oct-3-ylamine.

$^1$H NMR (DMSO-d$_6$) δ: 7.58 (1H, ddd), 7.25 (1H, t), 6.94 (1H, dd), 6.76 (2H, t), 6.62 (2H, m), 6.07 (1H, d), 4.13 (1H, t), 3.86 (1H, br s), 3.57 (3H, m), 3.16-2.87 (4H, m), 2.12 (1H, m), 2.01 (1H, m), 1.83 (3H, m), 1.64 (2H, m), 0.83 (1H, m), 0.67 (1H, m).

LCMS (Method C) r/t 3.15 (M+H) 470

Example 75

(1aRS,7bSR)-5-(2-{[((S)-1-ethylpyrrolidine-3-carbonyl)amino]methyl}-4-fluoro-benzenesulfonylamino)-1,1a,2,7b-tetrahydrocyclopropa[c]chromene-4-carboxylic acid

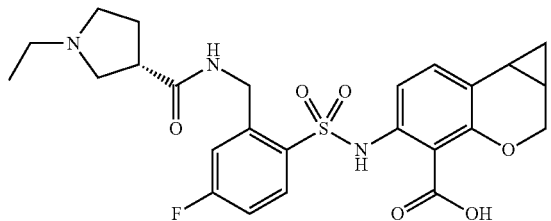 [SMILES: CCN1CC[C@H](C(=O)NCc2cc(F)ccc2S(=O)(=O)Nc2ccc3c(c2C(=O)O)OCC2CC32)C1]

Methyl (1aRS,7bSR)-5-(2-{[((S)-1-ethylpyrrolidine-3-carbonyl)amino]methyl}-4-fluoro-benzenesulfonylamino)-1,1a,2,7b-tetrahydrocyclopropa[c]chromene-4-carboxylate (Intermediate 188, 0.190 g) and lithium hydroxide monohydrate (0.150 g) were suspended in dioxane (5 mL) and water (5 mL) and the mixture was stirred and heated at 100° C. for 18.5 hours. After cooling, the volatiles were removed in vacuo and the residue was acidified by addition of aqueous citric acid solution (10%) and extracted with DCM. The organic layer was dried (Na$_2$SO$_4$) and filtered. The filtrate was evaporated to dryness and the residue was purified by preparative HPLC (C18) eluting with a mixture of acetonitrile and water, containing 0.1% formic acid, with a gradient of 25-60% to give (1aRS,7bSR)-5-(2-{[((S)-1-ethylpyrrolidine-3-carbonyl)amino]methyl}-4-fluorobenzenesulfonylamino)-1,1a,2,7b-tetrahydrocyclopropa[c]chromene-4-carboxylic acid (0.092 g) as a white solid.

$^1$H NMR (DMSO-d$_6$) δ: 8.78 (1H, q), 7.89-7.82 (1H, m), 7.19 (1H, td), 7.12 (1H, dt), 7.02 (1H, dd), 6.75 (1H, dd), 4.74 (2H, d), 4.19 (1H, d), 3.62 (1H, dt), 3.50-3.15 (5H, m), 3.10 (2H, q), 2.35-2.23 (1H, m), 2.10-1.99 (1H, m), 1.86 (1H, dt), 1.75-1.67 (1H, m), 1.20 (3H, t), 0.90 (1H, dt), 0.73 (1H, q)

LCMS (Method C) r/t 3.01 (M+H) 518

Example 76

(1aRS,7bSR)-5-{2-[2-((R)-1-Ethylpyrrolidin-3-ylamino)ethyl]-4-fluoro-benzenesulfonylamino}-1,1a,2,7b-tetrahydrocyclopropa[c]chromene-4-carboxylic acid

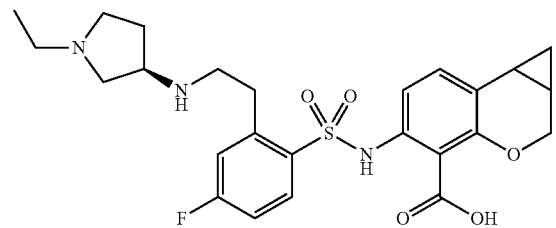 [SMILES: CCN1CC[C@@H](NCCc2cc(F)ccc2S(=O)(=O)Nc2ccc3c(c2C(=O)O)OCC2CC32)C1]

A solution of (1aRS,7bSR)-5-(4-fluoro-2-vinylbenzenesulfonylamino)-1,1a,2,7b-tetrahydro-cyclopropa[c]chromene-4-carboxylic acid (Intermediate 74, 0.150 g) and (R)-1-ethylpyrrolidin-3-ylamine (Intermediate 193, 0.25 g) in ethylene glycol (1 ml) was irradiated in the microwave at 200° C. for 30 minutes. After cooling, the mixture was diluted with water and loaded onto a SCX-2 SPE cartridge then washed with water, methanol and 2M ammonia in methanol. The basic fractions were combined and evaporated to dryness. The residue was purified by preparative HPLC (C18) eluting with a mixture of methanol and water, containing 0.1% ammonia, with a gradient of 10-98%. Then further purified by preparative HPLC (C18) eluting with a mixture of acetonitrile and water, containing 0.1% formic acid, with a gradient of 10-60% to give (1aRS,7bSR)-5-{2-[2-((R)-1-ethylpyrrolidin-3-ylamino)ethyl]-4-fluorobenzenesulfonylamino}-1,1a,2,7b-tetrahydro-cyclopropa[c]chromene-4-carboxylic acid (0.005 g) as a white solid.

$^1$H NMR (CDCl$_3$) δ: 7.86 (1H, dd), 7.43 (1H, dd), 7.31 (1H, dt), 7.27 (1H, d), 6.59 (1H, d), 4.31 (1H, d), 4.18-3.97 (1.5H, br), 3.82-3.64 (1.5H, br), 3.79 (1H, d), 3.33-3.20 (8H, br), 2.31 (1H, br s), 2.04 (1H, m), 1.84 (1H, q), 1.26 (4H, t), 1.07 (1H, m), 0.86 (1H, q).

LCMS (Method C) r/t 2.60 (M+H) 503.9

Example 77

(1aRS,7bSR)-5-{2-[((R)-1-Ethylpyrrolidin-3-yl)amino]benzenesulfonylamino}-1,1a,2,7b-tetrahydro-cyclopropa[c]chromene-4-carboxylic acid

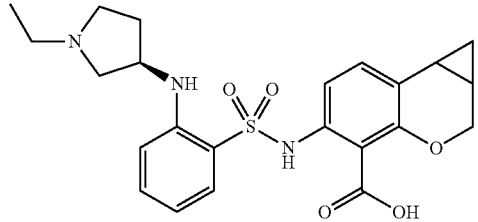 [SMILES: CCN1CC[C@@H](Nc2ccccc2S(=O)(=O)Nc2ccc3c(c2C(=O)O)OCC2CC32)C1]

A solution of (1aRS,7bSR)-5-(2-fluorobenzenesulfonylamino)-1,1a,2,7b-tetrahydrocyclopropa-[c]chromene-4-carboxylic acid (Intermediate 67, 0.13 g) and (R)-1-ethylpyrrolidin-3-ylamine (Intermediate 193, 1.22 g) in DMSO (0.7 mL) was stirred and heated in a sealed vessel at 120° C. for 22 hours. After cooling, the mixture was diluted with methanol and concentrated under vacuum. The residue was purified by HPLC (C18) to give (1aRS,7bSR)-5-{2-[((S)-1-ethylpyrrolidin-3-yl)amino]benzenesulfonylamino}-1,1a,2,7b-tetrahydrocyclopropa[c]chromene-4-carboxylic acid (0.107 g) as a white solid.

$^1$H NMR (DMSO-$d_6$) δ: 7.32 (2H, m), 7.04 (1H, d), 6.98 (1H, m), 6.72 (1H, d), 6.60 (1H, t), 5.55 (1H, br s), 4.18 (1H, br s), 4.11 (1H, t), 3.78 (1H, br s), 3.66-3.48 (2H, m), 3.18-2.94 (4H, m), 2.54 (1H, m), 1.86 (2H, m), 1.66 (1H, m), 1.22 (3H, t), 0.86 (1H, m), 0.68 (1H, m).

LCMS (Method C) r/t 3.40 (M+H) 458.

Example 78

(1aRS,7bSR)-5-{2-[((S)-1-Ethylpyrrolidin-3-yl)amino]benzenesulfonylamino}-1,1a,2,7b-tetrahydrocyclopropa[c]chromene-4-carboxylic acid

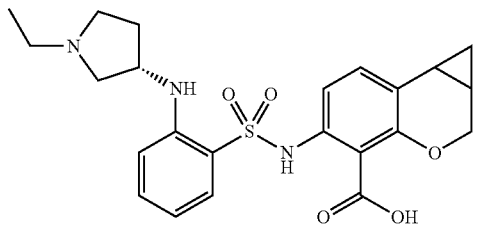 [SMILES: CCN1CC[C@H](Nc2ccccc2S(=O)(=O)Nc2ccc3c(c2C(=O)O)OCC2CC32)C1]

Prepared by proceeding in a similar manner to Example 77, starting from (1aRS,7bSR)-5-(2-fluorobenzenesulfonylamino)-1,1a,2,7b-tetrahydrocyclopropa-[c]chromene-4-carboxylic acid (Intermediate 67) and (S)-1-ethylpyrrolidin-3-ylamine (Intermediate 194).

$^1$H NMR (DMSO-$d_6$) δ: 7.32 (2H, m), 7.05 (1H, d), 6.98 (1H, m), 6.72 (1H, d), 6.60 (1H, t), 5.54 (1H, br s), 4.20 (1H, br s), 4.11 (1H, t), 3.80 (1H, br s), 3.69-3.48 (2H, m), 3.19-2.96 (4H, m), 2.56 (1H, m), 1.86 (2H, m), 1.66 (1H, m), 1.22 (3H, t), 0.87 (1H, m), 0.68 (1H, m).

LCMS (Method C) r/t 3.40 (M+H) 458.

Example 79

(1aRS,7bSR)-5-(2-{[((R)-1-Ethylpyrrolidine-3-ylcarbonyl)amino]methyl}-4-fluoro-benzenesulfonylamino)-1,1a,2,7b-tetrahydrocyclopropa[c]chromene-4-carboxylic acid

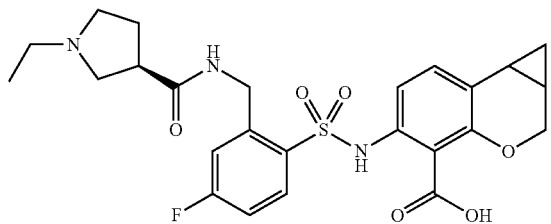 [SMILES: CCN1CC[C@@H](C(=O)NCc2cc(F)ccc2S(=O)(=O)Nc2ccc3c(c2C(=O)O)OCC2CC32)C1]

A mixture of methyl (1aRS,7bSR)-5-(2-{[((R)-1-ethylpyrrolidine-3-ylcarbonyl)amino]methyl}-4-fluoro-benzenesulfonylamino)-1,1a,2,7b-tetrahydrocyclopropa[c]chromene-4-carboxylate (Intermediate 195, 0.215 g) and lithium hydroxide monohydrate (0.170 g) was suspended in dioxane (5 mL) and water (5 mL) and the mixture was stirred and heated at 80° C. for 21 hours. The temperature was raised to 100° C. and the mixture was stirred and heated at that temperature for 2.5 hours. Further lithium hydroxide monohydrate (0.05 g) was added and the mixture was stirred and heated at 100° C. for 2 hours. After cooling, the volatiles were removed in vacuo and the residue was acidified by addition of aqueous citric acid solution (10%) and extracted with DCM. The organic layer was dried (Na$_2$SO$_4$) and filtered. The filtrate was evaporated to dryness and the residue was purified by preparative HPLC (C18) eluting with a mixture of acetonitrile and water, containing 0.1% formic acid, with a gradient of 25-60% to give (1aRS,7bSR)-5-(2-{[((R)-1-ethylpyrrolidine-3-ylcarbonyl)-amino]methyl}-4-fluorobenzenesulfonylamino)-1,1a,2,7b-tetrahydrocyclopropa[c]chromene-4-carboxylic acid (0.103 g) as a white solid.

$^1$H NMR (DMSO-$d_6$) δ: 8.78 (1H, q), 7.89-7.83 (1H, m), 7.18 (1H, td), 7.11 (1H, dt), 7.01 (1H, dd), 6.76 (1H, dd), 4.74 (2H, d), 4.19 (1H, d), 3.61 (1H, dt), 3.46-3.12 (5H, m), 3.07 (2H, q), 2.34-2.22 (1H, m), 2.10-1.98 (1H, m), 1.86 (1H, dt), 1.70 (1H, q), 1.19 (3H, t), 0.90 (1H, dt), 0.73 (1H, q).

LCMS (Method C) r/t 3.04 (M+H) 518.

Example 80

(1aRS,7bSR)5-[2-((Z)-3-Diethylamino-2-methylprop-1-enyl)-4-fluoro-benzenesulfonylamino]-1,1a,2,7b-tetrahydrocyclopropa[c]chromene-4-carboxylic acid

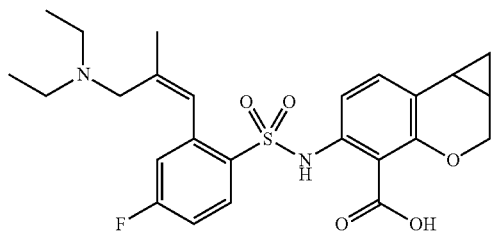 [SMILES: CCN(CC)C/C(C)=C\c1cc(F)ccc1S(=O)(=O)Nc1ccc2c(c1C(=O)O)OCC1CC21]

A mixture of methyl (1aRS,7bSR)-5-{N-[2-((Z)-3-diethylamino-2-methylprop-1-enyl)-4-fluorobenzenesulfonyl]-N-methoxycarbonylamino]-1,1a,2,7b-tetrahydrocyclopropa-[c]chromene-4-carboxylate (Intermediate 200, 0.264 g) and lithium hydroxide monohydrate (0.505 g) in dioxane (9 mL) and water (3 mL) was irradiated in the microwave at 130° C. for 40 minutes. After cooling, the mixture was diluted with methanol, acidified with formic acid and evaporated in vacuo then azeotroped with a mixture of ethanol and toluene. The residue was triturated with 15% methanol in DCM, filtered and the filtrate was evaporated in vacuo. The residue was purified by chromatography on silica, eluting with a mixture of methanol and DCM with a gradient of 0-40%. The resultant solid was triturated with ether and filtered to give (1aRS,7bSR)-5-[2-((Z)-3-diethylamino-2-methylprop-1-enyl)-4-fluorobenzene-sulfonylamino]-1,1a,2,7b-tetrahydrocyclopropa[c]chromene-4-carboxylic acid (0.202 g) as a white solid.

$^1$H NMR (DMSO-d$_6$) δ: 7.95 (1H, dd), 7.28 (1H, dt), 7.14 (1H, dd), 7.06 (1H, d), 6.92 (1H, s), 6.64 (1H, d), 4.25 (1H, d), 3.64 (1H, d), 3.36 (2H, br, s), 2.63 (4H, q), 1.96 (3H, s), 1.90 (1H, m), 1.74 (1H, m), 0.93 (1H, m), 0.86 (6H, t), 0.75 (1H, m).

LCMS (Method C) r/t 3.27 (M+H) 489

Example 81

(1aRS,7bSR)-5-{2-[2-((R)-1-Ethylpyrrolidin-3-yl)ethylamino]benzene-sulfonylamino}-1,1a,2,7b-tetrahydrocyclopropa[c]chromene-4-carboxylic acid

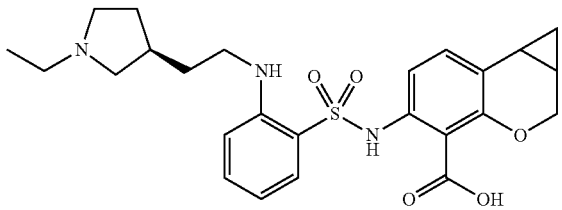 [SMILES: CCN1CC[C@@H](CCNc2ccccc2S(=O)(=O)Nc2ccc3c(c2C(=O)O)OCC2CC32)C1]

A mixture of (1aRS,7bSR)-5-(2-fluorobenzenesulfonylamino)-1,1a,2,7b-tetrahydrocyclopropa-[c]chromene-4-carboxylic acid (Intermediate 67, 0.2 g) and 2-((R)-1-ethylpyrrolidin-3-yl)ethylamine (Intermediate 203, 2.0 g) in DMSO (2 mL) was divided between two sealed vials and each was stirred and heated at 130° C. for 24 hours. After cooling, the combined mixture was diluted with methanol and then concentrated under vacuum. The residue was purified by HPLC (C18) to give (1aRS,7bSR)-5-{2-[2-((R)-1-ethylpyrrolidin-3-yl)ethylamino]-benzenesulfonylamino}-1,1a,2,7b-tetrahydrocyclopropa[c]chromene-4-carboxylic acid (0.125 g) as a white solid.

$^1$H NMR (DMSO-d$_6$) δ: 7.62 (1H, dt), 7.29 (1H, dt), 7.02 (2H, 2s), 6.70 (1H, d), 6.58 (1H, t), 5.84 (1H, br m), 4.14 (1H, d), 3.54 (1H, d), 3.36 (1H, m), 3.18 (3H, m), 3.06 (4H, m), 2.59 (1H, m), 2.01 (1H, m), 1.83 (1H, m), 1.80-1.49 (4H, m), 1.19 (3H, q), 0.85 (1H, m), 0.69 (1H, m).

LCMS (Method C) r/t 3.35 (M+H) 486.

Example 82

(1aRS,7bSR)-5-{2-[2-((S)-1-Ethylpyrrolidin-3-yl)ethylamino]benzenesulfonyl-amino}-1,1a,2,7b-tetrahydrocyclopropa[c]chromene-4-carboxylic acid

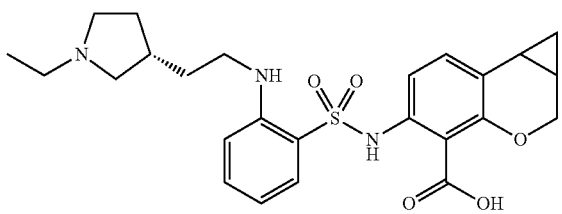 [SMILES: CCN1CC[C@H](CCNc2ccccc2S(=O)(=O)Nc2ccc3c(c2C(=O)O)OCC2CC32)C1]

Prepared by proceeding in a similar manner to Example 58, starting from (1aRS,7bSR)-5-(2-fluorobenzenesulfonylamino)-1,1a,2,7b-tetrahydrocyclopropa-[c]chromene-4-carboxylic acid (Intermediate 67) and 2-((S)-1-ethylpyrrolidin-3-yl)ethylamine (Intermediate 208).

$^1$H NMR (DMSO-d$_6$) δ: 7.62 (1H, dt), 7.29 (1H, dt), 7.02 (2H, 2s), 6.70 (1H, d), 6.57 (1H, t), 5.84 (1H, br m), 4.14 (1H, d), 3.54 (1H, d), 3.36 (1H, m), 3.17 (3H, m), 3.06 (4H, m), 2.57 (1H, m), 2.01 (1H, m), 1.83 (1H, m), 1.80-1.49 (4H, m), 1.19 (3H, q), 0.85 (1H, m), 0.68 (1H, m).

LCMS (Method C) r/t 3.34 (M+H) 486.

Example 83

(1aR,7bS)-5-[2-((S)-1-Ethylpyrrolidin-3-yloxymethyl)-4-fluorobenzene-sulfonylamino]-1,1a,2,7b-tetrahydrocyclopropa[c]chromene-4-carboxylic acid

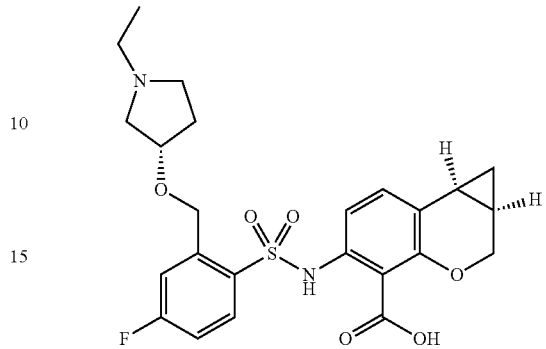

A mixture of methyl (1aR,7bS)-5-[2-((S)-1-ethylpyrrolidin-3-yloxymethyl)-4-fluorobenzene-sulfonylamino]-1,1a,2,7b-tetrahydrocyclopropa[c]chromene-4-carboxylate (Intermediate 213, 0.217 g) and lithium hydroxide monohydrate (0.168 g) in dioxane (3 mL) and water (1 mL) was irradiated in the microwave at 130° C. for 40 minutes. After cooling, the mixture was diluted with methanol, acidified with formic acid, evaporated in vacuo and azeotroped with a mixture of toluene and ethanol. The residue was triturated with 15% methanol in DCM, filtered and the filtrate was evaporated in vacuo. The residue was purified by chromatography on silica, eluting with a mixture of methanol and DCM with a gradient of 0-20%. The resultant gum was triturated with ether and ethyl acetate and filtered to give (1aR,7bS)-5-[2-((S)-1-ethylpyrrolidin-3-yloxymethyl)-4-fluorobenzenesulfonylamino]-1,1a,2,7b-tetrahydrocyclopropa[c]chromene-4-carboxylic acid (0.136 g) as a white solid.

$^1$H NMR (CDCl$_3$) δ: 7.35 (1H, dd), 7.23 (1H, d), 7.19 (1H, dd), 7.01 (1H, d), 6.83 (1H, dt), 4.87 (1H, br, d), 4.73 (1H, br, d), 4.36 (2H, br, m), 4.19 (1H, d), 3.88 (1H, m), 3.84 (1H, d), 3.38 (1H, m), 2.94 (1H, m), 2.86 (1H, m), 2.75 (1H, m), 2.26-2.45 (2H, m), 1.81 (1H, m), 1.60 (1H, m), 1.39 (3H, t), 0.90 (2H, m).

LCMS (Method C) r/t 3.25 (M+H) 491

Example 84

(1aR,7bS)-5-[2-((R)-1-Ethylpyrrolidin-3-yloxymethyl)-4-fluorobenzene-sulfonylamino]-1,1a,2,7b-tetrahydrocyclopropa[c]chromene-4-carboxylic acid

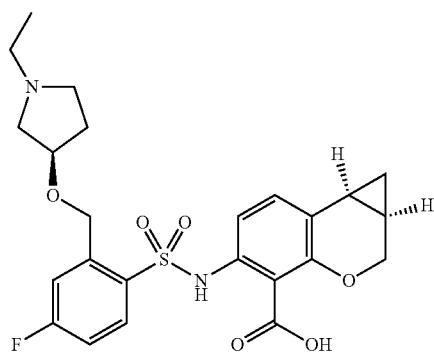 [SMILES: CCN1CC[C@@H](OCc2cc(F)ccc2S(=O)(=O)Nc2ccc3c(c2C(=O)O)OC[C@@H]2C[C@H]32)C1]

Prepared by proceeding in a similar manner to Example 83, starting from methyl (1aR,7bS)-5-[2-((R)-1-ethylpyrrolidin-3-yloxymethyl)-4-fluorobenzenesulfonylamino]-1,1a,2,7b-tetrahydro-cyclopropa[c]chromene-4-carboxylate (Intermediate 217).

$^1$H NMR (DMSO-d$_6$) δ: 7.83 (1H, dd), 7.44 (1H, dd), 7.20 (1H, dt), 7.07 (1H, d), 7.03 (1H, d), 4.99 (1H, d), 4.49 (2H, d), 4.19 (2H, d), 3.57 (2H, d), 2.93-3.30 (4H, m), 2.34 (1H, m), 2.13 (1H, m), 1.88 (1H, m), 1.72 (1H, m), 1.29 (3H, t), 0.92 (1H, m), 0.75 (1H, m).

LCMS (Method C) r/t 3.25 (M+H) 491.

Example 85

(1aR,7bS)-5-[2-(1-Ethylpiperidin-3-ylmethyl)-4-fluorobenzenesulfonylamino]-1,1a,2,7b-tetrahydro-cyclopropa[c]chromene-4-carboxylic acid

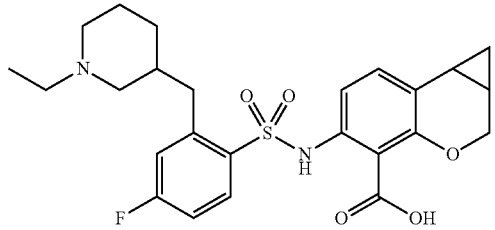 [SMILES: CCN1CCCC(Cc2cc(F)ccc2S(=O)(=O)Nc2ccc3c(c2C(=O)O)OCC2CC32)C1]

A mixture of methyl (1aR,7bS))-5-[2-(1-ethylpiperidin-3-ylmethyl)-4-fluorobenzenesulfonyl-amino]-1,1a,2,7b-tetrahydrocyclopropa[c]chromene-4-carboxylate (Intermediate 221, 0.071 g) and lithium hydroxide monohydrate (0.059 g) was suspended in dioxane (5 mL) and water (2 mL) and the mixture was stirred and heated at 100° C. for 25 hours. Further lithium hydroxide monohydrate (0.116 g) was added and the mixture was heated at 100° C. for a further 18 hours. After cooling, the volatiles were removed in vacuo and the residue was acidified by addition of aqueous citric acid solution (10%) and saturated with sodium chloride. The mixture was extracted with DCM and the organic layer was dried (Na$_2$SO$_4$) and filtered. The filtrate was evaporated to dryness and the residue was purified by preparative HPLC (C18), eluting with a mixture of acetonitrile and water, containing 0.1% formic acid, with a gradient of 25-60% to give (1aR,7bS)-5-[2-(1-ethyl-piperidin-3-ylmethyl)-4-fluorobenzenesulfonylamino]-1,1a,2,7b-tetrahydrocyclopropa-[c]chromene-4-carboxylic acid (0.032 g) as a white solid.

$^1$H NMR (DMSO-d$_6$) δ: 8.01-7.91 (1H, m), 7.26-7.18 (2H, m), 7.10-7.00 (2H, m), 4.22-4.17 (1H, m), 3.61 (1H, d), 3.45-2.92 (5H, m), 3.02-2.88 (4H, m), 1.94-1.85 (1H, m), 1.80-1.65 (3H, m), 1.65-1.50 (1H, m), 1.30-1.14 (4H, m), 0.97-0.87 (1H, m), 0.77-0.68 (1H, m).

LCMS (Method C) r/t 3.21 (M+H) 489.

Example 86

(1aR,7bS)-5-{2-[2-((R)-1-Ethylpyrrolidin-2-yl)ethyl]-4-fluorobenzenesulfonyl-amino}-1,1a,2,7b-tetrahydrocyclopropa[c]chromene-4-carboxylic acid

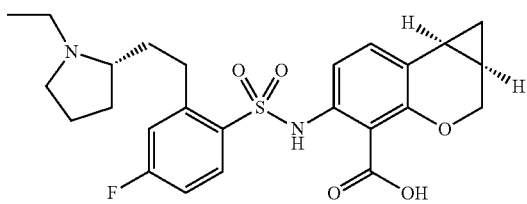 [SMILES: CCN1CCC[C@H]1CCc1cc(F)ccc1S(=O)(=O)Nc1ccc2c(c1C(=O)O)OC[C@@H]1C[C@H]21]

Lithium hydroxide (0.22 g) was added to a solution of methyl (1aR,7bS)-5-{2-[2-((R)-1-ethyl-pyrrolidin-2-yl)ethyl]-4-fluorobenzenesulfonylamino}-1,1a,2,7b-tetrahydrocyclopropa-[c]chromene-4-carboxylate (Intermediate 229, 0.26 g) in a mixture of dioxane (12 mL) and water (4 mL) and the mixture was irradiated in a microwave at 150° C. for 20 minutes. After cooling, the mixture was evaporated to dryness and the residue was acidified by addition of 10% aqueous citric acid (3 mL) and then extracted with DCM. The organic layer was dried (MgSO$_4$) and filtered and the filtrate was evaporated to dryness. The residue was purified by preparative HPLC (C18) eluting with a mixture of acetonitrile and water, containing 0.1% formic acid, with a gradient of 25-35% to give (1aR,7bS)-5-{2-[2-((R)-1-ethyl-pyrrolidin-2-yl)ethyl]-4-fluoro-benzenesulfonylamino}-1,1a,2,7b-tetrahydrocyclopropa[c]chromene-4-carboxylic acid (0.11 g) as a white solid.

$^1$H NMR (DMSO-d$_6$) δ: 7.88 (1H, dd), 7.33 (1H, dd), 7.15 (1H, dt), 7.08 (1H, d), 6.98 (1H, d), 4.18 (1H, d), 3.68 (1H, br m), 3.58 (1H, d), 3.56 (1H, m), 3.22-2.96 (5H, m), 2.23 (1H, m), 2.03 (4H, m), 1.87 (2H, m), 1.72 (1H, q), 1.31 (3H, t), 0.91 (1H, m), 0.72 (1H, q).

LCMS (Method C) r/t 3.24 (M+H) 489.

Intermediate 1

Methyl cis-(3aRS,9bRS)-7-(benzenesulfonylamino)-1,3a,4,9b-tetrahydro-2H-furo[2,3-c]chromene-6-carboxylate

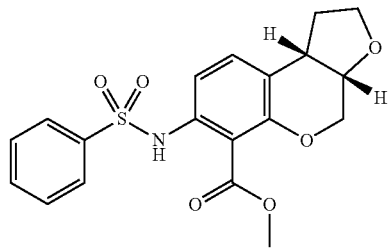

Mixture of cis enantiomers

Formic acid (5 mL) was added to methyl cis-(3aRS,9bRS)-7-[bis(tert-butoxycarbonyl)amino]-1,3a,4,9b-tetrahydro-2H-furo[2,3-c]chromene-6-carboxylate (Intermediate 2, 0.15 g) and the mixture was stirred at room temperature for 1 hour. The resultant mixture was evaporated to dryness and the residue was redissolved in toluene and evaporated to dryness three times. The residue was dissolved in DCM (2 mL) and pyridine (1 mL) was added followed by benzenesulfonyl chloride (0.07 g). The resultant mixture was stirred at room temperature for 90 minutes then diluted with DCM and washed with sodium hydroxide (1M) and brine. The sodium hydroxide washing was saturated with salt and then extracted with ethyl acetate, dried (MgSO$_4$) and filtered. The filtrate was evaporated to dryness to give methyl cis-(3aRS,9bRS)-7-(benzenesulfonylamino)-1,3a,4,9b-tetrahydro-2H-furo[2,3-c]chromene-6-carboxylate (0.082 g) as a gum.

$^1$H NMR (CDCl$_3$) δ: 7.73 (2H, dd), 7.53 (1H, t), 7.42 (2H, t), 7.25 (1H, d), 7.21 (1H, d), 4.29 (1H, m), 4.03 (1H, dd), 3.93 (1H, dd), 3.82 (2H, t), 3.70 (3H, s), 3.45 (1H, m), 2.48 (1H, m), 1.87 (1H, m).

Intermediate 2

Methyl cis-(3aRS,9bRS)-7-[bis-(tert-butoxycarbonyl)amino]-1,3a,4,9b-tetrahydro-2H-furo[2,3-c]chromene-6-carboxylate

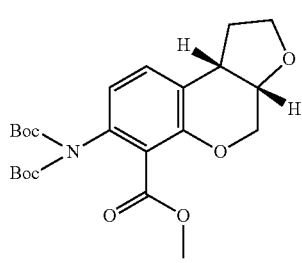

Mixture of cis enantiomers

A solution of methyl 7-[bis-(tert-butoxycarbonyl)amino]-4H-furo[2,3-c]-chromene-6-carboxylate (Intermediate 3, 0.15 g) in a mixture of dioxane (15 mL) and acetic acid (1.5 mL) was treated under an atmosphere of nitrogen with palladium on carbon (10%, 0.02 g). The mixture was stirred and the nitrogen was replaced by hydrogen then the mixture was stirred under an atmosphere of hydrogen for 3 hours. The mixture was filtered through Celite, the pad was washed thoroughly with dioxane and the filtrate was evaporated to dryness to give methyl cis-(3aRS,9bRS)-7-[bis-(tert-butoxycarbonyl)amino]-1,3a,4,9b-tetrahydro-2H-furo[2,3-c]chromene-6-carboxylate (0.15 g) as a gum.

$^1$H NMR (CDCl$_3$) δ: 7.22 (1H, dd), 6.80 (1H, d), 4.36 (1H, m), 4.07 (2H, d), 3.86 (2H, t), 3.84 (3H, s), 3.53 (1H, m), 2.50 (1H, m), 1.94 (1H, m), 1.40 (18H, s).

Intermediate 3

Methyl 7-[bis-(tert-butoxycarbonyl)amino]-4H-furo[2,3-c]-chromene-6-carboxylate

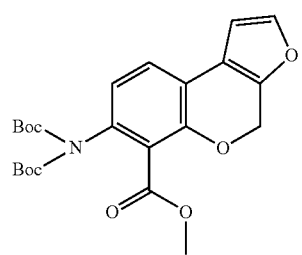 [SMILES: COC(=O)c1c(N(C(=O)OC(C)(C)C)C(=O)OC(C)(C)C)ccc2c1OCc1occc1-2]

Carbon tetrabromide (2.66 g) was added to a solution of methyl 6-[bis-(tert-butoxycarbonyl)amino]-2-hydroxy-3-(2-hydroxymethylfuran-3-yl)-benzoate (Intermediate 4, 2.65 g) and triphenyl phosphine (2.1 g) in DCM (40 mL) and the resultant solution was stirred at room temperature for 1 hour. The mixture was evaporated to dryness and DMF (60 mL) and cesium carbonate (5.59 g) were added to the residue. The resultant mixture was stirred for 1 hour, then partitioned between ethyl acetate and water. The organic layer was separated, dried (Na$_2$SO$_4$) and filtered. The filtrate was evaporated to dryness and the residue was purified by chromatography on silica, eluting with a mixture of ethyl acetate and cyclohexane with a gradient of 5-25% to give methyl 7-[bis-(tert-butoxycarbonyl)amino]-4H-furo[2,3-c]-chromene-6-carboxylate (0.735 g) as a gum which crystallised on standing.

$^1$H NMR (CDCl$_3$) δ: 7.45 (1H, m), 7.26 (1H, s), 6.79 (1H, d), 6.65 (1H, d), 5.44 (2H, s), 3.87 (3H, s), 1.42 (18H, s).

Intermediate 4

Methyl 6-[bis-(tert-butoxycarbonyl)amino]-2-hydroxy-3-(2-hydroxymethylfuran-3-yl)benzoate

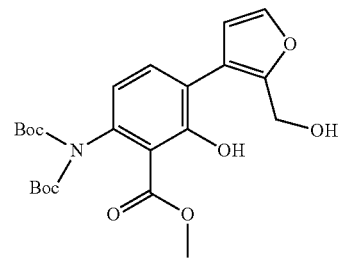 [SMILES: COC(=O)c1c(N(C(=O)OC(C)(C)C)C(=O)OC(C)(C)C)ccc(-c2ccoc2CO)c1O]

1M aqueous sodium hydroxide (50 mL) was added to a solution of methyl 6-[bis-(tert-butoxycarbonyl)amino]-3-(2-hydroxymethylfuran-3-yl)-2-(4-methylbenzene-sulfonyloxy)benzoate (Intermediate 5, 3.82 g) in methanol (100 mL) and the mixture was stirred and heated at 45° C. for 1.5 hours. The mixture was evaporated to dryness and the residue was dissolved in ethyl acetate and acidified with acetic acid. The organic layer was separated, dried (Na$_2$SO$_4$) and filtered. The filtrate was evaporated to dryness and the residue was purified by chromatography on silica, eluting with a mixture of ethyl acetate and cyclohexane with a gradient of 10-50% to give methyl 6-[bis-(tert-butoxycarbonyl)amino]-2-hydroxy-3-(2-hydroxymethylfuran-3-yl)benzoate (2.65 g) as a white foam.

$^1$H NMR (CDCl$_3$) a: 11.91 (1H, s), 7.50 (2H, m), 6.80 (1H, d), 6.57 (1H, d), 4.58 (2H, s), 3.97 (3H, s), 1.43 (18H, s).

Intermediate 5

Methyl 6-[bis-(tert-butoxycarbonyl)amino]-3-(2-hydroxymethyl-furan-3-yl)-2-(4-methylbenzenesulfonyloxy)benzoate

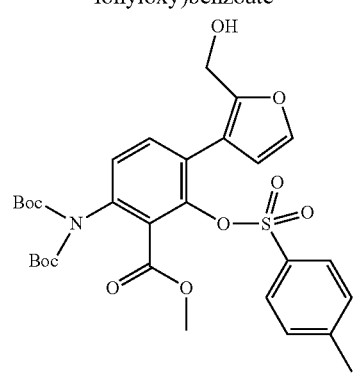

Sodium borohydride (0.304 g) was added to a solution of methyl 6-[bis-(tert-butoxycarbonyl)amino]-3-(2-formyl-furan-3-yl)-2-(4-methylbenzenesulfonyloxy)-benzoate (Intermediate 6, 3.9 g) in ethanol (50 mL) and the mixture was stirred for 15 minutes. The mixture was evaporated to dryness and the residue was partitioned between ethyl acetate and water. The organic layer was separated, dried (Na₂SO₄) and filtered. The filtrate was evaporated to dryness to give methyl 6-[bis-(tert-butoxycarbonyl)amino]-3-(2-hydroxymethylfuran-3-yl)-2-(4-methylbenzene-sulfonyloxy) benzoate (3.82 g) as a white solid.

¹H NMR (CDCl₃) δ: 7.40 (1H, d), 7.38 (2H, d), 7.30 (1H, d), 7.18 (1H, d), 7.11 (2H, d), 6.28 (1H, d), 4.33 (2H, s), 3.82 (3H, s), 2.40 (3H, s), 1.42 (18H, s).

Intermediate 6

Methyl 6-[bis-(tert-butoxycarbonyl)amino]-3-(2-formylfuran-3-yl)-2-(4-methylbenzenesulfonyloxy) benzoate

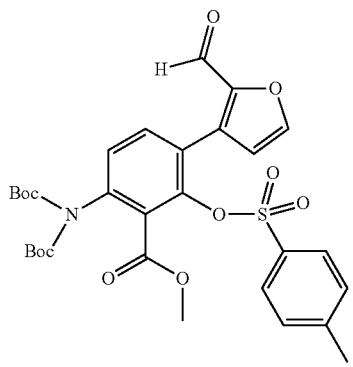 [SMILES: COC(=O)c1c(N(C(=O)OC(C)(C)C)C(=O)OC(C)(C)C)ccc(-c2ccoc2C=O)c1OS(=O)(=O)c1ccc(C)cc1]

Triethylamine (0.848 g) was added to a stirred solution of methyl 6-amino-3-(2-formylfuran-3-yl)-2-hydroxybenzoate (Intermediate 7, 1.72 g), 4-methylbenzenesulfonyl chloride (1.25 g) and DMAP (0.804 g) in DCM (30 mL) and the resultant mixture was stirred for 1 hour. The mixture was diluted with water and the organic layer was separated, dried (Na₂SO₄) and filtered. The filtrate was evaporated to dryness and the residue was dissolved in acetonitrile (30 mL) and DMAP (0.804 g) and di-tert-butyl bicarbonate (3.16 g) were added. The mixture was stirred for 2 hours then diluted with ethyl acetate and water. The organic layer was separated, dried (Na₂SO₄) and filtered. The filtrate was evaporated to dryness and the residue was purified by chromatography on silica, eluting with a mixture of ethyl acetate and cyclohexane with a gradient of 10-50% to give methyl 6-[bis-(tert-butoxycarbonyl)amino]-3-(2-formylfuran-3-yl)-2-(4-methylbenzenesulfonyloxy)-benzoate (3.91 g) as a white foam.

¹H NMR (CDCl₃) δ: 9.13 (1H, d), 7.54 (1H, dd), 7.38 (1H, d), 7.31 (2H, d), 7.23 (1H, d), 7.05 (2H, d), 6.75 (1H, d), 3.94 (3H, s), 2.37 (3H, s), 1.45 (18H, s).

Intermediate 7

Methyl 6-amino-3-(2-formylfuran-3-yl)-2-hydroxybenzoate

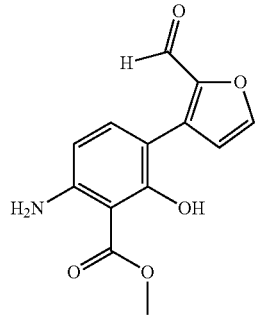 [SMILES: COC(=O)c1c(N)ccc(-c2ccoc2C=O)c1O]

A mixture of methyl 6-amino-3-bromo-2-hydroxybenzoate (prepared according to Wang et al, *Bioorg Med Chem Lett,* 2007, 17, 2817; 1.84 g), 2-formylfuran-3-boronic acid pinacol ester (1.99 g), tri-tert-butylphosphonium tetrafluoroborate (0.218 g), cesium carbonate (7.33 g) and tris-(dibenzylideneacetone)dipalladium (0.343 g) in dioxane (75 mL) and water (9.4 mL) was heated at 65° C., under nitrogen, for 1 hour. After cooling, the mixture was diluted with ethyl acetate and water and the organic layer was separated, dried (Na₂SO₄) and filtered. The filtrate was evaporated to dryness and the residue was purified by chromatography on silica, eluting with a mixture of ethyl acetate and cyclohexane with a gradient of 10-50% to give methyl 6-amino-3-(2-formylfuran-3-yl)-2-hydroxybenzoate (1.72 g) as a yellow solid. The material was used without further characterisation.

Intermediate 8

7-[2-((Z)-3-Diethylaminoprop-1-enyl)-4-fluorobenzene-sulfonylamino]-4H-furo[2,3-c]chromene-6-carboxylic acid

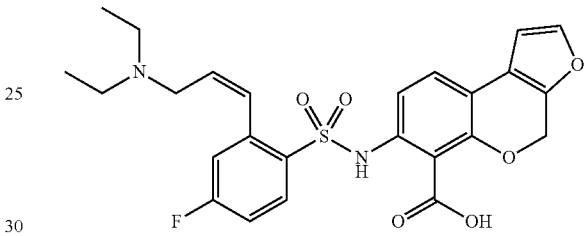

Methyl 7-[2-((Z)-3-diethylaminoprop-1-enyl)-4-fluorobenzenesulfonylamino]-4H-furo[2,3-c]chromene-6-carboxylate (Intermediate 9, 0.129 g) was added to a solution of lithium hydroxide monohydrate (0.42 g) in water (2 mL) and dioxane (8 mL), and the mixture was irradiated in the microwave at 130° C. for 1 hour. After cooling, the mixture was acidified with formic acid, and evaporated to dryness. The residue was triturated with 10% methanol in DCM, filtered and the filtrate was evaporated to dryness. The residue was purified by chromatography on silica, eluting with a mixture of methanol and DCM with a gradient of 0-10%. The isolated product was triturated with ethyl acetate and the solid was collected by filtration and dried in vacuo to give 7-[2-((Z)-3-diethylaminoprop-1-enyl)-4-fluorobenzenesulfonylamino]-4H-furo[2,3-c]chromene-6-carboxylic acid (0.056 g) as a white solid.

¹H NMR (DMSO-d₆) δ: 7.71 (1H, d), 7.68 (1H, d), 7.38 (1H, d), 7.28 (1H, dd), 7.26-7.19 (2H, m), 7.02 (1H, d), 6.86 (1H, d), 6.20-6.11 (1H, m), 5.28 (2H, s), 3.79 (2H, d), 3.12 (4H, q), 1.14 (6H, t).

LCMS (Method C) r/t 3.48 (M+H) 501.

Intermediate 9

Methyl 7-[2-((Z)-3-Diethylaminoprop-1-enyl)-4-fluorobenzene-sulfonylamino]-4H-furo[2,3-c]chromene-6-carboxylate

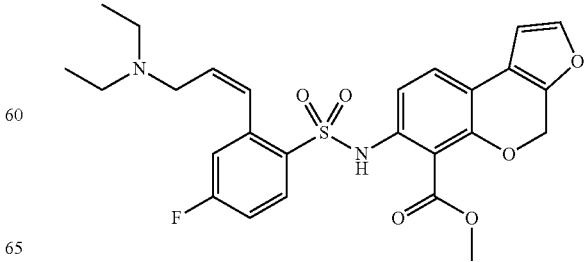

A mixture of methyl 7-(2-bromo-4-fluorobenzenesulfonylamino)-4H-furo[2,3-c]chromene-6-carboxylate (Intermediate 10, 2.04 g), N,N-diethyl-N—((Z)-1-tributylstannanylprop-1-en-3-yl)amine (Intermediate 11, 3.4 g), tri-tert-butylphosphonium tetrafluoroborate (0.246 g), tris-(dibenzylideneacetone)dipalladium (0.0.388 g) in dioxane (35 mL) was degassed and purged with argon then heated at 100° C. for 3.5 hours. After cooling, the mixture was diluted with ethyl acetate and filtered. The filtrate was washed with water, dried (Na$_2$SO$_4$) and filtered. The filtrate was evaporated to dryness and the residue was purified by chromatography on silica, eluting with a mixture of ammonia in methanol (2M) and DCM with a gradient of 0-10%. The product was triturated with ether and the solid was collected by filtration to give methyl 7-[2-((Z)-3-diethylaminoprop-1-en-1-yl)-4-fluorobenzenesulfonyl-amino]-4H-furo[2,3-c]chromene-6-carboxylate (1.47 g) as a pale orange solid.

$^1$H NMR (CDCl$_3$) δ: 8.06 (1H, dd), 7.40 (1H, m), 7.17 (1H, d), 7.14-6.98 (2H, m), 7.0-6.9 (2H, m), 6.56 (1H, d), 6.06 (1H, m), 5.37 (2H, s), 3.87 (3H, s), 3.17 (2H, m), 2.55 (4H, m), 0.97 (6H, t).

Intermediate 10

Methyl 7-(2-bromo-4-fluorobenzenesulfonylamino)-4H-furo[2,3-c]chromene-6-carboxylate

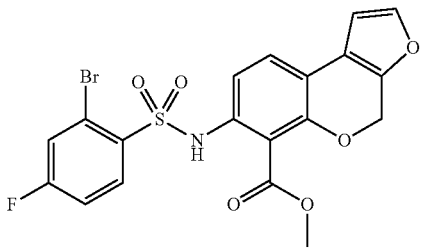 [SMILES: COC(=O)c1c(NS(=O)(=O)c2ccc(F)cc2Br)ccc2c1OCc1occc1-2]

Methyl 7-[bis-(tert-butoxycarbonyl)amino]-4H-furo[2,3-c]-chromene-6-carboxylate (Intermediate 3, 2.66 g) was dissolved in formic acid (50 mL) and the mixture was stirred at room temperature for 90 minutes. The mixture was evaporated to dryness and the crude residue was partitioned between ethyl acetate and aqueous potassium carbonate solution (10%). The organic layer was separated, dried (MgSO$_4$) and filtered. The filtrate was evaporated to dryness and the residue was dissolved in DCM (20 mL) and pyridine (10 mL) and 2-bromo-4-fluorobenzenesulfonyl chloride (1.95 g) was added. The resultant mixture was stirred for 3.5 hours then evaporated to dryness. The residue was dissolved in DCM washed with water and filtered through a phase separator. The filtrate was evaporated to dryness and the residue was purified by chromatography on silica, eluting with a mixture of ethyl acetate and cyclohexane with a gradient of 0-60% to give methyl 7-(2-bromo-4-fluorobenzenesulfonyl-amino)-4H-furo[2,3-c]chromene-6-carboxylate (0.47 g) as a pale yellow solid.

$^1$H NMR (CDCl$_3$) δ: 9.25 (1H, br s), 8.14 (1H, dd), 7.40 (2H, m), 7.16 (2H, m), 7.12 (1H, m), 6.55 (1H, d), 5.36 (2H, s), 3.92 (3H, s).

Intermediate 11

N,N-Diethyl-N—((Z)-1-tributylstannanylprop-1-en-3-yl)-amine

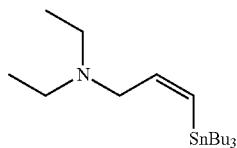

Diethylamine (19 mL) was added to a solution of ((Z)-3-bromoprop-1-enyl)-tributyl-stannane (Intermediate 12, 7.52 g) in THF (60 mL) and the mixture was stirred for 3 hours. The reaction mixture was evaporated to dryness and the residue was purified by chromatography on a silica column which had been pre-washed with 20% triethylamine in acetonitrile. The column was eluted with a mixture of ethyl acetate and pentane with a gradient of 0-10% to give N,N-diethyl-N—((Z)-1-tributylstannanylprop-1-en-3-yl)amine (4.75 g) as an orange oil.

$^1$H NMR (CDCl$_3$) δ: 6.59 (1H, dt), 5.97 (1H, dt), 3.08 (2H, dd), 2.53 (4H, q), 1.49 (6H, m), 1.37-1.24 (6H, m), 1.04 (6H, t), 0.92-0.89 (15H, m).

Intermediate 12

((Z)-3-Bromoprop-1-enyl)-tributylstannane

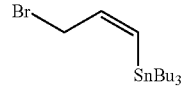

A solution of triphenylphosphine (5.32 g) in DCM (60 mL) was added to a solution of (Z)-3-tributylstannanylprop-2-en-1-ol (Intermediate 13, 6.4 g) and carbon tetrabromide (9.18 g) in DCM (60 mL) and the mixture was stirred for 2.5 hours. The mixture was evaporated to low volume and pentane was added. The solids were removed by filtration and the filtrate was evaporated to dryness. Pentane was added and the solids were again removed by filtration and the filtrate was evaporated to dryness to give ((Z)-3-bromoprop-1-enyl)-tributylstannane (12.14 g) as an oil.

$^1$H NMR (CDCl$_3$) δ: 6.71 (1H, dt), 6.11 (1H, d), 3.88 (2H, d), 1.52-1.50 (6H, m), 1.37-1.27 (6H, m), 0.99-0.97 (6H, m), 0.90 (9H, t).

Intermediate 13

(Z)-3-Tributylstannanylprop-2-en-1-ol

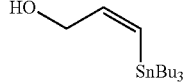

Propargyl alcohol (5 mL) was added to a solution of lithium aluminum hydride (1M in THF, 43 mL) in THF (70 mL) at −78° C. The resultant mixture was warmed to room temperature and stirred for 18 hours. It was re-cooled to −78° C. and a solution of tri-n-butyl tin chloride (8.32 mL) in diethyl ether (50 mL) was added and the mixture was stirred for 3 hours whilst gradually warming to room temperature. The reaction mixture was cooled to −5° C. and quenched by addition of water and 15% aqueous sodium hydroxide solution then warmed to room temperature. Ethyl acetate was added and the mixture was stirred for 1 hour. The mixture was filtered through Celite and the filtrate was evaporated to dryness. The residue was purified by chromatography on a silica column which had been pre-washed with 20% triethylamine in acetonitrile. The column was eluted with a mixture of ethyl acetate and pentane with a gradient of 0-10% to give (Z)-3-tributylstannanyl-prop-2-en-1-ol (5.06 g) as a clear oil.

$^1$H NMR (CDCl$_3$) δ: 6.70 (1H, dt), 6.08 (1H, dt), 4.12 (2H, dd), 1.49 (6H, m), 1.31 (6H, m), 0.98-0.84 (15H, m).

Intermediate 14

Methyl cis-(3aRS,9bRS)-7-[2-(3-{pyrrolidin-1-yl}propyl)-4-fluorobenzenesulfonylamino]-1,3a,4,9b-tetrahydro-2H-furo[2,3-c]chromene-6-carboxylate

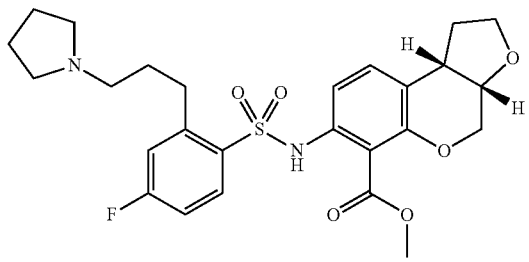

Mixture of cis enantiomers

A solution of methyl 7-[2-((Z)-3-{pyrrolidin-1-yl}prop-1-enyl)-4-fluorobenzene-sulfonylamino]-4H-furo[2,3-c]chromene-6-carboxylate (Intermediate 15, 0.06 g) in IMS (4 mL) and formic acid (2 drops) was treated under an atmosphere of nitrogen with palladium hydroxide on carbon (10%, 0.02 g). The nitrogen was replaced by hydrogen and the mixture was stirred under an atmosphere of hydrogen for 1 hour. The mixture was filtered through Celite and the filtrate was evaporated to dryness to give methyl cis-(3aRS,9bRS)-7-[2-(3-{pyrrolidin-1-yl}propyl)-4-fluorobenzene-sulfonylamino]-1,3a,4,9b-tetrahydro-2H-furo[2,3-c]chromene-6-carboxylate (0.06 g) which was used without further characterisation.

Intermediate 15

Methyl 7-[2-((Z)-3-{pyrrolidin-1-yl}prop-1-enyl)-4-fluorobenzene-sulfonylamino]-4H-furo[2,3-c]chromene-6-carboxylate

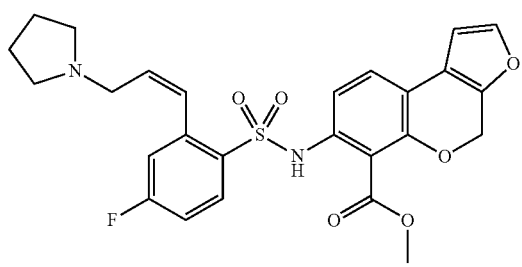 [SMILES: COC(=O)c1c(NS(=O)(=O)c2ccc(F)cc2/C=C\CN2CCCC2)ccc2c1OCc1occc1-2]

Prepared by proceeding in a similar manner to Intermediate 9, starting from methyl 7-(2-bromo-4-fluorobenzene-sulfonylamino)-4H-furo[2,3-c]chromene-6-carboxylate (Intermediate 10) and 1-((Z)-3-tributylstannanylallyl)pyrrolidine (Intermediate 16).

$^1$H NMR (CD$_3$OD) δ: 8.02 (1H, dd), 7.51 (1H, m), 7.16 (2H, d), 7.11-7.01 (2H, m), 6.76 (1H, d), 6.69 (1H, d), 5.93-5.83 (1H, m), 5.31 (2H, s), 3.80 (3H, s), 3.37-3.33 (2H, m), 2.69 (4H, m), 1.78 (4H, m).

Intermediate 16

1-((Z)-3-tributylstannanylallyl)pyrrolidine

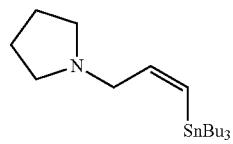

Prepared by proceeding in a similar manner to Intermediate 11 starting from ((Z)-3-bromoprop-1-enyl)tributylstannane (Intermediate 12) and pyrrolidine.

$^1$H NMR (CDCl$_3$) δ: 6.64 (1H, dt), 5.96 (1H, dt), 3.10 (2H, dd), 2.51 (4H, m), 1.79-1.78 (4H, m), 1.54-1.45 (6H, m), 1.36-1.26 (6H, m), 0.91-0.88 (15H, t).

Intermediate 17

Methyl cis-(3aRS,9bRS)-7-[2-((Z)-3-diethylamino-prop-1-enyl)-4-fluorobenzenesulfonylamino]-1,3a,4,9b-tetrahydro-2H-furo[2,3-c]chromene-6-carboxylate

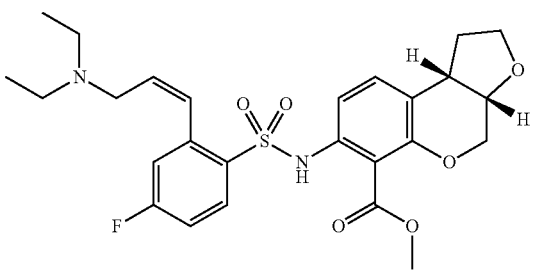

Mixture of cis enantiomers

Prepared by proceeding in a similar manner to Intermediate 9, starting from methyl cis-(3aRS,9bRS)-7-(2-bromo-4-fluorobenzenesulfonylamino)-1,3a,4,9b-tetrahydro-2H-furo[2,3-c]chromene-6-carboxylate (Intermediate 18) and N,N-diethyl-N—((Z)-1-tributylstannanylprop-1-en-3-yl)-amine (Intermediate 11) and heating at 80° C. for 2 hours.

LCMS (Method A) r/t 2.25 (M+H) 519.

Intermediate 18

Methyl cis-(3aRS,9bRS)-7-(2-bromo-4-fluorobenzenesulfonyl-amino)-1,3a,4,9b-tetrahydro-2H-furo[2,3-c]chromene-6-carboxylate

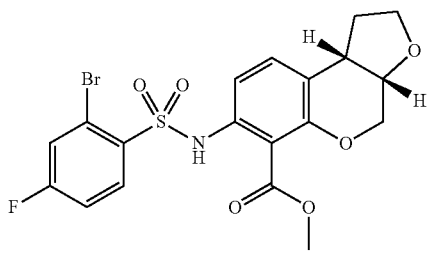

Mixture of cis enantiomers

2-Bromo-4-fluorobenzenesulfonyl chloride (0.335 g) was added to a solution of methyl cis-(3aRS,9bRS)-7-amino-1,3a,4,9b-tetrahydro-2H-furo[2,3-c]chromene-6-carboxylate (Intermediate 19, 0.255 g) in DCM (4 mL) and pyridine (2 mL) and the resultant mixture was stirred at room temperature overnight. The mixture was evaporated to dryness and the residue was purified by chromatography on silica eluting with a mixture of ethyl acetate and cyclohexane with a gradient of 0-100% to give methyl cis-(3aRS,9bRS)-7-(2-bromo-4-fluorobenzenesulfonylamino)-1,3a,4,9b-tetrahydro-2H-furo[2,3-c]chromene-6-carboxylate (0.486 g) as a yellow gum.

$^1$H NMR (CDCl$_3$) δ: 9.47 (1H, s), 8.17 (1H, m), 7.42 (1H, dd), 7.12 (1H, dt), 7.11 (2H, s), 4.28 (1H, m), 4.06 (1H, dd), 3.96 (1H, dd), 3.91 (3H, s), 3.82 (2H, m), 3.41 (1H, m), 2.45 (1H, m), 1.84 (1H, m).

Intermediate 19

Methyl cis-(3aRS,9bRS)-7-amino-1,3a,4,9b-tetrahydro-2H-furo[2,3-c]chromene-6-carboxylate

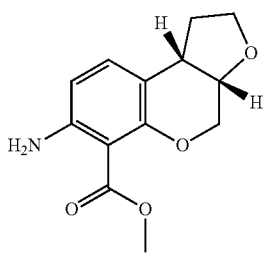

Mixture of cis enantiomers

Trifluoroacetic acid (7 mL) was added to a solution of methyl cis-(3aRS,9bRS)-7-[bis-(tert-butoxycarbonyl)amino]-1,3a,4,9b-tetrahydro-2H-furo[2,3-c]chromene-6-carboxylate (Intermediate 2, 0.66 g) in DCM (15 mL) and the mixture was stirred at room temperature for 1 hour. The mixture was evaporated to dryness and the residue was treated with aqueous sodium bicarbonate and extracted with DCM, dried (MgSO$_4$) and filtered. The filtrate was evaporated to dryness to give methyl cis-(3aRS,9bRS)-7-amino-1,3a,4,9b-tetrahydro-2H-furo[2,3-c]chromene-6-carboxylate (0.255 g) as a gum.

$^1$H NMR (CDCl$_3$) δ: 7.0 (1H, dd), 6.31 (1H, d), 4.32 (1H, m), 4.01 (2H, m), 3.88 (3H, s), 3.84 (2H, m), 3.39 (1H, m), 2.41 (1H, m), 1.86 (1H, m).

Intermediate 20

Methyl 7-[N-{2-((Z)-3-Diethylaminoprop-1-enyl)-4-fluoro-benzenesulfonyl}-N-(methoxycarbonyl)amino]-1,2-dihydrofuro[2,3-c]quinoline-6-carboxylate

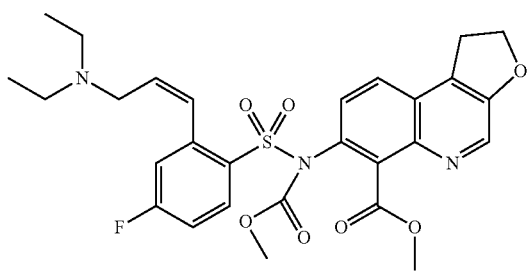 [SMILES: CCN(CC)C/C=C\c1cc(F)ccc1S(=O)(=O)N(C(=O)OC)c1ccc2c3c(cnc2c1C(=O)OC)OCC3]

Prepared by proceeding in a similar manner to Intermediate 9, starting from methyl 7-[N-(2-bromo-4-fluorobenzenesulfonyl)-N-(methoxycarbonyl)amino]-1,2-dihydro-furo[2,3-c]quinoline-6-carboxylate (Intermediate 21) and N,N-diethyl-N—((Z)-1-tributylstannanylprop-1-en-3-yl)amine (Intermediate 11) and heating at 60° C. for 1 hour.

$^1$H NMR (CDCl$_3$) δ: 8.72 (1H, s), 8.32 (1H, dd), 7.76 (1H, d), 7.62 (1H, d), 7.22-7.08 (3H, m), 6.03 (1H, m), 4.87 (2H, t), 3.93 (3H, s), 3.62 (3H, s), 3.56 (2H, t), 3.20 (2H, m), 2.52 (4H, m), 0.97 (6H, t).

Intermediate 21

Methyl 7-[N-(2-bromo-4-fluorobenzenesulfonyl)-N-(methoxy-carbonyl)amino]-1,2-dihydrofuro[2,3-c]quinoline-6-carboxylate

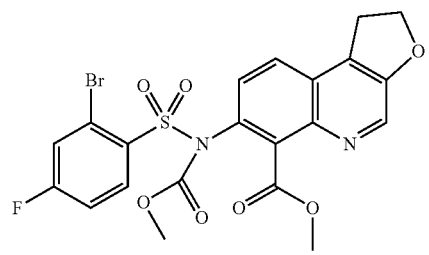 [SMILES: COC(=O)c1c(N(C(=O)OC)S(=O)(=O)c2ccc(F)cc2Br)ccc2c3c(cnc12)OCC3]

A solution of methyl 7-(2-bromo-4-fluorobenzenesulfonylamino)-1,2-dihydro-furo[2,3-c]quinoline-6-carboxylate (Intermediate 22, 0.29 g) in THF (5 mL) was added slowly to a suspension of sodium hydride (40% oil dispersion, 0.048 g) in THF (15 mL). Once the evolution of hydrogen had ceased, methyl chloroformate (0.147 g) was added and the mixture was stirred at room temperature for 1 hour. The mixture was diluted with ethyl acetate, washed with saturated sodium bicarbonate solution, dried (MgSO$_4$) and filtered. The filtrate was evaporated to dryness and the residue was triturated with a mixture of ether and cyclohexane (1:1) and the solid was collected by filtration to give methyl 7-[N-(2-bromo-4- fluorobenzenesulfonyl)-N-(methoxy-carbonyl)amino]-1,2-dihydrofuro[2,3-c]quinoline-6-carboxylate (0.3 g) as a pale orange solid.

¹H NMR (CDCl₃) δ: 8.73 (1H, s), 8.48 (1H, dd), 7.76 (2H, s), 7.51 (1H, dd), 7.25 (1H, m), 4.86 (2H, t), 4.01 (3H, s), 3.66 (3H, s), 3.56 (2H, t).

Intermediate 22

Methyl 7-(2-bromo-4-fluorobenzenesulfonylamino)-1,2-dihydro-furo[2,3-c]quinoline-6-carboxylate

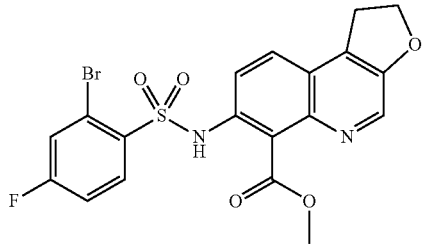 [SMILES: COC(=O)c1c(NS(=O)(=O)c2ccc(F)cc2Br)ccc2c3c(cnc12)OCC3]

Prepared by proceeding in a similar manner to Intermediate 18, starting from methyl 7-amino-1,2-dihydrofuro[2,3-c]quinoline-6-carboxylate (Intermediate 23) and 2-bromo-4-fluorobenzenesulfonyl chloride and stirring at room temperature for 3 days.

¹H NMR (CDCl₃) δ: 8.60 (1H, s), 8.07 (1H, dd), 7.84 (1H, d), 7.62 (1H, d), 7.43 (1H, dd), 7.06 (1H, m), 4.79 (2H, t), 4.02 (3H, s), 3.48 (2H, t).

Intermediate 23

Methyl 7-amino-1,2-dihydrofuro[2,3-c]quinoline-6-carboxylate

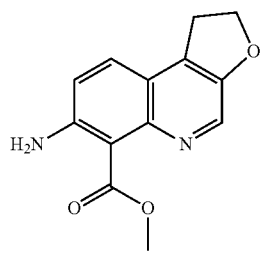 [SMILES: COC(=O)c1c(N)ccc2c3c(cnc12)OCC3]

A solution of methyl 7-aminofuro[2,3-c]quinoline-6-carboxylate (Intermediate 24, 1.13 g) in a mixture of dioxane (5 mL) and acetic acid (5 mL) was treated under an atmosphere of nitrogen with palladium hydroxide on carbon (10%, 0.1 g). The nitrogen was replaced by hydrogen and the mixture was stirred under an atmosphere of hydrogen for 24 hours. The mixture was diluted with ethyl acetate and filtered through Celite and the filtrate was washed with 1M aqueous sodium hydroxide solution, dried (MgSO₄) and filtered. The filtrate was evaporated to dryness and the residue was purified by chromatography on silica eluting with a mixture of methanol and ethyl acetate with a gradient of 0-10%. The isolated product was triturated with a mixture of ether and cyclohexane and the solid was collected by filtration to give methyl 7-amino-1,2-dihydrofuro[2,3-c]quinoline-6-carboxylate (0.666 g) as a yellow solid.

¹H NMR (CDCl₃) δ: 8.56 (1H, s), 7.51 (1H, d), 6.95 (1H, d), 5.16 (2H, br s), 4.74 (2H, t), 4.05 (3H, s), 3.46 (2H, t).

Intermediate 24

Methyl 7-aminofuro[2,3-c]quinoline-6-carboxylate

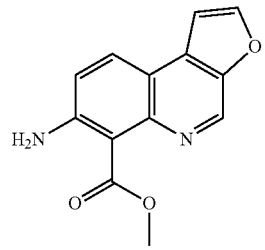 [SMILES: COC(=O)c1c(N)ccc2c1ncc1occc12]

A mixture of methyl 3-bromo-2,6-diaminobenzoate (Intermediate 25, 1.34 g), 2-formylfuran-3-boronic acid pinacol ester (1.46 g), tri-tert-butylphosphonium tetrafluoroborate (0.305 g), cesium carbonate (5.15 g) and tris-(dibenzylideneacetone)dipalladium (0.49 g) in a mixture of dioxane (80 mL) and water (30 mL) was degassed and purged with argon then heated at 60° C. for 1 hour. After cooling, the mixture was filtered through Celite and the pad was washed thoroughly with ethyl acetate. The filtrate was washed with water, dried (MgSO₄) and filtered. The filtrate was evaporated to dryness and the residue was purified by chromatography on silica eluting with a mixture of ethyl acetate and cyclohexane with a gradient of 0-100% to give methyl 7-aminofuro[2,3-c]quinoline-6-carboxylate (1.13 g) as a brown gum.

¹H NMR (CDCl₃) δ: 9.11 (1H, s), 7.95 (1H, d), 7.82 (1H, d), 7.14 (1H, dd), 7.05 (1H, d), 5.05 (2H, br s), 4.08 (3H, s).

Intermediate 25

Methyl 3-bromo-2,6-diaminobenzoate

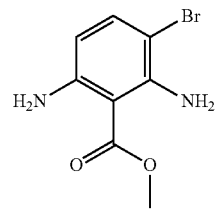

Iron powder (4.07 g) was added slowly with stirring and cooling to a solution of methyl 6-amino-3-bromo-2-nitrobenzoate (prepared according to Brock et al, Tetrahedron, 1963, 19, 1911; 2.0 g) in a mixture of absolute ethanol (49 mL), acetic acid (5 mL), formic acid (0.7 mL) and water (15 mL). On completion of the addition, the mixture was stirred at room temperature for 2 hours. The mixture was diluted with DCM and water (1:1) then filtered through Celite. The layers were separated and the aqueous layer was extracted with DCM. The combined organic layers were washed with 1M aqueous sodium hydroxide solution, dried (MgSO₄) and filtered. The filtrate was evaporated to dryness and the residue was triturated with ether and cyclohexane (1:1) and the solid was collected by filtration to give methyl 3-bromo-2,6-diaminobenzoate (1.34 g) as a pale yellow solid.

¹H NMR (CDCl₃) δ: 7.21 (1H, d), 6.11 (2H, br s), 5.88 (1H, d), 5.46 (2H, br s), 3.93 (3H, s).

Intermediate 26

Methyl 7-(benzenesulfonylamino)-1,2-dihydro[furo[2,3-c]quinoline-6-carboxylate

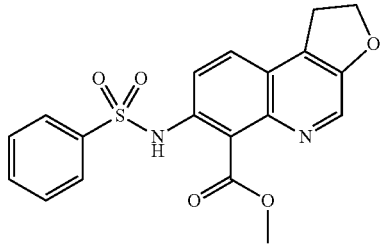 [SMILES: COC(=O)c1c(NS(=O)(=O)c2ccccc2)ccc2c3c(cnc12)OCC3]

Prepared by proceeding in a similar manner to Intermediate 18, starting from methyl 7-amino-1,2-dihydrofuro[2,3-c]quinoline-6-carboxylate (Intermediate 23) and benzenesulfonyl chloride and stirring at room temperature overnight.

¹H NMR (CDCl₃) δ: 8.59 (1H, s), 7.94 (1H, d), 7.70 (1H, d), 7.50 (1H, m), 7.40 (2H, t), 7.21 (2H, m), 4.81 (2H, t), 3.75 (3H, s), 3.51 (2H, t).

Intermediate 27

Methyl cis-(3aRS,9bRS)-5-acetyl-7-[2-((Z)-3-diethylaminoprop-1-enyl)-4-fluorobenzenesulfonylamino]-1,2,3a,4,5,9b-hexahydrofuro[2,3-c]quinoline-6-carboxylate

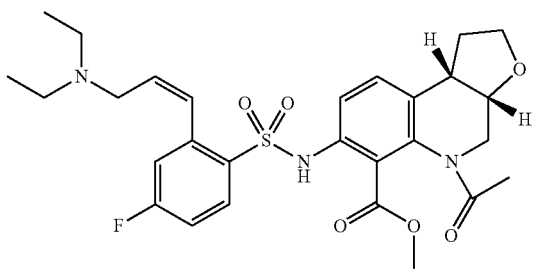

Mixture of cis enantiomers

Prepared by proceeding in a similar manner to Intermediate 9, starting from methyl cis-(3aRS,9bRS)-5-acetyl-7-(2-bromo-4-fluorobenzenesulfonylamino)-1,2,3a,4,5,9b-hexahydrofuro[2,3-c]quinoline-6-carboxylate (Intermediate 28) and heating at 80° C. for 2 hours.

LCMS (Method B) r/t 2.29 (M+H) 560.

Intermediate 28

Methyl cis-(3aRS,9bRS)-5-acetyl-7-(2-bromo-4-fluorobenzene-sulfonylamino)-1,2,3a,4,5,9b-hexahydrofuro[2,3-c]quinoline-6-carboxylate

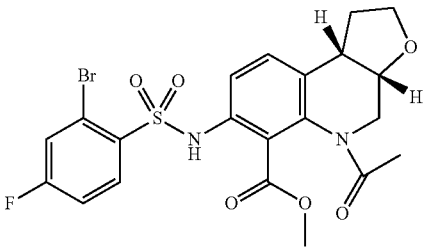

Mixture of cis enantiomers

Prepared by proceeding in a similar manner to Intermediate 18, starting from methyl cis-(3aRS,9bRS)-5-acetyl-7-amino-1,2,3a,4,5,9b-hexahydrofuro[2,3-c]quinoline-6-carboxylate (Intermediate 29) and 2-bromo-4-fluorobenzenesulfonyl chloride.

¹H NMR (CDCl₃) δ: 9.51 (1H, br s), 8.16 (1H, m), 7.42 (1H, dd), 7.34 (1H, d), 7.18 (1H, d), 7.12 (1H, dt), 4.46 (1H, d), 3.84 (2H, m), 3.81 (3H, s), 3.67 (1H, m), 3.49 (1H, m), 3.38-3.19 (1H, m), 2.41-2.30 (1H, m), 2.25 (3H, s), 1.57 (1H, m).

Intermediate 29

Methyl cis-(3aRS,9bRS)-5-acetyl-7-amino-1,2,3a,4,5,9b-hexahydrofuro[2,3-c]quinoline-6-carboxylate

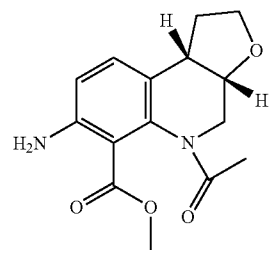

Mixture of cis enantiomers

Concentrated sulfuric acid (5 drops) was added to a solution of methyl cis-(3aRS,9bRS)-5-acetyl-7-(2,2-dimethylpropionylamino)-1,2,3a,4,5,9b-hexahydro-furo[2,3-c]quinoline-6-carboxylate (Intermediate 30, 0.15 g) in methanol (5 mL) and the solution was stirred and heated at reflux for 48 hours. After cooling, the mixture was evaporated to low volume and the residue was dissolved in ethyl acetate and carefully washed with saturated aqueous sodium bicarbonate solution. The organic layer was filtered through a phase separator and the filtrate was evaporated to dryness to give methyl cis-(3aRS,9bRS)-5-acetyl-7-amino-1,2,3a,4,5,9b-hexahydrofuro[2,3-c]quinoline-6-carboxylate (0.09 g) as a brown gum.

¹H NMR (CDCl₃) δ: 7.04 (1H, d), 6.53 (1H, d), 4.97 (2H, br s), 4.47 (1H, m), 3.90 (2H, m), 3.79 (3H, s), 3.67 (1H, m), 3.45 (1H, m), 3.30 (1H, m), 2.4-2.32 (1H, m), 2.27 (3H, s), 1.68-1.54 (1H, m).

Intermediate 30

Methyl cis-(3aRS,9bRS)-5-acetyl-7-(2,2-dimethylpropionylamino)-1,2,3a,4,5,9b-hexahydrofuro[2,3-c]quinoline-6-carboxylate

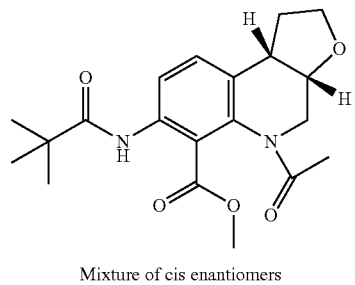 [SMILES: COC(=O)c1c(NC(=O)C(C)(C)C)ccc2c1N(C(C)=O)C[C@H]1OCC[C@@H]21]

Mixture of cis enantiomers

Sodium hydride (60% oil dispersion, 0.02 g) was added to a solution of methyl 2-acetylamino-6-(2,2-dimethylpropionylamino)-3-[cis-(2RS,3 RS)-2-(methanesulfonyl-oxymethyl)tetrahydrofuran-3-yl]benzoate (Intermediate 31, 0.166 g) in THF (3 mL) and the mixture was stirred at room temperature for 20 minutes. A saturated aqueous solution of ammonium chloride was added and the mixture was extracted with DCM, dried (MgSO$_4$) and filtered. The filtrate was evaporated to dryness to give methyl cis-(3aRS,9bRS)-5-acetyl-7-(2,2-dimethylpropionylamino)-1,2,3a,4,5,9b-hexahydrofuro[2,3-c]quinoline-6-carboxylate (0.15 g) as a tan coloured solid.

$^1$H NMR (CDCl$_3$) δ: 9.92 (1H, s), 8.29 (1H, d), 7.30 (1H, d), 4.51 (1H, d), 3.82 (3H, s), 3.75 (2H, m), 3.69 (1H, m), 3.56 (1H, m), 3.37-3.27 (1H, br m), 2.44-2.34 (1H, br m), 2.29 (3H, s), 1.68-1.58 (1H, br m), 1.29 (9H, s).

Intermediate 31

Methyl 2-acetylamino-6-(2,2-dimethylpropionylamino)-3-[cis-(2RS,3RS)-2-(methanesulfonyloxymethyl)tetrahydrofuran-3-yl]benzoate

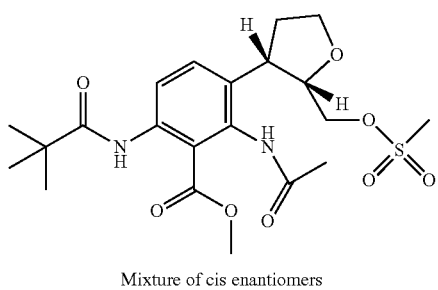 [SMILES: COC(=O)c1c(NC(=O)C(C)(C)C)ccc([C@@H]2CCO[C@@H]2COS(C)(=O)=O)c1NC(C)=O]

Mixture of cis enantiomers

Methanesulfonyl chloride (0.042 mL) was added to a mixture of methyl 2-acetylamino-6-(2,2-dimethylpropionylamino)-3-[cis-(2RS,3RS)-2-(hydroxymethyl)-tetrahydrofuran-3-yl]benzoate (Intermediate 32, 0.14 g) and triethylamine (0.15 mL) in DCM (5 mL) and the resultant mixture was stirred at room temperature for 30 minutes. The mixture was washed with 1M hydrochloric acid, dried (MgSO$_4$) and filtered. The filtrate was evaporated to dryness to give methyl 2-acetylamino-6-(2,2-dimethylpropionylamino)-3-[cis-(2RS,3RS)-2-(methanesulfonyloxymethyl)-tetrahydrofuran-3-yl]benzoate (0.166 g) as a gum.

LCMS (Method B) r/t 2.57 (M+Na) 493.

Intermediate 32

Methyl 2-acetylamino-6-(2,2-dimethylpropionylamino)-3-[cis-(2RS,3RS)-2-(hydroxymethyl)-tetrahydrofuran-3-yl]benzoate

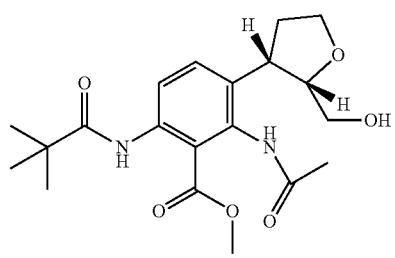

Mixture of cis enantiomers

A solution of methyl 2-acetylamino-6-(2,2-dimethylpropionylamino)-3-(2-hydroxymethylfuran-3-yl)benzoate (Intermediate 38, 0.2 g) in dioxane (4 mL) and acetic acid (1 mL) was treated under an atmosphere of nitrogen with palladium hydroxide on carbon (10%, 0.03 g). The nitrogen was replaced by hydrogen and the mixture was stirred under an atmosphere of hydrogen overnight. The mixture was filtered through Celite and the pad was washed thoroughly with ethyl acetate. The filtrate was evaporated to dryness and the residue was purified by chromatography on silica eluting with a mixture of methanol and ethyl acetate with a gradient of 0-10% to give methyl 2-acetylamino-6-(2,2-dimethylpropionylamino)-3-[cis-(2RS,3RS)-2-(hydroxymethyl)tetrahydrofuran-3-yl]benzoate (0.14 g) as a white solid.

$^1$H NMR (CDCl$_3$) δ: 9.70 (1H, br s), 8.29 (1H, d), 8.25 (1H, br s), 7.36 (1H, d), 4.22 (1H, m), 4.10 (1H, m), 3.91 (1H, m), 3.90 (3H, s), 3.64 (2H, m), 3.24 (1H, m), 2.41 (1H, m), 2.16 (3H, s), 2.11 (1H, m), 1.30 (9H, s).

Intermediate 33

Methyl 2-acetylamino-6-(2,2-dimethylpropionylamino)-3-(2-hydroxymethylfuran-3-yl)benzoate

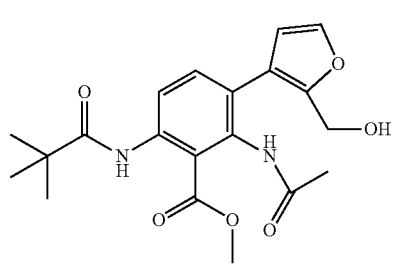 [SMILES: COC(=O)c1c(NC(=O)C(C)(C)C)ccc(-c2ccoc2CO)c1NC(C)=O]

Tetrabutylammonium fluoride (1M solution in THF, 1.1 mL) was added to a stirred, cooled solution of methyl 2-acetylamino-3-[2-(tert-butyldimethylsilanyloxymethyl)-furan-3-yl]-6-(2,2-dimethylpropionylamino)benzoate (Intermediate 34, 0.43 g) in THF (10 mL) at 0° C. and the mixture was stirred at 0° C. for 40 minutes then evaporated to dryness. The residue was partitioned between ethyl acetate and water and the organic layer was washed with brine, dried (MgSO$_4$) and filtered. The filtrate was evaporated to dryness and the residue was purified by chromatography on silica eluting with a mixture of methanol and ethyl acetate with a gradient of 0-2% to give methyl 2-acetylamino-6-(2,2-dimethylpropionylamino)-3-(2-hydroxymethylfuran-3-yl)benzoate (0.2 g) as a gum.

$^1$H NMR (CDCl$_3$) δ: 9.95 (1H, br s), 8.36 (1H, d), 8.00 (1H, br s), 7.46 (1H, s), 7.36 (1H, d), 6.32 (1H, s), 4.54 (2H, d), 3.90 (3H, s), 2.45 (1H, t), 1.99 (3H, s), 1.32 (9H, s).

Intermediate 34

Methyl 2-acetylamino-3-[2-(tert-butyldimethylsilanyloxymethyl)-furan-3-yl]-6-(2,2-dimethylpropionylamino)benzoate

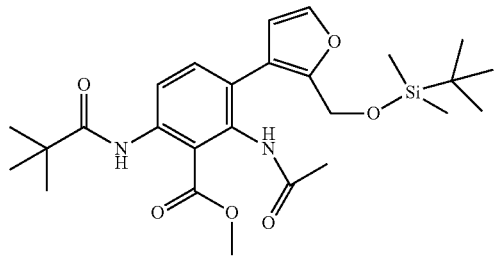 [SMILES: COC(=O)c1c(NC(=O)C(C)(C)C)ccc(-c2ccoc2CO[Si](C)(C)C(C)(C)C)c1NC(C)=O]

Acetyl chloride (0.09 mL) was added to a stirred solution of methyl 2-amino-3-[2-(tert-butyldimethylsilanyloxymethyl)furan-3-yl]-6-(2,2-dimethylpropionylamino)-benzoate (Intermediate 35, 0.47 g) in DCM (5 mL) and pyridine (0.16 mL) and the mixture was stirred at room temperature for 1 hour. The mixture was diluted with DCM and washed with water and brine, dried (MgSO$_4$) and filtered. The filtrate was evaporated to dryness and the residue was purified by chromatography on silica eluting with a mixture of ethyl acetate and cyclohexane with a gradient of 20-50% to give methyl 2-acetylamino-3-[2-(tert-butyldimethylsilanyloxymethyl)-furan-3-yl]-6-(2,2-dimethylpropionylamino)benzoate (0.442 g) as a colourless foam.

$^1$H NMR (CDCl$_3$) δ: 10.08 (1H, br s), 8.34 (1H, d), 8.15 (1H, br s), 7.46 (1H, s), 7.36 (1H, d), 6.32 (1H, s), 4.51 (2H, s), 3.93 (3H, s), 1.98 (3H, s), 1.32 (9H, s), 0.93 (9H, s), 0.13 (6H, s).

Intermediate 35

Methyl 2-amino-3-[2-(tert-butyldimethylsilanyloxymethyl)furan-3-yl]-6-(2,2-dimethylpropionylamino)-benzoate

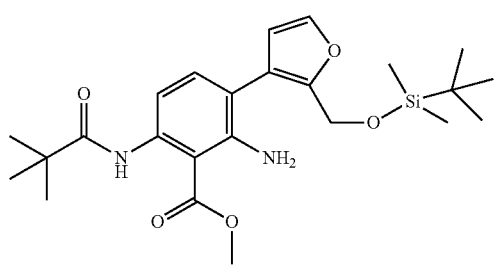 [SMILES: COC(=O)c1c(NC(=O)C(C)(C)C)ccc(-c2ccoc2CO[Si](C)(C)C(C)(C)C)c1N]

Pivaloyl chloride (0.353 g) was added to a stirred, cooled mixture of methyl 2,6-diamino-3-[2-(tert-butyldimethylsilanyloxymethyl)furan-3-yl]benzoate (Intermediate 36, 1.0 g) and sodium bicarbonate (0.268 g) in ethyl acetate (20 mL) and water (7 mL) at 0° C. The mixture was allowed to warm to room temperature and stirred for 1.5 hours. Further pivaloyl chloride (0.048 g) was added and the mixture was stirred for 1 hour. Ethyl acetate was added and the layers were separated. The organic layer was washed with aqueous sodium bicarbonate solution dried (MgSO$_4$) and filtered. The filtrate was evaporated to dryness and the residue was purified by chromatography on silica eluting with a mixture of ethyl acetate and cyclohexane with a gradient of 5-20% to give methyl 2-amino-3-[2-(tert-butyldimethylsilanyloxymethyl)furan-3-yl]-6-(2,2-dimethylpropionylamino)benzoate (0.744 g) as an oil.

$^1$H NMR (CDCl$_3$) δ: 10.81 (1H, br s), 7.97 (1H, d), 7.48 (1H, s), 7.18 (1H, d), 6.41 (1H, s), 5.67 (2H, s), 4.51 (2H, s), 3.98 (3H, s), 1.33 (9H, s), 0.87 (9H, s), 0.05 (6H, s).

Intermediate 36

Methyl 2,6-diamino-3-[2-(tert-butyldimethylsilanyloxymethyl)-furan-3-yl]benzoate

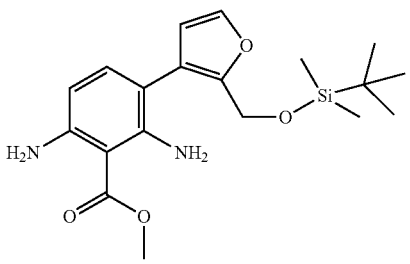 [SMILES: COC(=O)c1c(N)ccc(-c2ccoc2CO[Si](C)(C)C(C)(C)C)c1N]

A mixture of methyl 3-bromo-2,6-diaminobenzoate (Intermediate 25, 2.6 g), 2-(tert-butyldimethylsilanyloxymethyl)furan-3-boronic acid (Intermediate 37, 3.5 g), cesium carbonate (11.35 g), tri-tert-butylphosphonium tetrafluoroborate (0.334 g) and tris-(dibenzylideneacetone)dipalladium (0.529 g) in dioxane (72 mL) and water (18 mL) was degassed and purged with nitrogen then heated at 70° C. for 75 minutes. After cooling, ethyl acetate and water were added and the mixture was filtered through Celite. The filtrate was separated and the organic layer was washed with brine, dried (MgSO$_4$) and filtered. The filtrate was evaporated to dryness and the residue was purified by chromatography on silica eluting with a mixture of ethyl acetate and cyclohexane with a gradient of 5-20% to give methyl 2,6-diamino-3-[2-(tert-butyldimethylsilanyloxymethyl)furan-3-yl]benzoate (2.39 g) as a viscous oil which was used without further characterization.

Intermediate 37

2-(tert-Butyldimethylsilanyloxymethyl)furan-3-boronic acid

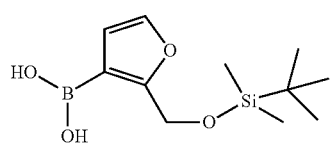 [SMILES: CC(C)(C)[Si](C)(C)OCc1occc1B(O)O]

n-Butyllithium (2.5M in hexanes, 11.25 mL) was added slowly to a stirred, cooled solution of 3-bromo-2-(tert-butyldimethylsilanyloxymethyl)furan (Intermediate 38, 7.5 g) in dry ether (150 mL) while maintaining the temperature below −70° C. The mixture was stirred at −78° C. for 2.5 hours. Tri-isopropyl borate (6.75 g) was added and the mixture was allowed to warm to room temperature and stirred for 1.75 hours. Ethyl acetate and aqueous ammonium chloride solution were added and the layers were separated. The organic layer was washed with aqueous ammonium chloride solution, dried (MgSO₄) and filtered. The filtrate was evaporated to dryness and the residue was purified by chromatography on silica eluting with a mixture of ethyl acetate and cyclohexane with a gradient of 10-35% to give 2-(tert-butyldimethylsilanyloxymethyl)furan-3-boronic acid (3.6 g) which was used directly without further characterization.

Intermediate 38

3-Bromo-2-(tert-butyldimethylsilanyloxymethyl)furan

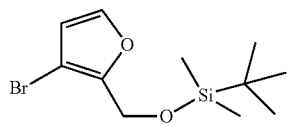

tert-Butyldimethylsilanyl triflate (17.13 g) was added slowly to a stirred, cooled solution of 3-bromo-2-hydroxymethylfuran (Intermediate 39, 10.1 g) in DCM (160 mL) and pyridine (9.57 g) while maintaining the temperature at 0° C. The mixture was allowed to warm to room temperature and stirred for 1 hour. The mixture was washed with aqueous citric acid solution, brine, dried (Na₂SO₄) and filtered. The filtrate was evaporated to dryness to give 3-bromo-2-(tert-butyldimethylsilanyloxymethyl)furan (17.1 g).
¹H NMR (CDCl₃) δ: 7.35 (1H, d), 6.38 (1H, d), 4.65 (2H, s), 0.90 (9H, s), 0.09 (6H, s).

Intermediate 39

3-Bromo-2-hydroxymethylfuran

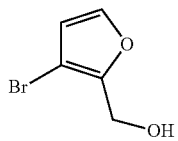

Sodium borohydride (1.14 g) was added slowly to a stirred, cooled solution of 3-bromo-2-formylfuran (5 g) in a mixture of THF (50 mL) and methanol (25 mL) while maintaining the temperature around 0° C. The mixture was allowed to warm to room temperature and stirred for 1 hour. The mixture was evaporated to dryness and the residue was partitioned between ethyl acetate and water. The aqueous layer was extracted with ethyl acetate and the combined organic layers were washed with brine, dried (Na₂SO₄) and filtered. The filtrate was evaporated to dryness to give 3-bromo-2-hydroxymethylfuran (5.31 g) as a colourless oil.

¹H NMR (CDCl₃) δ: 7.37 (1H, d), 6.42 (1H, d), 4.65 (2H, d), 1.71 (1H, t).

Intermediate 40

Methyl (1aRS,7bSR)-5-[2-((Z)-3-diethylaminoprop-1-enyl)-4-fluorobenzene-sulfonylamino]-1,1a,2,7b-tetrahydrocyclopropa[c]chromene-4-carboxylate

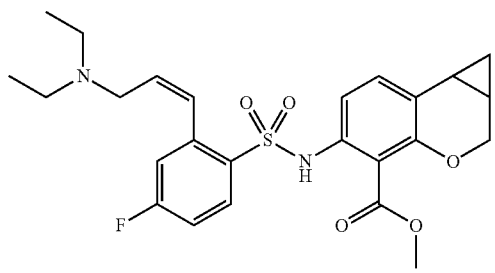 [SMILES: CCN(CC)C/C=C\c1cc(F)ccc1S(=O)(=O)Nc1ccc2c(c1C(=O)OC)OCC1CC21]

A solution of methyl (1aRS,7bSR)-5-(2-bromo-4-fluorobenzenesulfonylamino)-1,1a,2,7b-tetrahydrocyclopropa[c]chromene-4-carboxylate (Intermediate 41, 0.208 g) and N,N-diethyl-N—((Z)-1-tributylstannanylprop-1-en-3-yl)-amine (Intermediate 11, 0.367 g) in dioxane (5 mL) and DMSO (0.5 mL) was de-gassed and flushed with nitrogen. Tris-(dibenzylideneacetone)-dipalladium (0.021 g) and tri-tert-butylphosphonium tetrafluoroborate (0.013 g) were added and the mixture was again de-gassed and flushed with nitrogen. The resultant mixture was heated at 95° C. for 45 minutes. After cooling, the mixture was partitioned between ethyl acetate and water and the organic layer was dried (MgSO₄) and filtered. The filtrate was concentrated in vacuo and the residue was purified by chromatography on silica, eluting with a mixture of methanol and DCM, with a gradient of 0-12% to give methyl (1aRS,7bSR)-5-[2-((Z)-3-diethylaminoprop-1-enyl)-4-fluorobenzenesulfonylamino]-1,1a,2,7b-tetrahydrocyclopropa[c]chromene-4-carboxylate (0.188 g) as a yellow/brown oil.
¹H NMR (CDCl₃) δ: 8.06 (1H, dd), 7.16 (1H, d), 7.09-7.03 (2H, m), 6.94 (1H, d), 6.86 (1H, d), 6.10-6.02 (1H, m), 4.33 (1H, d), 3.84 (3H, s), 3.78 (1H, d), 3.13 (2H, br, d), 2.54 (4H, br, q), 1.88 (1H, m), 1.71 (1H, m), 1.03-0.92 (8H, m).

Intermediate 41

Methyl (1aRS,7bSR)-5-(2-bromo-4-fluorobenzene-sulfonylamino)-1,1a,2,7b-tetrahydrocyclopropa[c]chromene-4-carboxylate

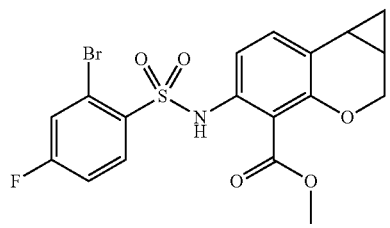 [SMILES: COC(=O)c1c(NS(=O)(=O)c2ccc(F)cc2Br)ccc2c1OCC1CC21]

Methyl (1aRS,7bSR)-5-amino-1,1a,2,7b-tetrahydrocyclopropa[c]chromene-4-carboxylate (Intermediate 42, 0.120 g) was suspended in DCM (5 mL). Pyridine (0.885 mL) and 2-bromo-4-fluorobenzenesufonyl chloride (0.180 g) were added. The mixture was stirred at room temperature for 5 hours then concentrated in vacuo. The residue was dissolved in ethyl acetate and washed with 0.5M aqueous hydrochloric acid solution, dried (MgSO$_4$) and filtered. The filtrate was concentrated in vacuo and the residue was purified by chromatography on silica, eluting with a mixture of ethyl acetate and cyclohexane, with a gradient of 5-10% to give methyl (1aRS,7bSR)-5-(2-bromo-4-fluorobenzenesulfonylamino)-1,1a,2,7b-tetrahydrocyclopropa[c]chromene-4-carboxylate (0.208 g) as a colourless oil.

$^1$H NMR (CDCl$_3$) δ: 9.31 (1H, br, s), 8.14 (1H, dd), 7.41 (1H, dd), 7.17 (1H, d), 7.11 (1H, ddd), 7.06 (1H, d), 4.34 (1H, dd), 3.90 (3H, s), 3.80 (1H, dd), 1.94-1.85 (1H, m), 1.75-1.67 (1H, m), 1.01 (2H, m).

Intermediate 42

Methyl (1aRS,7bSR)-5-amino-1,1a,2,7b-tetrahydrocyclopropa[c]chromene-4-carboxylate

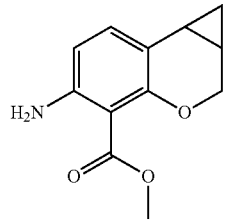 [SMILES: COC(=O)c1c(N)ccc2c1OCC1CC21]

Methyl (1aRS,7bSR)-5-(2,2-dimethylpropionylamino)-1,1a,2,7b-tetrahydrocyclopropa[c]chromene-4-carboxylate (Intermediate 43, 0.310 g) was suspended in methanol (7.5 mL) and concentrated sulphuric acid (4 drops) was added. The reaction mixture was heated to reflux, under an atmosphere of nitrogen, for 36 hours. A further 2 drops of concentrated sulphuric acid was added and heating was continued for a further 24 hours. After cooling, the mixture was concentrated in vacuo and the residue was partitioned between ethyl acetate and saturated aqueous potassium carbonate solution. The aqueous layer was extracted with ethyl acetate and the combined organic layers were dried (Na$_2$SO$_4$) and filtered. The filtrate was concentrated in vacuo and the residue was purified by chromatography on silica, eluting with a mixture of ethyl acetate and cyclohexane, with a gradient of 5-20% to give methyl (1aRS,7bSR)-5-amino-1,1a,2,7b-tetrahydrocyclopropa[c]chromene-4-carboxylate (0.120 g) as an off-white solid.

$^1$H NMR (CDCl$_3$) δ: 7.06 (1H, d), 6.26 (1H, d), 4.33 (1H, d), 3.87 (3H, s), 3.85 (1H, d), 1.83 (1H, td), 1.64 (1H, m), 0.99-0.89 (2H, m).

Intermediate 42A

Methyl (1aR,7bS)-5-amino-1,1a,2,7b-tetrahydrocyclopropa[c]chromene-4-carboxylate

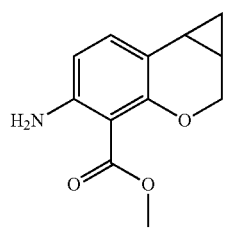 [SMILES: COC(=O)c1c(N)ccc2c1OCC1CC21]

Sample from Intermediate 42 was subjected to chiral SFC separation using a Lux C-3 column, 50 mm×250 mm, particle size 5 micron. Eluting with 5% methanol (+0.1% diethylamine) in CO$_2$ Absolute configuration of Intermediate 42A was confirmed by conversion of a sample to Example 12 and comparison with the analytical chiral HPLC.

Intermediate 43

Methyl (1aRS,7bSR)-5-(2,2-dimethylpropionylamino)-1,1a,2,7b-tetrahydrocyclopropa[c]chromene-4-carboxylate

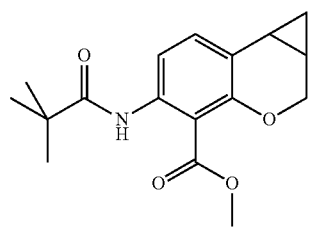 [SMILES: COC(=O)c1c(NC(=O)C(C)(C)C)ccc2c1OCC1CC21]

Methyl (1aRS,7bSR)-1,1-dibromo-5-(2,2-dimethylpropionylamino)-1,1a,2,7b-tetrahydro-cyclopropa[c]chromene-4-carboxylate (Intermediate 44, 1.13 g) was suspended in ethanol (30 mL). Zinc dust (1.17 g), followed by ammonium chloride (1.31 g) were added and the reaction mixture was heated to reflux, under an atmosphere of nitrogen, for 6 hours. After cooling, the solid was filtered off and washed with ethyl acetate. The filtrate was concentrated in vacuo and the residue was purified by chromatography on silica, eluting with a mixture of ether and cyclohexane, with a gradient of 5-12.5% to give methyl (1aRS,7bSR)-5-(2,2-dimethylpropionylamino)-1,1a,2,7b-tetrahydrocyclopropa[c]chromene-4-carboxylate (0.310 g) as a colourless oil.

$^1$H NMR (CDCl$_3$) δ: 9.72 (1H, br, s), 7.98 (1H, d), 7.30 (1H, d), 4.36 (1H, dd), 3.91 (3H, s), 3.84 (1H, dd), 1.95 (1H, td), 1.73 (1H, m), 1.28 (9H, s), 1.03 (2H, m).

Intermediate 44

Methyl (1aRS,7bSR)-1,1-dibromo-5-(2,2-dimethylpropionylamino)-1,1a,2,7b-tetrahydrocyclopropa[c]chromene-4-carboxylate

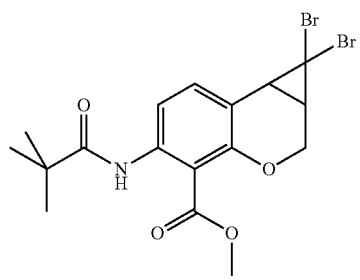 [SMILES: COC(=O)c1c(NC(=O)C(C)(C)C)ccc2c1OCC1C2C1(Br)Br]

Methyl 7-(2,2-dimethylpropionylamino)-2H-chromene-8-carboxylate (Intermediate 45, 2.372 g) and benzyl triethyl ammonium chloride (0.373 g) were suspended in bromoform (6.45 mL) and aqueous sodium hydroxide solution (50%, 3.64 mL) was added dropwise. The resultant black suspension was heated to 60° C. for 2 hours. After cooling, the mixture was partitioned between water and ethyl acetate. The emulsion formed was filtered through a pad of Celite and the organic layer was decanted off. The aqueous was re-extracted with ethyl acetate and the combined organic layers were dried (MgSO$_4$) and filtered. The filtrate was concentrated in vacuo and the residue was purified by chromatography on silica, eluting with a mixture of ethyl acetate and cyclohexane, with a gradient of 2.5-15% to give methyl 1,1-dibromo-5-(2,2-dimethylpropionylamino)-1,1a,2,7b-tetrahydrocyclopropa[c]chromene-4-carboxylate (1.557 g) as an off-white solid.

$^1$H NMR (CDCl$_3$) δ: 9.89 (1H, br, s), 8.13 (1H, d), 7.43 (1H, d), 4.47 (1H, dd), 4.32 (1H, dd), 3.91 (3H, s), 2.89 (1H, d), 2.45 (1H, ddd), 1.30 (9H, s).

Intermediate 45

Methyl 7-(2,2-dimethylpropionylamino)-2H-chromene-8-carboxylate

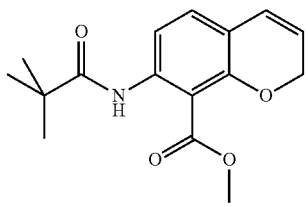 [SMILES: COC(=O)c1c(NC(=O)C(C)(C)C)ccc2c1OCC=C2]

A solution of methyl 2-(2,2-dimethylpropionylamino)-6-(prop-2-ynyloxy)benzoate (Intermediate 46, 4.74 g) and [bis(trifluoromethanesulfonyl)imidate]-(triphenylphosphine)gold (2:1) toluene adduct (0.060 g) in toluene (70 mL) was heated to 85° C., under an atmosphere of nitrogen for 3 hours. After cooling, the mixture was concentrated in vacuo and the residue was purified by chromatography on silica, eluting with a mixture of ethyl acetate and cyclohexane, with a gradient of 0-20% to give methyl 7-(2,2-dimethylpropionylamino)-2H-chromene-8-carboxylate (3.59 g) as a colourless oil.

$^1$H NMR (CDCl$_3$) δ: 10.02 (1H, br, s), 8.05 (1H, d), 7.05 (1H, d), 6.39 (1H, ddd), 5.76 (1H, dt), 4.83 (2H, dd), 3.93 (3H, s), 1.30 (9H, s).

Intermediate 46

Methyl 2-(2,2-dimethylpropionylamino)-6-(prop-2-ynyloxy)benzoate

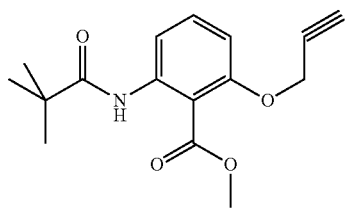 [SMILES: C#CCOc1cccc(NC(=O)C(C)(C)C)c1C(=O)OC]

A mixture of methyl 2-(2,2-dimethylpropionylamino)-6-hydroxybenzoate (Intermediate 47, 4.57 g), propargyl bromide (80% solution in toluene, 2.03 mL) and potassium carbonate (3.74 g) in acetone (35 mL) was heated at reflux for 8 hours. After cooling, the mixture was filtered and the filtrate was concentrated in vacuo. The residue was purified by chromatography on silica, eluting with a mixture of ethyl acetate and cyclohexane, with a gradient of 5-20% to give methyl 2-(2,2-dimethylpropionylamino)-6-(prop-2-ynyloxy)benzoate (4.74 g) as an oil which crystallised on standing to give a white solid.

$^1$H NMR (CDCl$_3$) δ: 9.89 (1H, br, s), 8.16 (1H, dd), 7.41 (1H, t), 6.83 (1H, dd), 4.74 (2H, d), 3.95 (3H, s), 2.53 (1H, t), 1.31 (9H, s).

Intermediate 47

Methyl 2-(2,2-dimethylpropionylamino)-6-hydroxybenzoate

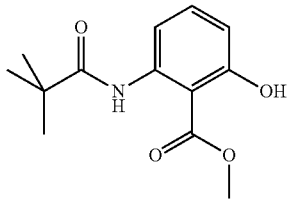 [SMILES: COC(=O)c1c(O)cccc1NC(=O)C(C)(C)C]

Trimethylacetyl chloride (3.69 g) was added to a mixture of methyl 2-amino-6-hydroxybenzoate (prepared according to Comess et al, US2004 0167128, 3.99 g) and sodium bicarbonate (2.57 g) in ethyl acetate (77 mL) and water (18 mL). The reaction mixture was stirred at room temperature for 1 hour. A further amount of trimethylacetyl chloride (1.85 g) was added and the mixture was stirred for 1 hour. A further amount of trimethylacetyl chloride (0.920 g) was added and the mixture was stirred for 30 minutes. The mixture was diluted with ethyl acetate, the layers were separated and the organic layer was dried (Na$_2$SO$_4$) and filtered. The filtrate was concentrated in vacuo and the residue was purified by chromatography on silica, eluting with a mixture of ethyl acetate and cyclohexane, with a gradient of 5-25% to give methyl 2-(2,2-dimethylpropionylamino)-6-hydroxybenzoate (5.79 g) as a white solid.

$^1$H NMR (CDCl$_3$) δ: 10.32 (1H, br, s), 8.22 (1H, dd), 7.41 (1H, t), 6.71 (1H, dd), 4.08 (3H, s), 1.33 (9H, s).

Intermediate 48

Methyl (1aRS,7bSR)-5-[2-((Z)-3-diethylaminoprop-1-enyl)-4-fluorobenzenesulfonylamino]-7b-methyl-1,1a,2,7b-tetrahydrocyclopropa[c]chromene-4-carboxylate

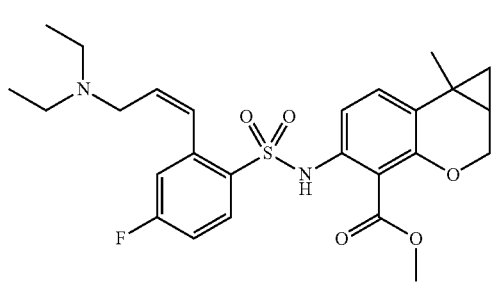 [SMILES: CCN(CC)C/C=C\c1cc(F)ccc1S(=O)(=O)Nc1ccc2c(c1C(=O)OC)OCC1CC21C]

Prepared by proceeding in a similar manner to Intermediate 40, starting from methyl (1aRS,7bSR)-5-(2-bromo-4-fluorobenzenesulfonylamino)-7b-methyl-1,1a,2,7b-tetrahydrocyclopropa[c]chromene-4-carboxylate (Intermediate 49) and N,N-diethyl-N—((Z)-1-tributylstannanylprop-1-en-3-yl)amine (Intermediate 11).

$^1$H NMR (CDCl$_3$) δ: 8.07 (1H, dd), 7.28 (1H, d), 7.05 (2H, m), 6.95 (1H, d), 6.88 (1H, d), 6.06 (1H, m), 4.28 (1H, d), 3.85 (3H, s), 3.83 (1H, d), 3.14 (2H, br d), 2.53 (4H, q), 1.41 (3H, s), 1.12 (1H, m), 1.07 (1H, t), 0.93 (6H, t), 0.84 (1H, dd).

Intermediate 49

Methyl (1aRS,7bSR)-5-(2-bromo-4-fluorobenzenesulfonylamino)-7b-methyl-1,1a,2,7b-tetrahydrocyclopropa[c]chromene-4-carboxylate

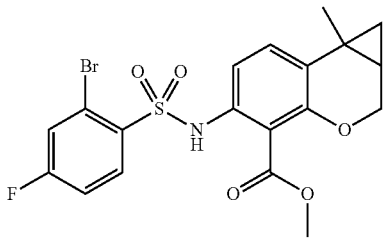 [SMILES: COC(=O)c1c(NS(=O)(=O)c2ccc(F)cc2Br)ccc2c1OCC1CC21C]

Prepared by proceeding in a similar manner to Intermediate 41, starting from methyl (1aRS,7bSR)-5-amino-7b-methyl-1,1a,2,7b-tetrahydrocyclopropa[c]chromene-4-carboxylate (Intermediate 50) and 2-bromo-4-fluorobenzenesulfonyl chloride.

$^1$H NMR (CDCl$_3$) δ: 9.18 (1H, br s), 8.14 (1H, dd), 7.41 (1H, dd), 7.29 (1H, d), 7.11 (1H, m), 7.08 (1H, d), 4.28 (1H, d), 3.89 (3H, s), 3.84 (1H, d), 1.44 (1H, m), 1.42 (3H, s), 1.10 (1H, t), 0.83 (1H, dd).

Intermediate 50

Methyl (1aRS,7bSR)-5-amino-7b-methyl-1,1a,2,7b-tetrahydrocyclopropa-[c]chromene-4-carboxylate

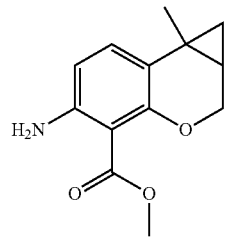 [SMILES: COC(=O)c1c(N)ccc2c1OCC1CC21C]

Trifluoroacetic acid (4 mL) was added to a solution of methyl (1aRS,7bSR)-5-(tert-butoxycarbonylamino)-7b-methyl-1,1a,2,7b-tetrahydrocyclopropa-[c]chromene-4-carboxylate (Intermediate 51, 0.6 g) in dichloromethane (4 mL) and the resultant dark solution was stirred at room temperature for 1 hour. The solution was evaporated to dryness and the residue was partitioned between water and ethyl acetate and treated with a small amount of solid sodium bicarbonate until the pH of the aqueous layer was >7. The layers were separated and the aqueous layer was extracted with ethyl acetate. The combined organic layers were washed with water, dried (MgSO$_4$) and filtered. The filtrate was evaporated to dryness to give methyl (1aRS,7bSR)-5-amino-7b-methyl-1,1a,2,7b-tetrahydrocyclopropa-[c]chromene-4-carboxylate (0.402 g) as a red/orange solid.

$^1$H NMR (CDCl$_3$) δ: 7.20 (1H, d), 6.30 (1H, d), 4.27 (1H, d), 3.90 (1H, d), 3.88 (3H, s), 1.42 (3H, s), 1.37 (1H, m), 1.06 (1H, t), 0.78 (1H, dd).

Intermediate 51

Methyl (1aRS,7bSR)-5-(tert-butoxycarbonylamino)-7b-methyl-1,1a,2,7b-tetrahydrocyclopropa-[c]chromene-4-carboxylate

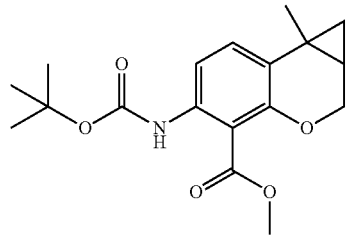 [SMILES: COC(=O)c1c(NC(=O)OC(C)(C)C)ccc2c1OCC1CC21C]

Prepared by proceeding in a similar manner to Intermediate 43, starting from methyl (1aRS,7bSR)-5-(tert-butoxycarbonylamino)-1,1-dibromo-7b-methyl-1,1a,2,7b-tetrahydro-cyclopropa-[c]chromene-4-carboxylate (Intermediate 52).

$^1$H NMR (CDCl$_3$) δ: 8.27 (1H, br s), 7.72 (1H, d), 7.38 (1H, d), 4.29 (1H, d), 3.91 (3H, s), 3.88 (1H, d), 1.50 (9H, s), 1.46 (3H, s), 1.44 (1H, m), 1.13 (1H, t), 0.84 (1H, dd).

Intermediate 52

Methyl (1aRS,7bSR)-1,1-dibromo-5-(tert-butoxycarbonylamino)-7b-methyl-1,1a,2,7b-tetrahydrocyclopropa-[c]chromene-4-carboxylate

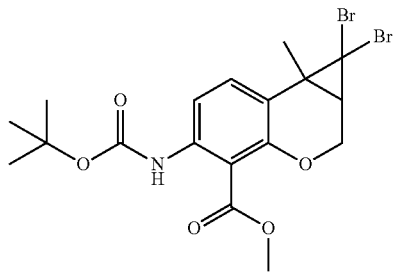 [SMILES: COC(=O)c1c(NC(=O)OC(C)(C)C)ccc2c1OCC1C(Br)(Br)C21C]

Prepared by proceeding in a similar manner to Intermediate 44, starting from methyl 4-methyl-7-(tert-butoxycarbonylamino)-2H-chromene-8-carboxylate (Intermediate 53).

$^1$H NMR (CDCl$_3$) δ: 8.55 (1H, br s), 7.87 (1H, d), 7.42 (1H, d), 4.75 (1H, dd), 4.13 (1H, dd), 3.92 (3H, s), 2.05 (1H, dd), 1.79 (3H, s), 1.50 (9H, s).

Intermediate 53

Methyl 4-methyl-7-(tert-butoxycarbonylamino)-2H-chromene-8-carboxylate

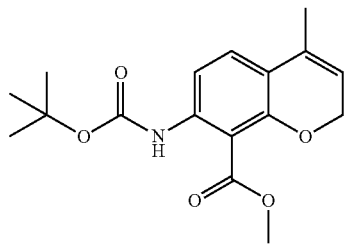 [SMILES: COC(=O)c1c(NC(=O)OC(C)(C)C)ccc2c1OCC=C2C]

Prepared by proceeding in a similar manner to Intermediate 45, starting from methyl 2-[bis-(tert-butyoxycarbonyl)amino]-6-(but-2-ynyloxy)benzoate (Intermediate 54).

$^1$H NMR (CDCl$_3$) δ: 8.66 (1H, br s), 7.77 (1H, d), 7.18 (1H, dd), 5.53 (1H, m), 4.73 (2H, m), 3.93 (3H, s), 1.99 (3H, q), 1.51 (9H, s).

Intermediate 54

Methyl 2-[bis-(tert-butyoxycarbonyl)amino]-6-(but-2-ynyloxy)benzoate

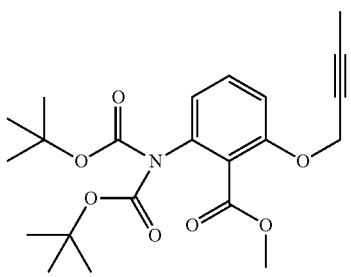 [SMILES: CC#CCOc1cccc(N(C(=O)OC(C)(C)C)C(=O)OC(C)(C)C)c1C(=O)OC]

Prepared by proceeding in a similar manner to Intermediate 46, starting from methyl 2-[bis-(tert-butyoxycarbonyl)amino]-6-hydroxybenzoate (Intermediate 55) and 1-bromobut-2-yne $^1$H NMR (CDCl$_3$) δ: 7.36 (1H, t), 7.08 (1H, dd), 6.82 (1H, dd), 4.70 (2H, q), 3.84 (3H, s), 1.84 (3H, t), 1.39 (18H, s).

Intermediate 55

Methyl 2-[bis-(tert-butyoxycarbonyl)amino]-6-hydroxybenzoate

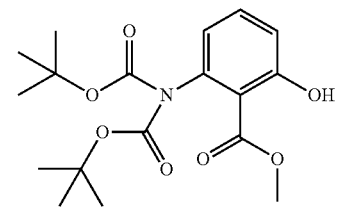 [SMILES: COC(=O)c1c(O)cccc1N(C(=O)OC(C)(C)C)C(=O)OC(C)(C)C]

Prepared by proceeding in a similar manner to Intermediate 4, starting from methyl 2-[bis-(tert-butoxycarbonyl)amino]-6-(4-methylbenzenesulfonyloxy)benzoate (Intermediate 56)

$^1$H NMR (CDCl$_3$) δ: 11.17 (1H, s), 7.40 (1H, t), 6.99 (1H, dd), 6.69 (1H, dd), 3.92 (3H, s), 1.37 (18H, s).

Intermediate 56

Methyl 2-[bis-(tert-butoxycarbonyl)amino]-6-(4-methylbenzenesulfonyloxy)-benzoate

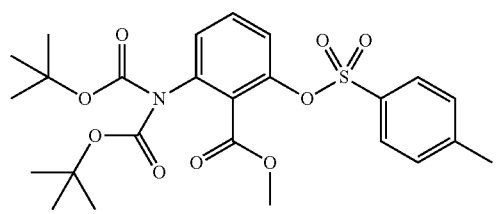 [SMILES: COC(=O)c1c(OS(=O)(=O)c2ccc(C)cc2)cccc1N(C(=O)OC(C)(C)C)C(=O)OC(C)(C)C]

Prepared by proceeding in a similar manner to Intermediate 6, starting from methyl 2-amino-6-hydroxybenzoate (prepared according to Comess et al, US2004 0167128)

$^1$H NMR (CDCl$_3$) δ: 7.72 (2H, d), 7.40 (1H, t), 7.31 (2H, d), 7.22 (1H, dd), 7.11 (1H, dd), 3.71 (3H, s), 2.44 (3H, s), 1.33 (18H, s).

Intermediate 57

Cis-(3aRS,9bRS)-7-(2-fluorobenzenesulfonylamino)-1,3a,4,9b-tetrahydro-2H-furo[2,3-c]chromene-6-carboxylic acid

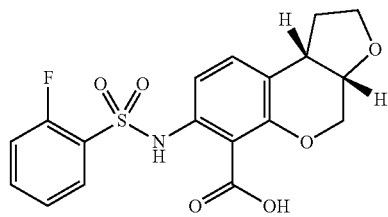

Mixture of cis enantiomers

A mixture of lithium hydroxide (0.5 g) and methyl cis-(3aRS,9bRS)-7-(2-fluorobenzenesulfonyl-amino)-1,3a,4,9b-tetrahydro-2H-furo[2,3-c]chromene-6-carboxylate (Intermediate 58, 0.217 g) in a mixture of dioxane (13 mL) and water (4 mL) was divided between two microwave vials and the mixtures were irradiated in the microwave at 150° C. for 10 minutes. After cooling, the combined mixture was acidified by addition of 10% aqueous citric acid (2 mL), extracted with DCM, dried (MgSO$_4$) and filtered. The filtrate was evaporated to dryness to give cis-(3aRS,9bRS)-7-(2-fluorobenzenesulfonylamino)-1,3a,4,9b-tetrahydro-2H-furo[2,3-c]chromene-6-carboxylic acid (0.518 g) as a glass.

$^1$H NMR (CDCl$_3$) δ: 12.00 (1H, br s), 11.57 (1H, br s), 7.97 (1H, dt), 7.55 (1H, m), 7.43 (1H, d), 7.26 (2H, m), 7.15 (1H, t), 4.43 (1H, dd), 4.37 (1H, m), 4.14 (1H, dd), 3.83 (2H, m), 3.50 (1H, m), 2.50 (1H, m), 1.87 (1H, m).

Intermediate 58

Methyl cis-(3aRS,9bRS)-7-(2-fluorobenzenesulfonylamino)-1,3a,4,9b-tetrahydro-2H-furo[2,3-c]chromene-6-carboxylate

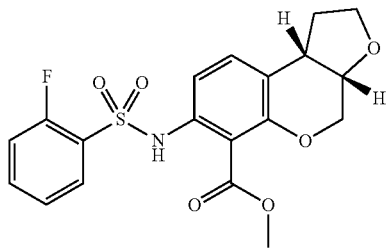

Mixture of cis enantiomers

2-Fluorobenzenesulfonyl chloride (0.5 g) was added to a solution of methyl cis-(3aRS,9bRS)-7-amino-1,3a,4,9b-tetrahydro-2H-furo[2,3-c]chromene-6-carboxylate (Intermediate 19, 0.53 g) in DCM (10 mL) and pyridine (20 mL) and the resultant mixture was stirred at room temperature for 48 hours. The mixture was evaporated to dryness and the residue was treated with water, extracted with DCM, dried (MgSO$_4$) and filtered. The filtrate was evaporated to dryness and the residue was purified by chromatography on silica, eluting with a mixture of ethyl acetate and cyclohexane with a gradient of 0-60% to give methyl cis-(3aRS,9bRS)-7-(2-fluorobenzenesulfonylamino)-1,3a,4,9b-tetrahydro-2H-furo[2,3-c]chromene-6-carboxylate (0.574 g) as a pale yellow solid.

$^1$H NMR (CDCl$_3$) δ: 9.11 (1H, s), 7.85 (1H, dt), 7.53 (1H, m), 7.23 (1H, d), 7.21 (1H, dt), 7.15 (1H, d), 7.13 (1H, dd), 4.28 (1H, m), 4.04 (1H, dd), 3.95 (1H, dd), 3.87 (3H, s), 3.82 (2H, m), 3.41 (1H, m), 2.45 (1H, m), 1.84 (1H, m).

Intermediate 59

Methyl (1aRS,7bSR)-5-[2-((Z)-3-diethylaminoprop-1-enyl)-4-fluorobenzenesulfonylamino]-1,1-difluoro-1,1a,2,7b-tetrahydro-cyclopropa[c]chromene-4-carboxylate

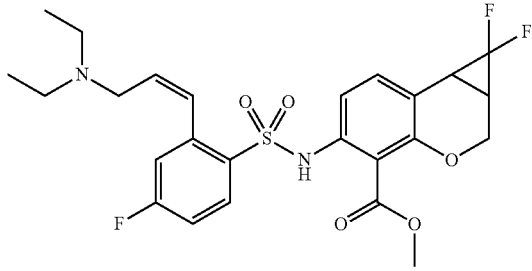 [SMILES: CCN(CC)C/C=C\c1cc(F)ccc1S(=O)(=O)Nc1ccc2c(c1C(=O)OC)OCC1C2C1(F)F]

Prepared by proceeding in a similar manner to Intermediate 9, starting from methyl (1aRS,7bSR)-5-(2-bromo-4-fluorobenzenesulfonylamino)-1,1-difluoro-1,1a,2,7b-tetrahydro-cyclopropa[c]chromene-4-carboxylate (Intermediate 60) and N,N-diethyl-N—((Z)-1-tributylstannanylprop-1-en-3-yl)amine (Intermediate 11) as a pale yellow gum.

$^1$H NMR (CDCl$_3$) δ: 8.11 (1H, dd), 7.18 (1H, d), 7.13-7.04 (2H, m), 6.98 (1H, d), 6.93 (1H, d), 6.08 (1H, m), 4.38 (1H, d), 4.02 (1H, m), 3.87 (3H, s), 3.23-3.04 (2H, br s), 2.67 (1H, t), 2.60-2.43 (4H, br s), 3.32 (1H, m), 0.94 (6H, t).

Intermediate 60

Methyl (1aRS,7bSR)-5-(2-bromo-4-fluorobenzenesulfonylamino)-1,1-difluoro-1,1a,2,7b-tetrahydrocyclopropa[c]chromene-4-carboxylate

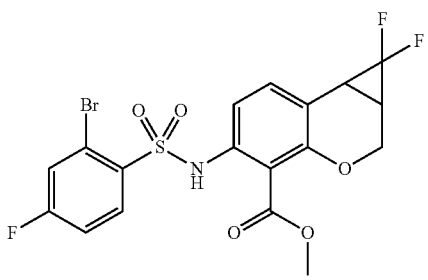 [SMILES: COC(=O)c1c(NS(=O)(=O)c2ccc(F)cc2Br)ccc2c1OCC1C2C1(F)F]

Prepared by proceeding in a similar manner to Intermediate 18, starting from methyl (1aRS,7bSR)-5-amino-1,1-difluoro-1,1a,2,7b-tetrahydrocyclopropa[c]chromene-4-carboxylate (Intermediate 61) and 2-bromo-4-fluorobenzene sulfonyl chloride, as a colourless foam.

$^1$H NMR (CDCl$_3$) δ: 9.58 (1H, s), 8.18 (1H, dd), 7.42 (1H, dd), 7.20 (1H, d), 7.13 (1H, d), 7.16-7.08 (1H, m), 4.38 (1H, d), 4.03 (1H, m), 3.91 (3H, s), 2.67 (1H, t), 2.32 (1H, m).

Intermediate 61

Methyl (1aRS,7bSR)-5-amino-1,1-difluoro-1,1a,2,7b-tetrahydrocyclopropa-[c]chromene-4-carboxylate

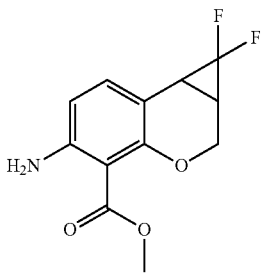 [SMILES: COC(=O)c1c(N)ccc2c1OCC1C2C1(F)F]

Prepared by proceeding in a similar manner to Intermediate 42, starting from methyl (1aRS,7bSR)-5-(2,2-dimethylpropionylamino)-1,1-difluoro-1,1a,2,7b-tetrahydro-cyclopropa[c]chromene-4-carboxylate (Intermediate 62) as an off white solid.

$^1$H NMR (CDCl$_3$) δ: 7.07 (1H, d), 6.30 (1H, d), 5.19-4.95 (2H, br s), 4.32 (1H, d), 4.11 (1H, m), 3.87 (3H, s), 2.60 (1H, t), 2.27 (1H, m).

Intermediate 62

Methyl (1aRS,7bSR)-5-(2,2-dimethylpropionylamino)-1,1-difluoro-1,1a,2,7b-tetrahydrocyclopropa[c]chromene-4-carboxylate

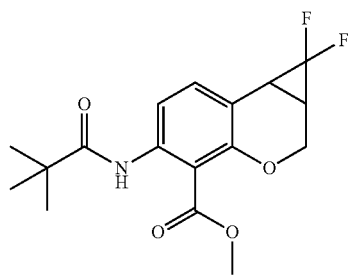 [SMILES: COC(=O)c1c(NC(=O)C(C)(C)C)ccc2c1OCC1C2C1(F)F]

Methyl 7-(2,2-dimethylpropionylamino)-2H-chromene-8-carboxylate (Intermediate 45, 1.0 g) was dissolved in diglyme (30 mL) and the solution was heated to 160° C. Sodium chlorodifluoroacetate (4.27 g) was added in portions over 15 minutes with the final portion being washed in with diglyme (15 mL). On completion of the addition the mixture was heated at 180° C. for 15 minutes. After cooling, the mixture was poured into water and extracted with ethyl acetate, washed with water, dried (MgSO$_4$) and filtered. The filtrate was evaporated to dryness and the residue was purified by chromatography on silica, eluting with a mixture of ethyl acetate and pentane with a gradient of 2.5-15% to give methyl (1aRS,7bSR)-5-(2,2-dimethylpropionylamino)-1,1-difluoro-1,1a,2,7b-tetrahydro-cyclopropa[c]chromene-4-carboxylate (0.66 g) as a colourless oil.

$^1$NMR (CDCl$_3$) δ: 9.86 (1H, br s), 8.12 (1H, d), 7.33 (1H, d), 4.41 (1H, d), 4.07 (1H, m), 3.92 (3H, s), 2.74 (1H, t), 2.34 (1H, m), 1.29 (9H, s).

Intermediate 63

Methyl (1aRS,7bSR)-5-[2-((Z)-3-ethylaminoprop-1-enyl)-4-fluorobenzenesulfonylamino]-1,1a,2,7b-tetrahydrocyclopropa[c]chromene-4-carboxylate

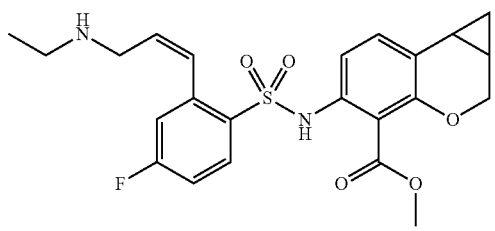 [SMILES: CCNC/C=C\c1cc(F)ccc1S(=O)(=O)Nc1ccc2c(c1C(=O)OC)OCC1CC21]

Methane sulfonic anhydride (0.09 g) was added to a stirred, cooled mixture of methyl (1aRS,7bSR)-5-{N-[methoxycarbonyl]-N-[2-((Z)-3-hydroxyprop-1-enyl)-4-fluorobenzenesulfonyl]amino}-1,1a,2,7b-tetrahydrocyclopropa[c]chromene-4-carboxylate (Intermediate 64, 0.17 g) and N,N-di-isopropyl-N-ethylamine (0.134 g) in DCM (10 mL) at 0° C. The temperature was allowed to rise to room temperature and the mixture was stirred for 2 hours. A solution of ethylamine (2M in toluene, 2 mL) was added and the resultant mixture was stirred at room temperature for 3 hours then diluted with water. The organic layer was separated, dried (Na$_2$SO$_4$) and filtered. The filtrate was evaporated to dryness to give methyl (1aRS,7bSR)-5-[2((Z)-3-ethylaminoprop-1-enyl)-4-fluorobenzenesulfonyl-amino]-1,1a,2,7b-tetrahydro-cyclopropa[c]chromene-4-carboxylate (0.09 g) as a white solid.

$^1$H NMR (DMSO-d$_6$) δ: 7.89 (1H, dd), 7.35 (1H, d), 7.16 (1H, m), 7.08 (1H, d), 6.83 (1H, d), 6.58 (1H, d), 5.69 (1H, m), 4.17 (1H, d), 3.84-3.04 (2H, br s), 3.67 (3H, s), 3.58 (1H, d), 2.78 (2H, m), 1.83 (1H, m), 1.66 (1H, m), 1.04 (3H, t), 0.88 (1H, m), 0.64 (1H, m).

Intermediate 64

Methyl (1aRS,7bSR)-5-{N-[2-((Z)-3-hydroxyprop-1-enyl)-4-fluorobenzene-sulfonyl]-N-[methoxycarbonyl]amino}-1,1a,2,7b-tetrahydrocyclopropa-[c]chromene-4-carboxylate

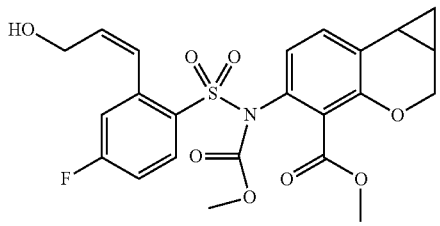 [SMILES: COC(=O)c1c(N(C(=O)OC)S(=O)(=O)c2ccc(F)cc2/C=C\CO)ccc2c1OCC1CC21]

A mixture of methyl (1aRS,7bSR)-5-[N-(2-bromo-4-fluorobenzenesulfonyl)-N-(methoxycarbonyl)amino]-1,1a,2,7b-tetrahydrocyclopropa-[c]chromene-4-carboxylate (Intermediate 65, 0.6 g), (Z)-3-tributylstannanylprop-2-en-1-ol (Intermediate 12, 0.81 g), tris-(dibenzylideneacetone)dipalladium (0.1 g) and tri-tert-butylphosphonium tetrafluoroborate (0.07 g) in dioxane (18 mL) and DMSO (2 mL) was stirred at room temperature for 30 minutes. The resultant mixture was diluted with ethyl acetate and washed with water, dried (Na$_2$SO$_4$) and filtered. The filtrate was evaporated to dryness and the residue was purified by chromatography on silica, eluting with a mixture of ethyl acetate and petroleum ether with a gradient of 30-50% to give methyl (1aRS,7bSR)-5-{N-[2-((Z)-3-hydroxyprop-1-enyl)-4-fluorobenzenesulfonyl]-N-[methoxycarbonyl]amino}-1,1a,2,7b-tetrahydrocyclopropa-[c]chromene-4-carboxylate (0.55 g) as an off-white solid.

$^1$H NMR (CDCl$_3$) δ: 8.19 (1H, m), 7.39 (1H, d), 7.16 (1H, m), 7.02 (1H, m), 6.96 (2H, m), 6.03 (1H, m), 4.41 (1H, m), 4.23 (2H, m), 3.88 (1H, dd), 3.71 (3H, 2s), 3.65 (3H, 2s), 2.06 (1H, m), 1.82 (1H, m), 1.25 (1H, m), 1.14 (1H, m).

Intermediate 65

Methyl (1aRS,7bSR)-5-[N-(2-bromo-4-fluorobenzenesulfonyl)-N-(methoxycarbonyl)amino]-1,1a,2,7b-tetrahydrocyclopropa-[c]chromene-4-carboxylate

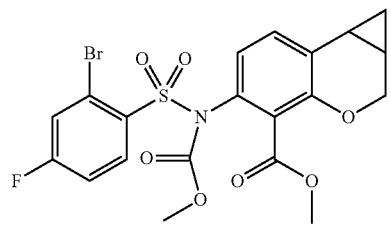 [SMILES: COC(=O)c1c(N(C(=O)OC)S(=O)(=O)c2ccc(F)cc2Br)ccc2c1OCC1CC21]

A solution of methyl (1aRS,7bSR)-5-(2-bromo-4-fluorobenzenesulfonylamino)-1,1a,2,7b-tetrahydrocyclopropa[c]chromene-4-carboxylate (Intermediate 41, 1.7 g) in THF (20 mL) was added to a suspension of sodium hydride (70% oil dispersion, 0.2 g) in THF (10 mL). The resultant solution was stirred for 30 minutes then methyl chloroformate (0.53 g) was added. The resultant mixture was stirred at room temperature overnight. Saturated aqueous sodium bicarbonate was added and the mixture was extracted with ethyl acetate, dried (Na₂SO₄) and filtered. The filtrate was evaporated to dryness and the residue was purified by chromatography on silica, eluting with a mixture of ethyl acetate and petroleum ether (30%) to give methyl (1aRS,7bSR)-5-[N-(2-bromo-4-fluorobenzenesulfonyl)-N-(methoxycarbonyl)amino]-1,1a,2,7b-tetrahydrocyclopropa-[c]chromene-4-carboxylate (1.6 g) as a white solid.

¹H NMR (CDCl₃) δ: 8.42 (1H, m), 7.48 (1H, dd), 7.37 (1H, d), 7.19 (2H, m), 4.42 (1H, m), 3.95 (1H, dd), 3.86 (3H, s), 3.69 (3H, s), 2.06 (1H, m), 1.84 (1H, m), 1.16 (2H, m).

Intermediate 66

Methyl (1aRS,7bSR)-5-{2[(Z)-3-(pyrrolidin-1-yl)prop-1-enyl]-4-fluorobenzenesulfonylamino}-1,1a,2,7b-tetrahydrocyclopropa[c]chromene-4-carboxylate

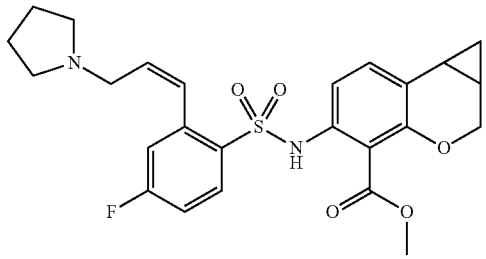 [SMILES: COC(=O)c1c(NS(=O)(=O)c2ccc(F)cc2/C=C\CN2CCCC2)ccc2c1OCC1CC21]

Prepared by proceeding in a similar manner to Intermediate 63, starting from methyl (1aRS,7bSR)-5-{N—[methoxycarbonyl]-N-[2-((Z)-3-hydroxyprop-1-enyl)-4-fluorobenzenesulfonyl]amino}-1,1a,2,7b-tetrahydrocyclopropa[c]chromene-4-carboxylate (Intermediate 64) and pyrrolidine as a brown oil.

LCMS (Method D) r/t 1.28 (M+H) 487

Intermediate 67

(1aRS,7bSR)-5-(2-Fluorobenzenesulfonylamino)-1,1a,2,7b-tetrahydro-cyclopropa[c]chromene-4-carboxylic acid

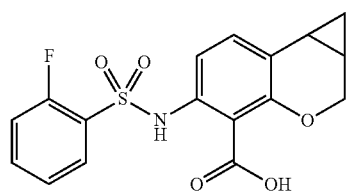 [SMILES: O=C(O)c1c(NS(=O)(=O)c2ccccc2F)ccc2c1OCC1CC21]

A mixture of methyl (1aRS,7bSR)-5-(2-Fluorobenzenesulfonylamino)-1,1a,2,7b-tetrahydrocyclopropa[c]chromene-4-carboxylate (Intermediate 68, 0.6 g) and lithium hydroxide monohydrate (1.5 g) in dioxane (45 mL) and water (13.8 mL) was stirred and heated at 100° C. overnight. After cooling, the mixture was concentrated under vacuum and the residue was diluted with water and acidified to pH3 with 1M hydrochloric acid. The precipitated solid was collected by filtration to give (1aRS,7bSR)-5-(2-fluorobenzenesulfonylamino)-1,1a,2,7b-tetrahydrocyclopropa[c]chromene-4-carboxylic acid (0.58 g) as a white solid.

¹H NMR (DMSO-d₆) ε: 13.05 (1H, br s), 9.96 (1H, s), 7.73 (2H, m), 7.45-7.31 (2H, m), 7.23 (1H, d), 6.64 (1H, d), 4.29 (1H, d), 3.74 (1H, d), 2.01 (1H, m), 1.80 (1H, m), 1.02 (1H, m), 0.81 (1H, m).

Intermediate 68

Methyl (1aRS,7bSR)-5-(2-fluorobenzenesulfonylamino)-1,1a,2,7b-tetrahydrocyclopropa[c]chromene-4-carboxylate

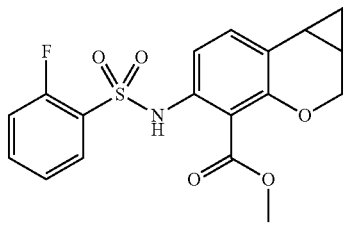

Prepared by proceeding in a similar manner to Intermediate 41, starting from methyl (1aRS,7bSR)-5-amino-1,1a,2,7b-tetrahydrocyclopropa[c]chromene-4-carboxylate (Intermediate 42) and 2-fluorobenzenesulfonyl chloride.

¹H NMR (CDCl₃) δ: 8.90 (1H, s), 7.84 (1H, dt), 7.53 (1H, m), 7.24-7.11 (4H, m), 4.34 (1H, d), 3.88 (3H, s), 3.80 (1H, dd), 1.91 (1H, m), 1.74 (1H, m), 1.02 (2H, m).

Intermediate 69

Methyl (1aRS,7bSR)-5-{2[(Z)-3-(propan-2-yl)aminoprop-1-enyl]-4-fluorobenzenesulfonylamino}-1,1a,2,7b-tetrahydrocyclopropa[c]chromene-4-carboxylate

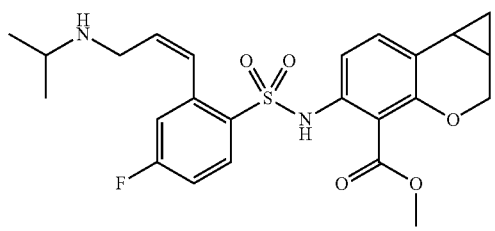

Prepared by proceeding in a similar manner to Intermediate 63, starting from methyl (1aRS,7bSR)-5-{N-[methoxycarbonyl]-N-[2-((Z)-3-hydroxyprop-1-enyl)-4-fluorobenzene-sulfonyl]amino}-1,1a,2,7b-tetrahydrocyclopropa[c]chromene-4-carboxylate (Intermediate 64) and 2-aminopropane.

LCMS (Method D) r/t 1.17 (M+H) 475.

Intermediate 70

Methyl (1aRS,7bSR)-5-{2[(Z)-3-((S)-3-hydroxypyrrolidin-1-yl)aminoprop-1-enyl]-4-fluorobenzenesulfonylamino}-1,1a,2,7b-tetrahydrocyclopropa[c]chromene-4-carboxylate

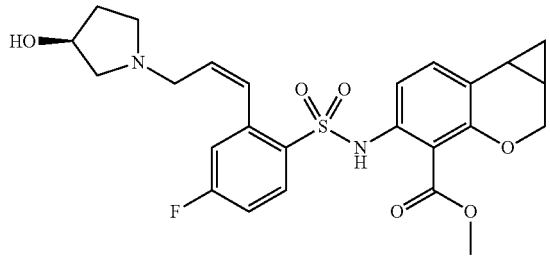 [SMILES: COC(=O)c1c(NS(=O)(=O)c2ccc(F)cc2/C=C\CN2CC[C@H](O)C2)ccc2c1OCC1CC21]

Prepared by proceeding in a similar manner to Intermediate 63, starting from methyl (1aRS,7bSR)-5-{N—[methoxycarbonyl]-N-[2-((Z)-3-hydroxyprop-1-enyl)-4-fluorobenzene-sulfonyl]amino}-1,1a,2,7b-tetrahydrocyclopropa[c]chromene-4-carboxylate (Intermediate 64) and (S)-3-hydroxypyrrolidine.
LCMS (Method D) r/t 1.14 (M+H) 503.

Intermediate 71

Methyl (1aRS,7bSR)-5-{2[(Z)-3-((R)-3-hydroxypyrrolidin-1-yl)aminoprop-1-enyl]-4-fluorobenzenesulfonylamino}-1,1a,2,7b-tetrahydro 1 cyclopropa[c]chromene-4-carboxylate

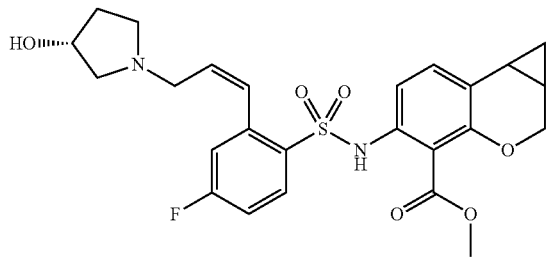 [SMILES: COC(=O)c1c(NS(=O)(=O)c2ccc(F)cc2/C=C\CN2CC[C@@H](O)C2)ccc2c1OCC1CC21]

Prepared by proceeding in a similar manner to Intermediate 63, starting from methyl (1aRS,7bSR)-5-{N—[methoxycarbonyl]-N-[2-((Z)-3-hydroxyprop-1-enyl)-4-fluorobenzene-sulfonyl]amino}-1,1a,2,7b-tetrahydrocyclopropa[c]chromene-4-carboxylate (Intermediate 64) and (R)-3-hydroxypyrrolidine and used without further characterisation.

Intermediate 72

Methyl (1aRS,7bSR)-5-{N-(methoxycarbonyl)-N—[2((Z)-4-diethylaminobut-1-enyl)-4-fluorobenzenesulfonyl]amino}-1,1a,2,7b-tetrahydrocyclopropa[c]chromene-4-carboxylate

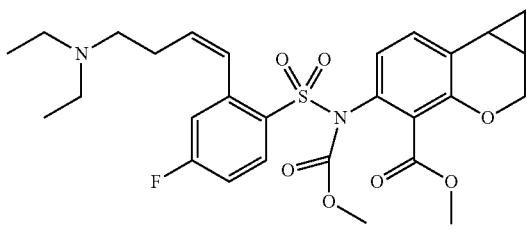 [SMILES: CCN(CC)CC/C=C\c1cc(F)ccc1S(=O)(=O)N(C(=O)OC)c1ccc2c(c1C(=O)OC)OCC1CC21]

Methyl sulfonic anhydride (0.062 g) was added to a stirred, cooled mixture of methyl (1aRS,7bSR)-5-{N-[methoxycarbonyl]-N-[2-((Z)-4-hydroxybut-1-enyl)-4-fluorobenzene-sulfonyl]amino}-1,1a,2,7b-tetrahydrocyclopropa[c]chromene-4-carboxylate (Intermediate 73, 0.12 g) and N,N-di-isopropyl-N-ethylamine (0.046 g) in DCM (15 mL) at 0° C. The resultant mixture was stirred at 0° C. for 20 minutes. Diethylamine (0.026 g) was added and the mixture was then stirred at room temperature for 24 hours. The mixture was diluted with water and extracted with DCM, dried ($Na_2SO_4$) and filtered. The filtrate was evaporated to dryness and the residue was purified by chromatography on silica, eluting with a mixture of methanol and DCM with a gradient of 2-10% to give methyl (1aRS,7bSR)-5-{N-(methoxycarbonyl)-N—[2((Z)-4-diethylaminobut-1-enyl)-4-fluorobenzenesulfonyl]amino}-1,1a,2,7b-tetrahydrocyclopropa-[c]chromene-4-carboxylate (0.08 g) as alight yellow solid.
LCMS (Method D) r/t1.22 (M+H) 561.

Intermediate 73

Methyl (1aRS,7bSR)-5-{N-[methoxycarbonyl]-N-[2-((Z)-4-hydroxybut-1-enyl)-4-fluorobenzenesulfonyl]amino}-1,1a,2,7b-tetrahydrocyclopropa[c]chromene-4-carboxylate

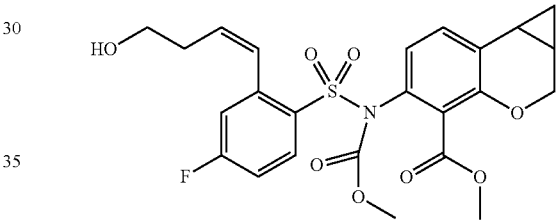

Prepared by proceeding in a similar manner to Intermediate 64, starting from methyl (1aRS,7bSR)-5-[N-(2-bromo-4-fluorobenzenesulfonyl)-N-(methoxycarbonyl)amino]-1,1a,2,7b-tetrahydrocyclopropa-[c]chromene-4-carboxylate (Intermediate 65) and (Z)-4-tributylstannanylprop-3-en-1-ol (prepared according to Miura et al, Organic Letters, 2005, 7(3) 503).
$^1$H NMR (CDCl$_3$) δ: 8.18 (1H, m), 7.38 (1H, d), 7.13 (3H, m), 6.96 (1H, d), 5.91 (1H, m), 4.44 (1H, m), 3.98 (1H, dd), 3.79 (3H, s), 3.75 (2H, m), 3.65 (3H, s), 2.49 (2H, m), 2.07 (1H, m), 1.81 (1H, m), 1.27 (1H, m), 1.15 (1H, m).

Intermediate 74

(1aRS,7bSR)-5-(4-Fluoro-2-vinylbenzenesulfonylamino)-1,1a,2,7b-tetrahydrocyclopropa[c]chromene-4-carboxylic acid

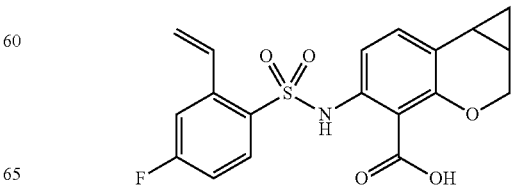

Lithium hydroxide (0.101 g) was added to a solution of methyl (1aRS,7bSR)-5-(4-fluoro-2-vinylbenzenesulfonylamino)-1,1a,2,7b-tetrahydrocyclopropa[c]chromene-4-carboxylate (Intermediate 75, 0.150 g) in a mixture of dioxane (3 mL) and water (0.6 mL) and the mixture was irradiated in the microwave at 130° C. for 30 minutes. After cooling, the mixture evaporated to dryness and the residue was acidified by addition of 10% aqueous citric acid (2 mL), extracted with DCM, dried (MgSO$_4$) and filtered. The filtrate was evaporated to dryness and the residue was purified by chromatography on silica eluting with a mixture of methanol and DCM with a gradient of 0-10% to give (1aRS,7bSR)-5-(4-fluoro-2-vinylbenzenesulfonylamino)-1,1a,2,7b-tetrahydrocyclopropa[c]chromene-4-carboxylic acid (0.0.35 g) as a glass.

$^1$H NMR (CDCl$_3$) δ: 11.69 (1H, br s), 8.10 (1H, dd), 7.50 (1H, dd), 7.31-7.17 (3H, m), 7.03 (1H, dt), 5.60 (1H, d), 5.50 (1H, d), 4.60 (1H, d), 4.04 (1H, d), 1.97 (1H, m), 1.81 (1H, m), 1.20 (1H, m), 0.99 (1H, m).

Intermediate 75

Methyl (1aRS,7bSR)-5-(4-fluoro-2-vinylbenzenesulfonylamino)-1,1a,2,7b-tetrahydrocyclopropa[c]chromene-4-carboxylate

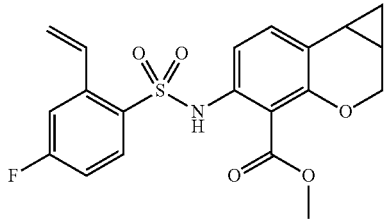 [SMILES: C=Cc1cc(F)ccc1S(=O)(=O)Nc1ccc2c(c1C(=O)OC)OCC1CC21]

A mixture of methyl (1aRS,7bSR)-5-(2-bromo-4-fluorobenzenesulfonylamino)-1,1a,2,7b-tetrahydrocyclopropa[c]chromene-4-carboxylate (Intermediate 41, 0.1 g), vinyl boronic acid pinacol ester (0.073 g), bis(triphenylphospine) palladium (II) chloride (0.034 g) and cesium carbonate (0.215 g) in dioxane (5 mL) and water (1 ml) was degassed and purged with argon then irradiated in a microwave at 130° C. for 20 minutes. After cooling, the mixture was partitioned between 1M hydrochloric acid and ethyl acetate. The organic layer was dried (MgSO$_4$) and filtered and the filtrate evaporated to dryness to give methyl (1aRS,7bSR)-5-(4-fluoro-2-vinylbenzenesulfonyl-amino)-1,1a,2,7b-tetrahydrocyclopropa[c]chromene-4-carboxylate (0.15 g) as a yellow glass.

$^1$H NMR (CDCl$_3$) δ: 8.99 (1H, br s), 7.97 (1H, dd), 7.38 (1H, dd), 7.21 (1H, dd), 7.18 (1H, d), 7.05 (1H, d), 7.00 (1H, m), 5.59 (1H, d), 5.38 (1H, d), 4.32 (1H, d), 3.77 (4H, m), 1.90 (1H, dt), 1.71 (1H, m), 1.00 (2H, m).

Intermediate 76

Methyl (1aRS,7bSR)-5-{2-[(Z)-3-(azetidin-1-yl)prop-1-enyl]-4-fluoro-benzenesulfonylamino}-1,1a,2,7b-tetrahydrocyclopropa[c]chromene-4-carboxylate

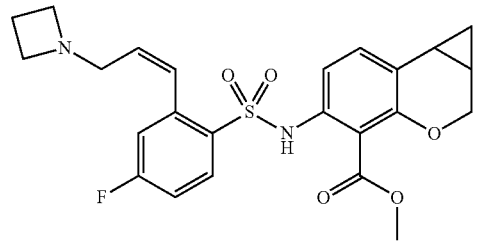 [SMILES: COC(=O)c1c(NS(=O)(=O)c2ccc(F)cc2/C=C\CN2CCC2)ccc2c1OCC1CC21]

Prepared by proceeding in a similar manner to Intermediate 63, starting from methyl (1aRS,7bSR)-5-{N—[methoxycarbonyl]-N-[2-((Z)-3-hydroxyprop-1-enyl)-4-fluorobenzene-sulfonyl]amino}-1,1a,2,7b-tetrahydrocyclopropa[c]chromene-4-carboxylate (Intermediate 64) and azetidine as a yellow oil.

LCMS (Method D) r/t 1.17 (M+H) 473.

Intermediate 77

Methyl (1aRS,7bSR)-5-{2-[(Z)-3-(3-hydroxyazetidin-1-yl)prop-1-enyl]-4-fluorobenzenesulfonylamino}-1,1a,2,7b-tetrahydrocyclopropa[c]chromene-4-carboxylate

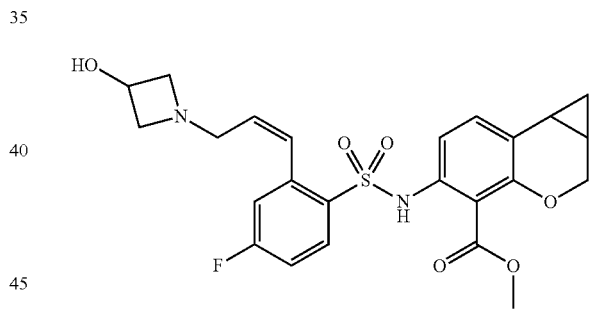

Prepared by proceeding in a similar manner to Intermediate 63, starting from methyl (1aRS,7bSR)-5-{N-[methoxycarbonyl]-N-[2-((Z)-3-hydroxyprop-1-enyl)-4-fluorobenzene-sulfonyl]amino}-1,1a,2,7b-tetrahydrocyclopropa[c]chromene-4-carboxylate (Intermediate 64) and 3-hydroxyazetidine as a yellow oil.

LCMS (Method D) r/t 1.15 (M+H) 489.

Intermediate 78

N-(4-Dimethylaminobutyl)-N-methylamine

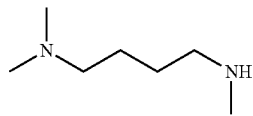

A solution of lithium aluminium hydride in THF (1M, 28 mL) was added dropwise to a stirred, cooled solution of N-(4-dimethylaminobutyl)formamide (Intermediate 79, 2.7 g) in THF (60 mL) while maintaining the temperature at 0° C. under an atmosphere of nitrogen. On completion of the addition, the mixture was stirred and heated at 75° C. for 2 hours. The reaction mixture was cooled to 0° C. and ethanol was added then the mixture was evaporated to dryness. The residue was diluted with a mixture of diethyl ether and DCM (30%) and the solid was filtered off. The filtrate was evaporated to dryness to give N-(4-dimethylaminobutyl)-N-methylamine (1.5 g) as a yellow oil.

$^1$H NMR (CDCl$_3$) δ: 2.56 (2H, m), 2.41 (3H, s), 2.25 (2H, m), 2.20 (6H, s), 1.47 (4H, m).

Intermediate 79

N-(4-Dimethylaminobutyl)formamide

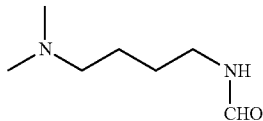

A solution of 4-dimethylaminobutylamine (3.0 g) in ethyl formate (30 mL) was stirred and heated at reflux under an atmosphere of nitrogen for 3 hours. After cooling, the mixture was evaporated to dryness and the residue was purified by chromatography on silica, eluting with a mixture of methanol and DCM (20%) to give N-(4-dimethylaminobutyl)formamide (2.7 g) as a pale yellow oil.

$^1$H NMR (CDCl$_3$) δ: 8.14 (1H, s), 6.80 (1H, s), 3.50 (2H, m), 2.28 (2H, m), 2.20 (6H, s), 1.61 (4H, m).

Intermediate 80

Methyl (1aRS,7bSR)-5-{2-[((S)-1-ethylpyrrolidin-3-ylcarbamoyl)methyl]-4-fluorobenzenesulfonylamino}-1,1a,2,7b-tetrahydrocyclopropa[c]chromene-4-carboxylate

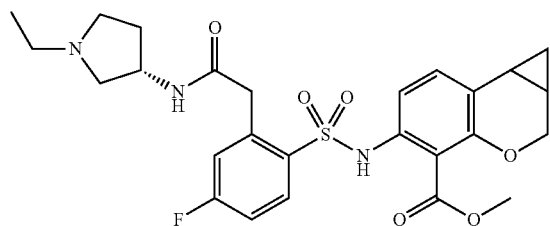 [SMILES: CCN1CC[C@H](NC(=O)Cc2cc(F)ccc2S(=O)(=O)Nc2ccc3c(c2C(=O)OC)OCC2CC32)C1]

A solution of methyl (1aRS,7bSR)-5-(2-carboxymethyl-4-fluorobenzenesulfonylamino)-1,1a,2,7b-tetrahydrocyclopropa[c]chromene-4-carboxylate (Intermediate 83, 0.180 g), (S)-1-ethylpyrrolidin-3-ylamine ditrifluoroacetic acid salt (Intermediate 81, 0.171 g), EDAC (0.144 g) and triethylamine (0.202 g) in DCM (5 mL) was allowed to stand at room temperature for 6 days then washed with water and filtered through a phase separator. The filtrate was directly purified by chromatography on silica, eluting with a mixture of methanol and DCM with a gradient of 0-20% to give methyl (1aRS,7bSR)-5-{2-[((S)-1-ethylpyrrolidin-3-ylcarbamoyl)methyl]-4-fluorobenzenesulfonylamino}-1,1a,2,7b-tetrahydrocyclopropa[c]chromene-4-carboxylate (0.178 g) as an off-white foam.

LCMS (Method E) r/t 2.57 (M+H) 532

Intermediate 81

(S)-1-Ethylpyrrolidin-3-ylamine ditrifluoroacetic acid salt

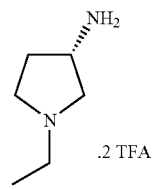

A solution of tert-butyl ((S)-1-ethylpyrrolidin-3-yl)carbamate (Intermediate 82, 0.107 g) in a solution of trifluoroacetic acid (2 mL) and DCM (2 mL) was left to stand at room temperature for 30 minutes then concentrated in vacuo. The residue was azeotroped with toluene to give (S)-1-ethylpyrrolidin-3-ylamine ditrifluoroacetic acid salt (0.231 g) as a light brown gum which was used without further characterisation.

Intermediate 82 tert-Butyl ((S)-1-ethylpyrrolidin-3-yl)carbamate

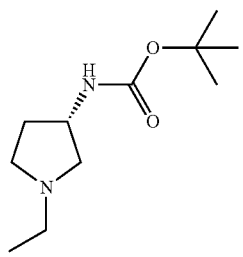

A mixture of tert butyl (S)-pyrrolidin-3-ylcarbamate (1.048 g), iodoethane (0.90 g) and potassium carbonate (1.55 g) in acetonitrile (15 mL) was stirred at room temperature for 17 hours then filtered. The filtrate was concentrated in vacuo and the residue was triturated with DCM and filtered. The filtrate was concentrated in vacuo and the residue was purified by chromatography on silica, eluting with a mixture of methanol and DCM with a gradient of 0-35% to give tert-butyl ((S)-1-ethylpyrrolidin-3-yl)carbamate (0.891 g) as a light coloured gum.

$^1$H NMR (CDCl$_3$) δ: 5.11 (1H, br, s), 4.29 (1H, br, s), 3.88 (1H, br, s), 3.18 (1H, br, s), 2.90 (2H, br, m), 2.76 (2H, br, m), 2.62 (1H, br, q), 2.38 (1H, m), 1.44 (9H, s), 1.28 (3H, t).

Intermediate 83

Methyl (1aRS,7bSR)-5-(2-carboxymethyl-4-fluorobenzenesulfonylamino)-1,1a,2,7b-tetrahydrocyclopropa[c]chromene-4-carboxylate

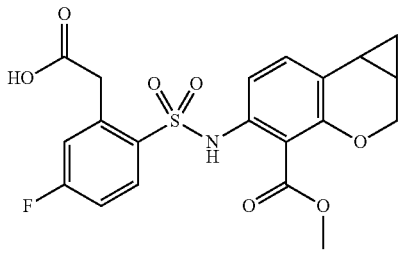 [SMILES: COC(=O)c1c(NS(=O)(=O)c2ccc(F)cc2CC(=O)O)ccc2c1OCC1CC21]

1M Sodium hydroxide solution (3 mL) was added to a solution of methyl (1aRS,7bSR)-5-(4-fluoro-2-methoxycarbonylmethylbenzenesulfonylamino)-1,1a,2,7b-tetrahydrocyclopropa-[c]chromene-4-carboxylate (Intermediate 84, 0.438 g) in methanol (6 mL) and the mixture was heated at 50° C. for 2 hours. After cooling, the mixture was evaporated to dryness and the residue was dissolved in ethyl acetate and water and acidified with concentrated hydrochloric acid. The organic layer was dried ($Na_2SO_4$) and filtered and the filtrate was concentrated in vacuo, the residue was dissolved in toluene and re-evaporated to give methyl (1aRS,7bSR)-5-(2-carboxymethyl-4-fluorobenzenesulfonylamino)-1,1a,2,7b-tetrahydrocyclopropa[c]chromene-4-carboxylate (0.422 g) as a white solid.

$^1$H NMR (CDCl$_3$) δ: 8.83 (1H, br, s), 7.86 (1H, dd), 7.22 (1H, d), 7.01 (3H, m), 4.32 (1H, d), 4.00 (2H, m), 3.76 (1H, d), 3.73 (3H, s), 1.94 (1H, m), 1.73 (1H, m), 1.02 (2H, m).

Intermediate 84

Methyl (1aRS,7bSR)-5-[4-fluoro-2-(methoxycarbonylmethyl)benzene-sulfonylamino]-1,1a,2,7b-tetrahydrocyclopropa[c]chromene-4-carboxylate

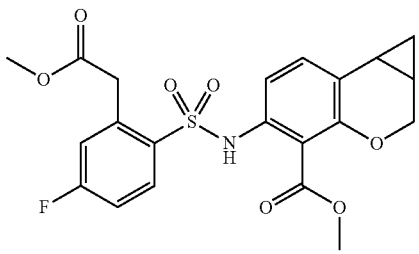 [SMILES: COC(=O)Cc1cc(F)ccc1S(=O)(=O)Nc1ccc2c(c1C(=O)OC)OCC1CC21]

A solution of methyl (2-chlorosulfonyl-5-fluorophenyl)acetate (Intermediate 85, 0.293 g) and methyl (1aRS,7bSR)-5-amino-1,1a,2,7b-tetrahydro-cyclopropa[c]chromene-4-carboxylate (Intermediate 42, 0.219 g) in pyridine (1 mL) and DCM (3 mL) was left to stand at room temperature for 4 days. The mixture was diluted with DCM, washed with 2M hydrochloric acid and filtered through a phase separator. The filtrate was concentrated in vacuo and the residue was purified by chromatography on silica, eluting with a mixture of ethyl acetate and cyclohexane with a gradient of 0-40% to give methyl (1aRS,7bSR)-5-[4-fluoro-2-(methoxycarbonylmethyl)-benzenesulfonylamino]-1,1a,2,7b-tetrahydrocyclopropa[c]chromene-4-carboxylate (0.438 g) as a colourless gum.

$^1$H NMR (CDCl$_3$) δ: 8.77 (1H, br, s), 7.84 (1H, dd), 7.22 (1H, d), 7.01 (3H, m), 4.33 (1H, d), 4.01 (2H, s), 3.79 (1H, d), 3.76 (3H, s), 3.69 (3H, s), 1.93 (1H, m), 1.73 (1H, m), 1.03 (2H, m).

Intermediate 85

Methyl (2-Chlorosulfonyl-5-fluorophenyl)acetate

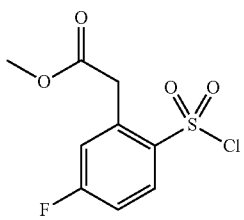 [SMILES: COC(=O)Cc1cc(F)ccc1S(=O)(=O)Cl]

Methyl (3-fluorophenyl)acetate (1.51 g) was added dropwise to chlorosulphonic acid (7 mL) with stirring and ice cooling. The cooling bath was removed and the mixture was allowed to stand at room temperature for 16 hours before being carefully added to a mixture of ice and ethyl acetate. The organic layer was separated, washed with water, dried (MgSO$_4$) and filtered. The filtrate was concentrated in vacuo and the residue was purified by chromatography on silica, eluting with a mixture of ethyl acetate and cyclohexane with a gradient of 0-20% to give methyl (2-chlorosulfonyl-5-fluorophenyl)acetate (1.42 g) as a white solid.

$^1$H NMR (CDCl$_3$) δ: 8.16 (1H, dd), 7.21 (2H, m), 4.19 (2H, s), 3.76 (3H, s).

Intermediate 86

Methyl (1aRS,7bSR)-5-[2-(1-ethylazetidin-3-yl)-4-fluorobenzene-sulfonylamino]-1,1a,2,7b-tetrahydrocyclopropa[c]chromene-4-carboxylate

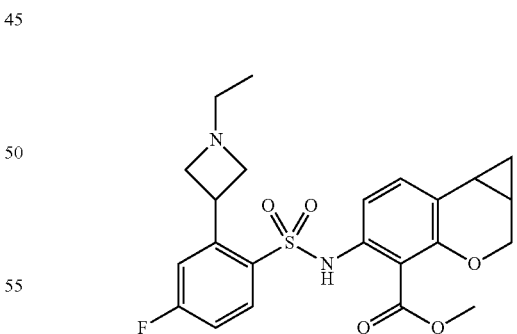

A mixture of methyl (1aRS,7bSR)-5-[2-(azetidin-3-yl)-4-fluorobenzenesulfonylamino]-1,1a,2,7b-tetrahydrocyclopropa[c]chromene-4-carboxylate (Intermediate 87, 0.216 g), iodoethane (0.078 g) and potassium carbonate (0.138 g) in acetonitrile (5 mL) was stirred at room temperature for 18 hours. The mixture was evaporated to dryness and the residue was purified by chromatography on silica, eluting with a mixture of methanol and DCM with a gradient of 0-15% to give methyl (1aRS,7bSR)-5-[2-(1-ethylazetidin-3- yl)-4-fluorobenzenesulfonylamino]-1,1a,2,7b-tetrahydrocyclopropa-[c]chromene-4-carboxylate (0.051 g).

¹H NMR (CDCl₃) δ: 7.97 (1H, dd), 7.62 (1H, dd), 7.24 (1H, d), 6.99 (1H, dt), 6.96 (1H, d), 4.35 (1H, d), 4.31 (1H, m), 3.79 (3H, s), 3.77 (1H, d), 3.58 (2H, m), 3.22 (2H, br, m), 2.53 (2H, q), 1.93 (1H, m), 1.74 (1H, q), 0.99 (5H, m).

Intermediate 87

Methyl (1aRS,7bSR)-5-[2-(azetidin-3-yl)-4-fluorobenzenesulfonylamino]-1,1a,2,7b-tetrahydrocyclopropa[c]chromene-4-carboxylate

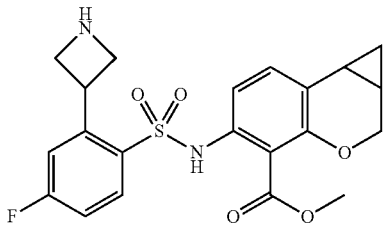 [SMILES: COC(=O)c1c(NS(=O)(=O)c2ccc(F)cc2C2CNC2)ccc2c1OCC1CC21]

A mixture of methyl (1aRS,7bSR)-5-{4-fluoro-2-[1-(2,2,2-trifluoroacetyl)azetidin-3-yl]benzene-sulfonylamino}-1,1a,2,7b-tetrahydrocyclopropa[c]chromene-4-carboxylate (Intermediate 88, 0.294 g) and potassium carbonate (0.155 g) in methanol (5 mL) and water (0.5 mL) was stirred at room temperature for 45 minutes. The mixture was concentrated in vacuo and the residue was triturated with 10% methanol in DCM and filtered. The filtrate was concentrated in vacuo and the residue was purified by chromatography on silica, eluting with a mixture of methanol and DCM with a gradient of 0-40% to give methyl (1aRS,7bSR)-5-[2-(azetidin-3-yl)-4-fluoro-benzenesulfonylamino)-1,1a,2,7b-tetrahydrocyclopropa[c]chromene-4-carboxylate (0.216 g) as a pale yellow foam.

¹H NMR (CDCl₃) δ: δ: 7.94 (1H, dd), 7.54 (1H, dd), 7.27 (1H, d), 7.09 (1H, dt), 6.99 (1H, d), 4.87 (1H, m), 4.32 (3H, m), 4.12 (2H, t), 3.78 (1H, m), 3.73 (3H, s), 1.94 (1H, m), 1.73 (1H, m), 0.99 (2H, m).

Intermediate 88

Methyl (1aRS,7bSR)-5-{4-fluoro-2-[1-(2,2,2-trifluoroacetyl)azetidin-3-yl]benzenesulfonylamino}-1,1a,2,7b-tetrahydrocyclopropa[c]chromene-4-carboxylate

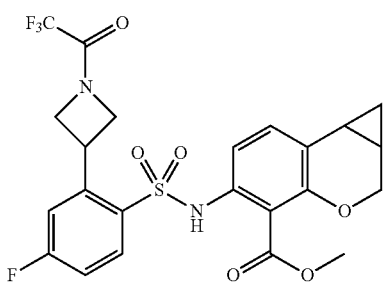 [SMILES: COC(=O)c1c(NS(=O)(=O)c2ccc(F)cc2C2CN(C(=O)C(F)(F)F)C2)ccc2c1OCC1CC21]

A solution of methyl 4-fluoro-2-[1-(2,2,2-trifluoroacetyl)azetidin-3-yl]benzenesulfonyl chloride (Intermediate 89, 0.192 g) and methyl (1aRS,7bSR)-5-amino-1,1a,2,7b-tetrahydrocyclopropa-[c]chromene-4-carboxylate (Intermediate 42, 0.122 g) in pyridine (1 mL) and DCM (3 mL) was left to stand at room temperature for 18 hours. The mixture was diluted with DCM, washed with 1M hydrochloric acid and filtered through a phase separator. The filtrate was concentrated in vacuo and the residue was purified by chromatography on silica, eluting with a mixture of ethyl acetate and cyclohexane with a gradient of 0-30% to give methyl (1aRS,7bSR)-5-{4-fluoro-2-[1-(2,2,2-trifluoro-acetyl)azetidin-3-yl]benzenesulfonylamino}-1,1a,2,7b-tetrahydrocyclopropa-[c]chromene-4-carboxylate (0.294 g) as a colourless gum.

¹H NMR (CDCl₃) δ: 8.99 (1H, br, s), 7.99 (1H, m), 7.81 (2H, m), 7.06 (2H, m), 4.68 (2H, m), 4.41 (1H, m), 4.34 (1H, d), 4.19 (1H, m), 4.08 (1H, m), 3.79 (1H, m), 3.72 (3H, s), 1.94 (1H, m), 1.75 (1H, m), 1.02 (2H, m).

Intermediate 89

4-Fluoro-2-[1-(2,2,2-trifluoroacetyl)-azetidin-3-yl]benzenesulfonyl chloride

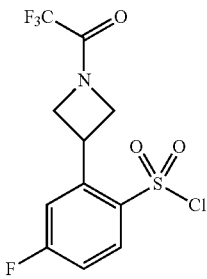 [SMILES: O=C(N1CC(c2cc(F)ccc2S(=O)(=O)Cl)C1)C(F)(F)F]

Chlorosulphonic acid (5 mL) was added to 2,2,2-trifluoro-1-[3-(3-fluorophenyl)azetidin-1-yl]ethanone (Intermediate 90, 1.15 g) with stirring and ice cooling. The mixture was stirred for 1 hour then poured carefully onto a mixture of ice and ethyl acetate. The organic layer was washed with water and concentrated in vacuo. The residue was purified by chromatography on silica, eluting with a mixture of ethyl acetate and cyclohexane with a gradient of 0-20% to give 4-fluoro-2-[1-(2,2,2-trifluoroacetyl)azetidin-3-yl]benzenesulfonyl chloride (0.910 g) as a white solid.

¹H NMR (CDCl₃) δ: 8.22 (1H, m), 7.51 (1H, dd), 7.26 (1H, m), 4.95 (2H, m), 4.70 (1H, t), 4.42 (1H, m), 4.31 (1H, m).

Intermediate 90

2,2,2-Trifluoro-1-[3-(3-fluorophenyl)azetidin-1-yl]ethanone

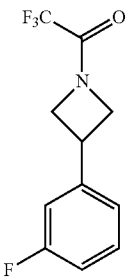 [SMILES: O=C(N1CC(c2cccc(F)c2)C1)C(F)(F)F]

A solution of tert-butyl 3-(3-fluorophenyl)azetidine-1-carboxylate (Intermediate 92, 2.51 g) in trifluoroacetic acid (15 mL) and DCM (15 mL) was left to stand at room temperature for 30 minutes. The mixture was concentrated in vacuo and the residue was azeotroped with toluene. The residue was dissolved in DCM (15 mL) and pyridine (5 mL) and trifluoroacetic anhydride (3.15 g) was added. The mixture was left to stand at room temperature for 30 minutes, then washed with 1M hydrochloric acid and filtered through a phase separator. The filtrate was concentrated in vacuo and the residue was purified by chromatography on silica, eluting with a mixture of ethyl acetate and cyclohexane with a gradient of 0-20% to give 2,2,2-trifluoro-1-[3-(3-fluorophenyl)azetidin-1-yl]ethanone (2.31 g) as a light brown oil.

$^1$H NMR (CDCl$_3$) δ: 7.36 (1H, m), 7.10 (1H, d), 7.02 (2H, m), 4.81 (1H, t), 4.57 (1H, t), 4.44 (1H, dd), 4.20 (1H, dd), 3.96 (1H, m).

Intermediate 91 tert-Butyl 3-(3-fluorophenyl)azetidine-1-carboxylate

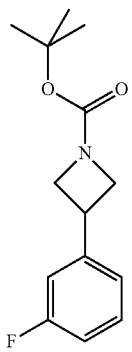 [SMILES: CC(C)(C)OC(=O)N1CC(c2cccc(F)c2)C1]

A solution of 1,2-dibromoethane (0.30 g) in anhydrous DMF (25 ml) was stirred with zinc dust (1.39 g) at 70° C. for 10 minutes then cooled to room temperature and chlorotrimethylsilane was (0.155 g) added. The resultant mixture was stirred at room temperature for 45 minutes. tert-Butyl 3-iodoazetidine-1-carboxylate (5 g) added and stirring was continued at 40° C. for 45 minutes then a solution of 3-fluoroiodobenzene (4.08 g), tris(dibenzylideneacetone)dipalladium(0) (0.325 g) and tris(2-furyl)phosphine (0.165 g) in DMF (15 mL) was added and the mixture was stirred at 70° C. for 3 hours. After cooling, the mixture was diluted with water and ethyl acetate and filtered through celite. The organic layer was washed twice with water, dried (Na$_2$SO$_4$) and filtered. The filtrate was concentrated in vacuo and the residue was purified by chromatography on silica, eluting with a mixture of ethyl acetate and cyclohexane with a gradient of 0-10%. The crude product was further purified by chromatography on silica, eluting with a mixture of DCM and cyclohexane with a gradient of 0-100% to give tert-butyl 3-(3-fluorophenyl)azetidine-1-carboxylate (2.52 g) as a colourless oil.

$^1$H NMR (CDCl$_3$) δ: 7.32 (1H, m), 6.90-7.11 (3H, m), 4.34 (2H, t), 3.95 (2H, dd), 3.72 (1H, m), 1.48 (9H, s).

Intermediate 92

Methyl (1aRS,7bSR)-5-{2-[((R)-1-ethylpyrrolidin-3-ylcarbamoyl)methyl]-4-fluorobenzenesulfonylamino}-1,1a,2,7b-tetrahydrocyclopropa[c]chromene-4-carboxylate

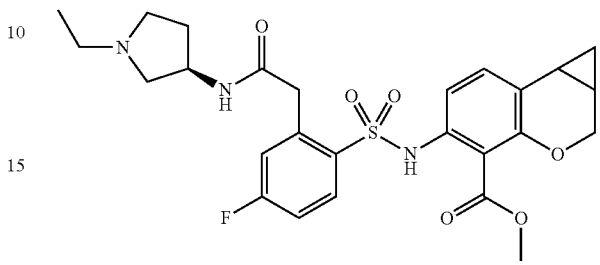

Prepared by proceeding in a similar manner to Intermediate 80, starting from methyl (1aRS,7bSR)-5-(2-carboxymethyl-4-fluorobenzenesulfonylamino)-1,1a,2,7b-tetrahydrocyclopropa[c]chromene-4-carboxylate (Intermediate 83) and (R)-1-ethylpyrrolidin-3-ylamine ditrifluoroacetic acid salt (Intermediate 93) as a light brown foam.

LCMS (Method E) r/t 2.57 (M+H) 532.

Intermediate 93

(R)-1-Ethylpyrrolidin-3-ylamine ditrifluoroacetic acid salt

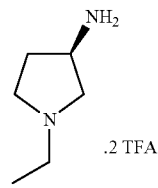

Prepared by proceeding in a similar manner to Intermediate 81, starting from tert-butyl ((R)-1-ethylpyrrolidin-3-yl)carbamate as a light brown gum which was used without further characterisation.

Intermediate 94 tert-Butyl ((R)-1-ethylpyrrolidin-3-yl)carbamate

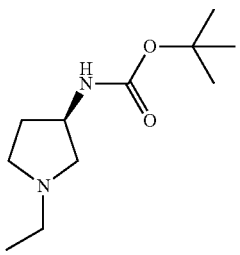

Prepared by proceeding in a similar manner to Intermediate 82, starting from tert butyl (R)-pyrrolidin-3-yl-carbamate and iodoethane as a light coloured gum.

¹H NMR (CDCl₃) δ: 5.09 (2H, br, s), 4.25 (1H, br, s), 3.08 (1H, br, s), 2.82 (2H, br, m), 2.69 (2H, br, q), 2.52 (1H, br, q), 2.35 (1H, m), 1.44 (9H, s), 1.21 (3H, t).

Intermediate 95

Methyl (1aS,7bR)-5-[2-((R)-1-ethylpyrrolidin-3-ylmethyl)-4-fluoro-benzenesulfonylamino]-1,1a,2,7b-tetrahydrocyclopropa[c]chromene-4-carboxylate

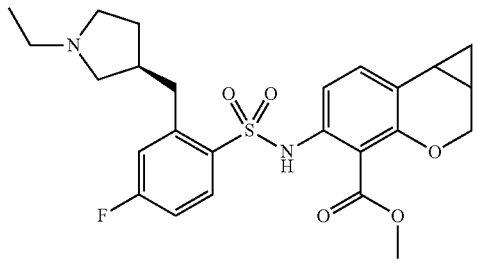 [SMILES: CCN1CC[C@@H](Cc2cc(F)ccc2S(=O)(=O)Nc2ccc3c(c2C(=O)OC)OCC2CC32)C1]

A solution of methyl (1aRS,7bSR)-5-amino-1,1a,2,7b-tetrahydrocyclopropa[c]chromene-4-carboxylate (Intermediate 42, 0.257 g) in DCM (10 mL) and pyridine (5 mL) was treated with a solution of 2-((R)-1-ethylpyrrolidin-3-ylmethyl)-4-fluorobenzenesulfonyl chloride (Intermediate 96, 0.36 g) in DCM (10 mL) and the mixture was stirred at room temperature overnight. The resultant mixture was evaporated to dryness and the residue was re-dissolved in DCM, washed with water, dried (MgSO₄) and filtered. The filtrate was evaporated to dryness and the residue was purified by chromatography on silica, eluting with a mixture of methanol and DCM with a gradient of 0-10%, then flushed with 100% methanol to give methyl (1 aS,7bR)-5-[2-((R)-1-ethylpyrrolidin-3-ylmethyl)-4-fluorobenzenesulfonylamino]-1,1a,2,7b-tetrahydrocyclopropa[c]chromene-4-carboxylate (0.13 g) as a gum.

¹H NMR (CDCl₃) δ: 7.88 (1H, br t), 7.23 (1H, d), 7.13 (1H, br d), 6.98 (2H, m), 4.33 (1H, d), 3.79 (1H, d), 3.77 (3H, s), 3.20-2.90 (6H, m) 2.24 (1H, br s), 2.04-1.18 (3H, br s), 1.93 (2H, dt), 1.74 (1H, q), 1.45 (3H, t), 1.02 (2H, m).

Intermediate 96

2-((R)-1-Ethylpyrrolidin-3-ylmethyl)-4-fluorobenzenesulfonyl chloride

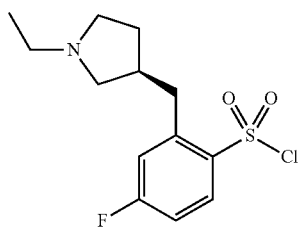 [SMILES: CCN1CC[C@@H](Cc2cc(F)ccc2S(=O)(=O)Cl)C1]

A solution of (R)-1-ethyl-3-(3-fluorobenzyl)pyrrolidine (Intermediate 97, 0.24 g) in DCE (1.2 mL) was added carefully to chlorosulfonic acid and the mixture was stirred at room temperature for 2 hours. The mixture was carefully poured into iced water and extracted with DCM, dried (MgSO₄) and filtered. The filtrate was evaporated to dryness to give 2-((R)-1-ethyl-pyrrolidin-3-ylmethyl)-4-fluorobenzenesulfonyl chloride (0.36 g) as an oil which was used without further characterization.

Intermediate 97

(R)-1-Ethyl-3-(3-fluorobenzyl)-pyrrolidine

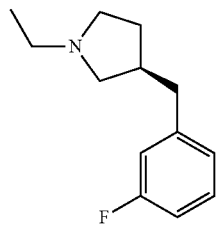

Ethyl bromide (0.22 g) was added to a suspension of 3-(R)-(3-fluorobenzyl)pyrrolidine (Intermediate 98, 0.36 g) and potassium carbonate (0.55 g) in acetonitrile and the mixture was stirred at room temperature for 2.5 hours. The mixture was diluted with ethyl acetate, filtered and the filtrate was evaporated to dryness. The residue was triturated with DCM, the solvent was decanted off and evaporated to dryness to give (R)-1-ethyl-3-(3-fluorobenzyl)pyrrolidine (0.24 g) as an oil.

¹H NMR (CDCl₃) δ: 7.22 (1H, m), 6.95 (1H, d), 6.88 (2H, m), 2.73-2.60 (4H, m), 2.52-2.38 (4H, m), 2.17 (1H, dd), 1.97 (1H, m), 1.49 (1H, m), 1.09 (3H, t).

Intermediate 98

3-(R)-(3-Fluorobenzyl)pyrrolidine

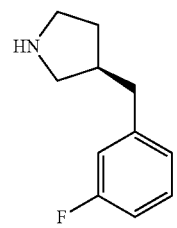

Trifluoroacetic acid (10 mL) was added to a solution of tert butyl (R)-3-(3-fluorobenzyl)-pyrrolidine-1-carboxylate (Intermediate 99, 0.515 g) in DCM (10 mL) and the mixture was stirred for 1 hour at room temperature. The mixture was evaporated to dryness and the residue was partitioned between DCM and saturated aqueous NaHCO₃. The organic extract was separated, dried (MgSO₄) and filtered. The filtrate was evaporated to dryness to give 3-(R)-(3-fluorobenzyl)pyrrolidine (0.402 g) as an oil.

¹H NMR (CDCl₃) δ: 7.30-7.23 (2H, m), 6.94 (1H, d), 6.88 (1H, dt), 3.45-3.16 (3H, br m), 2.90 (1H, m), 2.76 (2H, d), 2.63 (1H, m), 2.12 (1H, m), 1.74 (1H, m).

Intermediate 99 tert-Butyl (R)-3-(3-fluorobenzyl)pyrrolidine-1-carboxylate

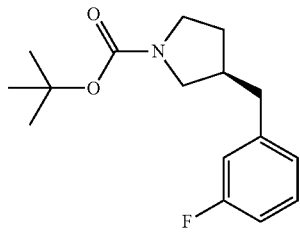 [SMILES: CC(C)(C)OC(=O)N1CC[C@@H](Cc2cccc(F)c2)C1]

Nickel Iodide (0.147 g), trans-2-aminocyclohexanol HCl salt (0.74 g), 3-fluorobenzene boronic acid (0.78 g) and sodium hexamethyldisilazide (0.208 g) were placed in a sealed tube and degassed and purged with argon. Isopropanol (8 mL) was added and the mixture was stirred at 40° C. for 5 minutes. A solution of tert-butyl (R)-3-iodomethylpyrrolidine-1-carboxylate (Intermediate 100, 1.44 g) in isopropanol (8 mL) was added and the mixture was stirred and heated at 70° C. overnight. After cooling, the mixture was diluted with ethyl acetate, filtered through Celite and the filtrate was evaporated to dryness. The residue was purified by chromatography on silica, eluting with a mixture of ethyl acetate and cyclohexane with a gradient of 0-60% to give tert-butyl (R)-3-(3-fluorobenzyl)pyrrolidine-1-carboxylate (0.515 g) as an oil.

$^1$H NMR (CDCl$_3$) δ: 7.27-7.21 (2H, m), 6.95-6.84 (2H, m), 3.46 (2H, m), 3.26 (1H, m), 2.98 (1H, dd), 2.67 (2H, m), 2.40 (1H, m), 1.92 (1H, m), 1.58 (1H, m), 1.46 (9H, s).

Intermediate 100 tert-Butyl (R)-3-iodomethylpyrrolidine-1-carboxylate

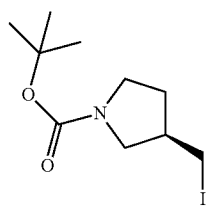

Iodine (1.91 g) was added in portions to a vigorously stirred, ice cooled suspension of imidazole (0.681 g) and triphenylphosphine (1.97 g) in diethyl ether (12 mL). The mixture was then stirred for 10 minutes before a solution of tert butyl (R)-3-hydroxymethylpyrrolidine-1-carboxylate (1 g) in dioxane (6 mL) was added dropwise. The resulting mixture was stirred at room temperature overnight, then diluted with diethyl ether and filtered. The solid was washed with diethyl ether and the combined filtrate was evaporated to dryness. The residue was purified by chromatography on silica, eluting with a mixture of ethyl acetate and pentane with a gradient of 0-20% to give tert-butyl (R)-3-iodomethylpyrrolidine-1-carboxylate (1.44 g) as an oil.

$^1$H NMR (CDCl$_3$) δ: 3.64-3.46 (2H, m), 3.33 (1H, m), 3.19 (2H, d), 3.02 (1H, dd), 2.49 (1H, m), 2.07 (1H, m), 1.65 (1H, m), 1.46 (9H, s).

Intermediate 101

Methyl (1aRS,7bSR)-5-{2-[((S)-1-ethylpyrrolidin-2-yl)cabonyl-aminomethyl]-4-fluorobenzenesulfonylamino}-1,1a,2,7b-tetrahydrocyclopropa-[c]chromene-4-carboxylate

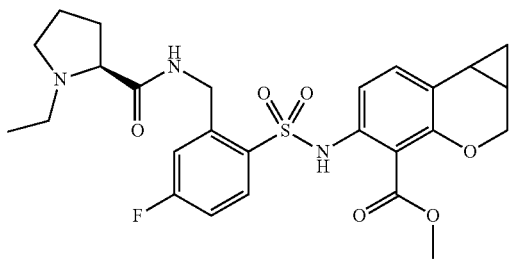 [SMILES: CCN1CCC[C@H]1C(=O)NCc1cc(F)ccc1S(=O)(=O)Nc1ccc2c(c1C(=O)OC)OCC1CC21]

A mixture of methyl (1aRS,7bSR)-5-(2-aminomethyl-4-fluorobenzenesulfonylamino)-1,1a,2,7b-tetrahydrocyclopropa[c]chromene-4-carboxylate (Intermediate 102, 0.515 g), HATU (0.483 g), (S)—N-ethylpyrrolidine-2-carboxylic acid (Intermediate 106, 0.182 g) and N,N-di-isopropyl-N-ethylamine (0.328 g) in dry DMF (25 mL) was stirred at room temperature for 2 hours. The mixture was concentrated under vacuum and the residue was diluted with water and extracted with ethyl acetate, washed with water, dried (MgSO$_4$) and filtered. The filtrate was evaporated to dryness and the residue was purified by chromatography on silica, eluting with a mixture of methanol and DCM, with a gradient of 1-2% to give methyl (1aRS,7bSR)-5-{2-[((S)-1-ethylpyrrolidin-2-yl)cabonyl-aminomethyl]-4-fluorobenzenesulfonylamino}-1,1a,2,7b-tetrahydrocyclopropa-[c]chromene-4-carboxylate (0.505 g) as a glassy solid.

$^1$H NMR (CDCl$_3$) δ: 9.2-8.9 (1H, br s), 7.82 (2H, m), 7.24 (2H, m), 7.00 (1H, dt), 6.95 (1H, dd), 4.75 (2H, m), 4.33 (1H, d), 3.99 (1H, br s), 3.79 (1H, m), 3.77 (3H, s), 3.67 (1H, m), 3.15-2.87 (3H, m), 2.48 (1H, m), 2.02 (2H, m), 1.93 (2H, m), 1.74 (1H, m), 1.20 (3H, m), 1.02 (2H, m).

Intermediate 102

Methyl (1aRS,7bSR)-5-(2-aminomethyl)-4-fluorobenzenesulfonylamino)-1,1a,2,7b-tetrahydrocyclopropa[c]chromene-4-carboxylate

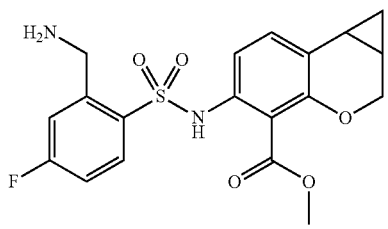 [SMILES: COC(=O)c1c(NS(=O)(=O)c2ccc(F)cc2CN)ccc2c1OCC1CC21]

A solution of potassium carbonate (2.1 g) in water was added to a solution of methyl (1aRS,7bSR)-5-(4-fluoro-2-trifluoroacetylaminomethyl)benzenesulfonylamino)-1,1a,2, 7b-tetrahydrocyclopropa[c]chromene-4-carboxylate (Intermediate 103, 1.53 g) in methanol (50 mL) and the resultant mixture was stirred and heated at 45° C. for 4 hours. After cooling, the mixture was concentrated under vacuum and the residue was diluted with water and saturated with salt. The resultant solid was collected by filtration, washed with water and ethyl acetate then dried under vacuum at 50° C. to give methyl (1aRS,7bSR)-5-(2-aminomethyl)-4-fluoro-benzenesulfonylamino)-1,1a,2,7b-tetrahydrocyclopropa[c]chromene-4-carboxylate (1.06 g) as a white solid.

$^1$H NMR (DMSO-$d_6$) δ: 8.52 (1H, br s), 7.99 (1H, dd), 7.32 (2H, m), 6.89 (1H, d), 6.74 (1H, d), 4.32 (2H, s), 4.17 (1H, d), 3.70 (3H, s), 3.64 (1H, d), 1.82 (1H, m), 1.65 (1H, m), 0.89 (1H, m), 0.61 (1H, m).

Intermediate 103

Methyl (1aRS,7bSR)-5-(4-fluoro-2-trifluoroacetylaminomethyl) benzenesulfonylamino)-1,1a,2,7b-tetrahydrocyclopropa[c]chromene-4-carboxylate

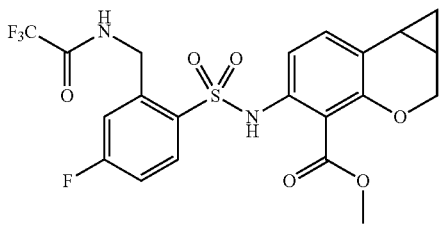 [SMILES: COC(=O)c1c(NS(=O)(=O)c2ccc(F)cc2CNC(=O)C(F)(F)F)ccc2c1OCC1CC21]

Methyl (1aRS,7bSR)-5amino-1,1a,2,7b-tetrahydrocyclopropa[c]chromene-4-carboxylate (Intermediate 42, 0.972 g) was added to a solution of 4-fluoro-2-(trifluoroacetylaminomethyl)-benzenesulfonyl chloride (Intermediate 104, 1.53 g) in DCM (25 mL) and pyridine (6 mL). The resultant mixture was stirred at room temperature for 2 hours. The mixture was diluted with DCM, washed with water, HCl (1M), water, dried (MgSO$_4$) and filtered. The filtrate was evaporated to dryness and the residue was purified by chromatography on silica, eluting with a mixture of ethyl acetate and pentane with a gradient of 5-30% to give methyl (1aRS,7bSR)-5-(2-trifluoroacetylaminomethyl)-4-fluorobenzenesulfonylamino)-1,1a,2,7b-tetrahydrocyclopropa-[c]chromene-4-carboxylate (1.76 g) as a glassy foam.

$^1$H NMR (CDCl$_3$) δ: 9.04 (1H, br s), 7.83 (1H, dd), 7.49 (1H, br t), 7.30 (1H, dd), 7.29 (1H, d), 7.09 (1H, d), 7.06 (1H, dt), 4.61 (2H, d), 4.34 (1H, d), 3.78 (1H, dd), 3.73 (3H, s), 1.95 (1H, m), 1.75 (1H, m), 1.04 (2H, m).

Intermediate 104

4-Fluoro-2-(trifluoroacetylaminomethyl)benzenesulfonyl chloride

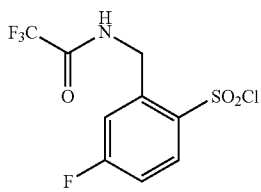 [SMILES: O=C(NCc1cc(F)ccc1S(=O)(=O)Cl)C(F)(F)F]

3-Fluoro-N-trifluoroacetylbenzylamine (Intermediate 105, 1.11 g) was added portionwise to chlorosulfonic acid (5 mL), while stirring and cooling in an ice bath. On completion of the addition, the ice bath was removed and the mixture was allowed to come to room temperature then heated to 70° C. for 3 hours. After cooling, the mixture was slowly added to ice and the resultant suspension was extracted with ethyl acetate, washed with water, dried (MgSO$_4$) and filtered. The filtrate was evaporated to dryness to give 4-fluoro-2-(trifluoroacetylaminomethyl)benzenesulfonyl chloride (1.53 g) as a brown solid.

$^1$H NMR (CDCl$_3$) δ: 8.18 (1H, dd), 7.47 (1H, m), 7.29 (1H, m), 7.18 (1H, br s), 4.92 (2H, d).

Intermediate 105

3-Fluoro-N-trifluoroacetylbenzylamine

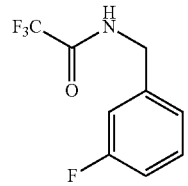

Trifluoroacetic anhydride (5.05 g) was added dropwise to an ice-cooled solution of 3-fluorobenzylamine (2.5 g) and triethylamine (2.22 g) in ethyl acetate (75 mL) while maintaining the temperature below 10° C. The mixture was stirred at 0-5° C. for 1 hour then allowed to warm to room temperature and stirred for 2 hours. Water was added and the layers were separated. The organic layer was washed with water, dried (MgSO$_4$) and filtered. The filtrate was evaporated to dryness to give 3-fluoro-N-trifluoroacetylbenzylamine (4.58 g) as an oil which crystallised on standing to a white solid.

$^1$H NMR (CDCl$_3$) δ: 7.34 (1H, m), 7.03 (3H, m), 6.72 (1H, br s), 4.53 (2H, d).

Intermediate 106

(S)—N-Ethylpyrrolidine-2-carboxylic acid

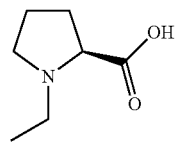

Palladium on carbon (10%, 0.2 g) was added to a solution of benzyl (S)—N-ethylpyrrolidine-2-carboxylate (Intermediate 107, 0.603 g) under an atmosphere of nitrogen. The mixture was then hydrogenated at 4 Bar for 3 hours. The mixture was filtered through Celite and the filtrate was evaporated to dryness to give (S)—N-ethylpyrrolidine-2-carboxylic acid (0.378 g) as a straw coloured gummy solid.

$^1$H NMR (CDCl$_3$) δ: 4.01 (1H, m), 3.78 (1H, m), 3.31 (1H, m), 3.18 (1H, m), 2.87 (1H, m), 2.38 (1H, m), 2.27 (1H, m), 2.02 (2H m), 1.39 (3H, t).

Intermediate 107

Benzyl (S)—N-ethylpyrrolidine-2-carboxylate hydrochloride

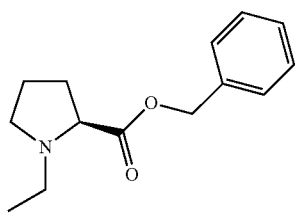 [SMILES: CCN1CCC[C@H]1C(=O)OCc1ccccc1]

Iodoethane (1.34 g) was added to a mixture of benzyl (S)-pyrrolidine-2-carboxylate (1.0 g) and potassium carbonate (1.77 g) in dry DMF (7 mL) and the resultant mixture was stirred at room temperature for 3 days. The mixture was diluted with water, extracted with ethyl acetate, washed with water, dried (MgSO$_4$) and filtered. The filtrate was evaporated to dryness and the residue was purified by chromatography on silica, eluting with a mixture of ethyl acetate and pentane with a gradient of 10-20% to give benzyl (S)—N-ethylpyrrolidine-2-carboxylate (0.643 g) as a pale straw coloured oil.

$^1$H NMR (CDCl$_3$) δ: 7.35 (5H, m), 5.17 (2H, s), 3.19 (2H, m), 2.74 (1H, m), 2.45 (1H, m), 2.34 (1H, m), 2.12 (1H, m) 1.93 (2H, m), 1.81 (1H, m), 1.10 (3H, t).

Intermediate 108

Methyl (1aRS,7bSR)-5-[2-(4-dimethylaminobutyrylamino)-4-fluorobenzene-sulfonylamino]-1,1a,2,7b-tetrahydrocyclopropa-[c]chromene-4-carboxylate

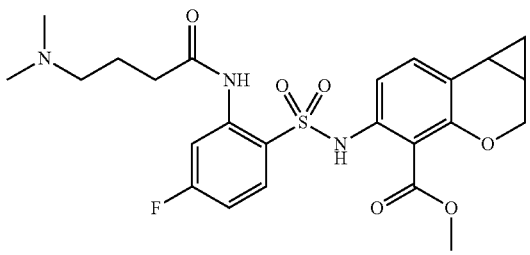 [SMILES: COC(=O)c1c(NS(=O)(=O)c2ccc(F)cc2NC(=O)CCCN(C)C)ccc2c1OCC1CC21]

A mixture of methyl (1aRS,7bSR)-5-{N-[methoxycarbonyl]-N-[2-(4-chlorobutyryl-amino)-4-fluorobenzenesulfonyl]amino}-1,1a,2,7b-tetrahydrocyclopropa-[c]chromene-4-carboxylate (Intermediate 109, 0.15 g) and dimethylamine (30% aqueous solution, 5 mL) in acetonitrile (10 mL) was stirred and heated at 40° C. for 10 hours. After cooling, the mixture was concentrated under vacuum and the residue was extracted with a mixture of ethyl acetate and THF (50%), dried (Na$_2$SO$_4$) and filtered. The filtrate was evaporated to dryness and the residue was purified by thick layer chromatography on silica, eluting with a mixture of methanol and DCM (10%) to give methyl (1aRS,7bSR)-5-[2-(4-dimethylaminobutyrylamino)-4-fluorobenzenesulfonyl-amino]-1,1a,2,7b-tetrahydrocyclopropa-[c]chromene-4-carboxylate (0.14 g) as a yellow oil.

LCMS (Method D) r/t 1.24 (M+H) 506.

Intermediate 109

Methyl (1aRS,7bSR)-5-{N-[methoxycarbonyl]-N-[2-(4-chlorobutyryl-amino)-4-fluorobenzenesulfonyl]amino}-1,1a,2,7b-tetrahydrocyclopropa-[c]chromene-4-carboxylate

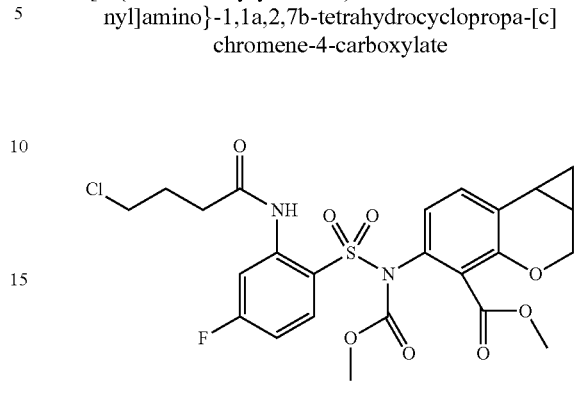

4-Chlorobutyryl chloride (3.0 g) was added to a stirred, cooled solution of methyl (1aRS,7bSR)-5-[N-(methoxycarbonyl)-N-(2-amino-4-fluorobenzenesulfonyl]amino}-1,1a,2,7b-tetrahydrocyclopropa-[c]chromene-4-carboxylate (Intermediate 110, 0.135 g) and triethylamine (1.0 g) in THF (100 mL) at 0° C. On completion of the addition, the mixture was stirred at room temperature for 4 hours. Saturated aqueous sodium bicarbonate was added and the mixture was extracted with ethyl acetate, dried (Na$_2$SO$_4$) and filtered. The filtrate was evaporated to dryness and the residue was purified by chromatography on silica, eluting with a mixture of ethyl acetate and petroleum ether, with a gradient of 20-25% to give methyl (1aRS,7bSR)-5-{N-[methoxycarbonyl]-N-[2-(4-chlorobutyrylamino)-4-fluoro-benzenesulfonyl]amino}-1,1a,2,7b-tetrahydrocyclopropa-[c]chromene-4-carboxylate (0.15 g) as a yellow oil.

LCMS (Method D) r/t 1.72 (M+H) 555.

Intermediate 110

Methyl (1aRS,7bSR)-5-[N-(methoxycarbonyl)-N-(2-amino-4-fluorobenzene-sulfonyl)amino]-1,1a,2,7b-tetrahydrocyclopropa[c]chromene-4-carboxylate

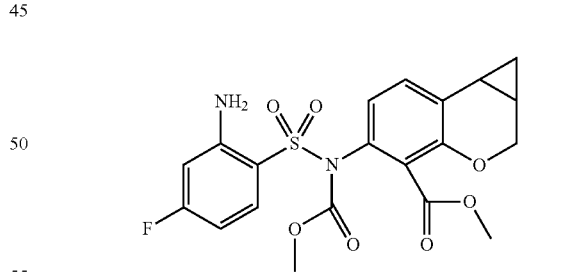

A mixture of methyl (1aRS,7bSR)-5-[N-(methoxycarbonyl)-N-(4-fluoro-2-nitrobenzene-sulfonyl)amino]-1,1a,2,7b-tetrahydro-cyclopropa[c]chromene-4-carboxylate (Intermediate 111, 0.2 g), zinc (0.54 g) and acetic acid (0.5 g) in ethanol (20 mL) was stirred and heated at reflux for 1 hour. After cooling, the solid was filtered off and the filtrate was evaporated to dryness. The residue was treated with saturated aqueous sodium bicarbonate and extracted with ethyl acetate, dried (Na$_2$SO$_4$) and filtered. The filtrate was evaporated to dryness and the residue was purified by chromatography on silica, eluting with a mixture of ethyl acetate and petroleum ether with a gradient of 30-50% to give methyl (1aRS,7bSR)-5-[N-(methoxycarbonyl)-N-(2-amino-4-fluorobenzenesulfonyl)amino]-1,1a,2,7b-tetrahydrocyclopropa[c]chromene-4-carboxylate (0.15 g) as a white solid.

$^1$H NMR (CDCl$_3$) δ: 7.74 (1H, m), 7.36 (1H, d), 6.95 (1H, d), 6.47 (1H, m), 6.39 (1H, d), 5.37 (2H, m), 4.42 (1H, m), 3.91 (1H, d), 3.74 (3H, 2s), 3.70 (3H, 2s), 2.06 (1H, m), 1.84 (1H, m), 1.28 (1H, m), 1.15 (1H, m).

Intermediate 111

Methyl (1aRS,7bSR)-5-[N-(methoxycarbonyl)-N-(4-fluoro-2-nitrobenzene-sulfonyl)amino]-1,1a,2,7b-tetrahydrocyclopropa[c]chromene-4-carboxylate

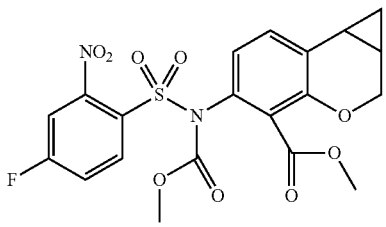 [SMILES: COC(=O)c1c(N(C(=O)OC)S(=O)(=O)c2ccc(F)cc2[N+](=O)[O-])ccc2c1OCC1CC21]

A solution of methyl (1aRS,7bSR)-5-(4-fluoro-2-nitrobenzenesulfonylamino)-1,1a,2,7b-tetrahydro-cyclopropa[c]chromene-4-carboxylate (Intermediate 112, 0.25 g) in THF (10 mL) was added dropwise with stirring to a cooled suspension of sodium hydride (0.1 g) in THF (5 mL) at 0° C. On completion of the addition, the mixture was stirred at room temperature for 30 minutes. Methyl chloroformate (0.3 g) was added dropwise and the mixture was stirred at room temperature for 1.5 hours. Saturated aqueous sodium bicarbonate was added and the mixture was extracted with ethyl acetate, dried (Na$_2$SO$_4$) and filtered. The filtrate was evaporated to dryness and the residue was purified by chromatography on silica, eluting with a mixture of ethyl acetate and petroleum ether to give methyl (1aRS,7bSR)-5-[N-(methoxycarbonyl)-N-(4-fluoro-2-nitrobenzenesulfonyl)amino]-1,1a,2,7b-tetrahydrocyclopropa-[c]chromene-4-carboxylate (0.2 g) as a white solid.

LCMS (Method D) r/t 1.58 (M+H) 481.

Intermediate 112

Methyl (1aRS,7bSR)-5-(4-fluoro-2-nitrobenzenesulfonylamino)-1,1a,2,7b-tetrahydrocyclopropa[c]chromene-4-carboxylate

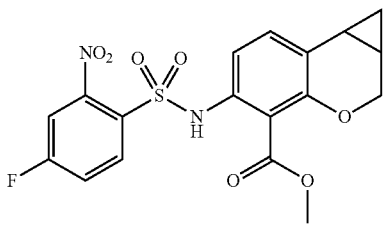 [SMILES: COC(=O)c1c(NS(=O)(=O)c2ccc(F)cc2[N+](=O)[O-])ccc2c1OCC1CC21]

A mixture of methyl (1aRS,7bSR)-5-amino-1,1a,2,7b-tetrahydrocyclopropa-[c]chromene-4-carboxylate (Intermediate 42, 0.1 g), 4-fluoro-2-nitrobenzenesulfonyl chloride (0.115 g) and pyridine (2 mL) in DCM (5 mL) was stirred at room temperature overnight. The mixture was concentrated under vacuum and the residue was partitioned between ethyl acetate and water. The organic layer was dried (Na$_2$SO$_4$) and filtered and the filtrate was evaporated to dryness. The residue was purified by chromatography on silica, eluting with a mixture of ethyl acetate and petroleum ether (20%) to give methyl (1aRS,7bSR)-5-(4-fluoro-2-nitrobenzenesulfonylamino)-1,1a,2,7b-tetrahydrocyclopropa[c]chromene-4-carboxylate (0.11 g) as a yellow oil.

$^1$H NMR (CDCl$_3$) δ: 8.56 (1H, br s), 7.92 (1H, m), 7.55 (1H, dd), 7.31 (2H, m), 7.24 (1H, m), 4.34 (1H, d), 3.85 (3H, s), 3.82 (1H, d), 1.98 (1H, m), 1.74 (1H, m), 1.08 (2H, m).

Intermediate 113

Methyl (1aS,7bR)-5-[2-((S)-1-ethyl-pyrrolidin-3-ylmethyl)-4-fluoro-benzenesulfonylamino]-1,1a,2,7b-tetrahydrocyclopropa[c]chromene-4-carboxylate

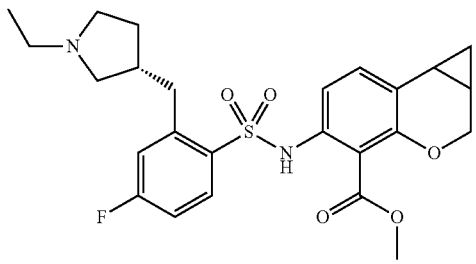 [SMILES: CCN1CC[C@H](Cc2cc(F)ccc2S(=O)(=O)Nc2ccc3c(c2C(=O)OC)OCC2CC32)C1]

A solution of methyl 5-amino-1,1a,2,7b-tetrahydrocyclopropa[c]chromene-4-carboxylate (Intermediate 42, 0.19 g) in DCM (10 mL) and pyridine (3.5 mL) was treated with a solution of 2-((S)-1-ethylpyrrolidin-3-ylmethyl)-4-fluorobenzenesulfonyl chloride (Intermediate 114, 0.26 g) in DCM (5 mL) and the mixture was stirred and heated at 40° C. for 1 hour. The resultant mixture was evaporated to dryness and the residue was purified by chromatography on silica, eluting with a mixture of DCM and methanol with a gradient of 0-25%, then flushed with 100% methanol to give methyl (1aS,7bR)-5-[2-((S)-1-ethylpyrrolidin-3-ylmethyl)-4-fluoro-benzenesulfonylamino]-1,1a,2,7b-tetrahydrocyclopropa[c]chromene-4-carboxylate (0.107 g) as a gum.

LCMS (Method A) r/t 2.29 (M+H) 489.

Intermediate 114

2-((S)-1-Ethylpyrrolidin-3-ylmethyl)-4-fluorobenzenesulfonyl chloride

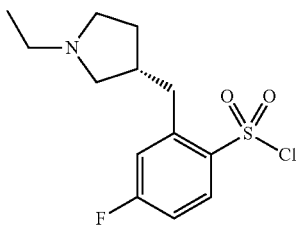 [SMILES: CCN1CC[C@H](Cc2cc(F)ccc2S(=O)(=O)Cl)C1]

Prepared by proceeding in a similar manner to Intermediate 96, starting from (S)-1-ethyl-3-(3-fluorobenzyl)pyrrolidine (Intermediate 115).

LCMS (Method A) r/t 1.95 (M+H) 308.

Intermediate 115

(S)-1-Ethyl-3-(3-fluorobenzyl)pyrrolidine

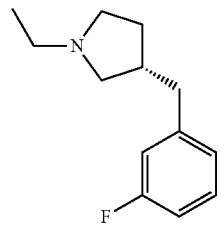

Prepared by proceeding in a similar manner to Intermediate 97 starting with 3-(S)-(3-fluoro-benzyl)pyrrolidine (Intermediate 116).

$^1$H NMR (CDCl$_3$) δ: 7.22 (1H, m), 6.95 (1H, d), 6.88 (2H, m), 2.81-2.62 (4H, br m), 2.61-2.39 (4H, br m), 2.21 (1H, br s), 1.99 (1H, m), 1.52 (1H, m), 1.11 (3H, t).

Intermediate 116

3-(S)-(3-Fluorobenzyl)-pyrrolidine

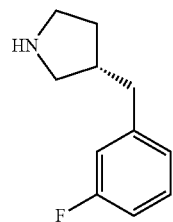

Prepared by proceeding in a similar manner to Intermediate 98 starting with tert-butyl (S)-3-(3-fluorobenzyl)-pyrrolidine-1-carboxylate (intermediate 117).

$^1$H NMR (CDCl$_3$) δ: 7.27 (1H, m), 6.96-6.84 (3H, m), 3.32 (1H, m), 3.25 (1H, dd), 3.16 (1H, m), 2.83 (1H, m), 2.73 (2H, d), 2.58 (1H, m), 2.08 (1H, m), 1.68 (1H, m).

Intermediate 117 tert-Butyl (S)-3-(3-fluorobenzyl)-pyrrolidine-1-carboxylate

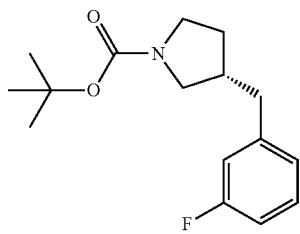 [SMILES: CC(C)(C)OC(=O)N1CC[C@H](Cc2cccc(F)c2)C1]

Prepared by proceeding in a similar manner to Intermediate 99 starting with tert-butyl (S)-3-iodomethylpyrrolidine-1-carboxylate (Intermediate 118).

$^1$H NMR (CDCl$_3$) δ: 7.27 (1H, m), 6.97-6.83 (3H, m), 3.46 (2H, m), 3.25 (1H, m), 2.98 (1H, m), 2.67 (2H, m), 2.40 (1H, m), 1.91 (1H, m), 1.58 (1H, m), 1.45 (9H, s).

Intermediate 118 tert-Butyl (S)-3-iodomethylpyrrolidine-1-carboxylate

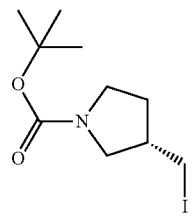

Prepared by proceeding in a similar manner to Intermediate 100 starting with tert-butyl (S)-3-hydroxymethylpyrrolidine-1-carboxylate.

$^1$H NMR (CDCl$_3$) δ: 3.59 (1H, dd), 3.51 (1H, m), 3.33 (1H, m), 3.19 (2H, d), 3.02 (1H, dd), 2.49 (1H, m), 2.07 (1H, m), 1.65 (1H, m), 1.46 (9H, s).

Intermediate 119 tert-Butyl (1aRS,7bSR)-5-{2-[N-(2,4-dimethoxybenzyl)-N-(3-dimethyl-aminopropyl)carbamoyl]benzenesulfonylamino}-1,1a,2,7b-tetrahydrocyclopropa[c]chromene-4-carboxylate

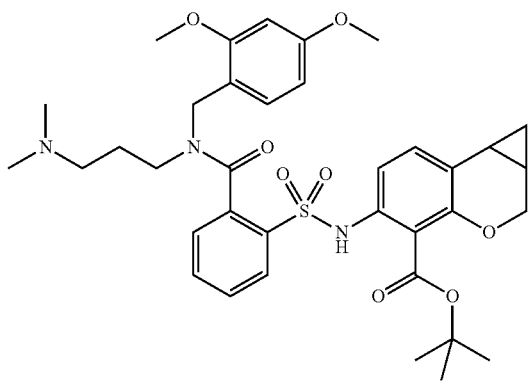 [SMILES: COc1ccc(CN(CCCN(C)C)C(=O)c2ccccc2S(=O)(=O)Nc2ccc3c(c2C(=O)OC(C)(C)C)OCC2CC32)c(OC)c1]

A solution of N-(2,4-dimethoxybenzyl)-N-(3-dimethylaminopropyl)amine (Intermediate 120, 0.179 g) in DCM (2 mL) was added dropwise with stirring to a cooled solution of 2-chlorosulfonylbenzoyl chloride (Intermediate 121, 0.17 g) in DCM (20 mL) at 0° C. The mixture was stirred at 0° C. for 1 hour then a solution of tert-butyl (1aRS,7bSR)-5-amino-1,1a,2,7b-tetrahydro-cyclopropa-[c]chromene-4-carboxylate (Intermediate 122, 0.185 g) in DCM (2 mL) was added. The resultant mixture was stirred and heated at 30-35° C. overnight. After cooling, the mixture was concentrated under vacuum and the residue was purified by HPLC (C18) to give tert-butyl (1aRS,7bSR)-5-{2-[N-(2,4-dimethoxybenzyl)-N-(3-dimethylaminopropyl)carbamoyl]-benzenesulfonylamino}-1,1a,2,7b-tetrahydro-cyclopropa-[c]chromene-4-carboxylate (0.03 g) as a yellow oil.

LCMS (Method D) r/t 3.16 (M+H) 680.

Intermediate 120

N-(2,4-Dimethoxybenzyl)-N-(3-dimethylaminopropyl)amine

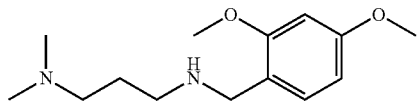

A mixture of 3-dimethylaminopropylamine (3.06 g), 2,4-dimethoxybenzaldehyde (6.0 g) and sodium triacetoxyborohydride (9.54 g) in methanol (20 mL) was stirred at room temperature for 10 hours. The mixture was concentrated under vacuum and the residue was dissolved in ethyl acetate and washed with water and brine, dried (Na$_2$SO$_4$) and filtered. The filtrate was evaporated to dryness to give N-(2,4-dimethoxybenzyl)-N-(3-dimethylaminopropyl)amine (7.2 g) as a brown oil which was used directly without further characterisation.

Intermediate 121

2-Chlorosulfonylbenzoyl chloride

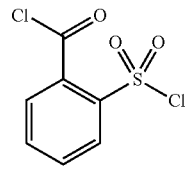 [SMILES: O=C(Cl)c1ccccc1S(=O)(=O)Cl]

A mixture of 1,1-dioxo-1H-1lambda*6*benzo[c][1,2]oxathiol-3-one (4.5 g) and phosphorous pentachloride (15 g) was stirred and heated at 60° C. overnight. After cooling, a mixture of ice and water was added and the solution was extracted with DCM, dried (Na$_2$SO$_4$) and filtered. The filtrate was evaporated to dryness to give 2-chlorosulfonylbenzoyl chloride (5 g) as a yellow solid which was used without further characterisation.

Intermediate 122 tert-Butyl (1aRS,7bSR)-5-amino-1,1a,2,7b-tetrahydrocyclopropa-[c]chromene-4-carboxylate

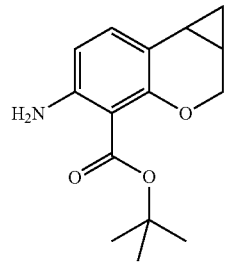 [SMILES: CC(C)(C)OC(=O)c1c(N)ccc2c1OCC1CC21]

Sodium borohydride (0.32 g) was added in portions to a stirred solution of tert-butyl (1aRS,7bSR)-5-(trifluoroacetylamino)-1,1a,2,7b-tetrahydro-cyclopropa-[c]chromene-4-carboxylate (Intermediate 123, 0.5 g) in ethanol (20 mL). The resultant mixture was stirred at room temperature for 1 hour then concentrated under vacuum. The residue was purified by chromatography on silica, eluting with a mixture of ethyl acetate and petroleum ether with a gradient of 2-4% to give tert-butyl (1aRS,7bSR)-5-amino-1,1a,2,7b-tetrahydrocyclopropa-[c]chromene-4-carboxylate (0.2 g) as a white solid.

$^1$H NMR (CDCl$_3$) δ: 7.04 (1H, d), 6.25 (1H, d), 4.57 (2H, br s), 4.32 (1H, d), 3.87 (1H, d), 1.86 (1H, m), 1.65 (1H, m), 1.60 (9H, s), 0.95 (2H, m).

Intermediate 123 tert-Butyl (1aRS,7bSR)-5-(trifluoroacetylamino)-1,1a,2,7b-tetrahydro-cyclopropa[c]chromene-4-carboxylate

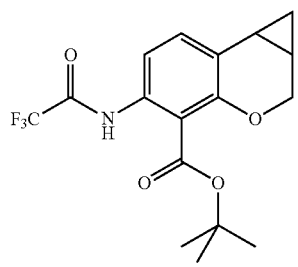 [SMILES: CC(C)(C)OC(=O)c1c(NC(=O)C(F)(F)F)ccc2c1OCC1CC21]

A mixture of (1aRS,7bSR)-5-(trifluoroacetylamino)-1,1a,2,7b-tetrahydrocyclopropa-[c]chromene-4-carboxylic acid (Intermediate 124, 0.97 g), DMAP (0.2 g), dicyclohexyl carbodiimide (1.33 g) and di-tert-butyl dicarbonate (3.51 g) in tert-butanol (20 mL) was stirred and heated at reflux for 7 hours. After cooling, the mixture was concentrated under vacuum and the residue was purified by chromatography on silica, eluting with a mixture of ethyl acetate and petroleum ether (2%) to give tert-butyl (1aRS,7bSR)-5-(trifluoroacetylamino)-1,1a,2,7b-tetrahydrocyclopropa[c]chromene-4-carboxylate (0.5 g) as a yellow oil.

$^1$H NMR (CDCl$_3$) δ: 10.47 (1H, br s), 7.89 (1H, d), 7.34 (1H, d), 4.39 (1H, d), 3.88 (1H, d), 2.02 (1H, m), 1.77 (1H, m), 1.60 (9H, s), 1.09 (2H, m).

Intermediate 124

(1aRS,7bSR)-5-(Trifluoroacetylamino)-1,1a,2,7b-tetrahydrocyclopropa-[c]chromene-4-carboxylic acid

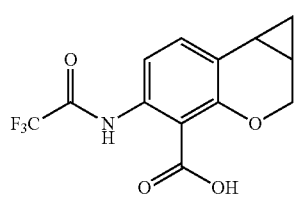 [SMILES: O=C(O)c1c(NC(=O)C(F)(F)F)ccc2c1OCC1CC21]

Trifluoroacetic anhydride (2.98 g) was added dropwise to a stirred, cooled solution of (1aRS,7bSR)-5-amino-1,1a,2, 7b-tetrahydro-cyclopropa-[c]chromene-4-carboxylic acid (Intermediate 125, 0.97 g) and triethylamine (2.39 g) in THF (20 mL). The resultant mixture was stirred at room temperature for 30 minutes. Water was added and the mixture was extracted with ethyl acetate, dried (Na$_2$SO$_4$) and filtered. The filtrate was evaporated to dryness and the residue was purified by chromatography on silica, eluting with a mixture of ethyl acetate and petroleum ether (2%) to give (1aRS,7bSR)-5-(trifluoroacetylamino)-1,1a,2,7b-tetrahydrocyclopropa-[c]chromene-4-carboxylic acid (0.97 g) as a white solid.

$^1$H NMR (DMSO-d$_6$) δ: 7.92 (1H, d), 7.28 (1H, d), 4.54 (1H, d), 3.94 (1H, d), 2.27 (1H, m), 2.02 (1H, m), 1.21 (1H, m), 0.95 (1H, m).

Intermediate 125

(1aRS,7bSR)-5-Amino-1,1a,2,7b-tetrahydrocyclopropa[c]chromene-4-carboxylic acid

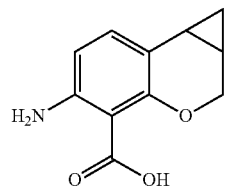 [SMILES: Nc1ccc2c(c1C(=O)O)OCC1CC21]

A mixture of methyl (1aRS,7bSR)-5-amino-1,1a,2,7b-tetrahydrocyclopropa[c]chromene-4-carboxylate (Intermediate 42, 1.0 g) and lithium hydroxide monohydrate (0.96 g) in dioxane (16 mL) and water (14 mL) was stirred and heated at 90° C. for 1 hour. After cooling, the mixture was concentrated under vacuum and the residue was diluted with water and neutralised to pH7 with formic acid. The mixture was then extracted with ethyl acetate, dried (Na$_2$SO$_4$) and filtered and the filtrate was evaporated to dryness to give (1aRS,7bSR)-5-amino-1,1a,2,7b-tetrahydro-cyclopropa-[c]chromene-4-carboxylic acid (0.97 g) as a yellow oil.

LCMS (Method D) r/t 2.13 (M+H) 206.

Intermediate 126

Methyl (1aRS,7bSR)-5-(2-{[N—((S)-1-ethylpyrrolidin-3-yl)-N-methyl-carbamoyl]-methyl}-4-fluorobenzenesulfonylamino)-1,1a,2,7b-tetrahydrocyclopropa[c]chromene-4-carboxylate

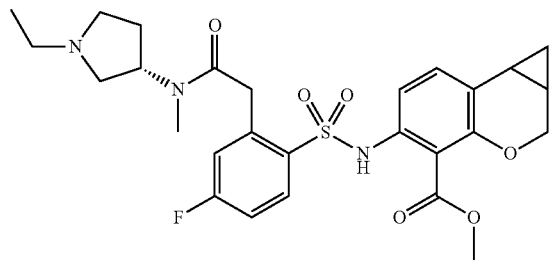 [SMILES: CCN1CC[C@H](N(C)C(=O)Cc2cc(F)ccc2S(=O)(=O)Nc2ccc3c(c2C(=O)OC)OCC2CC32)C1]

EDAC (0.058 g) was added to a stirred solution of methyl (1aRS,7bSR)-5-(2-carboxymethyl-4-fluorobenzenesulfonylamino)- 1,1a,2,7b-tetrahydrocyclopropa[c]chromene-4-carboxylate (Intermediate 83, 0.109 g) in DCM (3 mL) and the mixture was stirred at room temperature for 10 minutes. A solution of N—((S)-1-ethylpyrrolidin-3-yl)-N-methylamine dihydrochloride (Intermediate 127, 0.102 g) and triethylamine (0.151 g) in DCM (3 mL) was added and the mixture stirred for 17 hours. The mixture was evaporated in vacuo and the residue was dissolved in dioxane (4 mL) and the mixture was heated at 75° C. for 20 hours. After cooling, the mixture was diluted with DCM and water and filtered through a phase separator. The filtrate was evaporated in vacuo and the residue was combined with an identical reaction carried out earlier. The material was purified by chromatography on silica, eluting with a mixture of methanol and DCM with a gradient of 0-50% to give methyl (1aRS,7bSR)-5-(2-{[((S)-1-ethylpyrrolidin-3-yl)methylcarbamoyl]methyl}-4-fluoro-benzenesulfonylamino)-1,1a,2,7b-tetrahydro-cyclopropa[c]chromene-4-carboxylate (0.48 g) as a light brown foam.

LCMS (Method E) r/t 2.65 (M+H) 546.

Intermediate 127

N—((S)-1-Ethylpyrrolidin-3-yl)-N-methylamine dihydrochloride

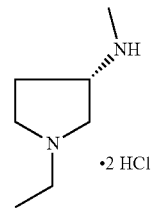

A mixture of benzyl N—((S)-1-ethylpyrrolidin-3-yl)-N-methylcarbamate (Intermediate 128, 0.682 g) and 10% palladium on carbon (0.10 g) in ethanol (20 mL) was stirred at room temperature under an atmosphere of hydrogen for 3 hours. The mixture was filtered, and concentrated hydrochloric acid (2 mL) was added. The solution was evaporated in vacuo then redissolved in a mixture of toluene and ethanol then re-evaporated to give N—((S)-1-ethylpyrrolidin-3-yl)-N-methylamine dihydrochloride (0.531 g) as a light coloured, viscous oil which was used without further characterisation.

Intermediate 128

Benzyl N—((S)-1-ethylpyrrolidin-3-yl)-N-methyl-carbamate

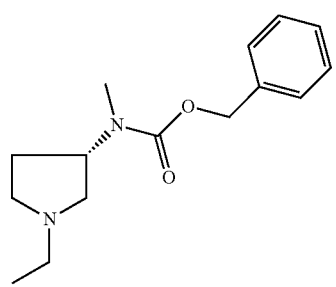 [SMILES: CCN1CC[C@H](N(C)C(=O)OCc2ccccc2)C1]

A mixture of benzyl N-methyl-(S)-pyrrolidin-3-ylcarbamate (Intermediate 129, 1.28 g), iodoethane (0.853 g), and potassium carbonate (1.51 g) in acetonitrile (12 mL) was stirred at room temperature for 4 hours. The mixture was evaporated in vacuo and the residue was basified with 5M sodium hydroxide and filtered through a phase separator. The filtrate was concentrated in vacuo and the residue was purified by chromatography on silica, eluting with a mixture of methanol and DCM with a gradient of 0-30% to give benzyl N—((S)-1-ethylpyrrolidin-3-yl)-N-methylcarbamate (0.686 g) as a colourless oil.

$^1$H NMR (CDCl$_3$) δ: 7.35 (5H, m), 5.13 (2H, s), 4.84 (1H, br, s), 2.91 (3H, s), 2.30-2.82 (6H, m), 2.12 (1H, br, m), 1.79 (1H, m), 1.10 (3H, t).

Intermediate 129

Benzyl N-methyl-(S)-pyrrolidin-3-ylcarbamate

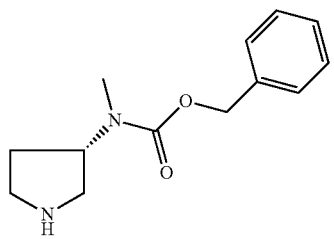 [SMILES: CN(C(=O)OCc1ccccc1)[C@H]1CCNC1]

A solution of tert-butyl (S)-3-(N-benzyloxycarbonyl-N-methylamino)pyrrolidine-1-carboxylate (Intermediate 130, 1.81 g) in trifluoroacetic acid (8 mL) and DCM (8 mL) was left to stand at room temperature for 30 minutes. The resultant mixture was concentrated in vacuo and the residue was dissolved in DCM and brine, basified with 2M sodium hydroxide and filtered through a phase separator. The filtrate was concentrated in vacuo to give benzyl N-methyl-(S)-pyrrolidin-3-ylcarbamate (1.46 g) as a light coloured oil.

$^1$H NMR (CDCl$_3$) δ: 7.35 (5H, m), 5.14 (2H, s), 4.68 (1H, br, m), 3.08 (2H, m), 2.88 (3H, s), 2.76-2.95 (3H, m), 2.01 (1H, m), 1.75 (1H, m).

Intermediate 130 tert-Butyl (S)-3-(N-benzyloxycarbonyl-N-methylamino)pyrrolidine-1-carboxylate

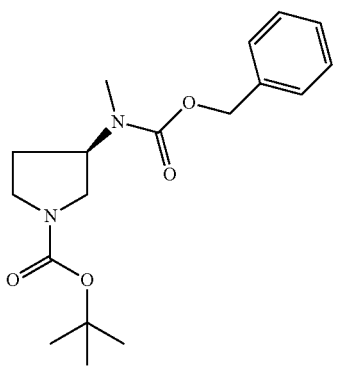 [SMILES: CN(C(=O)OCc1ccccc1)[C@@H]1CCN(C(=O)OC(C)(C)C)C1]

Sodium hydride (60% oil dispersion, 0.32 g) was added to a stirred solution of tert-butyl (S)-3-benzyloxycarbonylaminopyrrolidine-1-carboxylate (prepared according to Cheng et al, WO2007 142585, 1.73 g) in THF (20 mL) and the mixture was stirred for 15 minutes. Iodomethane (1.85 g) was added and the mixture was stirred at room temperature for 1 hour. Methanol was carefully added to destroy the excess sodium hydride then ethyl acetate and water were added and the organic layer was washed with brine, dried (Na$_2$SO$_4$), filtered. The filtrate was concentrated in vacuo to give tert-butyl (S)-3-(N-benzyloxycarbonyl-N-methylamino)pyrrolidine-1-carboxylate (1.66 g) as a pale coloured oil.

$^1$H NMR (CDCl$_3$) δ: 7.36 (5H, m), 5.15 (2H, s), 4.79 (1H, br, s), 3.54 (2H, br, m), 3.11-3.38 (2H, br, m), 2.86 (3H, s), 1.98 (2H, m), 1.46 (9H, s).

Intermediate 131

Methyl (1aRS,7bSR)-5-(2-{[N—((R)-1-ethylpyrrolidin-3-yl)-N-methyl-carbamoyl]methyl}-4-fluorobenzenesulfonylamino)-1,1a,2,7b-tetrahydrocyclopropa-[c]chromene-4-carboxylate

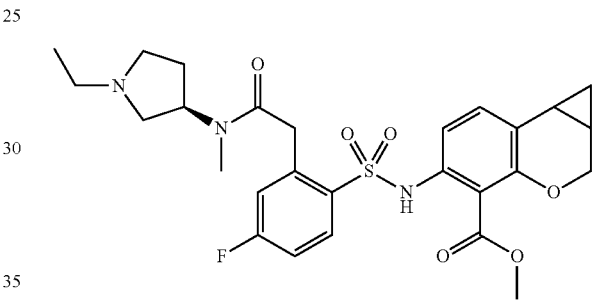

Prepared by proceeding in a similar manner to Intermediate 126, starting from methyl (1aRS,7bSR)-5-(2-carboxymethyl-4-fluorobenzenesulfonylamino)-1,1a,2,7b-tetrahydro-cyclopropa[c]chromene-4-carboxylate (Intermediate 83) and N—((R)-1-ethylpyrrolidin-3-yl)-N-methylamine dihydrochloride (Intermediate 132) as a light brown foam.

LCMS (Method E) r/t 2.63 (M+H) 546

Intermediate 132

N—((R)-1-Ethylpyrrolidin-3-yl)-N-methylamine dihydrochloride

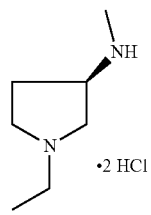

Prepared by proceeding in a similar manner to Intermediate 127, starting from benzyl N—((R)-1-ethylpyrrolidin-3-yl)-N-methylcarbamate (Intermediate 133) as a light coloured viscous oil, which was used without further characterization.

Intermediate 133

Benzyl N—((R)-1-ethylpyrrolidin-3-yl)-N-methyl-carbamate

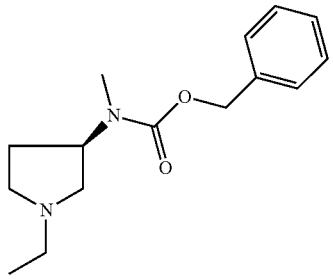 [SMILES: CCN1CC[C@@H](N(C)C(=O)OCc2ccccc2)C1]

Prepared by proceeding in a similar manner to Intermediate 128, starting from benzyl N-methyl-(R)-pyrrolidin-3-ylcarbamate (I including bridged or fused rings, and Intermediate 134) and iodoethane, as a light coloured oil.

$^1$H NMR (CDCl$_3$) δ: 7.35 (5H, m), 5.13 (2H, s), 4.84 (1H, br, s), 2.91 (3H, s), 2.30-2.87 (6H, m), 2.12 (1H, br, m), 1.80 (1H, m), 1.10 (3H, t).

Intermediate 134

Benzyl N-methyl-(R)-pyrrolidin-3-ylcarbamate

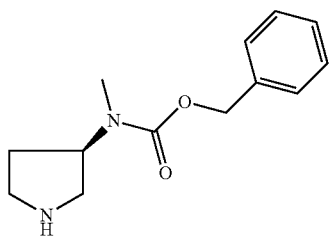 [SMILES: CN(C(=O)OCc1ccccc1)[C@@H]1CCNC1]

Prepared by proceeding in a similar manner to Intermediate 129, starting from tert-butyl (R)-3-(N-benzyloxycarbonyl-N-methylamino)-pyrrolidine-1-carboxylate (Intermediate 135) as a pale coloured oil.

$^1$H NMR (CDCl$_3$) δ: 7.35 (5H, m), 5.14 (2H, s), 4.79 (1H, br, s), 3.08 (2H, m), 2.88 (3H, s), 2.76-2.95 (3H, m), 2.01 (1H, m), 1.75 (1H, m).

Intermediate 135 tert-Butyl (R)-3-(N-benzyloxycarbonyl-N-methyl-amino)pyrrolidine-1-carboxylate

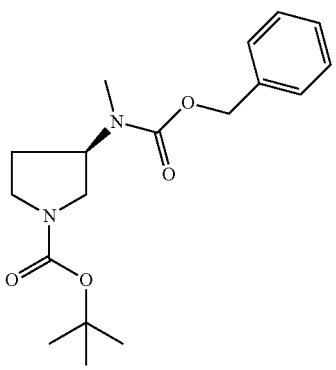 [SMILES: CN(C(=O)OCc1ccccc1)[C@@H]1CCN(C(=O)OC(C)(C)C)C1]

Prepared by proceeding in a similar manner to Intermediate 130, starting from tert-butyl (R)-3-benzyloxycarbonylaminopyrrolidine-1-carboxylate (prepared according to Zhou et al, US 2008 0293771) and iodomethane, as a pale coloured oil.

$^1$H NMR (CDCl$_3$) δ: 7.35 (5H, m), 5.15 (2H, s), 4.69 (1H, br, s), 3.54 (2H, br, m), 3.11-3.38 (2H, br, m), 2.86 (3H, s), 1.98 (2H, m), 1.46 (9H, s).

Intermediate 136

2((S)-1-Ethylpyrrolidin-2-yl)ethylamine

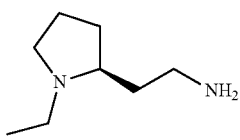

((S)-1-Acetylpyrrolidin-2-yl)acetonitrile (Intermediate 137, 1.0 g) was added portionwise to a stirred, cooled solution of lithium aluminium hydride (0.36 g) in THF (30 mL) under an atmosphere of nitrogen while maintaining the temperature at 0° C. The mixture was allowed to warm to room temperature then heated at reflux for 2 hours. After cooling, ethanol (4 mL) was added dropwise and the resultant solid was filtered off. The filtrate was evaporated to dryness to give 2((S)-1-ethylpyrrolidin-2-yl)ethylamine (0.6 g) as a colourless oil.

$^1$H NMR (D$_2$O) δ: 3.59 (1H, m), 3.37 (2H, m), 3.01 (4H, m), 2.24 (2H, m), 1.98 (3H, m), 1.65 (1H, m), 1.21 (3H, t).

Intermediate 137

((S)-1-Acetylpyrrolidin-2-yl)acetonitrile

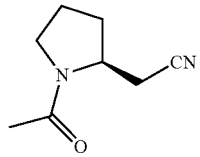

Acetyl chloride (8.6 g) was added dropwise to a stirred, cooled solution of ((S)-pyrrolidin-2-yl)acetonitrile hydrochloride (Intermediate 138, 8.0 g) and triethylamine (16.5 g) in DCM (80 mL) while maintaining the temperature at 0° C. The resultant solution was stirred at 0° C. for 30 minutes. Water was added and the layers were separated. The aqueous layer was further extracted with DCM and the combined organic layers were washed with brine, dried (Na$_2$SO$_4$) and filtered. The filtrate was evaporated to dryness and the residue was purified by HPLC (C18) to give ((S)-1-acetylpyrrolidin-2-yl)acetonitrile (5.0 g) as a light yellow oil which was used directly without further characterisation.

Intermediate 138

((S)-Pyrrolidin-2-yl)acetonitrile hydrochloride

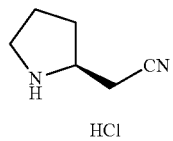

A solution of tert-butyl (S)-2-cyanomethylpyrrolidine-1-carboxylate (Intermediate 139, 13.0 g) in methanol (130 mL) and concentrated hydrochloric acid (13 mL) was stirred and heated at 40° C. overnight. After cooling, the mixture was concentrated under vacuum and the residue was diluted with toluene and reconcentrated. Ethanol (20 mL) was added and the resultant solid was collected by filtration and washed with hexane to give ((S)-pyrrolidin-2-yl)acetonitrile hydrochloride (8.0 g) as a white solid.
LCMS (Method D) r/t 0.50 (M+H) 111.

Intermediate 139 tert-Butyl (S)-2-cyanomethylpyrrolidine-1-carboxylate

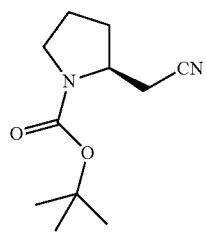

Sodium cyanide (8.2 g) was added to a solution of tert-butyl (S)-2-(4-methylbenzenesulfonyloxymethyl)pyrrolidine-1-carboxylate (Intermediate 140, 29.6 g) in DMSO (300 mL) and the resultant mixture was stirred and heated at 90° C. for 5.5 hours. After cooling, the mixture was treated with saturated aqueous iron (II) sulphate solution and the mixture was stirred for a further 5 hours then extracted with ethyl acetate. The organic layer was washed with brine, dried ($Na_2SO_4$) and filtered. The filtrate was evaporated to dryness and the residue was purified by chromatography on silica, eluting with a mixture of ethyl acetate and petroleum ether (5%) to give tert-butyl (S)-2-cyanomethylpyrrolidine-1-carboxylate (13.0 g) as a light yellow oil which was used without further characterisation.

Intermediate 140 tert-Butyl (S)-2-(4-methylbenzenesulfonyloxymethyl)pyrrolidine-1-carboxylate

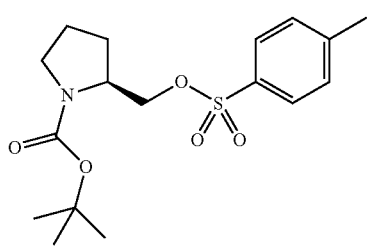 [SMILES: Cc1ccc(S(=O)(=O)OC[C@@H]2CCCN2C(=O)OC(C)(C)C)cc1]

4-Methylbenzenesulfonyl chloride (22.7 g) was added portionwise to a stirred, cooled solution of tert-butyl (S)-2-hydroxyoxymethylpyrrolidine-1-carboxylate (20.0 g) in pyridine (70 mL) while maintaining the temperature at 0° C. The resultant mixture was stirred at room temperature overnight. The mixture was concentrated under vacuum and the residue was dissolved in DCM and washed with saturated aqueous sodium bicarbonate solution and brine, dried ($Na_2SO_4$) and filtered. The filtrate was evaporated to dryness to give tert-butyl (S)-2-(4-methylbenzenesulfonyl-oxymethyl)pyrrolidine-1-carboxylate (34 g) as a yellow oil which was used without further characterisation.

Intermediate 141

2-((R)-1-Ethylpyrrolidin-2-yl)ethylamine

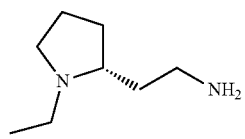

Prepared by proceeding in a similar manner to Intermediate 136, starting from ((S)-1-acetylpyrrolidin-2-yl)acetonitrile (Intermediate 142) and used without further characterisation.

Intermediate 142

((R)-1-Acetylpyrrolidin-2-yl)acetonitrile

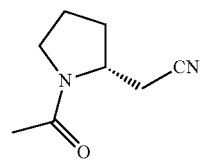

Prepared by proceeding in a similar manner to Intermediate 137, starting from ((R)-pyrrolidin-2-yl)acetonitrile hydrochloride (Intermediate 143) and used without further characterisation.

Intermediate 143

((R)-Pyrrolidin-2-yl)acetonitrile hydrochloride

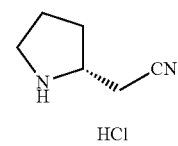

Prepared by proceeding in a similar manner to Intermediate 138, starting from tert-butyl (R)-2-cyanomethylpyrrolidine-1-carboxylate (Intermediate 144) and used without further characterisation.

Intermediate 144 tert-Butyl (R)-2-cyanomethylpyrrolidine-1-carboxylate

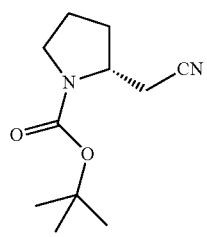

Prepared by proceeding in a similar manner to Intermediate 139, starting from tert-butyl (R)-2-(4-methylbenzenesulfonyloxymethyl)pyrrolidine-1-carboxylate (Intermediate 145) and used without further characterisation.

Intermediate 145 tert-Butyl (R)-2-(4-methylbenzenesulfonyloxymethyl)pyrrolidine-1-carboxylate

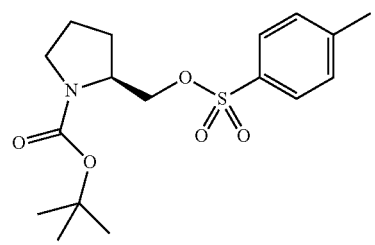 [SMILES: Cc1ccc(S(=O)(=O)OC[C@@H]2CCCN2C(=O)OC(C)(C)C)cc1]

Prepared by proceeding in a similar manner to Intermediate 140, starting from tert-butyl (R)-2-hydroxymethylpyrrolidine-1-carboxylate and used without further characterisation.

Intermediate 146

Methyl (1aRS,7bSR)-5-(2-{[((R)-1-ethylpyrrolidine-2-yl)carbonylamino]-methyl}-4-fluorobenzenesulfonylamino)-1,1a,2,7b-tetrahydrocyclopropa[c]chromene-4-carboxylate

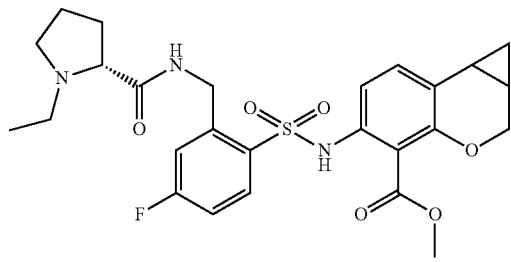 [SMILES: CCN1CCC[C@@H]1C(=O)NCc1cc(F)ccc1S(=O)(=O)Nc1ccc2c(c1C(=O)OC)OCC1CC21]

Prepared by proceeding in a similar manner to Intermediate 101, starting from methyl (1aRS,7bSR)-5-(2-aminomethyl-4-fluorobenzenesulfonylamino)-1,1a,2,7b-tetrahydrocyclopropa[c]chromene-4-carboxylate (Intermediate 102) and (R)-1-ethylpyrrolidine-2-carboxylic acid (Intermediate 147) as a solid.

LCMS (Method B) r/t 2.37 (M+H) 532

Intermediate 147

(R)-1-Ethyl-pyrrolidine-2-carboxylic acid

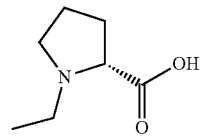

Prepared by proceeding in a similar manner to Intermediate 106, starting from tert-butyl (R)-1-ethylpyrrolidine-2-carboxylate (Intermediate 148) as a solid.
$^1$H NMR (CDCl$_3$) δ: 3.99 (1H, m), 3.76 (1H, dd), 3.37-3.23 (1H, m), 3.21-3.08 (1H, m), 2.84 (1H, dt), 2.45-2.21 (2H, m), 2.07-1.94 (2H, m), 1.39 (3H, t).

Intermediate 148

Benzyl (R)-1-ethylpyrrolidine-2-carboxylate

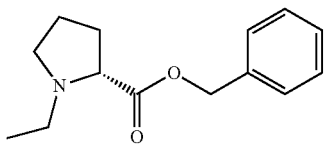 [SMILES: CCN1CCC[C@@H]1C(=O)OCc1ccccc1]

Prepared by proceeding in a similar manner to Intermediate 107, starting from benzyl (R)-pyrrolidine-2-carboxylate as a colourless oil.
$^1$H NMR (CDCl$_3$) δ: 7.34 (5H, m), 5.17 (2H, s), 3.19 (2H, m), 2.75 (1H, m), 2.45 (1H, m), 2.33 (1H, m), 2.12 (1H, m), 1.93 (2H, m), 1.81 (1H, m), 1.09 (3H, t).

Intermediate 149

(1-Ethylazetidin-3-yl)methylamine

A solution of 3-[bis-(tert-butoxycarbonylamino)methyl]-1-ethylazetidine (Intermediate 150, 0.83 g) in a mixture of methanol (6 mL) and concentrated hydrochloric acid (1 mL) was stirred and heated at 50° C. for 3 hours. After cooling, the mixture was concentrated under vacuum and the residue was dissolved in isopropanol and treated with potassium carbonate (3 g). The mixture was stirred at room temperature for 48 hours, then the solid was filtered off and the filtrate was evaporated to dryness to give (1-ethylazetidin-3-yl)methylamine (0.18 g) as a light sticky gum which was used without further characterisation.

Intermediate 150

3-[bis-(tert-Butoxycarbonylamino)methyl]-1-ethyl-azetidine

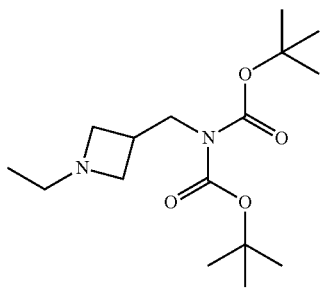 [SMILES: CCN1CC(CN(C(=O)OC(C)(C)C)C(=O)OC(C)(C)C)C1]

A mixture of acetaldehyde (1.5 g) and 3-[bis-(tert-butoxycarbonyl-amino)methyl]azetidine (Intermediate 151, 1.0 g) in ethanol (20 mL) was stirred at room temperature for 30 minutes and then 10% palladium on carbon (0.3 g) was added. The mixture was stirred under an atmosphere of hydrogen overnight. The solid was filtered off and the filtrate was evaporated to dryness. The residue was purified by chromatography on silica, eluting with a mixture of methanol and DCM (10%) to give 3-[bis-(tert-butoxycarbonylamino)methyl]-1-ethylazetidine (0.83 g) as a colourless liquid, which was used without further characterization.

Intermediate 151

3-[bis-(tert-Butoxycarbonylamino)methyl]azetidine

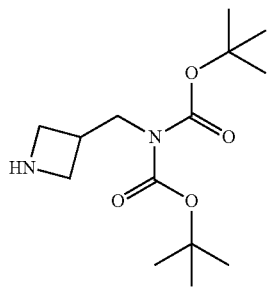 [SMILES: CC(C)(C)OC(=O)N(CC1CNC1)C(=O)OC(C)(C)C]

A mixture of 3-[bis-(tert-butoxycarbonylamino)methyl]-1-(diphenylmethyl)azetidine (Intermediate 152, 6.4 g) and 10% palladium on carbon (3 g) in ethanol (100 mL) and acetic acid (2 mL) was stirred under an atmosphere of hydrogen overnight. The solid was filtered off and the filtrate was evaporated to dryness. The residue was dissolved in ethyl acetate and washed with saturated aqueous sodium carbonate, dried (Na$_2$SO$_4$) and filtered. The filtrate was evaporated to dryness and the residue was purified by chromatography on silica, eluting with a mixture of methanol and DCM (10%) to give 3-[bis-(tert-butoxycarbonylamino)methyl]azetidine (4.0 g) as a colourless liquid, which was used without further characterisation.

Intermediate 152

3-[bis-(tert-Butoxycarbonylamino)methyl]-1-(diphenylmethyl)-azetidine

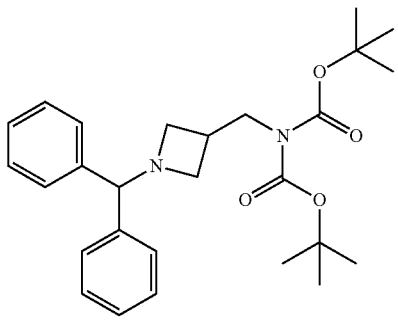 [SMILES: CC(C)(C)OC(=O)N(CC1CN(C(c2ccccc2)c2ccccc2)C1)C(=O)OC(C)(C)C]

Di-tert-butyl dicarbonate (22 g) was added to a solution of 1-(diphenylmethyl)azetidin-3-ylmethylamine (5 g), DMAP (0.5 g) and triethylamine (12 g) in THF (150 mL) and the resultant solution was stirred and heated at 60° C. for 5 hours. After cooling, the mixture was added to brine solution and extracted with ethyl acetate, washed with brine, dried (Na$_2$SO$_4$) and filtered. The filtrate was evaporated to dryness and the residue was purified by chromatography on silica, eluting with a mixture of ethyl acetate and petroleum ether (10%) to give 3-[bis-(tert-butoxycarbonylamino)methyl]-1-(diphenylmethyl)azetidine (6.4 g) as a white solid, which was used without further characterisation.

Intermediate 153

Methyl (1aRS,7bSR)-5-[2-((Z)-3-diethylaminoprop-1-enyl)benzene-sulfonylamino]-1,1a,2,7b-tetrahydrocyclopropa[c]chromene-4-carboxylate

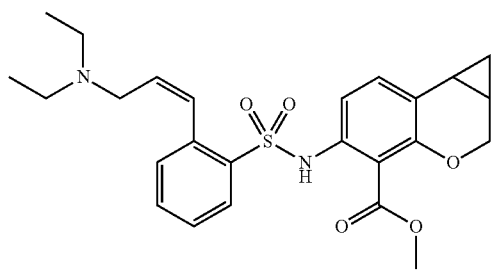 [SMILES: CCN(CC)C/C=C\c1ccccc1S(=O)(=O)Nc1ccc2c(c1C(=O)OC)OCC1CC21]

A mixture of methyl (1aRS,7bSR)-5-(2-bromobenzenesulfonylamino)-1,1a,2,7b-tetrahydro-cyclopropa[c]chromene-4-carboxylate (Intermediate 154, 0.612 g), N,N-diethyl-N—((Z)-1-tributylstannanylprop-1-en-3-yl)amine (Intermediate 11, 1.13 g), tri-tert-butylphosphonium tetrafluoroborate (0.041 g), tris-(dibenzylideneacetone)dipalladium (0.064 g) in dioxane (12 mL) and DMSO (0.4 mL) was degassed and purged with nitrogen then heated at 100° C. for 1.5 hours. After cooling, the mixture was diluted with brine and extracted with ethyl acetate. The organic layer was washed with water, dried (Na$_2$SO$_4$) and filtered. The filtrate was evaporated to dryness and the residue was purified by chromatography on silica, eluting with a mixture of methanol and DCM with a gradient of 0-15% to give methyl (1aRS,7bSR)-5-[2-((Z)-3-diethylamino-prop-1-enyl)benzenesulfonylamino]-1,1a,2,7b-tetrahydrocyclopropa[c]chromene-4-carboxylate (0.495 g) as a solid.

¹H NMR (CDCl₃) δ: 8.06 (1H, dd), 7.52 (1H, m), 7.40 (1H, m), 7.30 (1H, m), 7.14 (1H, d), 7.01 (1H, m), 6.86 (1H, d), 6.02 (1H, m), 4.33 (1H, d), 3.84 (3H, s), 3.77 (1H, d), 3.12 (2H, br s), 2.51 (4H, br s), 1.87 (1H, m), 1.70 (1H, m), 1.05-0.85 (8H, m).

Intermediate 154

Methyl (1aRS,7bSR)-5-(2-bromobenzenesulfonylamino)-1,1a,2,7b-tetrahydrocyclopropa[c]chromene-4-carboxylate

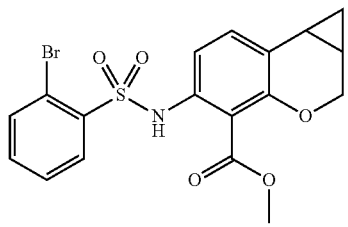

2-Bromobenzenesulfonyl chloride (0.559 g) was added to a solution of methyl (1aRS,7bSR)-5-amino-1,1a,2,7b-tetrahydrocyclopropa[c]chromene-4-carboxylate (Intermediate 42, 0.40 g) in DCM (12 mL) and pyridine (4 mL) and the resultant mixture was stirred at room temperature for 1 hour. The mixture was evaporated to dryness and the residue was dissolved in DCM and washed with 2N HCl, dried (Na₂SO₄) and filtered. The filtrate was evaporated to dryness and the residue was purified by chromatography on silica, eluting with a mixture of ethyl acetate and cyclohexane with a gradient of 0-35% to give methyl (1aRS,7bSR)-5-(2-bromobenzenesulfonylamino)-1,1a,2,7b-tetrahydrocyclopropa[c]chromene-4-carboxylate (0.612 g) as a solid.

¹H NMR (CDCl₃) δ: 9.85 (1H, s), 7.89 (1H, dd), 7.85 (1H, dd), 7.57-7.49 (2H, m), 7.26 (1H, d), 6.64 (1H, d), 4.27 (1H, d), 3.72 (1H, d), 3.66 (3H, s), 2.05-1.95 (1H, m), 1.86-1.76 (1H, m), 1.08-0.98 (1H, m), 0.84-0.76 (1H, m).

Intermediate 155

Methyl (1aRS,7bSR)-5-(2-{N—[((R)-1-ethylpyrrolidine-2-yl)carbonyl]-N-methylaminomethyl}-4-fluorobenzenesulfonylamino)-1,1a,2,7b-tetrahydrocyclopropa-[c]chromene-4-carboxylate

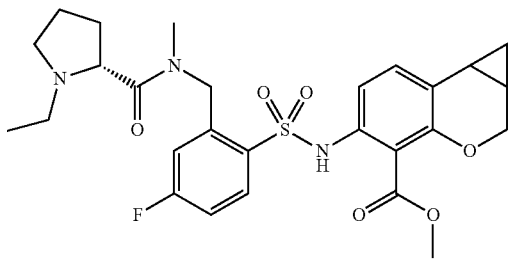 [SMILES: CCN1CCC[C@@H]1C(=O)N(C)Cc1cc(F)ccc1S(=O)(=O)Nc1ccc2c(c1C(=O)OC)OCC1CC21]

HATU (0.136 g) was added to a mixture of methyl (1aRS,7bSR)-5-(4-fluoro-2-methylaminomethylbenzenesulfonylamino)-1,1a,2,7b-tetrahydrocyclopropa[c]chromene-4-carboxylate (Intermediate 156, 0.150 g), (R)-1-ethylpyrrolidine-2-carboxylic acid (Intermediate 147, 0.061 g) and N,N-diisopropyl-N-ethylamine (0.124 mL) in DMF (5 mL) and the mixture was stirred for 3 days at room temperature. The volatiles were removed in vacuo and the residue was extracted with ethyl acetate (50 mL). The organic layer was washed with water (50 mL), brine, dried (Na₂SO₄) and filtered. The filtrate was evaporated to dryness and the residue was purified by chromatography on silica eluting with a mixture of methanol and DCM with a gradient of 0-10% to give methyl (1aRS,7bSR)-5-(2-{N—[((R)-1-ethylpyrrolidine-2-yl)carbonyl]methylamino]-methyl}-4-fluorobenzenesulfonylamino)-1,1a,2,7b-tetrahydrocyclopropa[c]chromene-4-carboxylate (0.177 g) as a solid.

LCMS (Method F) r/t 2.33 (M+H) 546.

Intermediate 156

Methyl (1aRS,7bSR)-5-(4-fluoro-2-methylaminomethylbenzenesulfonyl-amino)-1,1a,2,7b-tetrahydrocyclopropa[c]chromene-4-carboxylate

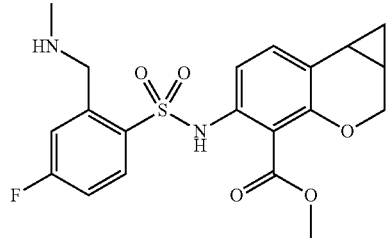 [SMILES: CNCc1cc(F)ccc1S(=O)(=O)Nc1ccc2c(c1C(=O)OC)OCC1CC21]

A solution of potassium carbonate (0.345 g) in water (2 mL) was added to a solution of methyl (1aRS,7bSR)-5-(4-fluoro-2-[N-methyl-N-(2,2,2-trifluoroacetyl)-aminomethyl]-benzenesulfonyl-amino)-1,1a,2,7b-tetrahydrocyclopropa[c]chromene-4-carboxylate (Intermediate 157, 0.257 g) in methanol (12 mL) and the mixture was heated at 45° C. for 3 hours. After cooling, the volatiles were removed in vacuo and the residue was treated with water (30 mL) and saturated with sodium chloride and extracted with ethyl acetate (50 mL). The organic layer was dried (Na₂SO₄) and filtered and the filtrate was evaporated to dryness to give methyl (1aRS,7bSR)-5-(4-fluoro-2-methylaminomethylbenzenesulfonylamino)-1,1a,2,7b-tetrahydrocyclopropa[c]chromene-4-carboxylate (0.156 g) as a solid.

LCMS (Method B) r/t 2.14 (M+H) 421.

Intermediate 157

Methyl (1aRS,7bSR)-5-(4-fluoro-2-[N-methyl-N-(2,2,2-trifluoroacetyl)-aminomethyl]benzenesulfonylamino)-1,1a,2,7b-tetrahydrocyclopropa[c]chromene-4-carboxylate

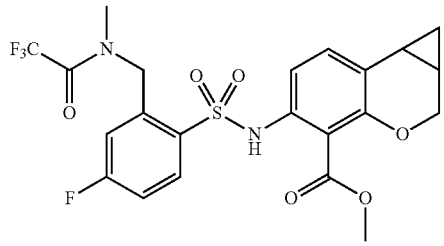 [SMILES: COC(=O)c1c(NS(=O)(=O)c2ccc(F)cc2CN(C)C(=O)C(F)(F)F)ccc2c1OCC1CC21]

A mixture of 4-fluoro-2-[N-methyl-N-(2,2,2-trifluoroacetyl)aminomethyl]benzenesulfonyl chloride (Intermediate 158, 0.182 g) was added to a solution of methyl (1aRS,7bSR)-5-amino-1,1a,2,7b-tetrahydrocyclopropa[c]chromene-4-carboxylate (Intermediate 42, 0.100 g) in DCM (3 mL) and pyridine (1 mL) and the resultant mixture was stirred at room temperature for 1 hour. The mixture was evaporated to dryness and the residue was purified by chromatography on silica eluting with a mixture of ethyl acetate and cyclohexane with a gradient of 0-40% to give methyl (1aRS,7bSR)-5-(4-fluoro-2-[N-methyl-N-(2,2,2-trifluoroacetyl)aminomethyl]benzenesulfonyl-amino)-1,1a,2,7b-tetrahydrocyclopropa[c]chromene-4-carboxylate (0.257 g) as a solid.

LCMS (Method F) r/t 3.77 (M+H) 517.

Intermediate 158

4-Fluoro-2-[N-methyl-N-(2,2,2-trifluoroacetyl)aminomethyl]benzene-sulfonyl chloride

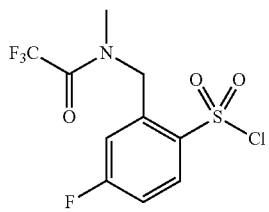 [SMILES: CN(Cc1cc(F)ccc1S(=O)(=O)Cl)C(=O)C(F)(F)F]

A solution of 3-fluoro-N-methyl-N-(trifluoroacetyl)benzylamine (Intermediate 159, 0.497 g) in DCE (0.5 mL) was added to stirred, cooled chlorosulfonic acid (3 mL). The mixture was allowed to come up to room temperature and then heated at 70° C. for 3 hours. After cooling, the mixture was added carefully to a mixture of ice and water, then extracted with ethyl acetate, washed with water, dried (MgSO$_4$) and filtered. The filtrate was evaporated to dryness and the residue was purified by chromatography on silica, eluting with a mixture of ethyl acetate and pentane with a gradient of 2.5-10% to give 4-fluoro-2-[N-methyl-N-(2,2,2-trifluoroacetyl)aminomethyl]-benzenesulfonyl chloride (0.21 g) as a clear oil.

$^1$H NMR (CDCl$_3$) δ: 8.20 (1H, m), 7.24 (1H, m), 7.01 (1H, d), 5.21 (2H, s), 3.24 (2H, s), 3.13 (1H, s).

Intermediate 159

3-Fluoro-N-methyl-N-(trifluoroacetyl)benzylamine

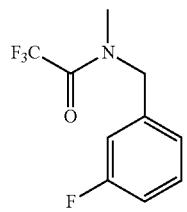 [SMILES: CN(Cc1cccc(F)c1)C(=O)C(F)(F)F]

A solution of 3-fluoro-N-(trifluoroacetyl)benzylamine (Intermediate 105, 0.508 g) in THF (5 mL) was added to a stirred suspension of sodium hydride (60% oil dispersion, 0.096 g) in THF (5 mL). The resultant mixture was stirred at room temperature for 30 minutes. Iodomethane (0.653 g) was added and the mixture was stirred at room temperature overnight. The mixture was poured into water and extracted with ethyl acetate, washed with water, dried (MgSO$_4$) and filtered. The filtrate was evaporated to dryness to give 3-fluoro-N-methyl-N-(trifluoroacetyl)benzylamine (0.497 g) as a white solid.

$^1$H NMR (CDCl$_3$) δ: 7.34 (1H, m), 7.10-6.90 (3H, m), 4.63 (2H, s), 3.07 (2H, q), 2.94 (1H, s).

Intermediate 160

Methyl (1aRS,7bSR)-5-(2-[N—((S)-1-ethylpyrrolidine-2-yl)carbonyl-N-methylaminomethyl]-4-fluorobenzenesulfonylamino)-1,1a,2,7b-tetrahydrocyclopropa-[c]chromene-4-carboxylate

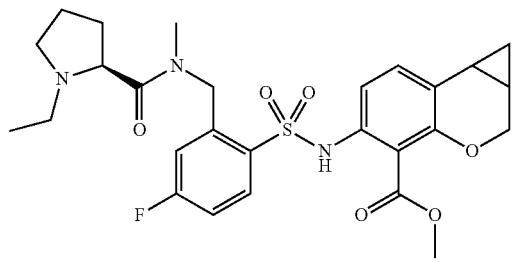 [SMILES: CCN1CCC[C@H]1C(=O)N(C)Cc1cc(F)ccc1S(=O)(=O)Nc1ccc2c(c1C(=O)OC)OCC1CC21]

Prepared by proceeding in a similar manner to Intermediate 155, starting from methyl (1aRS,7bSR)-5-(4-fluoro-2-methylaminomethylbenzenesulfonylamino)-1,1a,2,7b-tetrahydro-cyclopropa[c]chromene-4-carboxylate (intermediate 156) and (S)-1-ethylpyrrolidine-2-carboxylic acid (Intermediate 106) as a solid/

LCMS (Method B) r/t 2.47 (M+H) 546.

Intermediate 161

Methyl (1aRS,7bSR)-5-[2-(4-dimethylaminobutylamino)-4-fluoro-benzenesulfonylamino]-1,1a,2,7b-tetrahydrocyclopropa[c]chromene-4carboxylate

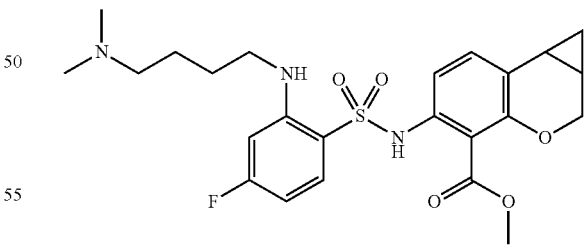

A solution of methyl (1aRS,7bSR)-5-(2,4-difluorobenzenesulfonylamino)-1,1a,2,7b-tetrahydro-cyclopropa[c]chromene-4-carboxylate (Intermediate 162, 0.675 g) and N,N-dimethylbutane-diamine (0.496 g) in dioxane (20 mL) was stirred and heated at 80° C. for 17 hours then left at room temperature for 3 days. The solution was diluted with ethyl acetate, washed with potassium carbonate solution and water then dried (Na$_2$SO$_4$) and filtered. The filtrate was concentrated in vacuo and the residue was purified by chromatography on silica, eluting with a mixture of methanol and DCM with a gradient of 0-40% to give methyl (1aRS,7bSR)-5-[2-(4-dimethyl-aminobutylamino)-4-fluorobenzene-sulfonylamino]-1,1a,2,7b-tetrahydrocyclopropa[c]chromene-4carboxylate (0.499 g) as a colourless gum.

$^1$H NMR (CDCl$_3$) δ: 7.51 (1H, dd), 7.26 (1H, d), 7.12 (1H, d), 6.29 (2H, m), 6.00 (1H, br, s), 4.31 (1H, d), 3.75 (1H, d), 3.50 (3H, s), 3.01 (2H, m), 2.25 (6H, s), 2.11 (2H, t), 1.94 (1H, m), 1.73 (1H, m), 1.58 (4H, m), 1.03 (2H, m).

Intermediate 162

Methyl (1aRS,7bSR)-5-(2,4-difluorobenzenesulfonylamino)-1,1a,2,7b-tetrahydrocyclopropa[c]chromene-4-carboxylate

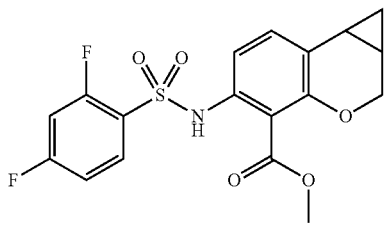 [SMILES: COC(=O)c1c(NS(=O)(=O)c2ccc(F)cc2F)ccc2c1OCC1CC21]

2,4-Difluorobenzenesulphonyl chloride (0.468 g) was added to a solution of methyl (1aRS,7bSR)-5-amino-1,1a,2,7b-tetrahydrocyclopropa[c]chromene-4-carboxylater (Intermediate 42, 0.438 g) in pyridine (2 mL) and DCM (4 mL) and the solution was left at room temperature for 2 hours. The mixture was diluted with DCM, washed with 2M hydrochloric acid, dried (Na$_2$SO$_4$) and filtered. The filtrate was concentrated in vacuo and the residue was purified by chromatography on silica, eluting with a mixture of ethyl acetate and cyclohexane with a gradient of 0-30% to give methyl (1aRS,7bSR)-5-(2,4-difluorobenzenesulfonylamino)-1,1a,2,7b-tetrahydrocyclopropa[c]chromene-4-carboxylate (0.761 g) as a light coloured gum.

$^1$H NMR (CDCl$_3$) δ: 8.90 (1H, br, s), 7.82 (1H, m), 7.22 (1H, d), 7.13 (1H, d), 6.88 (2H, m), 4.32 (1H, d), 3.89 (3H, s), 3.79 (1H, d), 1.90 (1H, m), 1.71 (1H, m), 1.01 (2H, m).

Intermediate 163

((R)-1-Ethylpyrrolidin-3-ylmethyl)amine

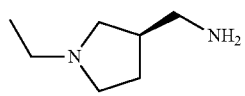

Lithium aluminium hydride was added to a stirred solution of ((R)-1-acetylpyrrolidin-3-ylmethyl)amine (Intermediate 164, 1.5 g) in THF (50 mL) and the resulting mixture was stirred and heated at reflux for 2 hours. After cooling, ethanol was slowly added and the mixture was concentrated under vacuum. The residue was diluted with DCM and the solid was filtered off. The filtrate was evaporated to dryness to give ((R)-1-ethylpyrrolidin-3-ylmethyl)amine (0.9 g) as a yellow solid.

LCMS (Method D) r/t 0.396 (M+H) 129.

Intermediate 164

((R)-1-Acetylpyrrolidin-3-ylmethyl)amine

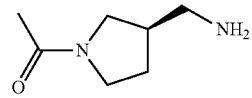

A mixture of benzyl N—((S)-1-acetylpyrrolidin-3-ylmethyl)-N-benzylcarbamate (Intermediate 165, 4.2 g) and palladium hydroxide on carbon (0.4 g) in methanol (42 mL) was stirred under an atmosphere of hydrogen at 60° C. for 48 hours. The mixture was filtered and the filtrate was evaporated to dryness to give ((R)-1-acetylpyrrolidin-3-ylmethyl)amine (1.5 g) as a light yellow oil.

LCMS (Method D) r/t 0.49 (M+H) 143.

Intermediate 165

Benzyl N—((S)-1-acetylpyrrolidin-3-ylmethyl)-N-benzylcarbamate

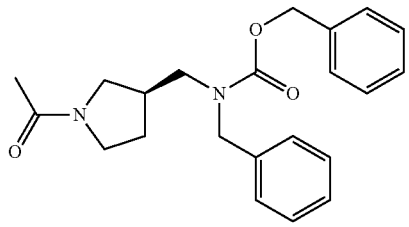 [SMILES: CC(=O)N1CC[C@H](CN(Cc2ccccc2)C(=O)OCc2ccccc2)C1]

Acetyl chloride (2.86 g) was added to a stirred solution of benzyl N—((S)-pyrrolidin-3-ylmethyl)-N-benzylcarbamate (Intermediate 166, 5.9 g) and triethylamine (3.68 g) in DCM (80 mL) with ice cooling. The resultant mixture was stirred at room temperature for 2 hours then concentrated under vacuum. The residue was treated with saturated aqueous sodium bicarbonate and extracted with ethyl acetate, dried (Na$_2$SO$_4$) and filtered. The filtrate was evaporated to dryness and the residue was purified by chromatography on silica, eluting with ethyl acetate to give benzyl N—((S)-1-acetylpyrrolidin-3-ylmethyl)-N-benzylcarbamate (4.2 g) as a yellow oil.

LCMS (Method D) r/t 1.65 (M+H) 367.

Intermediate 166

Benzyl N—((S)-pyrrolidin-3-ylmethyl)-N-benzylcarbamate

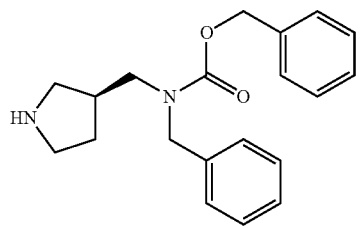 [SMILES: O=C(OCc1ccccc1)N(Cc1ccccc1)C[C@H]1CCNC1]

tert-Butyl (S)-3-[N-benzyl-N-(benzyloxycarbonyl)aminomethyl]pyrrolidine-1-carboxylate (Intermediate 167, 1 g) was added dropwise to a solution of acetyl chloride (15 g) in methanol (50 mL) and the resultant mixture was stirred at room temperature overnight. The mixture was concentrated under vacuum and the residue was purified by HPLC (C18) to give benzyl N—((S)-pyrrolidin-3-ylmethyl)-N-benzylcarbamate (8.0 g) as an off white solid which was used without further characterisation.

Intermediate 167 tert-Butyl (S)-3-[N-benzyl-N-(benzyloxycarbonyl)aminomethyl]-pyrrolidine-1-carboxylate

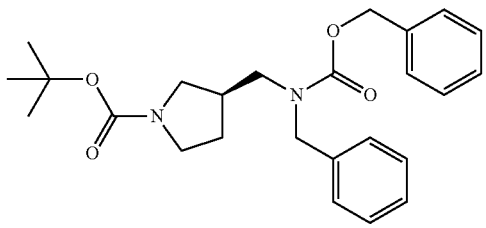 [SMILES: CC(C)(C)OC(=O)N1CC[C@H](CN(Cc2ccccc2)C(=O)OCc2ccccc2)C1]

A solution of tert-butyl (R)-3-(N-benzyloxycarbonyl)aminomethylpyrrolidine-1-carboxylate (Intermediate 168, 19 g) in DMF (90 mL) was added dropwise to a suspension of sodium hydride (60%, 4.55 g) in DMF (100 mL) After stirring for 30 minutes, benzyl bromide (11.7 g) was added dropwise. The resultant mixture was stirred and heated at 70° C. overnight.

After cooling, saturated aqueous sodium bicarbonate was added and the mixture was extracted with ethyl acetate, dried (Na₂SO₄) and filtered. The filtrate was purified by chromatography on silica, eluting with a mixture of ethyl acetate and petroleum ether (10%) to give tert-butyl (S)-3-[N-benzyl-N-(benzyloxycarbonyl)aminomethyl]-pyrrolidine-1-carboxylate (11.0 g) as a light yellow oil, which was used without further characterisation.

Intermediate 168 tert-Butyl (R)-3-(N-benzyloxycarbonyl)aminomethylpyrrolidine-1-carboxylate

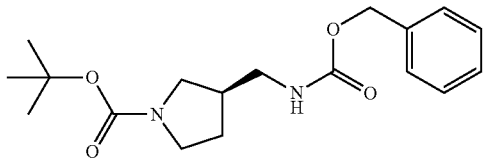 [SMILES: CC(C)(C)OC(=O)N1CC[C@H](CNC(=O)OCc2ccccc2)C1]

Benzyl chloroformate (14.1 g) was added dropwise to a cooled solution of tert-butyl (R)-3-aminomethylpyrrolidine-1-carboxylate (15 g) in THF (150 mL) while maintaining the temperature below 0° C. On completion of the addition, triethylamine (15.2 g) was added dropwise. The resultant mixture was stirred at −5° C. for 30 minutes then at room temperature overnight. Brine was added and the mixture was extracted with ethyl acetate, washed with brine, dried (Na₂SO₄) and filtered. The filtrate was evaporated to dryness to give tert-butyl (R)-3-(N-benzyloxycarbonyl)aminomethylpyrrolidine-1-carboxylate (23 g) as a colourless sticky gum, which was used without further characterisation.

Intermediate 169

((S)-1-Ethylpyrrolidin-3-yl)methylamine

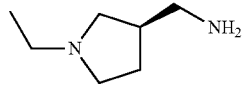

Palladium on carbon (10%, 0.3 g) was added to a solution of benzyl N—((S)-1-ethylpyrrolidin-3-ylmethyl)carbamate (Intermediate 170, 1.8 g) in methanol (20 mL) and the resultant mixture was stirred under an atmosphere of hydrogen for 24 hours. The mixture was filtered and the filtrate was evaporated to dryness to give ((S)-1-ethylpyrrolidin-3-yl)methylamine (0.8 g) as a colourless oil, which was used without further characterisation.

Intermediate 170

Benzyl N—((S)-1-ethylpyrrolidin-3-ylmethyl)carbamate

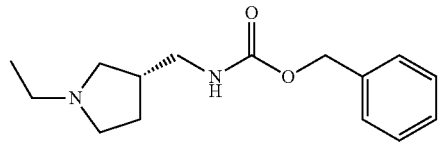 [SMILES: CCN1CC[C@@H](CNC(=O)OCc2ccccc2)C1]

Iodoethane (4.1 g) was added to a cooled mixture of benzyl N—((R)-pyrrolidin-3-ylmethyl)carbamate trifluoroacetate salt (Intermediate 171, 7.6 g) and potassium carbonate (12.2 g) in DMF (100 mL) while maintaining the temperature at 0° C. The mixture was then stirred at room temperature for 4 hours. Water was added and the mixture was extracted with ethyl acetate, washed with brine, dried (Na₂SO₄) and filtered. The filtrate was evaporated to dryness to give benzyl N—((S)-1-ethylpyrrolidin-3-ylmethyl)carbamate (1.8 g) as a colourless oil, which was used without further characterisation.

Intermediate 171

Benzyl N—((R)-pyrrolidin-3-ylmethyl)carbamate trifluoroacetate salt

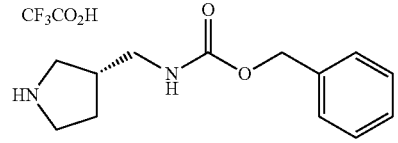 [SMILES: "CF3CO2H" ; O=C(NC[C@@H]1CCNC1)OCc1ccccc1]

A mixture of tert-butyl (S)-3-(N-benzyloxycarbonyl)aminomethylpyrrolidine-1-carboxylate (Intermediate 172, 8.0 g) in trifluoroacetic acid (10 mL) was stirred at room temperature for 5 hours. The mixture was concentrated under vacuum to give crude benzyl N—((R)-pyrrolidin-3-ylmethyl)carbamate trifluoroacetate salt (7.6 g) as a light brown oil which was used without further purification or characterisation.

Intermediate 172 tert-Butyl (S)-3-(N-benzyloxycarbonyl)aminomethylpyrrolidine-1-carboxylate

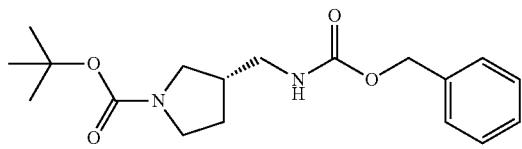 [SMILES: CC(C)(C)OC(=O)N1CC[C@@H](CNC(=O)OCc2ccccc2)C1]

Prepared by proceeding in a similar manner to Intermediate 168, starting form tert-butyl (S)-3-aminomethylpyrrolidine-1-carboxylate and used without further characterisation.

Intermediate 173

Methyl (1aRS,7bSR)-5-[2-(4-Ethyl-2-oxopiperazin-1-ylmethyl)-4-fluorobenzene-sulfonylamino]-1,1a,2,7b-tetrahydrocyclopropa[c]chromene-4-carboxylate

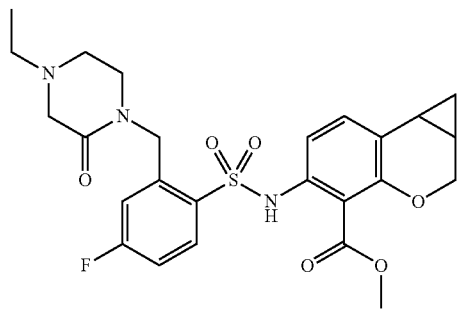 [SMILES: CCN1CCN(Cc2cc(F)ccc2S(=O)(=O)Nc2ccc3c(c2C(=O)OC)OCC2CC32)C(=O)C1]

A solution of 2-(4-ethyl-2-oxopiperazin-1-ylmethyl)-4-fluorobenzenesulfonyl chloride (Intermediate 174, 0.368 g) and methyl (1 aRS,7bSR)-5-amino-1,1a,2,7b-tetrahydro-cyclopropa[c]chromene-4-carboxylate (Intermediate 42, 0.219 g) in pyridine (3 mL) and DCM (3 mL) was left to stand at room temperature for 17 hours. The mixture was evaporated in vacuo and the residue was dissolved in water and DCM and the organic layer was dried (Na$_2$SO$_4$) and filtered. The filtrate was concentrated in vacuo and the residue was purified by chromatography on silica, eluting with a mixture of ethyl acetate and cyclohexane with a gradient of 50-100% to give a gum which was triturated with ether and filtered to give methyl (1aRS,7bSR)-5-[2-(4-ethyl-2-oxopiperazin-1-ylmethyl)-4-fluorobenzenesulfonylamino]-1,1a,2,7b-tetrahydro-cyclopropa[c]chromene-4-carboxylate (0.312 g) as a white solid.

$^1$H NMR (DMSO-d$_6$) δ: 9.95 (1H, br, s), 7.81 (1H, dd), 7.26 (2H, m), 6.89 (1H, dd), 6.59 (1H, d), 4.75 (2H, s), 4.29 (1H, d), 3.71 (1H, d), 3.62 (3H, s), 3.15 (4H, m), 2.70 (2H, t), 2.45 (2H, q), 2.02 (1H, m), 1.72 (1H, m), 1.06 (1H, m), 1.02 (3H, t), 0.80 (1H, q).

Intermediate 174

2-(4-Ethyl-2-oxopiperazin-1-ylmethyl)-4-fluorobenzenesulfonyl chloride

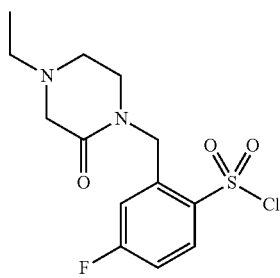 [SMILES: CCN1CCN(Cc2cc(F)ccc2S(=O)(=O)Cl)C(=O)C1]

Chlorosulphonic acid (2 mL) was added to 4-ethyl-1-(3-fluorobenzyl)-piperazin-2-one (Intermediate 175, 0.59 g) with stirring and cooling in ice. The cooling was removed and the solution was stirred at room temperature for 4 hours before being carefully added to a mixture of ethyl acetate, ice and sodium bicarbonate. The organic layer was dried (Na$_2$SO$_4$) and filtered and the filtrate was concentrated in vacuo to give 2-(4-ethyl-2-oxopiperazin-1-ylmethyl)-4-fluoro-benzenesulfonyl chloride (0.37 g) as a colourless gum.

LCMS (Method E) r/t 1.99 (M–H) 335, 337

Intermediate 175

4-Ethyl-1-(3-fluoro-benzyl)-piperazin-2-one

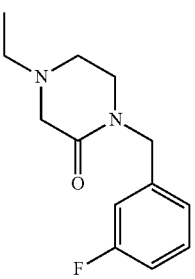 [SMILES: CCN1CCN(Cc2cccc(F)c2)C(=O)C1]

Sodium hydride (60% oil dispersion, 0.176 g) was added to a stirred solution of 4-ethyl-piperazin-2-one (Intermediate 176, 0.512 g) in anhydrous THF (100 mL) and the mixture was stirred at room temperature for 10 minutes. 3-Fluorobenzyl bromide (0.827 g) was added and stirring was continued for 2 hours. The solution was diluted with water and ethyl acetate and the organic layer was dried (Na$_2$SO$_4$) and filtered. The filtrate was concentrated in vacuo and the residue was purified by chromatography on silica, eluting with a mixture of methanol and DCM with a gradient of 0-5% to give 4-ethyl-1-(3-fluorobenzyl)piperazin-2-one (0.595 g) as a colourless oil.

$^1$H NMR (CDCl$_3$) δ: 7.26 (1H, m), 6.91-7.10 (3H, m), 4.61 (2H, s), 3.27 (2H, t), 3.23 (2H, s), 2.65 (2H, t), 2.48 (2H, q), 1.09 (3H, t).

Intermediate 176

4-Ethylpiperazin-2-one

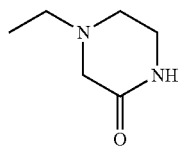

A mixture of 2-oxopiperazine (1.07 g), iodoethane (1.72 g) and potassium carbonate (2.76 g) in acetonitrile (50 mL) was stirred at 55° C. for 3 hours. After cooling, the mixture was filtered and the filtrate was concentrated in vacuo. The residue was triturated with DCM and filtered and the filtrate was concentrated in vacuo. The residue was purified by chromatography on silica, eluting with a mixture of methanol and DCM with a gradient of 0-40% to give 4-ethylpiperazin-2-one (0.991 g) as a colourless oil.

$^1$H NMR (CDCl$_3$) δ: 6.81 (1H, br, s), 3.37 (2H, m), 3.14 (2H, s), 2.66 (2H, t), 2.50 (2H, q), 1.11 (3H, t).

Intermediate 177

Methyl (1aRS,7bSR)-5-[2-(1-ethylpiperidin-4-ylmethyl)-4-fluorobenzene-sulfonylamino]-1,1a,2,7b-tetrahydrocyclopropa[c]chromene-4-carboxylate

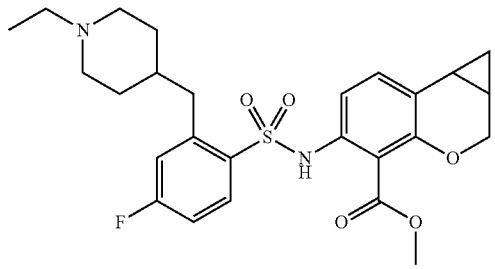 [SMILES: CCN1CCC(Cc2cc(F)ccc2S(=O)(=O)Nc2ccc3c(c2C(=O)OC)OCC2CC32)CC1]

2-(1-Ethylpiperidine-4-ylmethyl)-4-fluorobenzenesulfonyl chloride (Intermediate 178, 0.165 g) was added to a solution of methyl (1aRS,7bSR)-5-amino-1,1a,2,7b-tetrahydrocyclopropa-[c]chromene-4-carboxylate (Intermediate 42, 0.290 g) in DCM (5 mL) and pyridine (1 mL) and the resultant mixture was stirred at room temperature for 21 hours. The mixture was evaporated to dryness and the residue was purified by chromatography on silica eluting with a mixture of 2M NH$_3$ in methanol and DCM with a gradient of 0-20% to give methyl (1aRS,7bSR)-5-[2-(1-ethyl-piperidin-4-ylmethyl)-4-fluorobenzenesulfonylamino]-1,1a,2,7b-tetrahydrocyclopropa-[c]chromene-4-carboxylate (0.200 g) as a solid.

LCMS (Method F) r/t 2.34 (M+H) 503

Intermediate 178

2-(1-Ethylpiperidin-4-ylmethyl)-4-fluorobenzenesulfonyl chloride

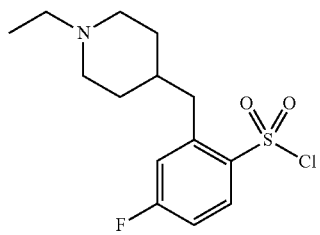 [SMILES: CCN1CCC(Cc2cc(F)ccc2S(=O)(=O)Cl)CC1]

A solution of 1-ethyl-4-(3-fluorobenzyl)piperidine (Intermediate 179, 0.210 g) in DCE (1 mL) was added to chlorosulfonic acid (2 mL) at 0° C. The mixture was allowed to warm to room temperature and stirred for 2 hours. The resultant mixture was added carefully to ice/water and extracted with DCM. The organic layer was dried (Na$_2$SO$_4$) and filtered and the filtrate was evaporated to dryness to give 2-(1-ethylpiperidin-4-ylmethyl)-4-fluorobenzenesulfonyl chloride (0.290 g) as a solid.

$^1$H NMR (CDCl$_3$) δ: 8.17 (1H, dd), 7.17 (1H, m), 7.08 (1H, dd), 3.59 (2H, d), 3.13-2.99 (4H, m), 2.57 (2H, m), 2.24 (2H, m), 1.95-1.77 (3H, m), 1.47 (3H, t).

Intermediate 179

1-Ethyl-4-(3-fluorobenzyl)piperidine

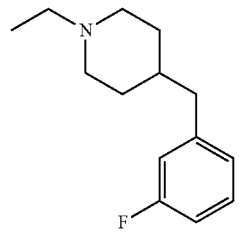 [SMILES: CCN1CCC(Cc2cccc(F)c2)CC1]

Bromoethane (0.1 mL) was added to a mixture of 4-(3-fluorobenzyl)piperidine (Intermediate 180, 0.259 g) and potassium carbonate (0.204 g) in acetonitrile (10 mL). The mixture was stirred for 20 hours then filtered. The filtrate acidified by addition of few drops of 2M HCl and the solution was passed through a SCX-2 column (10 g). The product was eluted with 2M ammonia in methanol and the residue after evaporation was triturated with diethyl ether. The solid was filtered off and the filtrated was concentrated in vacuo to give 1-ethyl-4-(3-fluorobenzyl)piperidine (0.210 g)

$^1$H NMR (CDCl$_3$) δ: 7.24-7.16 (1H, m), 6.94-6.79 (3H, m), 2.91 (2H, dt), 2.52 (2H, d), 2.36 (2H, q), 1.82 (2H, td), 1.68-1.57 (2H, m), 1.56-1.44 (1H, m), 1.30 (2H, m), 1.06 (3H, t).

Intermediate 180

4-(3-Fluorobenzyl)piperidine

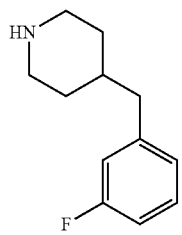 [SMILES: Fc1cccc(CC2CCNCC2)c1]

A mixture of benzyl 4-(3-fluorobenzylidene)piperidine-1-carboxylate (Intermediate 181, 1.05 g), 20% palladium hydroxide on carbon (0.227 g), IMS (30 mL) and acetic acid (10 mL) was degassed by nitrogen/vacuum purging. The mixture was placed under an atmosphere of hydrogen with rapid stirring. After 2 hours the mixture was filtered and the filtrate was diluted with water (40 mL) and neutralized with $Na_2CO_3$. The solution was saturated with sodium chloride, extracted with ethyl acetate dried ($MgSO_4$) and filtered. The filtrate was concentrated in vacuo and the residue was dissolved in a mixture of methanol and water (20 mL, 1:1) and passed down a SCX-2 column. The product was eluted with 2M ammonia to give 4-(3-fluorobenzyl)piperidine (0.532 g)

$^1$H NMR ($CDCl_3$) δ: 7.24-7.16 (1H, m), 6.95-6.77 (3H, m), 3.04 (2H, dt), 2.56 (2H, dd), 2.51 (2H, d), 1.71-1.54 (3H, m), 1.42 (1H, s), 1.14 (2H, m)

Intermediate 181

Benzyl 4-(3-fluorobenzylidene)piperidine-1-carboxylate

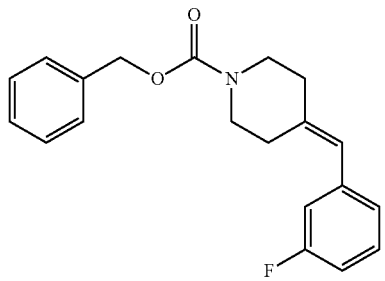 [SMILES: O=C(OCc1ccccc1)N1CCC(=Cc2cccc(F)c2)CC1]

Sodium hydride (0.245 g) was added portionwise to a solution of diethyl (3-fluorobenzyl)phosphonate (Intermediate 182, 1 g) in THF (40 mL) at 0° C. The mixture was stirred for 30 minutes then benzyl 4-oxopiperidine-1-carboxylate (0.947 g) was added at 0° C. The mixture was allowed to warm to room temperature and stirred for 21.5 hours. The mixture was partitioned between water and ethyl acetate and the organic layer was washed with brine, dried ($Na_2SO_4$) and filtered. The filtrate was evaporated to dryness and the residue was purified by chromatography on silica eluting with a mixture of ethyl acetate and cyclohexane with a gradient of 0-25% to give benzyl 4-(3-fluorobenzylidene)piperidine-1-carboxylate (1.05 g)

$^1$H NMR ($CDCl_3$) δ: 7.39-7.22 (6H, m), 6.98-6.83 (3H, m), 6.33 (1H, s), 5.15 (2H, s), 3.54 (4H, dt), 2.41 (4H, dt).

Intermediate 182

Diethyl (3-fluorobenzyl)phosphonate

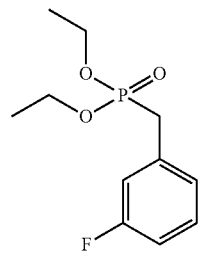 [SMILES: CCOP(=O)(Cc1cccc(F)c1)OCC]

A mixture of 3-fluorobenzyl bromide (2 g) and triethyl phosphite (2.2 mL) was heated at 160° C. under nitrogen for 4 hours. After cooling, the were volatiles removed in vacuo and the residue was purified by chromatography on silica eluting with a mixture of ethyl acetate and cyclohexane with a gradient of 0-100% to give diethyl (3-fluorobenzyl)phosphonate (2.46 g)

$^1$H NMR ($CDCl_3$) δ: 7.31-7.22 (1H, m), 7.11-6.89 (3H, m), 4.09-3.97 (4H, m), 3.13 (2H, d), 1.25 (6H, t).

Intermediate 183

Methyl (1aRS,7bSR)-5-{2-[2-(1-ethylazetidin-3-yl)ethyl]-4-fluorobenzene-sulfonylamino}-1,1a,2,7b-tetrahydrocyclopropa[c]chromene-4-carboxylate

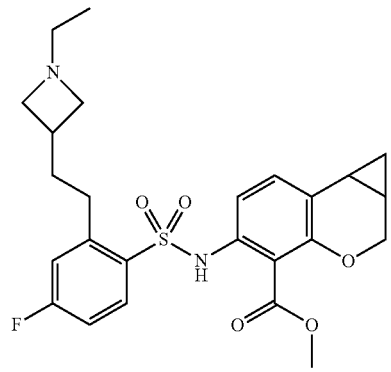 [SMILES: CCN1CC(CCc2cc(F)ccc2S(=O)(=O)Nc2ccc3c(c2C(=O)OC)OCC2CC32)C1]

A solution of tert-butyl (1aRS,7bSR)-3-{2-[5-fluoro-2-(4-methoxycarbonyl-1,1a,2,7b-tetrahydrocyclopropa[c]chromen-5-ylsulfamoyl)phenyl]ethyl}azetidine-1-carboxylate (Intermediate 184, 0.397 g) in DCM (5 mL) and trifluoroacetic acid (5 mL) was left at room temperature for 30 minutes then evaporated in vacuo and the residue was dissolved in toluene and re-evaporated. The residue was dissolved in DCM (15 mL) and acetaldehyde (0.063 g) was added followed by sodium triacetoxyborohydride (0.301 g). The mixture was stirred at room temperature for 2 hours then diluted with ethyl acetate and water and the organic layer was dried ($Na_2SO_4$) and filtered. The filtrate was concentrated in vacuo and the residue was purified by chromatography on silica, eluting with a mixture of methanol and DCM with a gradient of 0-25% to give methyl (1aRS,7bSR)-5-{2-[2-(1-ethylazetidin-3-yl)ethyl]-4-fluorobenzenesulfonylamino}-1,1a,2,7b-tetrahydrocyclopropa[c]chromene-4-carboxylate (0.312 g) as a white foam.

LCMS (Method E) r/t 2.75 (M+H) 489.

Intermediate 184 tert-butyl (1aRS,7bSR)-3-{2-[5-fluoro-2-(4-methoxycarbonyl-1,1a,2,7b-tetrahydro-cyclopropa[c]chromen-5-ylsulfamoyl)phenyl]ethyl}azetidine-1-carboxylate

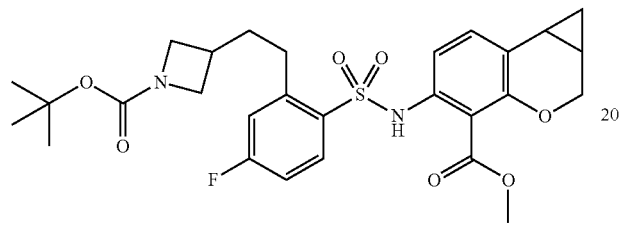

A mixture of tert-butyl (1aRS,7bSR)-3-{(E/Z)-2-[5-fluoro-2-(4-methoxycarbonyl-1,1a,2,7b-tetrahydrocyclopropa[c]chromen-5-ylsulfamoyl)phenyl]vinyl}azetidine-1-carboxylate (Intermediate 185, 0.502 g) and 10% palladium on carbon (0.05 g) in ethanol (25 mL) was stirred under an atmosphere of hydrogen for 30 minutes. The suspension was filtered and the filtrate was concentrated in vacuo. The residue was purified by chromatography on silica, eluting with a mixture of ethyl acetate and cyclohexane with a gradient of 0-40% to give tert-butyl (1aRS,7bSR)-3-{2-[5-fluoro-2-(4-methoxycarbonyl-1,1a,2,7b-tetrahydrocyclopropa[c]chromen-5-ylsulfamoyl)phenyl]-ethyl}azetidine-1-carboxylate (0.401 g) as a colourless gum.

$^1$H NMR (CDCl$_3$) δ: 9.01 (1H, br, s), 7.90 (1H, dd), 7.21 (1H, d), 7.02 (1H, d), 6.94 (2H, m), 4.32 (1H, d), 4.00 (2H, t), 3.79 (1H, d), 3.77 (3H, s), 3.56 (2H, dd), 2.79 (2H, dd), 2.56 (1H, m), 1.89 (3H, m), 1.72 (1H, m), 1.45 (9H, s), 0.99 (2H, m).

Intermediate 185 tert-Butyl (1aRS,7bSR)-3-{(E/Z)-2-[5-fluoro-2-(4-methoxycarbonyl-1,1a,2,7b-tetrahydro-cyclopropa[c]chromen-5-ylsulfamoyl)phenyl]vinyl}azetidine-1-carboxylate

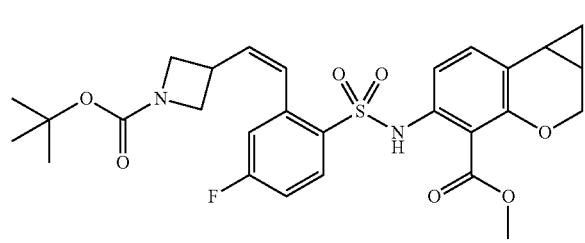 [SMILES: COC(=O)c1c(NS(=O)(=O)c2ccc(F)cc2/C=C\C2CN(C(=O)OC(C)(C)C)C2)ccc2c1OCC1CC21]

A mixture of methyl (1aRS,7bSR)-5-(2-bromo-4-fluorobenzenesulfonylamino)-1,1a,2,7b-tetrahydrocyclopropa[c]chromene-4-carboxylate (Intermediate 41, 0.456 g), tert-butyl 3-((E/Z)-2-trimethylstannanylvinyl)azetidine-1-carboxylate (Intermediate 186, 0.433 g), tris(dibenzylideneacetone)dipalladium(0) (0.046 g) and tri-tert-butylphosphonium tetrafluoroborate (0.029 g) in dioxane (15 mL) and DMSO (1.5 mL) was stirred and heated at 90° C. under nitrogen for 1 hour. After cooling, the solution was diluted with ethyl acetate, washed with water, dried (Na$_2$SO$_4$) and filtered. The filtrate was concentrated in vacuo and the residue was purified by chromatography on silica, eluting with a mixture of ethyl acetate and cyclohexane with a gradient of 0-40% to give tert-butyl (1aRS,7bSR)-3-{(E/Z)-2-[5-fluoro-2-(4-methoxycarbonyl-1,1a,2,7b-tetrahydrocyclopropa[c]chromen-5-ylsulfamoyl)phenyl]vinyl}-azetidine-1-carboxylate (0.508 g) as a colourless gum.

LCMS (Method E) r/t 4.47 (M–H) 557

Intermediate 186 tert-Butyl 3-((E/Z)-2-trimethylstannanylvinyl)azetidine-1-carboxylate

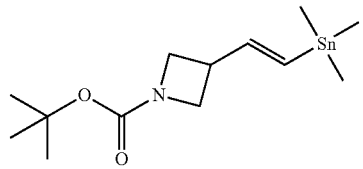 [SMILES: CC(C)(C)OC(=O)N1CC(/C=[CH]/[Sn]([CH3])([CH3])[CH3])C1]

A solution of tert-butyl 3-((E/Z)-2-iodovinyl)azetidine-1-carboxylate (Intermediate 187, 1.39 g), hexamethylditin (2.95 g), and tetrakis(triphenylphosphine)palladium(0) (0.52 g) in anhydrous THF (40 mL) was stirred and heated at 50° C. under nitrogen for 2 hours. After cooling, the mixture was evaporated in vacuo and the residue was purified by chromatography on silica, eluting with a mixture of ethyl acetate and cyclohexane with a gradient of 0-10% to give tert-butyl 3-((E/Z)-2-trimethylstannanylvinyl)azetidine-1-carboxylate (0.601 g) as a pale yellow oil.

$^1$H NMR (CDCl$_3$) δ: 5.79-6.5 (2H, m), 3.95 (2H, m), 3.62 (2H, m), 2.88-3.12 (1H, m), 1.32 (9H, s), 0.0 (9H, s).

Intermediate 187 tert-Butyl 3-((E/Z)-2-iodovinyl)azetidine-1-carboxylate

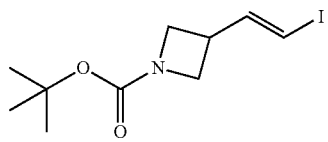

A solution of tert-butyl 3-formylazetidine-1-carboxylate (1.97 g) and iodoform (8.37 g) in anhydrous THF (25 mL) was added to a stirred suspension of anhydrous chromium (II) chloride in anhydrous THF (100 mL) under nitrogen and the mixture was stirred at room temperature for 4 hours. The resulting mixture was diluted with water and ethyl acetate and the organic layer was dried (Na$_2$SO$_4$) and filtered. The filtrate was concentrated in vacuo and the residue was purified by chromatography on silica, eluting with a mixture of ethyl acetate and cyclohexane with a gradient of 0-15% to give tert-butyl 3-((E/Z)-2-iodovinyl)azetidine-1-carboxylate (2.01 g) as a pale yellow oil.

$^1$H NMR (CDCl$_3$) δ: 6.71 (0.8H, dd), 6.55 (0.2H, t), 6.33 (0.2H, d), 6.18 (0.8H, d), 4.20 (0.4H, t), 4.08 (1.6H, t), 3.76 (2H, m), 3.45 (0.2H, m), 3.19 (0.8H, m), 1.44 (9H, s).

Intermediate 188

Methyl (1aRS,7bSR)-5-(2-{[((S)-1-ethylpyrrolidine-3-carbonyl)amino]-methyl}-4-fluorobenzenesulfonylamino)-1,1a,2,7b-tetrahydrocyclopropa[c]chromene-4-carboxylate

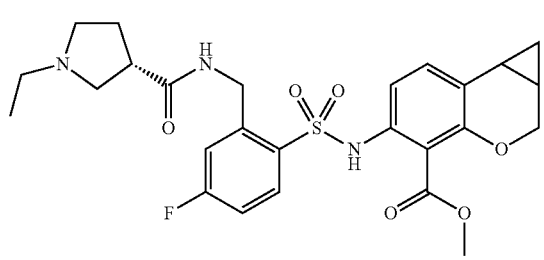 [SMILES: CCN1CC[C@H](C(=O)NCc2cc(F)ccc2S(=O)(=O)Nc2ccc3c(c2C(=O)OC)OCC2CC32)C1]

HATU (0.234 g) was added to a mixture of (S)-1-ethylpyrrolidine-3-carboxylic acid (Intermediate 189, 0.089 g) and NMM (0.068 mL) in DMF (4 mL) and the mixture was stirred for 15 minutes. Methyl (1aRS,7bSR)-5-(2-aminomethyl-4-fluorobenzenesulfonylamino)-1,1a,2,7b-tetrahydrocyclopropa[c]chromene-4-carboxylate (Intermediate 102, 0.250 g) was added and the mixture was stirred for 20 hours. The mixture was diluted with water and extracted with ethyl acetate. The organic layer was washed with saturated NaHCO$_3$ solution, dried (Na$_2$SO$_4$) and filtered. The filtrate was evaporated to dryness and the residue was purified by chromatography on silica eluting with a mixture of 2M ammonia in methanol and DCM with a gradient of 0-15% to give methyl (1aRS,7bSR)-5-(2-{[((S)-1-ethylpyrrolidine-3-carbonyl)amino]methyl}-4-fluoro-benzenesulfonylamino)-1,1a,2,7b-tetrahydrocyclopropa[c]chromene-4-carboxylate (0.190 g) as a solid.

$^1$H NMR (CDCl$_3$) δ: 7.81 (1H, dd), 7.46-7.38 (1H, m), 7.30-7.20 (3H, m), 7.06-6.93 (2H, m), 4.58 (2H, d), 4.32 (1H, dd), 3.79 (1H, dd), 3.76 (3H, s), 2.93-2.78 (3H, m), 2.70-2.49 (4H, m), 2.24-2.08 (1H, m), 2.00-1.87 (2H, m), 1.78-1.68 (1H, m), 1.15 (3H, t), 1.06-0.98 (2H, m)

Intermediate 189

(S)-1-Ethyl-pyrrolidine-3-carboxylic acid

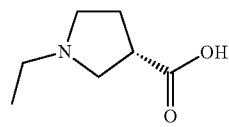

A mixture of benzyl (S)-1-ethylpyrrolidine-3-carboxylate (Intermediate 190, 0.563 g), 20% palladium hydroxide on carbon (0.056 g), ethyl acetate (9 mL) and IMS (1 mL) was degassed and hydrogenated for 4 hours. The catalyst was removed by filtration, washed with ethyl acetate and the filtrate was concentrated in vacuo to give (S)-1-ethylpyrrolidine-3-carboxylic acid (0.318 g) as a solid.

$^1$H NMR (CDCl$_3$) δ: 12.46-10.55 (1H, br s), 3.84-3.57 (1H, br s), 3.49-3.26 (1H, br s), 3.26-2.93 (5H, m), 2.50-2.33 (1H, m), 2.28-2.11 (1H, m), 1.35 (3H, t).

Intermediate 190

Benzyl (S)-1-ethylpyrrolidine-3-carboxylate

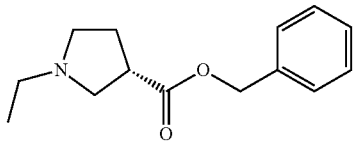 [SMILES: CCN1CC[C@H](C(=O)OCc2ccccc2)C1]

Ethyl bromide (0.21 mL) was added to a mixture of benzyl (S)-pyrrolidine-3-carboxylate trifluoroacetic acid salt (Intermediate 191, 0.897 g), potassium carbonate (0.971 g) and DMF (10 mL) at room temperature and the mixture was stirred for 25 hours. Further ethyl bromide (0.11 mL) was added and stirring was continued for 24 hours. Further ethyl bromide (0.05 mL) was added and stirring was continued for 22 hours. The resultant mixture was diluted with water and extracted with diethyl ether, washed with brine, dried (Na$_2$SO$_4$) and filtered. The filtrate was concentrated in vacuo to give benzyl (S)-1-ethylpyrrolidine-3-carboxylate (0.563 g).

$^1$H NMR (CDCl$_3$) δ: 7.38-7.30 (5H, m), 5.13 (2H, s), 3.09 (1H, m), 2.93 (1H, t), 2.76-2.66 (1H, m), 2.63 (1H, dd), 2.56-2.41 (3H, m), 2.16-2.05 (2H, m), 1.10 (3H, t).

Intermediate 191

Benzyl (S)-pyrrolidine-3-carboxylate trifluoroacetic acid salt

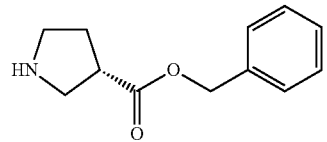 [SMILES: O=C(OCc1ccccc1)[C@H]1CCNC1]

Trifluoroacetic acid (2.5 mL) was added to a solution of benzyl (S)-1-tert-butoxycarbonylpyrrolidine-3-carboxylate (Intermediate 192, 0.859 g) and DCM (10 mL) at room temperature. The mixture was stirred for 4 hours then concentrated in vacuo. The residue was azetroped with toluene then ethyl acetate to give benzyl (S)-pyrrolidine-3-carboxylate trifluoroacetic acid salt (1 g).

$^1$H NMR (CDCl$_3$) δ: 7.41-7.29 (5H, m), 5.16 (2H, dd), 3.64-3.45 (2H, m), 3.44-3.23 (3H, m), 2.42-2.20 (2H, m).

Intermediate 192

Benzyl (S)-1-tert-butoxycarbonylpyrrolidine-3-carboxylate

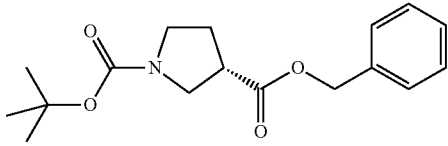 [SMILES: CC(C)(C)OC(=O)N1CC[C@H](C(=O)OCc2ccccc2)C1]

DBU (0.764 mL) was added to a mixture of benzyl bromide (0.61 mL), (S)-1-tert-butoxycarbonyl-pyrrolidine-3-carboxylic acid (1 g) in anhydrous toluene (10 mL) and the mixture was stirred at room temperature for 24 hours. The mixture was filtered and the filtrate was concentrated in vacuo. The residue was purified by chromatography on silica eluting with a mixture of ethyl acetate and cyclohexane with a gradient of 0-35% to give benzyl (S)-1-tert-butoxycarbonylpyrrolidine-3-carboxylate (0.859 g)
$^1$H NMR (CDCl$_3$) δ: 7.39-7.29 (5H, m), 5.14 (2H, s), 3.70-3.41 (3H, m), 3.41-3.27 (1H, m), 3.08 (1H, m), 2.13 (2H, q), 1.45 (9H, s).

Intermediate 193

(R)-1-Ethylpyrrolidin-3-ylamine

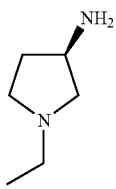

Acetyl chloride (15 mL) was added to methanol (120 mL) and the resultant solution was stirred for 20 minutes. A solution of tert-butyl N—((R)-1-ethylpyrrolidin-3-yl)carbamate (Intermediate 94, 8.4 g) in methanol (30 mL) was then added and the mixture was stirred and heated at 80° C. overnight. After cooling, the mixture was concentrated under vacuum and the residue was redissolved in methanol (150 mL) and potassium carbonate (25.8 g) was added. The mixture was stirred and heated at 30° C. for 30 hours. After cooling, the solid was filtered off and the filtrate was distilled, collecting the product at 100° C. to give (R)-1-ethylpyrrolidin-3-ylamine (2.10 g) as a yellow oil, which was used without further characterisation.

Intermediate 194

(S)-1-Ethylpyrrolidin-3-ylamine

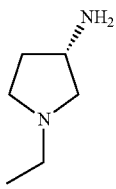

Prepared by proceeding in a similar manner to Intermediate 193, starting from tert-butyl N—((S)-1-ethylpyrrolidin-3-yl)carbamate (Intermediate 82) and used without further characterisation.

Intermediate 195

Methyl (1aRS,7bSR)-5-(2-{[((R)-1-ethylpyrrolidine-3-carbonyl)amino]-methyl}-4-fluorobenzenesulfonylamino)-1,1a,2,7b-tetrahydrocyclopropa[c]chromene-4-carboxylate

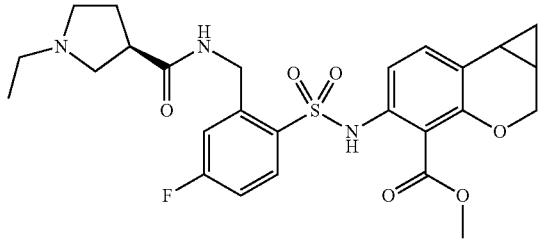 [SMILES: CCN1CC[C@@H](C(=O)NCc2cc(F)ccc2S(=O)(=O)Nc2ccc3c(c2C(=O)OC)OCC2CC32)C1]

Prepared by proceeding in a similar manner to Intermediate 188, starting from methyl (1aRS,7bSR)-5-(2-aminomethyl-4-fluorobenzenesulfonylamino)-1,1a,2,7b-tetrahydrocyclopropa[c]chromene-4-carboxylate (intermediate 102) and (R)-1-ethylpyrrolidine-3-carboxylic acid (Intermediate 196).
$^1$H NMR (CDCl$_3$) δ: 7.81 (1H, dd), 7.43-7.34 (1H, m), 7.30-7.20 (3H, m), 7.05-6.93 (2H, m), 4.59 (2H, d), 4.32 (1H, dd), 3.79 (1H, dd), 3.76 (3H, s), 2.99-2.84 (3H, m), 2.81-2.73 (1H, m), 2.73-2.60 (3H, m), 2.27-2.12 (1H, m), 2.01-1.88 (2H, m), 1.78-1.67 (1H, m), 1.17 (3H, s), 1.08-0.98 (2H, m).

Intermediate 196

(R)-1-Ethylpyrrolidine-3-carboxylic acid

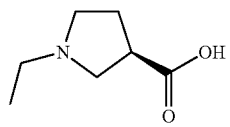

Prepared by proceeding in a similar manner to Intermediate 189, starting from benzyl (R)-1-ethylpyrrolidine-3-carboxylate (Intermediate 197).
$^1$H NMR (CDCl$_3$) δ: 11.05-9.55 (1H, br s), 3.71 (1H, br s), 3.37 (1H, br s), 3.27-2.94 (5H, m), 2.49-2.32 (1H, m), 2.29-2.13 (1H, m), 1.35 (3H, t).

Intermediate 197

Benzyl (R)-1-ethylpyrrolidine-3-carboxylate

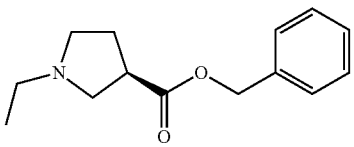 [SMILES: CCN1CC[C@@H](C(=O)OCc2ccccc2)C1]

Prepared by proceeding in a similar manner to Intermediate 190, starting from benzyl (R)-pyrrolidine-3-carboxylate trifluoroacetic acid salt (Intermediate 198).

$^1$H NMR (CDCl$_3$) δ: 7.38-7.30 (5H, m), 5.13 (2H, s), 3.09 (1H, m), 2.93 (1H, t), 2.76-2.66 (1H, m), 2.63 (1H, dd), 2.52-2.42 (3H, m), 2.16-2.06 (2H, m), 1.11 (3H, t).

Intermediate 198

Benzyl (R)-pyrrolidine-3-carboxylic trifluoroacetic acid salt

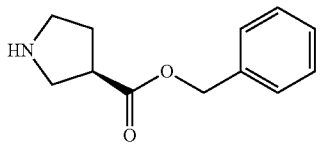 [SMILES: O=C(OCc1ccccc1)[C@@H]1CCNC1]

Prepared by proceeding in a similar manner to Intermediate 191, starting from benzyl (R)-1-tert-butoxycarbonylpyrrolidine-3-carboxylate (Intermediate 199).

$^1$H NMR (CDCl$_3$) δ: 7.41-7.29 (5H, m), 5.16 (2H, dd), 3.64-3.45 (2H, m), 3.42-3.23 (3H, m), 2.41-2.20 (2H, m).

Intermediate 199

Benzyl (R)-1-tert-butoxycarbonylpyrrolidine-3-carboxylate

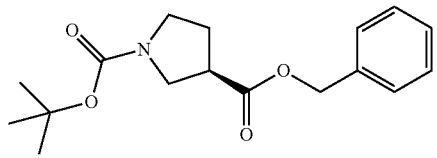 [SMILES: CC(C)(C)OC(=O)N1CC[C@@H](C(=O)OCc2ccccc2)C1]

Prepared by proceeding in a similar manner to Intermediate 192, starting from (R)-1-tert-butoxycarbonyl-pyrrolidine-3-carboxylic acid.

$^1$H NMR (CDCl$_3$) δ: 7.42-7.29 (5H, m), 5.15 (2H, s), 3.72-3.42 (3H, m), 3.42-3.26 (1H, m), 3.08 (1H, m), 2.13 (2H, q), 1.45 (9H, s).

Intermediate 200

Methyl (1aRS,7bSR)-5-{N-[2-((Z)-3-diethylamino-2-methylprop-1-enyl)-4-fluorobenzenesulfonyl]-N-(methoxycarbonyl)amino}-1,1a,2,7b-tetrahydrocyclopropa-[c]chromene-4-carboxylate

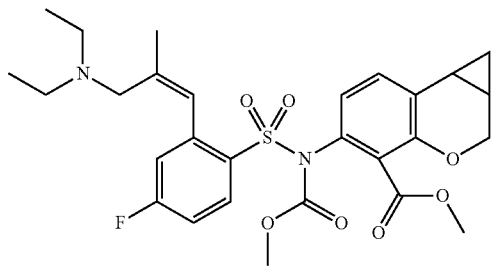 [SMILES: CCN(CC)C/C(C)=C\c1cc(F)ccc1S(=O)(=O)N(C(=O)OC)c1ccc2c(c1C(=O)OC)OCC1CC21]

Methanesulphonic anhydride (0.159 g) was added to a solution of methyl (1aRS,7bSR)-5-{N-[4-fluoro-2-((Z)-3-hydroxy-2-methylprop-1-enyl)benzenesulfonyl]-N-(methoxycarbonyl)amino}-1,1a,2,7b-tetrahydrocyclopropa[c]chromene-4-carboxylate (Intermediate 201, 0.310 g) and N,N-diisopropyl-N-ethylamine (0.118 g) in DCM (100 mL) and the mixture was left at room temperature for 1 hour. Diethylamine (1 mL) was added and the solution was left for a further 16 hours. The mixture was washed with water and filtered through a phase separator. The filtrate was concentrated in vacuo and the residue was purified by chromatography on silica, eluting with a mixture of methanol and DCM with a gradient of 0-8% to give methyl (1aRS,7bSR)-5-{N-[2-((Z)-3-diethylamino-2-methylprop-1-enyl)-4-fluorobenzene-sulfonyl]-N-methoxy-carbonylamino}-1,1a,2,7b-tetrahydrocyclopropa[c]chromene-4-carboxylate (0.268 g) as a white foam.

LCMS (Method E) r/t 2.79 (M+H) 561.

Intermediate 201

Methyl (1aRS,7bSR)-5-{N-[4-fluoro-2-((Z)-3-hydroxy-2-methylprop-1-enyl)benzenesulfonyl]-N-(methoxycarbonyl)amino}-1,1a,2,7b-tetrahydrocyclopropa-[c]chromene-4-carboxylate

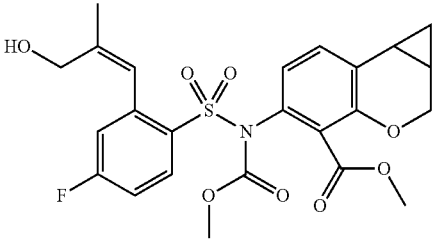 [SMILES: COC(=O)c1c(N(C(=O)OC)S(=O)(=O)c2ccc(F)cc2/C=C(/C)CO)ccc2c1OCC1CC21]

Concentrated hydrochloric acid (1 mL) was added to a solution of methyl (1aRS,7bSR)-5-(N-{2-[(Z)-3-(tert-butyldimethylsilanyloxy)-2-methylprop-1-enyl]-4-fluorobenzenesulfonyl]-N-methoxycarbonyl-amino}-1,1a,2,7b-tetrahydrocyclopropa[c]chromene-4-carboxylate (Intermediate 202, 0.385 g) in methanol (20 mL) and the mixture was left at room temperature for 45 minutes. The solution was concentrated in vacuo and the residue was purified by chromatography on silica, eluting with a mixture of ethyl acetate and cyclohexane with a gradient of 0-60% to give methyl (1aRS,7bSR)-5-{N-[4-fluoro-2-((Z)-3-hydroxy-2-methylprop-1-enyl)benzenesulfonyl]-N-methoxycarbonylamino}-1,1a,2,7b-tetrahydrocyclopropa-[c]chromene-4-carboxylate (0.314 g) as a white foam.

$^1$H NMR (CDCl$_3$) δ: 8.18 (1H, dd), 7.35 (1H, d), 7.11 (1H, dt), 6.94 (1H, d), 6.89 (1H, d), 6.74 (1H, s), 4.39 (1H, d), 3.82-4.17 (3H, m), 3.76 (1.5H, s), 3.72 (1.5H, s), 3.64 (3H, s), 1.98 (4H, m), 1.82 (1H, q), 1.14 (2H, m).

Intermediate 202

Methyl (1aRS,7bSR)-5-(N-{2-[(Z)-3-(tert-butyldimethylsilanyloxy)-2-methylprop-1-enyl]-4-fluorobenzenesulfonyl]-N-(methoxycarbonyl)amino}-1,1a,2,7b-tetrahydrocyclopropa-[c]chromene-4-carboxylate

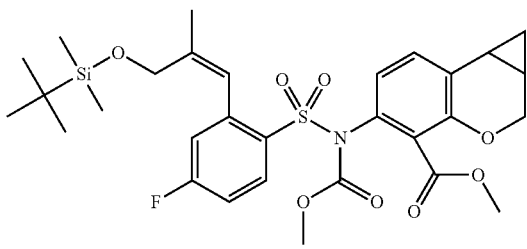 [SMILES: COC(=O)c1c(N(C(=O)OC)S(=O)(=O)c2ccc(F)cc2/C=C(/C)CO[Si](C)(C)C(C)(C)C)ccc2c1OCC1CC21]

A mixture of methyl (1aRS,7bSR)-5-[N-(2-bromo-4-fluorobenzenesulfonyl)-N-(methoxy-carbonyl)amino]-1,1a,2,7b-tetrahydrocyclopropa-[c]chromene-4-carboxylate (Intermediate 65, 0.257 g), tert-butyl-dimethyl-((Z)-2-methyl-3-tributylstannanylallyloxy)silane (0.475 g), tris (dibenzylideneacetone)dipalladium(0) (0.023 g) and tri-tert-butylphosphonium tetrafluoroborate (0.015 g) in dioxane (8 mL) and DMSO (0.8 mL) was stirred and heated at 90° C. under nitrogen for 1 hour. Further tris(dibenzylideneacetone)dipalladium(0) (0.023 g) and tri-tert-butylphosphonium tetrafluoroborate (0.015 g) were added and heating was continued for a further 40 minutes. After cooling, the mixture was diluted with ethyl acetate, washed with water, dried (Na$_2$SO$_4$) and filtered. The filtrate was concentrated in vacuo and the residue was purified by chromatography on silica, eluting with a mixture of ethyl acetate and cyclohexane with a gradient of 0-20% to give methyl (1aRS,7bSR)-5-(N-{2-[(Z)-3-(tert-butyldimethylsilanyloxy)-2-methylprop-1-enyl]-4-fluorobenzenesulfonyl]-N-methoxycarbonyl-amino}-1,1a,2,7b-tetrahydrocyclopropa[c]chromene-4-carboxylate (0.231 g) as a colourless gum.

LCMS (Method E) r/t 5.22 (M+Na) 642.

Intermediate 203

2-((R)-1-Ethylpyrrolidin-3-yl)ethylamine

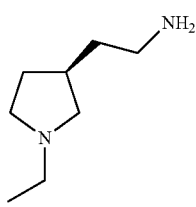

Lithium aluminium hydride (1.0 g) was added in portions to a stirred, cooled solution of 2-((S)-1-ethylpyrrolidin-3-yl)acetonitrile (Intermediate 204, 3.8 g) in THF (20 mL) at 0° C. On completion of the addition, the mixture was stirred at room temperature for 4 hours. Water was added cautiously, followed by addition of 15% aqueous sodium hydroxide solution and more water. The solid was filtered off and the filtrate was evaporated to dryness. The residue was dissolved in DCM, dried (Na$_2$SO$_4$) and filtered. The filtrate was evaporated to dryness to give 2-((R)-1-ethylpyrrolidin-3-yl)ethylamine (2.0 g) as a colourless oil, which was used without further characterisation.

Intermediate 204

2-((S)-1-Ethylpyrrolidin-3-yl)acetonitrile

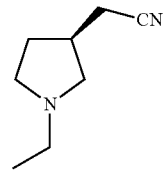

Iodoethane (10.1 g) was added to a mixture of 2-((S)-pyrrolidin-3-yl)acetonitrile hydrochloride (Intermediate 205, 7.9 g) and potassium carbonate (29.7 g) in DMF (20 mL) and the resultant mixture was stirred at room temperature for 5 hours. Water was added and the mixture was extracted with ethyl acetate, washed with brine, dried (Na$_2$SO$_4$) and filtered. The filtrate was evaporated to dryness to give 2-((S)-1-ethylpyrrolidin-3-yl)acetonitrile (3.8 g) as a yellow oil which was used without further characterisation.

Intermediate 205

2-((S)-Pyrrolidin-3-yl)acetonitrile hydrochloride

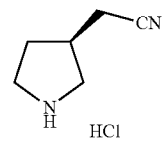

A solution of tert-butyl (S)-3-cyanomethylpyrrolidine-1-carboxylate (Intermediate 206, 12.3 g) in methanol (150 mL) and concentrated hydrochloric acid (12 mL) was stirred and heated at 50° C. overnight. After cooling, the mixture was concentrated under vacuum to give crude 2-((S)-pyrrolidin-3-yl)acetonitrile hydrochloride (9.0 g) as a white solid which was used without further characterisation.

Intermediate 206 tert-Butyl (S)-3-cyanomethylpyrrolidine-1-carboxylate

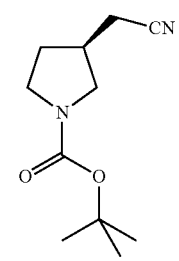

A mixture of tert-butyl ((R)-3-(4-methylbenzenesulfonyloxymethyl)pyrrolidine-1-carboxylate (Intermediate 207, 22.3 g) and sodium cyanide (6.13 g) in DMSO (100 mL) was stirred and heated at 100° C. for 4 hours. After cooling, a saturated aqueous solution of iron (II) sulphate was added and the mixture was stirred at room temperature for 8 hours. The resultant mixture was extracted with ethyl acetate, washed with brine, dried ($Na_2SO_4$) and filtered. The filtrate was evaporated to dryness and the residue was purified by chromatography on silica, eluting with an mixture of ethyl acetate and petroleum ether (20%) to give tert-butyl (S)-3-cyanomethylpyrrolidine-1-carboxylate (12.3 g) as a white solid which was used without further characterisation.

Intermediate 207 tert-Butyl ((R)-3-(4-methylbenzenesulfonyloxymethyl)-pyrrolidine-1-carboxylate

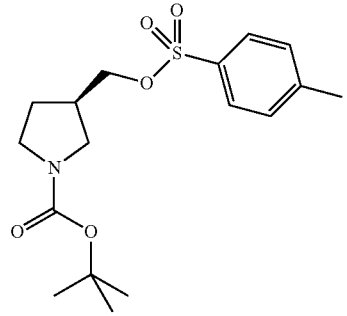 [SMILES: Cc1ccc(S(=O)(=O)OC[C@@H]2CCN(C(=O)OC(C)(C)C)C2)cc1]

Prepared by proceeding in a similar manner to Intermediate 140, starting from tert-butyl (R)-3-hydroxymethylpyrrolidine-1-carboxylate and 4-methylbenzenesulfonyl chloride and used without further characterisation.

Intermediate 208

2-((S)-1-Ethylpyrrolidin-3-yl)ethylamine

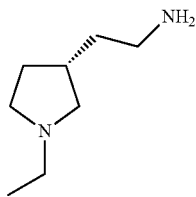

Prepared by proceeding in a similar manner to Intermediate 203, starting from 2-((R)-1-ethylpyrrolidin-3-yl)acetonitrile (Intermediate 209) and used without further characterisation.

Intermediate 209

2-((R)-1-Ethylpyrrolidin-3-yl)acetonitrile

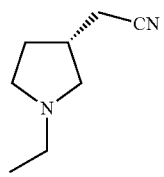

Iodoethane (6.46 g) was added in portions to a cooled mixture of 2-((R)-pyrrolidin-3-yl)acetonitrile (Intermediate 210, 4.6 g) and potassium carbonate (8.6 g) in acetonitrile (30 mL) at 0° C. The mixture was stirred for 3 hours at 0° C. then concentrated under vacuum. The residue was partitioned between water and DCM. The organic layer was washed with brine, dried ($Na_2SO_4$) and filtered. The filtrate was evaporated to dryness to give 2-((R)-1-ethylpyrrolidin-3-yl)acetonitrile (2.1 g) as a colourless liquid which was used without further characterisation.

Intermediate 210

2-((R)-Pyrrolidin-3-yl)acetonitrile hydrochloride

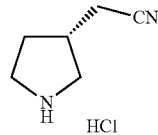

Prepared by proceeding in a similar manner to Intermediate 205, starting from tert-butyl (R)-3-cyanomethylpyrrolidine-1-carboxylate (Intermediate 211) and used without further characterisation.

Intermediate 211 tert-Butyl (R)-3-cyanomethylpyrrolidine-1-carboxylate

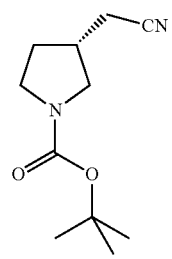

Prepared by proceeding in a similar manner to Intermediate 206, starting from tert-butyl ((S)-3-(4-methylbenzenesulfonyloxymethyl)pyrrolidine-1-carboxylate (Intermediate 212) and used without further characterisation.

Intermediate 212 tert-Butyl ((S)-3-(4-methylbenzenesulfonyloxymethyl)-pyrrolidine-1-carboxylate

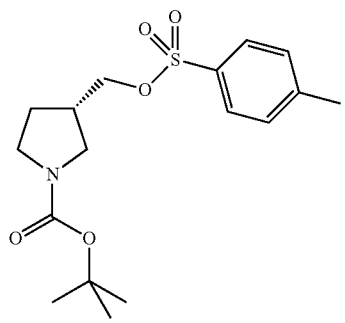 [SMILES: Cc1ccc(S(=O)(=O)OC[C@H]2CCN(C(=O)OC(C)(C)C)C2)cc1]

Prepared by proceeding in a similar manner to Intermediate 140, starting from tert-butyl (S)-3-hydroxymethylpyrrolidine-1-carboxylate and 4-methylbenzenesulfonyl chloride and used without further characterisation.

Intermediate 213

Methyl (1aR,7bS)-5-[2-((S)-1-ethylpyrrolidin-3-yloxymethyl)-4-fluoro-benzenesulfonylamino]-1,1a,2,7b-tetrahydrocyclopropa[c]chromene-4-carboxylate

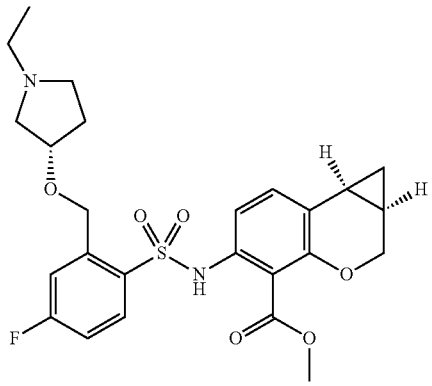 [SMILES: CCN1CC[C@H](OCc2cc(F)ccc2S(=O)(=O)Nc2ccc3c(c2C(=O)OC)OC[C@@H]2C[C@H]32)C1]

A solution of tert-butyl (S)-3-[(1aR,7bS)-5-fluoro-2-(4-methoxycarbonyl-1,1a,2,7b-tetrahydro-cyclopropa[c]chromen-5-ylsulfamoyl)benzyloxy]pyrrolidine-1-carboxylate (Intermediate 214, 0.284 g) in trifluoroacetic acid (4 mL) and DCM (4 mL) was left at room temperature for 30 minutes. The mixture was evaporated in vacuo and the residue was azeotroped with toluene. The residue was dissolved in DCM (4 mL) and acetaldehyde (0.044 g) was added followed by sodium triacetoxyborohydride (0.212 g). The mixture was stirred at room temperature for 1 hour. The resulting solution was diluted with DCM and 1M sodium hydroxide solution and the organic layer was dried (Na$_2$SO$_4$) and filtered. The filtrate was evaporated in vacuo and the residue was purified by chromatography on silica, eluting with a mixture of methanol and DCM with a gradient of 0-20% to give methyl (1aR,7bS)-5-[2-((S)-1-ethylpyrrolidin-3-yloxymethyl)-4-fluorobenzenesulfonylamino]-1,1a,2,7b-tetrahydrocyclopropa[c]chromene-4-carboxylate (0.221 g) as a white foam.

$^1$H NMR (CDCl$_3$) δ: 7.76 (1H, dd), 7.32 (1H, dd), 7.16 (1H, d), 6.94 (1H, dt), 6.87 (1H, d), 4.86 (1H, d), 4.68 (1H, d), 4.32 (1H, d), 4.19 (1H, m), 3.79 (1H, d), 3.73 (3H, s), 3.13 (1H, d), 2.92 (1H, q), 2.35-2.75 (4H, m), 2.10 (2H, m), 1.92 (1H, m), 1.72 (1H, m), 1.14 (3H, t), 1.03 (2H, m).

Intermediate 214 tert-Butyl (S)-3-[(1aR,7bS)-5-fluoro-2-(4-methoxycarbonyl-1,1a,2,7b-tetrahydrocyclopropa[c]chromen-5-ylsulfamoyl)benzyloxy]pyrrolidine-1-carboxylate

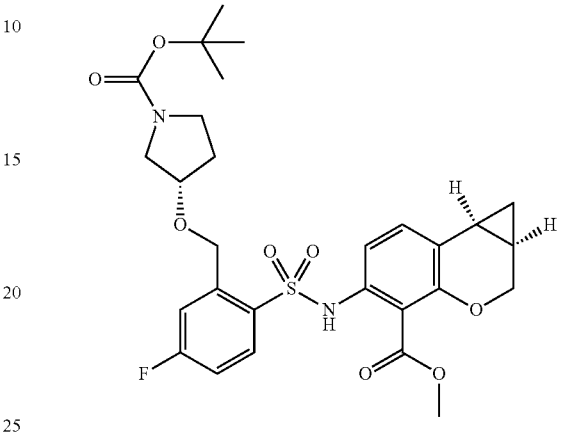

A solution of tert-butyl (S)-3-(2-chlorosulfonyl-5-fluorobenzyloxy)pyrrolidine-1-carboxylate (Intermediate 215, 0.295 g) in DCM (2 mL) was added to a solution of methyl (1aR,7bS)-5-amino-1,1a,2,7b-tetrahydrocyclopropa[c]chromene-4-carboxylate (Intermediate 42A, 0.1 g) in DCM (2 mL) and the mixture was left at room temperature for 5 days. The mixture was diluted with DCM, washed with 1M hydrochloric acid and filtered through a phase separator. The filtrate was evaporated in vacuo and the residue was purified by chromatography on silica, eluting with a mixture of ethyl acetate and cyclohexane with a gradient of 0-30% to give tert-butyl (S)-3-[5-fluoro-2-((1aR,7bS)-4-methoxycarbonyl-1,1a,2,7b-tetrahydrocyclopropa-[c]chromen-5-ylsulfamoyl)benzyloxy]pyrrolidine-1-carboxylate (0.288 g) as a white foam.

$^1$H NMR (CDCl$_3$) δ: 8.86 (1H, br, s), 7.76 (1H, dd), 7.41 (1H, dd), 7.25 (1H, d), 7.07 (1H, d), 6.95 (1H, dt), 4.69-4.91 (2H, br, q), 4.32 (1H, d), 4.19 (1H, m), 3.77 (1H, d), 3.71 (3H, s), 3.49 (4H, br, m), 1.89-2.18 (3H, m), 1.73 (1H, m), 1.47 (9H, s), 1.00 (2H, m).

Intermediate 215 tert-Butyl (S)-3-(2-chlorosulfonyl-5-fluorobenzyloxy)pyrrolidine-1-carboxylate

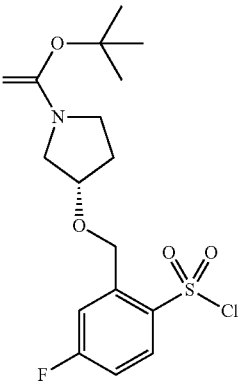

n-Butyllithium (1.6M in hexanes, 3.3 mL) was added to a solution of tert-butyl (S)-3-(2-bromo-5-fluorobenzyloxy)pyrrolidine-1-carboxylate (Intermediate 216, 1.87 g), in anhydrous THF (20 mL) at −78° C. under an atmosphere of nitrogen and the mixture was stirred for 30 minutes. Sulphur dioxide was passed through the resulting solution for 30 minutes, then the cooling bath was removed and the mixture was allowed to warm to room temperature and stirred for 15 minutes. The solution was evaporated in vacuo and the residue was dissolve in DCM (20 mL) and N-chlorosuccinimide (0.668 g) was added. The mixture was stirred for 30 minutes then diluted with ether and water. The organic layer was dried (MgSO$_4$) and filtered and the filtrate was evaporated in vacuo. The residue was purified by chromatography on silica, eluting with a mixture of ethyl acetate and cyclohexane with a gradient of 0-25% to give tert-butyl (S)-3-(2-chlorosulfonyl-5-fluorobenzyloxy)pyrrolidine-1-carboxylate (1.01 g) as a colourless, viscous oil.

$^1$H NMR (CDCl$_3$) δ: 8.09 (1H, dd), 7.58 (1H, dd), 7.18 (1H, dt), 4.98 (2H, q), 4.28 (1H, m), 3.40-3.61 (4H, m), 1.92-2.20 (2H, m), 1.47 (9H, s).

Intermediate 216 tert-Butyl (S)-3-(2-bromo-5-fluorobenzyloxy)pyrrolidine-1-carboxylate

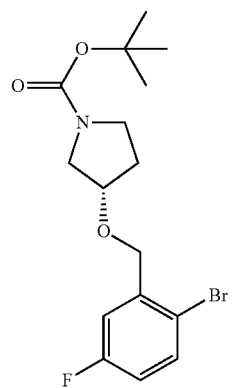 [SMILES: CC(C)(C)OC(=O)N1CC[C@H](OCc2cc(F)ccc2Br)C1]

Sodium hydride (60% oil dispersion, 0.24 g) was added to a stirred solution of tert-butyl (S)-3-hydroxypyrrolidine-1-carboxylate (0.935 g) in THF (15 mL) and the mixture was stirred for 5 minutes. 2-Bromo-5-fluorobenzyl bromide (1.608 g) was added and stirring was continued for 20 hours. The resultant suspension was filtered and the filtrate was evaporated to dryness. The residue was purified by chromatography on silica, eluting with a mixture of ethyl acetate and cyclohexane with a gradient of 0-15% to give tert-butyl (S)-3-(2-bromo-5-fluorobenzyloxy)-pyrrolidine-1-carboxylate (1.88 g) as a colourless oil.

$^1$H NMR (CDCl$_3$) δ: 7.46 (1H, dd), 7.22 (1H, dd), 6.88 (1H, dt), 4.52 (2H, s), 4.19 (1H, m), 3.40-3.65 (4H, br, m), 1.91-2.18 (2H, m), 1.49 (9H, s).

Intermediate 217

Methyl (1aR,7bS)-5-[2-((R)-1-ethylpyrrolidin-3-yloxymethyl)-4-fluoro-benzenesulfonylamino]-1,1a,2,7b-tetrahydrocyclopropa[c]chromene-4-carboxylate

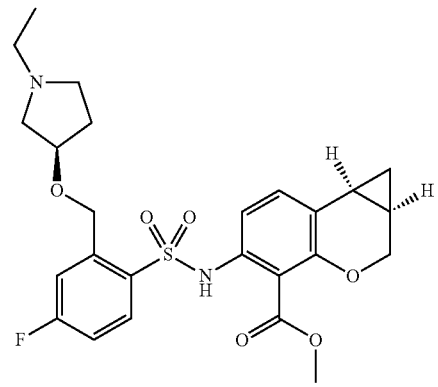 [SMILES: CCN1CC[C@@H](OCc2cc(F)ccc2S(=O)(=O)Nc2ccc3c(c2C(=O)OC)OC[C@@H]2C[C@H]32)C1]

Prepared by proceeding in a similar manner to Intermediate 213, starting from tert-butyl (R)-3-[(1aR,7bS)-5-fluoro-2-(4-methoxycarbonyl-1,1a,2,7b-tetrahydrocyclopropa[c]chromen-5-ylsulfamoyl)benzyloxy]-pyrrolidine-1-carboxylate (Intermediate 218).

$^1$H NMR (CDCl$_3$) δ: 7.76 (1H, dd), 7.32 (1H, dd), 7.17 (1H, d), 6.95 (1H, dt), 6.88 (1H, d), 4.85 (1H, d), 4.68 (1H, d), 4.32 (1H, d), 4.18 (1H, m), 3.81 (1H, d), 3.72 (3H, s), 3.11 (1H, d), 2.92 (1H, q), 2.25-2.75 (4H, m), 2.09 (2H, m), 1.91 (1H, m), 1.72 (1H, m), 1.14 (3H, t), 1.03 (2H, m).

Intermediate 218 tert-Butyl (R)-3-[(1aR,7bS)-5-fluoro-2-(4-methoxycarbonyl-1,1a,2,7b-tetrahydrocyclopropa[c]chromen-5-ylsulfamoyl)benzyloxy]pyrrolidine-1-carboxylate

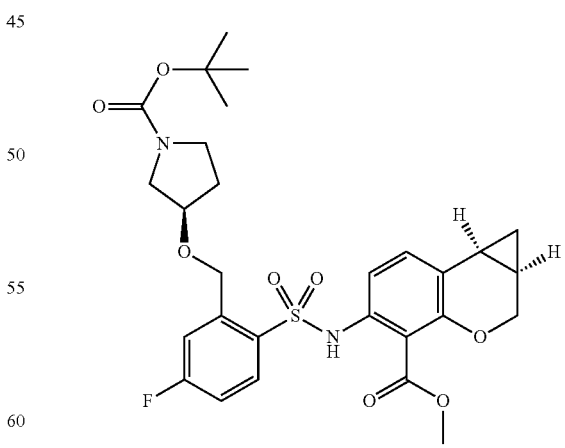

Prepared by proceeding in a similar manner to Intermediate 214, starting from tert-butyl (R)-3-(2-chlorosulfonyl-5-fluorobenzyloxy)pyrrolidine-1-carboxylate (Intermediate 219) and methyl (1aR,7bS)-5-amino-1,1a,2,7b-tetrahydrocyclopropa[c]chromene-4-carboxylate (Intermediate 42A).

¹H NMR (CDCl₃) δ: 8.86 (1H, br, s), 7.76 (1H, dd), 7.41 (1H, dd), 7.25 (1H, d), 7.07 (1H, d), 6.95 (1H, dt), 4.78 (2H, br, s), 4.32 (1H, d), 4.19 (1H, m), 3.77 (1H, d), 3.71 (3H, s), 3.49 (4H, br, m), 1.89-2.18 (3H, m), 1.73 (1H, m), 1.47 (9H, s), 1.00 (2H, m).

Intermediate 219 tert-Butyl (R)-3-(2-chlorosulfonyl-5-fluorobenzyloxy)pyrrolidine-1-carboxylate

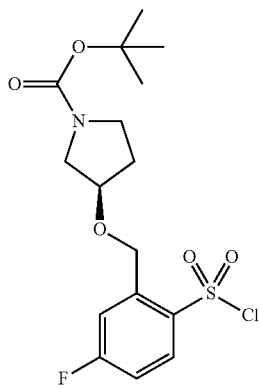 [SMILES: CC(C)(C)OC(=O)N1CC[C@@H](OCc2cc(F)ccc2S(=O)(=O)Cl)C1]

Prepared by proceeding in a similar manner to Intermediate 215, starting from tert-butyl (R)-3-(2-bromo-5-fluorobenzyloxy)pyrrolidine-1-carboxylate (Intermediate 220).

¹H NMR (CDCl₃) δ: 8.10 (1H, dd), 7.58 (1H, dd), 7.17 (1H, dt), 4.99 (2H, q), 4.28 (1H, m), 3.40-3.61 (4H, m), 1.92-2.20 (2H, m), 1.48 (9H, s).

Intermediate 220 tert-Butyl (R)-3-(2-bromo-5-fluorobenzyloxy)pyrrolidine-1-carboxylate

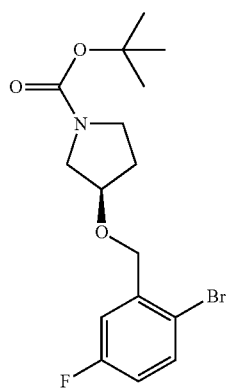 [SMILES: CC(C)(C)OC(=O)N1CC[C@@H](OCc2cc(F)ccc2Br)C1]

Prepared by proceeding in a similar manner to Intermediate 216, starting from tert-butyl(R)-3-hydroxy-pyrrolidine-1-carboxylate.

¹H NMR (CDCl₃) δ: 7.46 (1H, dd), 7.22 (1H, dd), 6.88 (1H, dt), 4.52 (2H, s), 4.19 (1H, m), 3.40-3.65 (4H, br, m), 1.91-2.18 (2H, m), 1.49 (9H, s).

Intermediate 221

Methyl (1aR,7bS)-5-[2-(1-ethylpiperidin-3-ylmethyl)-4-fluorobenzene-sulfonylamino]-1,1a,2,7b-tetrahydrocyclopropa[c]chromene-4-carboxylate

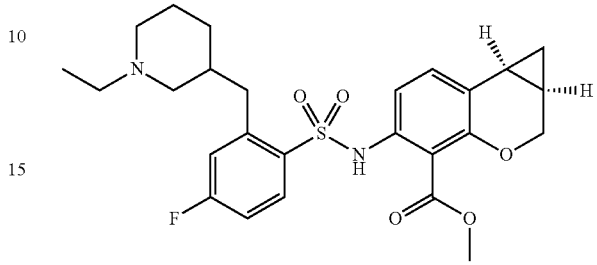

2-(1-Ethylpiperidin-3-ylmethyl)-4-fluorobenzenesulfonyl chloride (Intermediate 222, 0.21 g) was added to a solution of methyl (1aR,7bS)-5-amino-1,1a,2,7b-tetrahydrocyclopropa[c]chromene-4-carboxylate (Intermediate 42A 0.290 g) in DCM (100 mL) and pyridine (2 mL) and the resultant mixture was stirred at room temperature for 4 hours. The mixture was evaporated to dryness and the residue was partitioned between DCM and water. The organic layer was dried (Na₂SO₄), filtered and the filtrate was concentrated in vacuo. The residue was purified by chromatography on silica eluting with a mixture of 2M ammonia in methanol and DCM with a gradient of 0-15% to give methyl (1aR,7bS)-5-[2-(1-ethylpiperidin-3-ylmethyl)-4-fluoro-benzenesulfonylamino]-1,1a,2,7b-tetrahydrocyclopropa[c]chromene-4-carboxylate (0.071 g).

¹H NMR (CDCl₃) δ: 7.95-7.88 (1H, m), 7.21-7.15 (1H, m), 7.03-6.86 (3H, m), 4.31 (1H, d), 3.81-3.73 (4H, m), 2.89-2.63 (4H, m), 2.39-2.28 (2H, m), 2.09-2.08-1.95 (1H, m), 1.94-1.44 (8H, m), 1.06-0.94 (6H, m).

Intermediate 222

2-(1-Ethylpiperidin-3-ylmethyl)-4-fluoro-benzenesulfonyl chloride

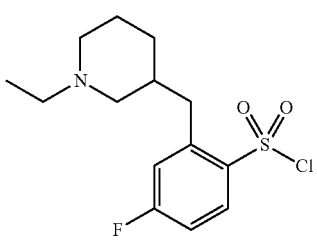 [SMILES: CCN1CCCC(Cc2cc(F)ccc2S(=O)(=O)Cl)C1]

A solution of 1-ethyl-3-(3-fluorobenzyl)piperidine (Intermediate 223, 0.214 g) in DCE (1 mL) was added to chlorosulfonic acid (2 mL) at 0° C. The mixture was allowed to warm to room temperature and stirred for 2 hours. The mixture was added dropwise to a mixture of ice and brine and extracted with DCM. The organic layer was dried (Na₂SO₄) and filtered and the filtrate was evaporated to dryness to give 2-(1-ethylpiperidin-4-ylmethyl)-4-fluorobenzene-sulfonyl chloride (0.44 g) as a solid.

¹H NMR (CDCl₃) δ: 8.17-8.11 (1H, m), 7.43-7.37 (1H, m), 7.19-7.12 (1H, m), 3.62-3.52 (1H, m), 3.42-3.32 (1H, m), 3.16 (2H, d), 3.11-2.92 (3H, m), 2.64-2.29 (3H, m), 1.91 (2H, d), 1.43 (3H, t), 1.39-1.23 (1H, m).

Intermediate 223

1-Ethyl-3-(3-fluorobenzyl)-piperidine

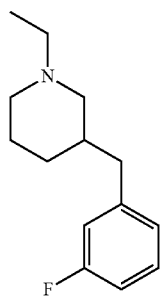 [SMILES: CCN1CCCC(Cc2cccc(F)c2)C1]

A solution of lithium aluminium hydride (2M in THF, 2.8 mL) was added dropwise to a solution of 1-[3-(3-fluorobenzyl)piperidin-1-yl]ethanone (Intermediate 224, 0.66 g) in anhydrous THF (20 mL) at 0° C. under argon. The mixture was stirred for 30 minutes then allowed to warm to room temperature and stirred for 2 hours. The mixture was recooled to 0° C. and water was added. The mixture was extracted with ether, washed with brine, dried (Na₂SO₄) and filtered. The filtrate was evaporated to dryness to give 1-ethyl-3-(3-fluorobenzyl)piperidine (0.535 g).

¹H NMR (CDCl₃) δ: 7.25-7.17 (1H, m), 6.95-6.80 (3H, m), 2.92-2.73 (2H, m), 2.58-2.42 (2H, m), 2.42-2.26 (2H, m), 1.96-1.76 (2H, m), 1.74-1.48 (4H, m), 1.04 (3H, t), 1.00-0.84 (1H, m).

Intermediate 224

1-[3-(3-Fluorobenzyl)piperidin-1-yl]ethanone

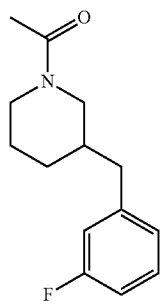 [SMILES: CC(=O)N1CCCC(Cc2cccc(F)c2)C1]

A mixture of 1-{3-[1-(3-fluorophenyl)methylidene]piperidin-1-yl}ethanone (Intermediate 225, 0.7 g), palladium hydroxide (20% on carbon, 0.07 g) in ethyl acetate (20 mL) and IMS (1 mL) was degassed by nitrogen/vacuum purging. The mixture was stirred under an atmosphere of hydrogen for 21.5 hours. The mixture was filtered the filtrate was evaporated to dryness to give 1-[3-(3-fluorobenzyl)piperidin-1-yl]ethanone (0.66 g).

¹H NMR (CDCl₃) δ: 7.31-7.17 (1H, m), 6.97-6.80 (3H, m), 4.52-4.43 (0.5H, m), 4.41-4.31 (0.5H, m), 3.76-3.65 (0.5H, m), 3.65-3.55 (0.5H, m), 3.07-2.95 (0.5H, m), 2.82-2.62 (1.5H, m), 2.60-2.49 (1H, m), 2.45-2.33 (1H, m), 2.08 (1.5H, s), 1.95 (1.5H, s), 1.83-1.63 (3H, m), 1.50-1.32 (1H, m), 1.29-1.09 (1H, m).

Intermediate 225

1-{3-[1-(3-Fluorophenyl)methylidene]piperidin-1-yl}ethanone

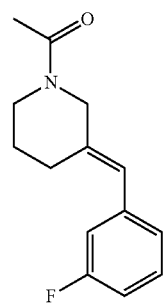 [SMILES: CC(=O)N1CCC/C(=C\c2cccc(F)c2)C1]

Acetyl chloride (0.515 mL) was added to a mixture of 3-[1-(3-fluorophenyl)methylidene]-piperidine hydrochloride (Intermediate 226, 1.5 g) and N,N-di-isopropyl-N-ethylamine (2.52 mL) in anhydrous THF (50 mL) at 0° C. under nitrogen. The mixture was allowed to warm to room temperature and was stirred for 2 hours. The mixture was diluted with water (100 mL) and extracted with ether, washed with brine, dried (Na₂SO₄) and filtered. The filtrate was evaporated to dryness and the residue was purified by chromatography on silica eluting with a mixture of ethyl acetate and cyclohexane with a gradient of 75-100% to give 1-{3-[1-(3-fluorophenyl)-methylidene]piperidin-1-yl}ethanone (1.38 g).

¹H NMR (CDCl₃) δ: 7.37-7.21 (1H, m), 7.04-6.82 (3H, m), 6.48-6.26 (1H, 4s), 4.39-4.00 (2H, m), 3.72-3.48 (2H, m), 2.61-2.41 (2H, m), 2.18-2.02 (3H, 4s), 1.83-1.61 (2H, m).

Intermediate 226

3-[1-(3-Fluorophenyl)methylidene]piperidine hydrochloride

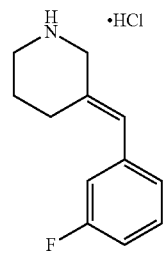 [SMILES: Cl ; Fc1cccc(/C=C2\CCCNC2)c1]

A solution of HCl in dioxane (4M, 30 mL) was added to a solution of tert-butyl 3-[1-(3-fluorophenyl)methylidene]piperidine-1-carboxylate (Intermediate 227, 2.38 g) in ether (30 mL) and the mixture was stirred at room temperature for 5 hours. The mixture was concentrated in vacuo and the residue was treated with ether. The solid was collected by filtration, washed with ether and dried under vacuum to give 3-[1-(3-fluorophenyl)methylidene]piperidine hydrochloride (1.64 g).

$^1$H NMR (CDCl$_3$) 3:2 ratio of E and Z isomers δ: 9.34 (2H, br s), 7.48-7.37 (1H, m), 7.22-7.00 (3H, m), 6.59 (1H, s), 3.78-3.68 (2H, m), 3.13 (2H, m), 2.52 (1.2H, m), 2.43 (0.8H, m), 1.84 (1.2H, m), 1.76 (0.8H, m).

Intermediate 227 tert-Butyl 3-[1-(3-fluorophenyl)methylidene]piperidine-1-carboxylate

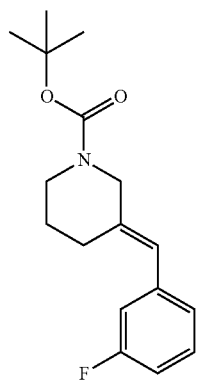 [SMILES: CC(C)(C)OC(=O)N1CCC/C(=C\c2cccc(F)c2)C1]

(3-Fluorobenzyltriphenylphosphonium bromide (Intermediate 228, 5.3 g) was added in portions to a solution of sodium tert-butoxide (1.06 g) in anhydrous THF (20 mL) at room temperature and the mixture was stirred for 30 minutes. A solution of tert-butyl 3-oxopiperidine-1-carboxylate (2 g) in anhydrous THF (100 mL) was added dropwise at room temperature and the mixture was stirred for 24 hours. The mixture was diluted with water (100 mL) and extracted with ether (100 mL), washed with brine, dried (Na$_2$SO$_4$) and filtered. The filtrate was concentrated in vacuo and the residue was purified by chromatography on silica eluting with a mixture of ethyl acetate and cyclohexane with a gradient of 0-20% to give tert-butyl 3-[1-(3-fluorophenyl)-methylidene]piperidine-1-carboxylate (1.42 g).

$^1$H NMR (CDCl$_3$) 3:2 ratio of E and Z isomers δ: 7.33-7.21 (1H, m), 7.05-6.85 (3H, m), 6.37 (0.6H, s), 6.28 (0.4H, s), 4.16 (0.8H, s), 4.00 (1.2H, s), 3.50 (2H, t), 2.50 (1.2H, m), 2.39 (0.8H, m), 1.72 (0.8H, m), 1.62 (1.2H, m), 1.48 (5.4H, s), 1.34 (3.6H, br s).

Intermediate 228

(3-Fluorobenzyl)triphenylphosphonium bromide

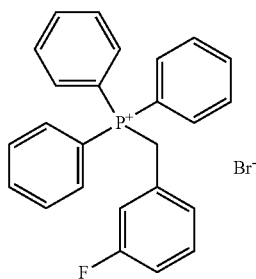 [SMILES: Fc1cccc(C[P+](c2ccccc2)(c2ccccc2)c2ccccc2)c1 ; [Br-]]

A mixture of 3-fluorobenzyl bromide (5 g) and triphenyl phosphine (6.94 g) in toluene (50 mL) was heated at reflux for 3 hours. After cooling, the solid was collected by filtration, washed with toluene and dried under vacuum at 50° C. to give (3-fluorobenzyl)triphenylphosphonium bromide (10.1 g).

$^1$H NMR (DMSO-d$_6$) δ: 7.96-7.87 (3H, m), 7.81-7.64 (12H, m), 7.35-7.26 (1H, m), 7.20-7.11 (1H, m), 6.88-6.82 (1H, m), 6.78-6.70 (1H, m), 5.21 (2H, d).

Intermediate 229

Methyl (1aR,7bS)-5-{2-[2-((R)-1-ethylpyrrolidin-2-yl)ethyl]-4-fluoro-benzenesulfonylamino}-1,1a,2,7b-tetrahydrocyclopropa[c]chromene-4-carboxylate

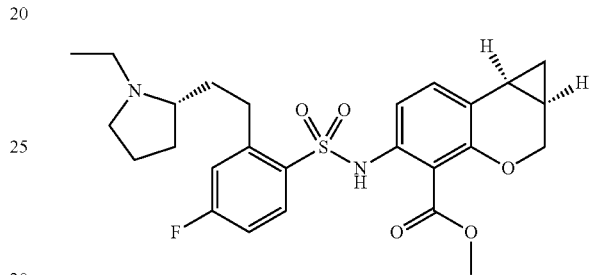

Prepared by proceeding in a similar manner to Intermediate 95, starting from 2-[2-((R)-1-ethyl-pyrrolidin-2-yl)-ethyl]-4-fluorobenzenesulfonyl chloride (intermediate 230) and methyl (1aR,7bS)-5-amino-1,1a,2,7b-tetrahydrocyclopropa[c]chromene-4-carboxylate (Intermediate 42A).

LCMS (Method A) r/t 2.30 (M+H) 503.

Intermediate 230

2-[2-((R)-1-Ethylpyrrolidin-2-yl)ethyl]-4-fluorobenzenesulfonyl chloride

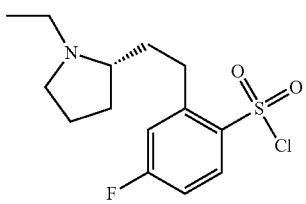 [SMILES: CCN1CCC[C@H]1CCc1cc(F)ccc1S(=O)(=O)Cl]

Prepared by proceeding in a similar manner to intermediate 96, starting from (R)-1-ethyl-2-[2-(3-fluorophenyl)ethyl]pyrrolidine (intermediate 231).

$^1$H NMR (CDCl$_3$) δ: 8.11 (1H, dd), 7.42 (1H, dd), 7.14 (1H, t), 3.93 (1H, m), 3.46-3.21 (2H, m), 3.13 (1H, m), 2.91 (2H, m), 2.43 (2H, m), 2.32 (2H, m), 2.11 (3H, m), 1.50 (3H, t).

Intermediate 231

(R)-1-Ethyl-2-[2-(3-fluorophenyl)ethyl]pyrrolidine

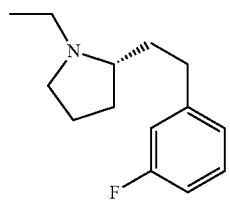 [SMILES: CCN1CCC[C@H]1CCc1cccc(F)c1]

A solution of 1-{(R)-2-[2-(3-fluorophenyl)ethyl]pyrrolidin-1-yl}ethanone (Intermediate 232, 0.48 g) in THF (20 mL) was cooled to 0° C. and treated with a solution of lithium aluminum hydride (2M in THF, 3.6 mL) under an atmosphere of nitrogen. The resultant mixture was allowed to warm to room temperature before heating to 60° C. overnight. The mixture was cooled to 0° C. and treated with water (0.35 ml), 4N sodium hydroxide solution (0.35 ml) and further water (0.9 ml). Sodium bisulphate powder was added to the suspension and the slurry was filtered through Celite and the filtrate was evaporated to dryness to give (R)-1-ethyl-2-[2-(3-fluoro-phenyl)ethyl]pyrrolidine (0.41 g) as an oil.

$^1$H NMR (CDCl$_3$) δ: 7.22 (1H, m), 6.96 (1H, d), 6.87 (2H, m), 3.18 (1H, dd), 2.87 (1H, m), 2.69 (1H, m), 2.55 (1H, m), 2.20 (1H, dq), 2.12-1.91 (4H, m), 1.75 (2H, m), 1.54 (2H, m), 1.10 (3H, t). HNMR 205205

Intermediate 232

1-{(R)-2-[2-(3-Fluorophenyl)ethyl]pyrrolidin-1-yl}ethanone

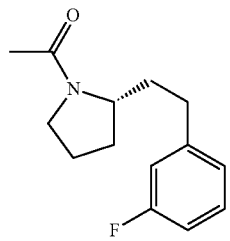 [SMILES: CC(=O)N1CCC[C@H]1CCc1cccc(F)c1]

Acetyl chloride (0.29 ml) was added to a solution of N,N-diisopropyl-N-ethylamine (0.71 ml) and (R)-2-[2-(3-fluorophenyl)ethyl]-pyrrolidine (Intermediate 233, 0.39 g) in DCM (30 ml) and the mixture was stirred for 1.5 hours. The mixture was washed with 1M HCl, dried (MgSO$_4$) and filtered. The filtrate was evaporated to dryness to give 1-{(R)-2-[2-(3-fluorophenyl)ethyl]-pyrrolidin-1-yl}ethanone (0.48 g) as an oil.

$^1$H NMR (d$_6$-DMSO, 80° C.) δ: 7.28 (1H, q), 7.02 (2H, t), 6.92 (1H, t), 3.93 (1H, br s), 3.41 (2H, m), 2.60 (2H, m), 2.05-1.54 (6H, m), 1.90 (3H, t).

Intermediate 233

(R)-2-[2-(3-Fluorophenyl)ethyl]pyrrolidine

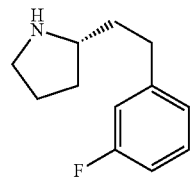 [SMILES: Fc1cccc(CC[C@@H]2CCCN2)c1]

Trifluoroacetic acid (5 mL) was added to a solution of tert-butyl (R)-2-[2-(3-fluorophenyl)ethyl]-pyrrolidine-1-carboxylate (Intermediate 234, 0.55 g) in DCM (5 mL) and the mixture was stirred at room temperature for 1.5 hours. The mixture was evaporated to dryness and the residue was dissolved in a small amount of methanol and loaded onto a 20 g SCX-2 SPE cartridge, washed with methanol then eluted with 2M ammonia in methanol to give (R)-2-[2-(3-fluorophenyl)-ethyl]pyrrolidine (0.39 g).

$^1$H NMR (CDCl$_3$) δ: 7.23 (1H, q), 6.97 (1H, d), 6.88 (2H, m), 2.99 (2H, m), 2.85 (1H, m), 2.69 (2H, m), 1.91 (1H, m), 1.75 (3H, m), 1.61 (1H, br s), 1.28 (1H, m).

Intermediate 234 tert-Butyl (R)-2-[2-(3-fluorophenyl)ethyl]pyrrolidine-1-carboxylate

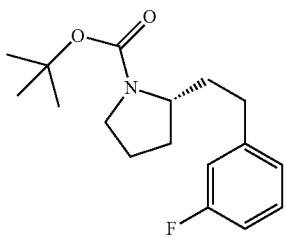 [SMILES: CC(C)(C)OC(=O)N1CCC[C@H]1CCc1cccc(F)c1]

A solution of tert-butyl (S)-2-(3-fluorophenylethynyl)pyrrolidine-1-carboxylate (Intermediate 235, 1.26 g) in IMS (70 mL) was carefully added to 20% palladium on carbon (0.6 g) under a carbon dioxide atmosphere. The mixture was degassed under vacuum and placed under an atmosphere of hydrogen. This was repeated three times then the mixture was stirred under an atmosphere of hydrogen for 18 hours. The mixture was filtered through Celite and the filtrate was evaporated to dryness. The residue was purified by chromatography on silica, eluting with a mixture of DCM and pentane with a gradient of 0-100% to give tert-butyl (R)-2-[2-(3-fluoro-phenyl)ethyl]pyrrolidine-1-carboxylate (0.55 g) as an oil.

$^1$H NMR (CDCl$_3$) δ: 7.21 (1H, br m), 6.99-6.81 (3H, br m), 3.80 (1H, br d), 3.37 (2H, br d), 2.61 (2H, br m), 1.97 (2H, br m), 1.83 (2H, m), 1.65 (2H, br m), 1.45 (9H, s).

Intermediate 235 tert-Butyl (S)-2-(3-fluorophenylethynyl)pyrrolidine-1-carboxylate

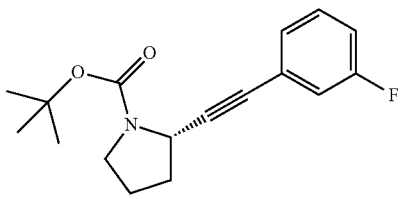 [SMILES: CC(C)(C)OC(=O)N1CCC[C@H]1C#Cc1cccc(F)c1]

A suspension of 3-fluorobromobenzene (0.62 ml), tris(dibenzylideneacetone) dipalladium(0) (0.276 g), tri-tert-butylphosphonium tetrafluoroborate (0.165 g) and tert-butyl (S)-2-tributyl-stannanylethynylpyrrolidine-1-carboxylate (Intermediate 236, 2.94 g) in anhydrous toluene (40 ml) was degassed under nitrogen and stirred at room temperature for 1.5 hours. The mixture was evaporated to dryness and the residue was purified by chromatography on silica, eluting with a mixture of DCM and pentane with a gradient of 0-100% to give tert-butyl (S)-2-(3-fluoro-phenylethynyl)pyrrolidine-1-carboxylate (1.26 g) as an oil.

$^1$H NMR (CDCl$_3$) δ: 7.25 (1H, m), 7.16 (1H, br d), 7.08 (1H, br d), 6.99 (1H, br t), 4.69 (1H, br d), 3.51 (1H, br s), 3.37 (1H, br s), 2.11 (3H, br m), 1.94 (1H, br s), 1.49 (9H, s).

Intermediate 236 tert-Butyl-2-tributylstannanylethynylpyrrolidine-1-carboxylate

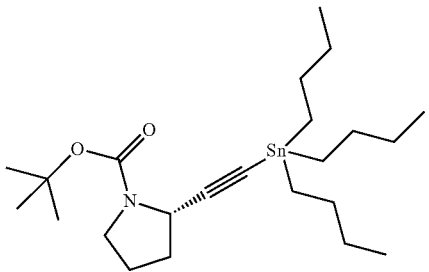 [SMILES: CCC[CH2][Sn]([C]#C[C@@H]1CCCN1C(=O)OC(C)(C)C)([CH2]CCC)[CH2]CCC]

n-Butyl lithium (2.5M solution in hexanes, 11 mL) was added dropwise to a cooled solution of tert-butyl (S)-2-ethynylpyrrolidine-1-carboxylate (prepared according A Paul et al, Tetrahedron, 2006, 62, 8919, 4.49 g) in dry THF (230 ml) under an atmosphere of nitrogen while maintaining the temperature below −65° C. When the addition was completed, the mixture was stirred at −78° C. for 15 minutes then allowed to warm to 0° C. and stirred for 2.5 hours. Tributyl tin chloride (7.7 mL) was added dropwise over five minutes and the mixture was stirred at room temperature for 1.5 hours. The mixture was cooled to 0° C. and saturated sodium bicarbonate was added while maintaining the temperature below 15° C. The layers were separated and the aqueous layer was extracted with ethyl acetate, washed with saturated sodium bicarbonate, water, dried (MgSO$_4$) and filtered. The filtrate was evaporated to dryness and the residue was purified by chromatography on silica, eluting with a mixture of pentane and ethyl acetate with a gradient of 0-7.5% to give tert-butyl (S)-2-tributylstannanylethynylpyrrolidine-1-carboxylate (0.39 g) as an oil.

$^1$H NMR (CDCl$_3$) δ: 4.41 (1H, br s), 3.45 (1H, br m), 3.28 (1H, br s), 2.03 (3H, br m), 1.86 (1H, br s), 1.54 (6H, m), 1.48 (9H, s), 1.33 (6H, q), 0.95 (6H, t), 0.90 (9H, t).

Biological Example 1

Compounds are tested for their capacity to inhibit recombinant human MetAP2 activity using the following assay.

Human recombinant MetAP2 expressed in Sf9 cells followed by affinity purification and EDTA treatment to remove endogenous active site cation was dialysed against MnCl$_2$ to produce the manganese enzyme used in the assay. The assay was carried out for 30 minutes at 25° C. in 50 mM HEPES buffer containing 100 mM NaCl, pH 7.5 the presence of 0.75 mM Methionine-Alanine-Serine (MAS) substrate and 50 g/ml amino acid oxidase using a dilution of purified MetAP2 giving >3-fold signal: noise. Cleavage of the substrate by MetAP2 and oxidation of free methionine by amino acid oxidase was detected and quantified using fluorescence generated by Amplex red (10-acetyl-3,7-dihydroxyphenoxazine) in combination with horseradish peroxidase which detects H$_2$O$_2$ released during the oxidation step. The fluorescent signal was detected using a multiwell fluorimeter. Compounds were diluted in DMSO prior to addition to assay buffer, the final DMSO concentration in the assay being 1%.

The IC$_{50}$ is defined as the concentration at which a given compound achieves 50% inhibition of control. IC$_{50}$ values are calculated using the XLfit software package (version 2.0.5).

Compounds of the invention demonstrated activity in the assay of this Example as indicated in the following table, wherein A represents <0.05 μM, B represents IC$_{50}$ between 0.05 μM and 0.5 μM, and C represents IC$_{50}$>0.5 μM.

| Compound name | Activity |
| --- | --- |
| Cis-(3aRS,9bRS)-7-(Benzenesulfonylamino)-1,3a,4,9b-tetrahydro-2H-furo[2,3-c]chromene-6-carboxylic acid | B |
| Cis-(3aRS,9bRS)-7[2-(3-Diethylaminopropyl)-4-fluorobenzenesulfonyl-amino]-1,3a,4,9b-tetrahydro-2H-furo[2,3-c]chromene-6-carboxylic acid | B |
| Cis-(3aRS,9bRS)-7-[2-(3-{Pyrrolidin-1-yl}propyl)-4-fluorobenzene-sulfonylamino]-1,3a,4,9b-tetrahydro-2H-furo[2,3-c]chromene-6-carboxylic acid | A |
| Cis-(3aRS,9bRS)-7-[2-((Z)-3-Diethylaminoprop-1-enyl)-4-fluoro-benzenesulfonylamino]-1,3a,4,9b-tetrahydro-2H-furo[2,3-c]chromene-6-carboxylic acid | A |
| First eluting enantiomer of cis-(3aRS,9bRS)-7-[2-((Z)-3-Diethylaminoprop-1-enyl)-4-fluoro-benzenesulfonylamino]-1,3a,4,9b-tetrahydro-2H-furo[2,3-c]chromene-6-carboxylic acid | A |
| Second eluting enantiomer of cis-(3aRS,9bRS)-7-[2-((Z)-3-Diethylaminoprop-1-enyl)-4-fluoro-benzenesulfonylamino]-1,3a,4,9b-tetrahydro-2H-furo[2,3-c]chromene-6-carboxylic acid | B |
| 7-[2-((Z)-3-Diethylaminoprop-1-enyl)-4-fluorobenzenesulfonyl-amino]-1,2-dihydrofuro[2,3-c]quinoline-6-carboxylic acid formate salt | A |
| 7-(Benzenesulfonylamino))-1,2-dihydrofuro[2,3-c]quinoline-6-carboxylic acid formate salt | A |
| Cis-(3aRS,9bRS)-7-[2-((Z)-3-Diethylaminoprop-1-enyl)-4-fluorobenzenesulfonylamino]-1,2,3a,4,5,9b-hexahydrofuro[2,3-c]quinoline-6-carboxylic acid | A |
| 5-[2-((Z)-3-Diethylaminoprop-1-enyl)-4-fluorobenzenesulfonyl-amino]-1,1a,2,7b-tetrahydrocyclopropa[c]chromene-4-carboxylic acid | A |
| (1aS,7bR)5-[2-((Z)-3-Diethylaminoprop-1-enyl)-4-fluorobenzenesulfonyl-amino]-1,1a,2,7b-tetrahydrocyclopropa[c]chromene-4-carboxylic acid | B |

| Compound name | Activity |
|---|---|
| (1aR,7bS)5-[2-((Z)-3-Diethylaminoprop-1-enyl)-4-fluorobenzenesulfonyl-amino]-1,1 a,2,7b-tetrahydrocyclopropa[c]chromene-4-carboxylic acid | A |
| (1aRS,7bSR)-5-[2-((Z)-3-Diethylaminoprop-1-enyl)-4-fluorobenzenesulfonylamino]-7b-methyl-1,1a,2,7b-tetrahydrocyclopropa[c]chromene-4-carboxylic acid | A |
| (1aRS,7bSR)-5-[2-((E)-3-Diethylaminoprop-1-enyl)-4-fluorobenzenesulfonylamino]-7b-methyl-1,1a,2,7b-tetrahydrocyclopropa[c]chromene-4-carboxylic acid | B |
| Cis-(3aRS,9bRS)-7-[2-(4-dimethylamino-butylamino)-benzenesulfonylamino]-1,3a,4,9b-tetrahydro-2H-furo[2,3-c]chromene-6-carboxylic acid | B |
| (1aR,7bS)-5-[2-(3-Diethylaminopropyl)-4-fluorobenzenesulfonyl-amino]-1,1a,2,7b-tetrahydrocyclopropa[c]chromene-4-carboxylic acid | A |
| (1aRS,7bSR)-5-[2-((Z)-3-Diethylaminoprop-1-enyl)-4-fluorobenzene-sulfonylamino]-1,1-difluoro-1,1a,2,7b-tetrahydrocyclopropa[c]chromene-4-carboxylic acid | A |
| First eluting enantiomer of (1aRS,7bSR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid | B |
| Second eluting enantiomer of (1aRS,7bSR)-5-[2-((Z)-3-diethylaminoprop-1-enyl)-4-fluorobenzene-sulfonylamino]-1,1-difluoro-1,1a,2,7b-tetrahydrocyclopropa[c]chromene-4-carboxylic acid | A |
| (1aRS,7bSR)-5-[2((Z)-3-Ethylaminoprop-1-enyl)-4-fluoro-benzenesulfonylamino]-1,1a,2,7b-tetrahydrocyclopropa-[c]chromene-4-carboxylic acid | A |
| First eluting enantiomer of (1aRS,7bSR)-5-[2((Z)-3-ethylaminoprop-1-enyl)-4-fluorobenzenesulfonylamino]-1,1a,2,7b-tetrahydrocyclopropa[c]chromene-4-carboxylic acid | A |
| Second eluting enantiomer of (1aRS,7bSR)-5-[2((Z)-3-ethylaminoprop-1-enyl)-4-fluorobenzene-sulfonylamino]-1,1a,2,7b-tetrahydro-cyclopropa[c]chromene-4-carboxylic acid | B |
| (1aRS,7bSR)-5-{2[(Z)-3-(Pyrrolidin-1-yl)prop-1-enyl]-4-fluorobenzenesulfonylamino}-1,1 a,2,7b-tetrahydro-cyclopropa[c]chromene-4-carboxylic acid | A |
| First eluting enantiomer of (1aRS,7bSR)-5-{2[(Z)-3-(pyrrolidin-1-yl)prop-1-enyl]-4-fluorobenzenesulfonylamino}-1,1a,2,7b-tetrahydro-cyclopropa[c]chromene-4-carboxylic acid | B |
| Second eluting enantiomer of (1aRS,7bSR)-5-{2[(Z)-3-(pyrrolidin-1-yl)prop-1-enyl]-4-fluorobenzenesulfonylaminol}-1,1a,2,7b-tetrahydro-cyclopropa[c]chromene-4-carboxylic acid | B |
| (1aRS,7bSR)-5-[2-(3-Dimethylaminopropylamino)benzene-sulfonylamino]-1,1a,2,7b-tetrahydrocyclopropa[c]chromene-4-carboxylic acid | A |
| First eluting enantiomer of (1aRS,7bSR)-5-[2-(3-dimethylaminopropylamino)benzene-sulfonylamino]-1,1a,2,7b-tetrahydrocyclopropa[c]chromene-4-carboxylic acid | C |
| Second eluting enantiomer of (1aRS,7bSR)-5-[2-(3-dimethylaminopropylamino)benzene-sulfonylamino]-1,1a,2,7b-tetrahydrocyclopropa[c]chromene-4-carboxylic acid | A |
| (1aRS,7bSR)-5-[2-(4-Dimethylaminobutylamino)benzene-sulfonylamino]-1,1a,2,7b-tetrahydrocyclopropa[c]chromene-4-carboxylic acid | A |
| First eluting enantiomer of (1aRS,7bSR)-5-[2-(4-dimethylaminobutylamino)benzene-sulfonylamino]-1,1a,2,7b-tetrahydrocyclopropa[c]chromene-4-carboxylic acid | B |
| Second eluting enantiomer of (1aRS,7bSR)-5-[2-(4-dimethylaminobutylamino)benzene-sulfonylamino]-1,1a,2,7b-tetrahydrocyclopropa[c]chromene-4-carboxylic acid | A |
| (1aRS,7bSR)-5-[2-(5-Dimethylaminopentylamino)benzene-sulfonylamino]-1,1a,2,7b-tetrahydrocyclopropa[c]chromene-4-carboxylic acid | A |
| (1aRS,7bSR)-5-{2[(Z)-3-(propan-2-yl)aminoprop-1-enyl]-4-fluorobenzene-sulfonylamino}-1,1a,2,7b-tetrahydrocyclopropa[c]chromene-4-carboxylic acid | B |
| (1aRS,7bSR)-5-{2[(Z)-3-((S)-3-hydroxypyrrolidin-1-yl)aminoprop-1-enyl]-4-fluorobenzenesulfonylamino]-1,1a,2,7b-tetrahydrocyclopropa[c]chromene-4-carboxylic acid | B |
| (1aRS,7bSR)-5-{2[(Z)-3-((R)-3-Hydroxypyrrolidin-1-yl)aminoprop-1-enyl]-4-fluorobenzene-sulfonylamino}-1,1a,2,7b-tetrahydro-cyclopropa[c]chromene-4-carboxylic acid | B |
| (1aRS,7bSR)-5-{2((Z)-4-Diethylaminobut-1-enyl)-4-fluorobenzenesulfonyl-amino]-1,1a,2,7b-tetrahydrocyclopropa[c]chromene-4-carboxylic acid | A |
| First eluting enantiomer of (1aRS,7bSR)-5-[2((Z)-4-diethylaminobut-1-enyl)-4-fluorobenzenesulfonyl-amino]-1,1a,2,7b-tetrahydrocyclopropa[c]chromene-4-carboxylic acid | B |
| Second eluting enantiomer of (1aRS,7bSR)-5-[2((Z)-4-diethylaminobut-1-enyl)-4-fluorobenzenesulfonylamino]-1,1a,2,7b-tetrahydrocyclopropa[c]chromene-4-carboxylic acid | B |
| (1aRS,7bSR)-5-{2-[2-(4-Ethylpiperazin-1-yl)-4-fluorobenzenesulfonylamino]-1,1 a,2,7b-tetrahydrocyclopropa[c]chromene-4-carboxylic acid | B |
| (1aRS,7bSR)-5-{2[(Z)-3-(Azetidin-1-yl)prop-1-enyl]-4-fluorobenzene-sulfonylamino}-1,1a,2,7b-tetrahydro-cyclopropa[c]chromene-4-carboxylic acid | B |
| (1aRS,7bSR)-5-{2[(Z)-3-(3-Hydroxyazetidin-1-yl)prop-1-enyl]-4-fluorobenzene-sulfonylamino)}-1,1a,2,7b-tetrahydrocyclopropa[c]chromene-4-carboxylic acid | A |
| (1aRS,7bSR)-5-{2[(Z)-3-(Azetidin-1-yl)propyl]-4-fluorobenzenesulfonylamino}-1,1a,2,7b-tetrahydrocyclopropa[c]chromene-4-carboxylic acid | B |
| (1aRS,7bSR)-5-{2((Z)-4-Diethylaminobutyl)-4-fluorobenzenesulfonylamino]-1,1a,2,7b-tetrahydrocyclopropa[c]chromene-4-carboxylic acid | B |
| (1aRS,7bSR)-5-{2[N-(4-Dimethylaminobutyl)-N-methylamino]-benzenesulfonyl-aminol}-1,1a,2,7b-tetrahydrocyclopropa-[c]chromene-4-carboxylic acid | C |
| (1aRS,7b SR)-5-{2-R(S)-1-Ethylpyrrolidin-3-ylcarbamoyl)-methyl]-4-fluoro-benzenesulfonyl-amino}-1,1a,2,7b-tetrahydrocyclopropa-[c]chromene-4-carboxylic acid | B |
| (1aRS,7bSR)-5-[2-(1-Ethylazetidin-3-yl)-4-fluorobenzene-sulfonylamino]-1,1a,2,7b-tetrahydro-cyclopropa[c]chromene-4-carboxylic acid | B |
| (1aRS,7bSR)-5-{2-[((R)-1-Ethylpyrrolidin-3-ylcarbamoyl)-methyl]-4-fluorobenzenesulfonyl-amino}-1,1a,2,7b-tetrahydrocyclopropa[c]chromene-4-carboxylic acid | B |
| (1aRS,7bSR)-5-{2[2-(Pyrrolidin-1-yl)-ethyl]-4-fluorobenzene-sulfonylamino}-1,1a,2,7b-tetrahydrocyclopropa[c]chromene-4-carboxylic acid | B |
| (1aRS,7bSR)-5-[2-((R)-1-Ethylpyrrolidin-3-ylmethyl)-4-fluorobenzenesulfonyl-amino]-1,1a,2,7b-tetrahydro-cyclopropa[c]chromene-4-carboxylic acid | A |
| First eluting enantiomer of (1aRS,7bSR)-5-[2-((R)-1-ethyl-pyrrolidin-3-ylmethyl)-4-fluorobenzenesulfonylamino]-1,1a,2,7b-tetrahydro-cyclopropa[c]chromene-4-carboxylic acid | B |
| Second eluting enantiomer of (1aRS,7bSR)-5-[2-((R)-1-Ethylpyrrolidin-3-ylmethyl)-4-fluorobenzenesulfonyl-amino]-1,1a,2,7b-tetrahydro-cyclopropa[c]chromene-4-carboxylic acid | A |
| (1aRS,7bSR)-5-{2-[((S)-1-Ethylpyrrolidin-2-yl)cabonyl-aminomethyl]-4-fluorobenzenesulfonylamino}-1,1a,2,7b-tetrahydrocyclopropa[c]chromene-4-carboxylic acid | A |
| (1aRS,7bSR)-5-[2-(4-Dimethylaminobutyrylamino)-4-fluorobenzenesulfonyl-amino]-1,1a,2,7b-tetrahydrocyclopropa-[c]chromene-4-carboxylic acid | B |
| (1aRS,7bSR)-5-[2-((S)-1-Ethyl-pyrrolidin-3-ylmethyl)-4-fluorobenzenesulfonyl-amino]-1,1a,2,7b-tetrahydrocyclopropa[c]chromene-4-carboxylic acid | B |
| (1aRS,7bSR)-5-[2-(3-Dimethylaminopropylcarbamoyl)benzene-sulfonylamino]-1,1a,2,7b-tetrahydrocyclopropa[c]chromene-4-carboxylic acid | B |
| (1aRS,7bSR)-5-(2-{[N-((S)-1-Ethyl-pyrrolidin-3-yl)-N-methyl-carbamoyl]methyl}-4-fluoro-benzenesulfonyl-amino)-1,1a,2,7b-tetrahydrocyclopropa-[c]chromene-4-carboxylic acid | B |
| (1aRS,7bSR)-5-(2-{[N-((R)-1-Ethylpyrrolidin-3-yl)-N-methyl-carbamoyl]methyl}-4-fluoro-benzenesulfonyl-amino)-1,1a,2,7b-tetrahydrocyclopropa-[c]chromene-4-carboxylic acid | B |
| (1aRS,7bSR)-5-{2[2((S)-1-Ethylpyrrolidin-2yl)ethylamino]-benzenesulfonyl-amino]-1,1a,2,7b-tetrahydrocyclopropa-[c]chromene-4-carboxylic acid | A |

| Compound name | Activity |
|---|---|
| (1aRS,7bSR)-5-{2-[2-((R)-1-Ethylpyrrolidin-2-yl)ethylamino]-benzenesulfonyl-amino}-1,1a,2,7b-tetrahydrocyclopropa-[c]chromene-4-carboxylic acid | A |
| (1aRS,7bSR)-5-[2-(3-N,N,-Diethylaminopropylamino)benzene-sulfonylamino]-1,1a,2,7b-tetrahydrocyclopropa[c]chromene-4-carboxylic acid | A |
| (1aRS,7bSR)-5-(2-{[((R)-1-Ethylpyrrolidine-2-yl)carbonyl-amino]methyl}-4-fluorobenzenesulfonylamino)-1,1a,2,7b-tetrahydrocyclopropa[c]chromene-4-carboxylic acid | B |
| (1aRS,7bSR)-5-{2-[(1-Ethylazetidin-3-ylmethyl)amino]benzene-sulfonylamino}-1,1a,2,7b-tetrahydrocyclopropa[c]chromene-4-carboxylic acid | B |
| First eluting enantiomer of (1aRS,7bSR)-5-[2-((Z)-3-diethylaminoprop-1-enyl)benzenesulfonylamino]-1,1a,2,7b-tetrahydrocyclopropa[c]chromene-4-carboxylic acid | B |
| Second eluting enantiomer of (1aRS,7bSR)-5-[2-((Z)-3-diethylaminoprop-1-enyl)benzenesulfonylamino]-1,1a,2,7b-tetrahydrocyclopropa[c]chromene-4-carboxylic acid | A |
| (1aRS,7bSR)-5-(2-{N-R(R)-1-Ethylpyrrolidine-2-yl)carbonyl]-N-methylaminomethyl}-4-fluorobenzenesulfonylamino)-1,1a,2,7b-tetrahydrocyclopropa[c]chromene-4-carboxylic acid | B |
| (1aRS,7bSR)-5-(2-{N-[((S)-1-Ethylpyrrolidine-2-yl)carbonyl]-N-methylamino-methyl}-4-fluorobenzenesulfonylamino)-1,t1a,2,7b-etrahydrocyclopropa[c]chromene-4-carboxylic acid | B |
| (1aRS,7bSR)-5-[2-(4-Dimethylaminobutylamino)-4-fluoro-benzenesulfonyl-amino]-1,1a,2,7b-tetrahydrocyclopropa-[c]chromene-4-carboxylic acid | B |
| (1aRS,7bSR)-5-{2-[((R)-1-Ethylpyaolidin-3-ylmethyl)amino]-benzenesulfonylamino}-1,1a,2,7b-tetrahydrocyclopropa-[c]chromene-4-carboxylic acid | B |
| (1aRS,7bSR)-5-{2-[((S)-1-Ethylpyrrolidin-3-ylmethyl)amino]-benzenesulfonylamino}-1,1a,2,7b-tetrahydrocyclopropa-[c]chromene-4-carboxylic acid | B |
| (1aRS,7bSR)-5-[2-(4-Ethyl-2-oxopiperazin-1-ylmethyl)-4-fluorobenzene-sulfonylamino]-1,1a,2,7b-tetrahydrocyclopropa-[c]chromene-4-carboxylic acid | B |
| (1aRS,7bSR)-5-[2-(1-Ethylpiperidin-4-ylmethyl)-4-fluoro-benzenesulfonylamino]-1,1a,2,7b-tetrahydrocyclopropa-[c]chromene-4-carboxylic acid | A |
| (1aRS,7bSR)-5-{2[2-(1-Ethylazetidin-3-yl)ethyl]-4-fluoro-benzenesulfonyl-amino}-1,1a,2,7b-tetrahydrocyclopropa-[c]chromene-4-carboxylic acid | B |
| (1aRS,7bSR)-5-{2[((S)-1-Azabicyclo[2.2.2]oct-3-yl)amino]benzenesulfonyl-amino]-1,1a,2,7b-tetrahydrocyclopropa[c]chromene-4-carboxylic acid | B |
| (1aRS,7bSR)-5-{2-[((R)-1-Azabicyclo[2.2.2]oct-3-yl)amino]benzenesulfonyl-amino}-1,1a,2,7b-tetrahydrocyclopropa[c]chromene-4-carboxylic acid | A |
| (1aRS,7bSR)-5-(2-{[((S)-1-ethylpyrrolidine-3-carbonyl)amino]methyl}-4-fluoro-benzenesulfonylamino)-1,1a,2,7b-tetrahydrocyclopropa[c]chromene-4-carboxylic acid | B |
| (1aRS,7bSR)-5-{2-[2-((R)-1-Ethylpyrrolidin-3-ylamino)ethyl]-4-fluoro-benzenesulfonylamino}-1,1a,2,7b-tetrahydrocyclopropa-[c]chromene-4-carboxylic acid | B |
| (1aRS,7bSR)-5-{2[((R)-1-Ethylpyrrolidin-3-yl)amino]-benzenesulfonylamino}-1,1a,2,7b-tetrahydrocyclopropa-[c]chromene-4-carboxylic acid | B |
| (1aRS,7bSR)-5-{2-[((S)-1-Ethylpyrrolidin-3-yl)amino]-benzenesulfonylamino}-1,1a,2,7b-tetrahydrocyclopropa-[c]chromene-4-carboxylic acid | B |
| (1aRS,7bSR)-5-(2-{[((R)-1-Ethylpyrrolidine-3-carbonyl)amino]-methyl}-4-fluoro-benzenesulfonylamino)-1,1 a,2,7b-tetrahydro-cyclopropa[c]chromene-4-carboxylic acid | B |
| (1aRS,7bSR)-5-[2-((Z)-3-Diethylamino-2-methylprop-1-enyl)-4-fluorobenzene-sulfonylamino]-1,1a,2,7b-tetrahydrocyclopropa-[c]chromene-4-carboxylic acid | A |
| (1aRS,7bSR)-5-{2-[2-((R)-1-Ethylpyrrolidin-3-yl)ethylamino]-benzenesulfonylamino}-1,1a,2,7b-tetrahydrocyclopropa-[c]chromene-4-carboxylic acid | B |
| (1aRS,7bSR)-5-{2-[2-((S)-1-Ethylpyrrolidin-3-yl)ethylamino]-benzenesulfonyl-amino}-1,1a,2,7b-tetrahydrocyclopropa-[c]chromene-4-carboxylic acid | B |
| (1aR,7bS)-5-[2-((S)-1-Ethylpyrrolidin-3-yloxymethyl)-4-fluoro-benzenesulfonylamino]-1,1a,2,7b-tetrahydrocyclopropa-[c]chromene-4-carboxylic acid | B |
| (1aR,7bS)-5-[2-((R)-1-Ethylpyrrolidin-3-yloxymethyl)-4-fluoro-benzenesulfonylamino]-1,1a,2,7b-tetrahydrocyclopropa-[c]chromene-4-carboxylic acid | B |
| (1aR,7bS)-5-[2-(1-Ethylpiperidin-3-ylmethyl)-4-fluorobenzene-sulfonylamino]-1,1a,2,7b-tetrahydrocyclopropa[c]chromene-4-carboxylic acid | B |
| (1aR,7bS)-5-{2-[2-((R)-1-Ethylpyrrolidin-2-yl)ethyl]-4-fluorobenzenesulfonyl-amino}-1,1a,2,7b-tetrahydrocyclopropa-[c]chromene-4-carboxylic acid | B |

In vitro pharmacology and ADME testing of the compound of Example 12 as follows:

| Parameter | Compound |
|---|---|
| MetAP2/MetAP1 $IC_{50}$ (nM) | 25/50,000 |
| MetAP2 off-rate ($T_{1/2}$) | 3 hours |
| HT1080 $EC_{50}$ | 28/8 |
| Cell cycle (G1 attenuation, nM) | 3 |
| Microsomal Stability | 72/88/77 |
| Hepatocyte Stability | 99/88/62 |
| CYP $IC_{50}$ (nM), HLM | >10* |
| Plasma protein binding (h/r/m, %) | 77.2/81.1/<70 |
| hERG $IC_{50}$ | >33 µM |
| AMES | negative |
| CEREP screen | <35% inhibition at10 µM across 72 receptors and enzymes |

*CYP3A4 signal observed with pre-incubation

Biological Example 2

Compounds were tested in diet induced obese mice (C57BL6) that were on a 65% high fat diet for 8-10 weeks. Mice were dosed for 10 days by oral gavage with 30 mg/kg of the compounds listed. Their body weights were recorded along with serum chemistries including cholesterol.

| Compound | Body Weight Change | Cholesterol Change |
|---|---|---|
| 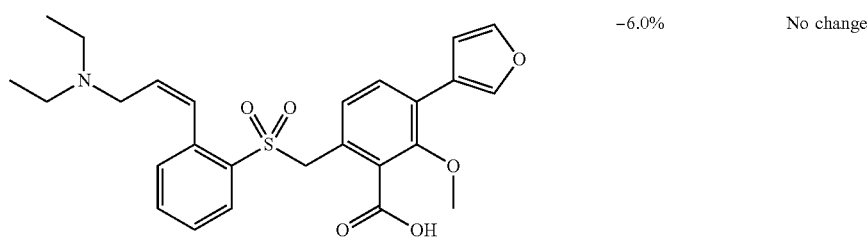 | −6.0% | No change |

-continued

| Compound | Body Weight Change | Cholesterol Change |
|---|---|---|
| [structure] | −7.0 | −35% |
| [structure] | −2.1% | No change |
| [structure] | −16% | No change |
| [structure] | −2.0% | −24% |

Biological Example 3

Mouse, rat and dog studies were conducted to assess i.v. and p.o. (oral) exposure. Results of the studies using compound A are shown in the table below:

|  | Mouse | Rat | Dog |
|---|---|---|---|
| i.v. | | | |
| Cl (mL/min/kg) | 126 | 54 | 14 |
| Vss (L/kg) | 3.1 | 3.4 | 1.3 |
| Plasma $T_{1/2}$ (h) | 0.9 | 1.2 | 3.6 |
| p.o. | | | |
| F (%) | 53 | 22 | 20 |
| plasma AUC | 497 | 356 | 711 |
| liver/plasma ratio | 38 | 39 | ND |

Biological Example 4

Diet Induced Obese Mouse Study

FIG. 1 shows the results of a mouse study. Diet induced obese (DIO) C57BL6 mice were provided with varying doses of compound A and fumagillin (fum). Tissue biomarkers in peri-renal fat, mesenteric fat and the liver were measured. The results in FIG. 1 indicate that compound A primarily targets the liver.

Figure 2:
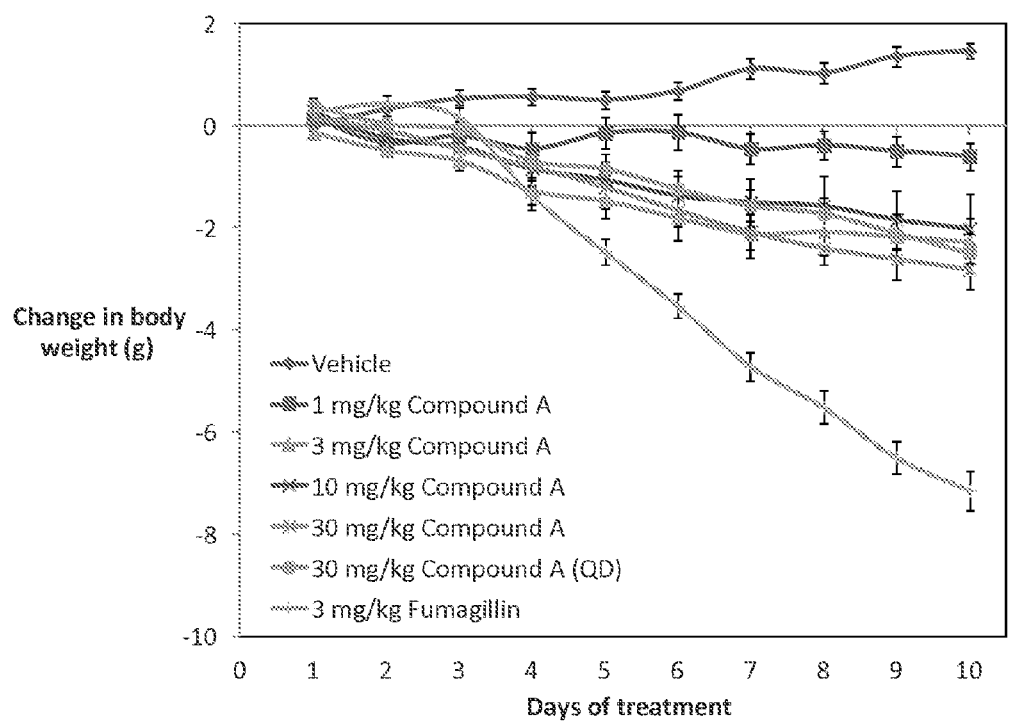
FIG. 2 shows the results from a body weight change study in obese mice 10 days after administration of a disclosed compound versus fumagillin or vehicle.
Figure 3:
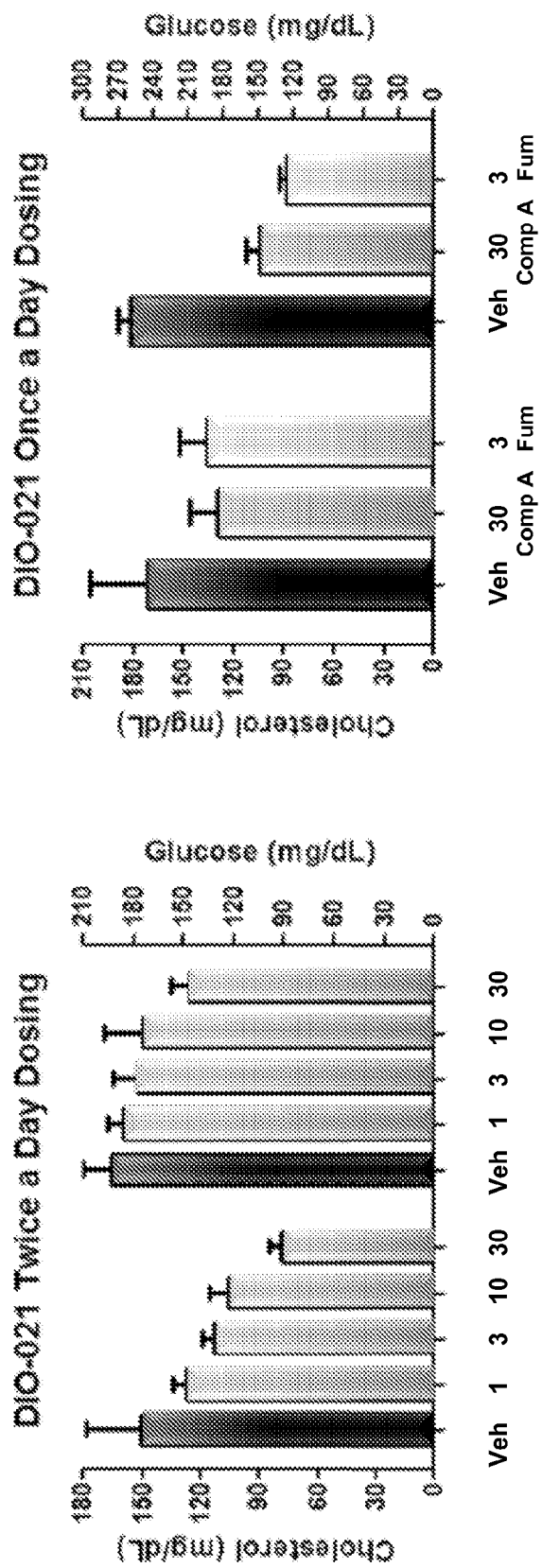
FIG. 3 shows the results from a mouse study examining the effect of once a day or twice a day administration of a disclosed compound.
Figure 4:
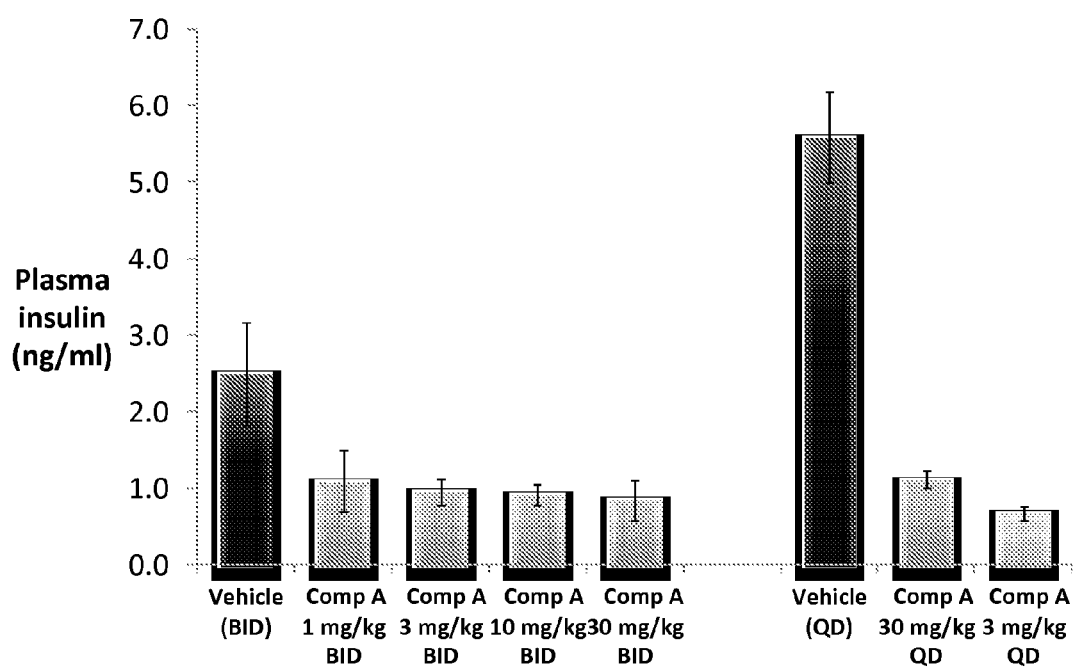
FIG. 4 indicates the reduction in the level of plasma insulin after administration of a disclosed compound.
Figure 5:
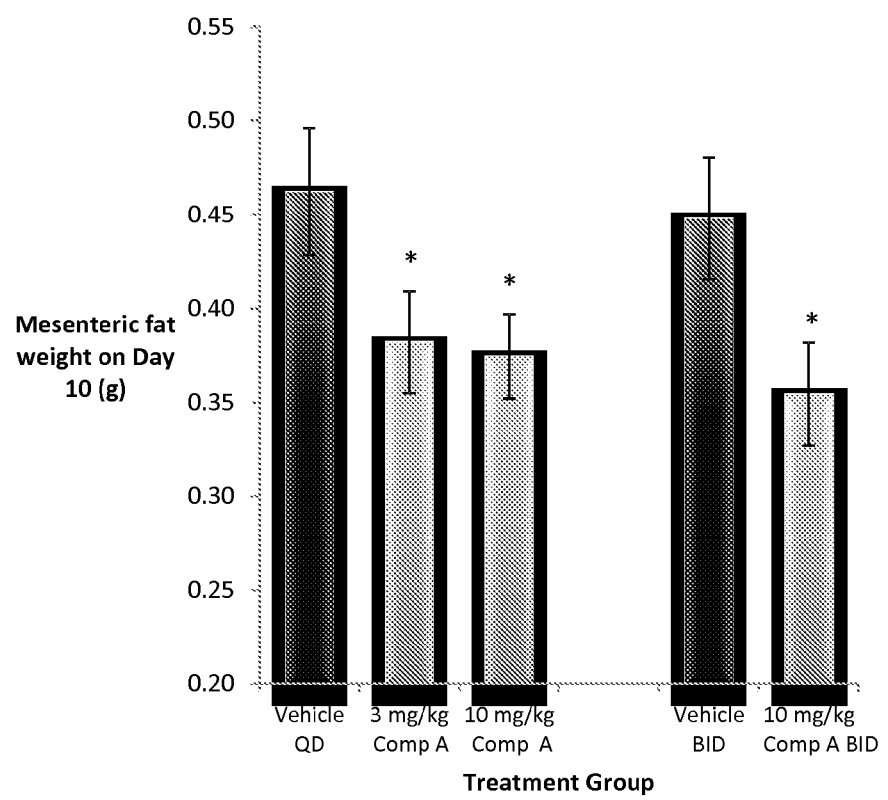
FIG. 5 shows a reduction in liver and mesenteric fat pad weight in an animal model.
Figure 5:
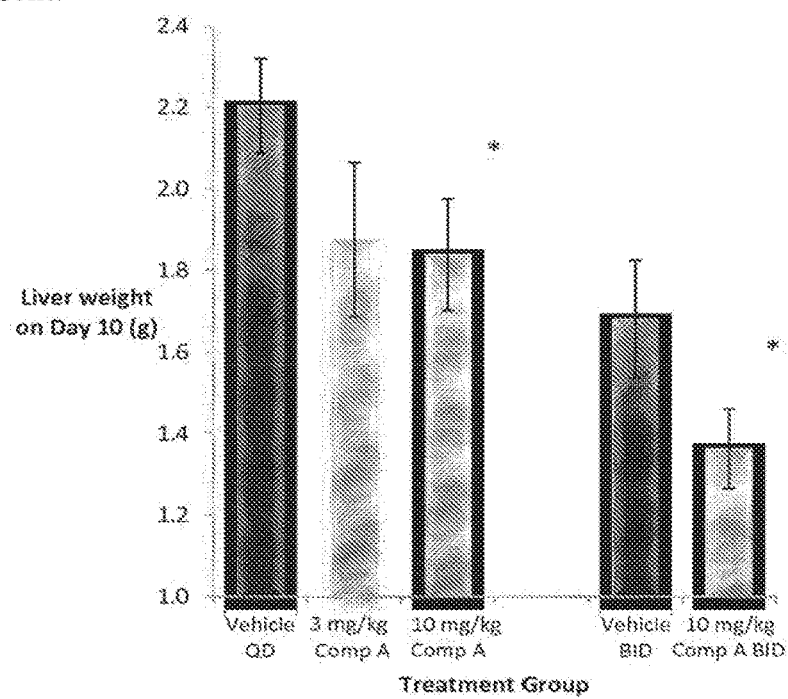

The change in bodyweight after 10 days, after administration of vehicle, fumagillin and compound A are shown in FIG. 2. Obese mice given increasing doses of compound A over a period of 10 days showed a marked decrease in body weight compared to control vehicle. Obese mice showed further marked lowering of blood cholesterol and glucose compared to vehicle. (FIG. 3). Decrease in plasma insulin in mice, after once or twice a day administration of compound A vs. vehicle is also observed (FIG. 4). As shown in FIG. 5, reduction in mesenteric adipose tissue weight and liver weight also occurred in compound A administered animals.

Figure 6:
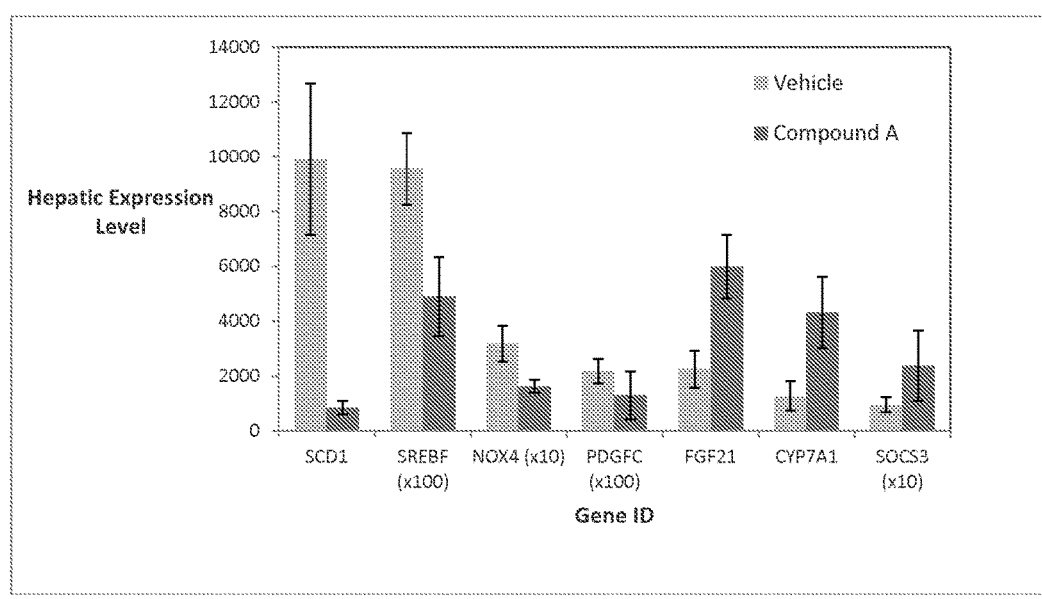
FIG. 6 indicates regulation of the expression of genes implicated in pathogenesis of fatty liver and fibrosis after treatment of obese mice with a disclosed compound.

The expression of genes implicated in pathogenesis of fatty liver and fibrosis are favorably regulated. FIG. 6 shows data from an Illumina Mouse microarray analysis of liver mRNA after Compound A (3 mg/kg/bid×10 days) was administered to DIO obese mice and hepatic gene expression levels were analyzed.

Biological Example 5

Non-Alcoholic Steatohepatitis Mouse Model

NASH was induced in 48 male mice by a single subcutaneous injection of 200 g streptozotocin (STZ; Sigma-Aldrich) in the back of mice 2 days after birth, and by feeding with high fat diet (HFD; 57 kcal % fat) after 4 weeks of age. At 5 weeks of age, the NASH mice were randomized into 6 groups of 8 mice based on body weight. Eight male littermates, fed with normal diet (without STZ treatment, were used for the Normal group. Vehicle, Compound A and Telmisartan were administered by the oral route in a volume of 10 mL/kg body weight.

Compound A was administered twice daily at doses of 1, 3 or 10 mg/kg body weight (i.e., 2, 6 or 20 mg/kg/day) and once daily at dose of 30 mg/kg body weight. Telmisartan was administered once daily at a dose of 10 mg/kg body weight.

C57BL/6 mice (15-day pregnant female) were obtained from Charles River Laboratories Japan (Japan). The animals were maintained in a SPF facility under controlled conditions of temperature (23±2° C.), humidity (45±10%), lighting (12-hour artificial light and dark cycles; light from 8:00 to 20:00) and air exchange. A high pressure (20±4 Pa) was maintained in the experimental room to prevent contamination of the facility.

Mice were fasted for 4 hours before blood was collected at the time of sacrifice. $HbA_{1c}$ levels were quantified in whole blood samples by DCA Vantage Analyzer (Siemens Healthcare Diagnostics, USA). For plasma biochemistry, blood was collected in polypropylene tubes with anticoagulant (Novo-Heparin) and centrifuged at 1,000×g for 15 minutes at 4° C. The supernatant was collected and stored at −80° C. until use. Plasma levels of glucose, ALT, TG and total cholesterol were measured by FUJI DRI-CHEM 7000 (Fujifilm, Japan). Plasma insulin concentration was quantified by the Ultra Sensitive Mouse Insulin ELISA Kit.

Liver total lipid-extracts were obtained by Folch's method (Folch J. et al., *J. Biol. Chem.* 1957; 226: 497). Liver samples were homogenized in chloroform-methanol (2:1, v/v) and incubated overnight at room temperature. After washing with chloroform-methanol-water (8:4:3, v/v/v), the extracts were evaporated to dryness, and dissolved in isopropanol. Liver TG levels were measured by Triglyceride E-test (Wako Pure Chemical Industries). Extracts were diluted 2-fold in isopropanol when the TG content exceeded the detection limit.

For HE staining, sections were cut from paraffin blocks of liver tissue prefixed in Bouin's solution and stained with Lillie-Mayer's Hematoxylin (Muto Pure Chemicals, Japan) and eosin solution (Wako Pure Chemical Industries). NAFLD Activity score (NAS) was calculated according to the criteria of Kleiner (Kleiner D E. et al., *Hepatology,* 2005; 41:1313). To visualize collagen deposition, Bouin's fixed liver sections were stained using picro-Sirius red solution (Waldeck, Germany). To visualize macro- and microvesicular fat, cryosections were cut from frozen liver tissues, prefixed in 10% neutral buffered formalin, embedded in Tissue-Tek O.C.T. compound (Sakura Finetek Japan, Japan), and stained with Oil Red O (Sigma-Aldrich). For immunohistochemistry, sections were cut from frozen liver tissues embedded in Tissue-Tek O.C.T. compound and fixed in acetone. Endogenous peroxidase activity was blocked using 0.03% $H_2O_2$ for 5 minutes, followed by incubation with Block Ace (Dainippon Sumitomo Pharma, Japan) for 10 minutes. The sections were incubated with a 200-fold dilution of anti-F4/80 antibody (BMA Biomedicals, Switzerland) over night at 4° C. After incubation with secondary antibody (HRP-Goat anti-rat antibody, Invitrogen, USA), enzyme-substrate reactions were performed using 3,3'-diaminobenzidine/$H_2O_2$ solution (Nichirei, Japan).

For quantitative analysis of fibrosis, fat deposition and inflammation areas, bright field images of Sirius red-stained, oil red-stained and F4/80-immunostained sections were captured around the central vein using a digital camera (DFC280; Leica, Germany) at 200-fold magnification, and the positive areas in 5 fields/section were measured using ImageJ software (National Institute of Health, USA).

All results were expressed as mean±SD and statistical analyses were performed using Prism Software 4 (GraphPad Software, USA).

Seven study groups were included in the study: Group 1 (Normal): Eight normal mice were fed with a normal diet ad libitum without any treatment until 9 weeks of age. Group 2 (Vehicle): Eight NASH mice were orally administered vehicle (0.5% CMC) in a volume of 10 mL/kg twice daily from 5 to 9 weeks of age. Group 3 (telmisartan): Eight NASH mice were orally administered the vehicle in the morning and pure water supplemented with Telmisartan at a dose of 10 mg/kg in the evening from 5 to 9 weeks of age. Telmisartan has been shown to have anti-steatotic, anti-inflammatory and anti-fibrotic effects in STAM mice and was used as the positive control in the present study. Treatment with Telmisartan decreased liver TG, NAS and the fibrosis area with statistical significance.

Group 4: (Compound A [1 mg/kg (BID)]): Eight NASH mice were orally administered the vehicle supplemented with Compound A at a dose of 1 mg/kg twice daily (2 mg/kg/day) from 5 to 9 weeks of age. Group 5: (Compound A [3 mg/kg (BID)]): Eight NASH mice were orally administered the vehicle supplemented with Compound A at a dose of 3 mg/kg twice daily (6 mg/kg/day) from 5 to 9 weeks of age. Group 6 (Compound A [10 mg/kg (BID)]): Eight NASH mice were orally administered the vehicle supplemented with Compound A at a dose of 10 mg/kg twice daily (20 mg/kg/day) from 5 to 9 weeks of age. Group 7: (Compound A [30 mg/kg (QD)]): Eight NASH mice were orally administered the vehicle in the morning and the vehicle supplemented with Compound A at a dose of 30 mg/kg in the evening from 5 to 9 weeks of age.

The table below summarizes the treatment schedule:

| Group | No. mice | Test substance | Dose (mg/kg/day) | Volume (mL/kg) | Regimens | Sacrifice (wks) |
|---|---|---|---|---|---|---|
| 1 | 8 | — | — | — | — | 9 |
| 2 | 8 | Vehicle | — | 10 | Oral, BID, 5 wks-9 wks | 9 |
| 3 | 8 | AM: Vehicle PM: Telmisartan | 10 | 10 | Oral, QD, 5 wks-9 wks | 9 |
| 4 | 8 | Compound A | 2 | 10 | Oral, BID, 5 wks-9 wks | 9 |
| 5 | 8 | Compound A | 6 | 10 | Oral, BID, 5 wks-9 wks | 9 |

| Group | No. mice | Test substance | Dose (mg/kg/day) | Volume (mL/kg) | Regimens | Sacrifice (wks) |
|---|---|---|---|---|---|---|
| 6 | 8 | Compound A | 20 | 10 | Oral, BID, 5 wks-9 wks | 9 |
| 7 | 8 | AM: Vehicle PM: Compound A | 30 | 10 | Oral, QD, 5 wks-9 wks | 9 |

The viability, clinical signs and behavior were monitored daily. Body weight was recorded daily before drug administration in the morning. Mice were observed for significant clinical signs of toxicity, moribundity, and mortality approximately 60 minutes after each administration. The animals were sacrificed by exsanguination through direct cardiac puncture under ether anesthesia.

Body weight gradually increased during the treatment period in all except the Telmisartan group. Mean body weight of Vehicle group was lower than that of Normal group throughout the treatment period. Mean body weight of Telmisartan group was lower than that of Vehicle group from day 7 to day 27 after the start of treatment. There were no differences in mean body weight between the Vehicle group and any of the groups during the treatment period. None of the animals in the study showed deterioration in general condition throughout the treatment period.

Mean body weight at the day before sacrifice was significantly lower in the Vehicle group compared with the Normal group (Normal: 25.1±2.0 g, Vehicle: 18.8±1.0 g). The Telmisartan group showed a decrease in mean body weight compared with the Vehicle group (Telmisartan: 15.6±1.8 g). There were no differences in mean body weight between the Vehicle group and any of the other groups (1 mg/kg (BID): 19.2±1.4 g, 3 mg/kg (BID): 18.7±1.4 g, 10 mg/kg (BID): 18.7±1.0 g, 30 mg/kg (QD): 17.9±0.9 g).

Liver TG content increased in the Vehicle group compared with the Normal group (Normal: 13.9±3.8 mg/g liver, Vehicle: 67.3±29.0 mg/g liver). The Telmisartan group showed a significant decrease in liver TG content compared with the Vehicle group (Telmisartan: 30.7±11.4 mg/g liver). Liver TG content was reduced by doses of 3, 10 and 30 mg/kg of Compound A (1 mg/kg (BID): 71.7±30.3 mg/g liver, 3 mg/kg (BID): 52.9±18.5 mg/g liver, 10 mg/kg (BID): 56.7±25.8 mg/g liver, 30 mg/kg (QD): 62.4±18.1 mg/g liver).

Liver sections from the Vehicle group exhibited severe micro- and macrovesicular fat deposition, hepatocellular ballooning and inflammatory cell infiltration. Consistent with these observations, NAS increased in the Vehicle group compared with the Normal group (Normal: 0.0±0.0, Vehicle: 5.4±0.9). The Telmisartan group showed marked improvements in fat deposition, hepatocellular ballooning and inflammatory cell infiltration, with a reduction in NAS compared with the Vehicle group (Telmisartan: 2.3±0.7). The 3 mg/kg (BID) and 10 mg/kg (BID) groups showed a decrease in hepatocellular ballooning and inflammatory cell infiltration compared with the Vehicle group. NAS decreased in the 3 mg/kg (BID) and 10 mg/kg (BID) groups compared with the Vehicle group (3 mg/kg (BID): 3.6±1.6, 10 mg/kg (BID): 3.4±1.5). No obvious differences were found in HE-stained liver sections between the Vehicle group and the 1 mg/kg (BID) and 30 mg/kg (QD) groups.

Liver sections from the Vehicle group showed increased collagen deposition in the pericentral region of liver lobule compared with the Normal group. The percentage of fibrosis area (Sirius red-positive area) increased in the Vehicle group compared with the Normal group (Normal: 0.17±0.03%, Vehicle: 1.07±0.18%). The fibrosis area decreased in the Telmisartan group compared with the Vehicle group (Telmisartan: 0.42±0.08%). There was no difference in the fibrosis area between the Vehicle group and any of the other groups (1 mg/kg (BID): 1.12±0.46%, 3 mg/kg (BID): 0.89±0.32%, 10 mg/kg (BID): 1.07±0.31%, 30 mg/kg (QD): 0.99±0.43%).

Liver sections from the Vehicle group showed increased micro- and macrovesicular fat deposition in the hepatocytes compared with the Normal group. The percentage of fat deposition area (oil red-positive area) increased in the Vehicle group compared with the Normal group (Normal: 0.97±1.53%, Vehicle: 23.57±6.52%). The fat deposition area tended to decrease in the Telmisartan group compared with the Vehicle group (Telmisartan: 17.29±7.66%). Fat deposition area was reduced in the 1 mg/kg, 3 mg/kg, and 10 mg/kg groups dosed twice daily (1 mg/kg (BID): 18.47±5.22%, 3 mg/kg (BID): 19.53±4.64%, 10 mg/kg (BID): 23.31±9.18%, 30 mg/kg (QD): 22.30±9.59%).

F4/80 immunostaining of liver sections revealed the number and size of F4/80$^+$ cells in the liver lobule region obviously increased in the Vehicle group compared to the Normal group. The percentage of inflammation area (F4/80-positive area) significantly increased in the Vehicle group compared with the Normal group (Normal: 1.40±0.35%, Vehicle: 3.57±0.88%). There were no apparent differences in the inflammation area between the Vehicle group and any of the other groups (Telmisartan: 3.84±0.86%, 1 mg/kg (BID): 3.67±0.91%, 3 mg/kg (BID): 3.47±0.65%, 10 mg/kg (BID): 3.82±0.57%, 30 mg/kg (QD): 3.90±0.78%).

Figure 7:
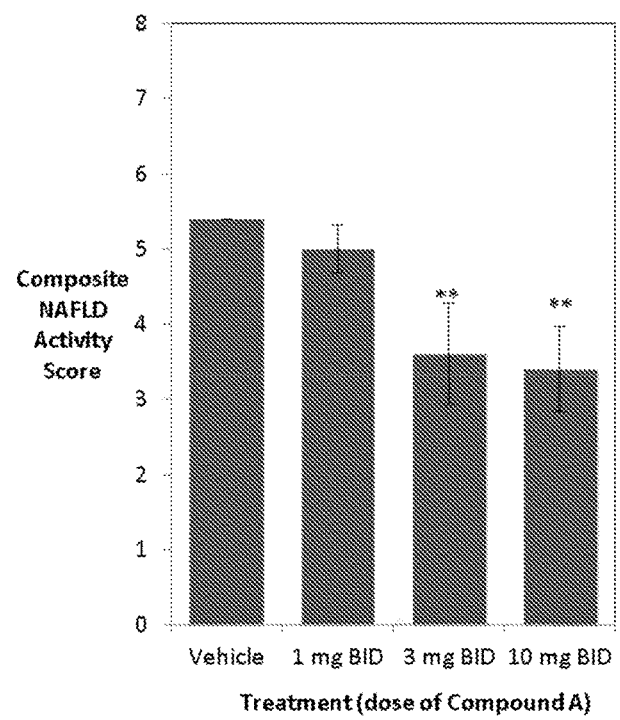
FIG. 7 shows the composite NAFLD (non-alcoholic fatty liver disease) activity score after treatment of mice with a disclosed compound.
Figure 8:
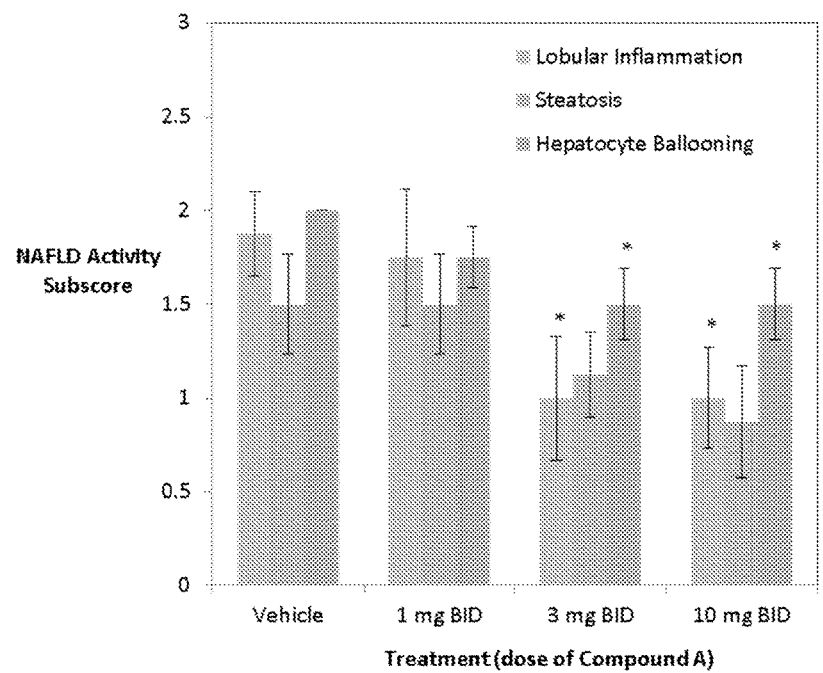
FIG. 8 shows the NAFLD activity subscore (lobular inflammation, steatotis, hepatocyte ballooning) in a NASH/NAFLD mouse model after treatment with a disclosed compound.
Figure 9:
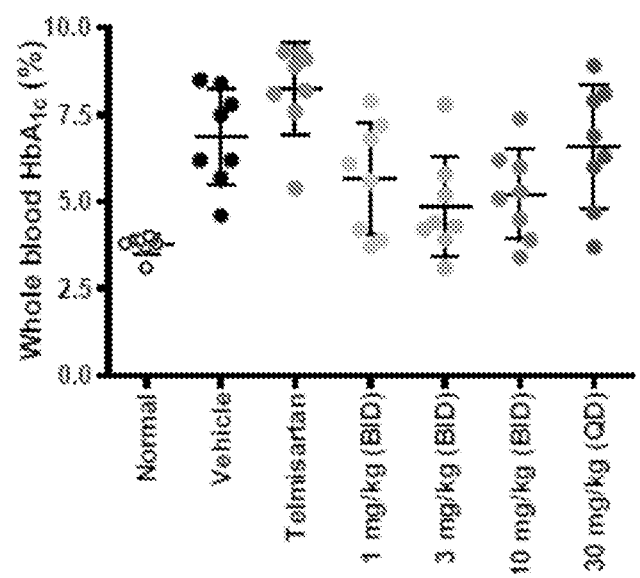
FIG. 9 shows the decrease in whole blood $HbA_{1c}$ after treatment with a disclosed compound.
Figure 10:
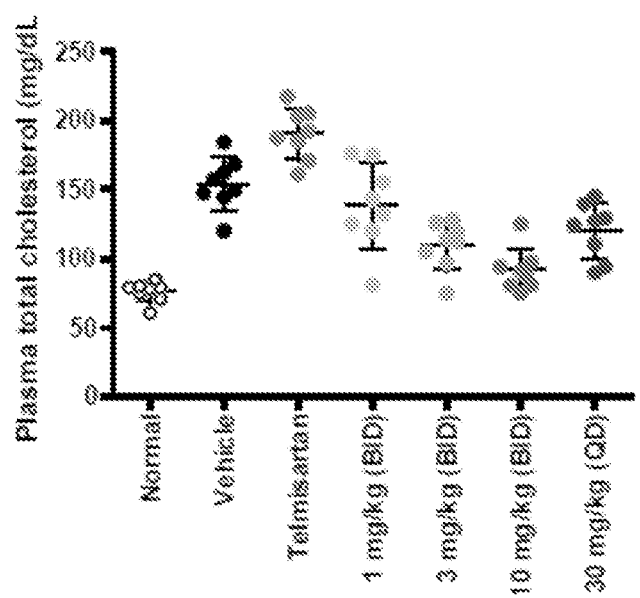
FIG. 10 shows the decrease in plasma total cholesterol after treatment with a disclosed compound.

For BID dosing, treatment with Compound A decreased in plasma total cholesterol levels (FIG. 10) and ameliorated NAS in a dose dependent manner. Further, whole blood HbA$_{1c}$ levels was decreased in 3 mg/kg (BID) and 10 mg/kg (BID) doses of Compound A groups. (FIG. 9) Treatment with Compound A improved in glucose and lipid metabolism as evidenced by reduction of whole blood HbA$_{1c}$ levels and plasma total cholesterol levels. The improvement in NAS was attributable to the changes in lobular inflammation and hepatocyte ballooning, both of which decreased in the 3 mg/kg (BID) and 10 mg/kg (BID) doses of Compound A groups compared with the Vehicle group. Because NAS is one of the clinical endpoints for assessing the activity of NASH (Sanyal A J. et al., *Hepatology*, 2011; 54:344), the observed changes in the treatment groups suggest potential clinical efficacy of Compound A as an anti-NASH therapeutic. As shown in FIGS. 7 and 8, Compound A reduced the composite (FIG. 7) and individual components (lobular inflammation, steaotosis, hepatocyte ballooning) (FIG. 8) of NAFLD activity.

On the other hand, treatment with QD dosing of Compound A did not show evident improvement in whole blood HbA$_{1c}$ and NAS, which was found with BID dosing of Compound A, although it significantly decreased plasma total cholesterol levels to a similar extent as BID dosing of Compound A. This may be due to the pharmokinetics in e.g., mice or other rodents. These results suggest that the dosing frequency of Compound A is suitable for BID dosing in mice, which may predict daily administration in humans or other larger animal species with slower rates of drug metabolism. Further, Compound A showed an anti-NASH effect and amelioration of glucose and lipid metabolism.

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method of treating a fatty liver disease or liver fibrosis, wherein the fatty liver disease is selected from the group consisting of non-alcoholic steatohepatitis, liver cirrhosis, focal fatty liver, and hepatocellular carcinoma, comprising administering to a patient in need thereof a therapeutically effective amount of compound represented by:

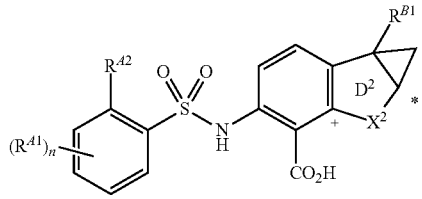

Formula IV wherein:

$X^2$ is $^+$—$W^2$—$C(R^{D5}R^{D6})$—*; wherein the $^+$ and * indicate the attachment points of $X^2$ as indicated in Formula IV;

$W^2$ is O;

$R^{B1}$ is selected from the group consisting of H, F, OH, CN, $C_{1-2}$alkoxy or $C_{1-3}$alkyl; wherein $C_{1-3}$alkyl and $C_{1-2}$alkoxy are optionally substituted by a group selected from OH, $C_{1-2}$alkoxy, CN or one or more fluorine atoms;

$R^{A1}$ is selected, independently for each occurrence, from the group consisting of hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n is 0, 1, or 2;

$R^{A2}$ is selected from the group consisting of hydrogen, $R^iR^jN$—, heterocyclyl, heterocyclyloxy and heterocyclyl-$(NR^a)$—; wherein said heterocyclyl may optionally be substituted by one or more substituents selected from $R^g$ and wherein if said heterocyclyl contains a —NH moiety that nitrogen may optionally be substituted by one or more groups $R^h$; or $R^{A2}$ is selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$— (wherein w is 0, 1 or 2), $C_{1-6}$alkyl-$N(R^a)$—, $C_{1-6}$alkyl-$N(R^a)$-carbonyl-, $C_{1-6}$alkylcarbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-$N(R^a)$—, $C_{1-6}$alkylcarbonyl-$N(R^a)$—$C_{1-6}$alkyl-, $C_{1-6}$alkyl-$N(R^a)$-carbonyl-$C_{1-6}$alkyl-, $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$—, $C_{1-6}$alkyl-$N(R^a)$—, $C_{1-6}$alkyl-$N(R^a)$-carbonyl-, $C_{1-6}$alkylcarbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-$N(R^a)$—, $C_{1-6}$alkylcarbonyl-$N(R^a)C_{1-6}$alkyl-, $C_{1-6}$alkyl-$N(R^a)$-carbonyl-$C_{1-6}$alkyl-, $C_{1-6}$alkoxy-$C_{1-6}$alkyl may optionally be substituted by $R^p$, phenyl, phenoxy, heteroaryl, heteroaryloxy, heteroaryl-$(NR^a)$—, heterocyclyl, heterocyclyloxy or heterocyclyl-$N(R^a)$—; and wherein said heteroaryl or phenyl may optionally be substituted with one or more substituents selected from $R^f$; and wherein said heterocyclyl may optionally be substituted by one or more substituents selected from $R^g$; and wherein if said heterocyclyl contains a —NH moiety that nitrogen may optionally be substituted by one or more groups $R^h$;

$R^{D5}$ and $R^{D6}$ are each independently selected from the group consisting of hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by a substituent or substituents selected from the group consisting of: one or more fluorine atoms, cyano, hydroxyl or $N(R^aR^b)$;

$R^a$ and $R^b$ are independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;

or $R^a$ and $R^b$, together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

$R^f$ is independently selected, for each occurrence, from the group consisting of $R^p$, hydrogen, $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-$S(O)_w$—, (wherein w is 0, 1 or 2), $C_{1-6}$alkylcarbonyl-$N(R^a)$— and $C_{1-6}$alkoxycarbonyl-$N(R^a)$—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-$S(O)_w$—, $C_{1-6}$alkylcarbonyl-N($R^a$)—, $C_{1-6}$alkoxycarbonyl-N($R^a$)— may be optionally substituted by one or more substituents selected from $R^P$;

$R^g$ is independently selected for each occurrence from the group consisting of $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, (wherein w is 0, 1 or 2), $C_{1-6}$alkylcarbonyl-N($R^a$)— and $C_{1-6}$alkoxycarbonyl-N($R^a$)—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$—, $C_{1-6}$ alkylcarbonyl-N($R^a$)—, $C_{1-6}$alkoxycarbonyl-N($R^a$)— may be optionally substituted by one or more substituents selected from $R^P$;

$R^h$ is independently selected for each occurrence from the group consisting of hydrogen, $C_{1-6}$ alkyl, $C_{3-6}$alkenyl, $C_{3-6}$alkynyl, $C_{3-6}$cycloalkyl, $C_{1-6}$ alkyl-S(O)$_2$—, $C_{1-6}$ alkoxycarbonyl-, $R^iR^jN$-carbonyl- and $R^iR^jN$—SO$_2$—; wherein $C_{1-6}$alkyl, $C_{3-6}$alkenyl, $C_{3-6}$alkynyl $C_{3-6}$cycloalkyl and $C_{1-6}$alkyl-S(O)$_2$—, $C_{1-6}$alkylcarbonyl- may optionally be substituted by one or more substituents selected from $R^P$;

$R^i$ and $R^j$ are selected independently for each occurrence from the group consisting of hydrogen, $C_{1-4}$alkyl, $C_{3-6}$cycloalkyl, heterocyclyl and heterocyclylcarbonyl; wherein $C_{1-4}$alkyl and $C_{3-6}$cycloalkyl may be optionally substituted by one or more substituents selected from fluorine, hydroxyl, cyano, $R^aR^bN$—, $R^aR^bN$-carbonyl- and $C_{1-3}$alkoxy and wherein heterocyclyl and heterocyclylcarbonyl may be optionally substituted by one or more substituents selected from $C_{1-6}$alkyl, $C_{2-6}$alkenyl, $C_{2-6}$alkynyl, $C_{3-6}$cycloalkyl, $C_{1-6}$alkoxy, halo-$C_{1-6}$-alkyl, hydroxyl-$C_{1-6}$-alkyl, $R^aR^bN$—$C_{1-6}$alkyl- and $C_{1-6}$-alkoxy-$C_{1-6}$-alkyl group; and wherein if said heterocyclyl or heterocyclylcarbonyl contains a —NH moiety that nitrogen may optionally be substituted by one or more groups $C_{1-6}$alkyl, $C_{3-6}$alkenyl, $C_{3-6}$alkynyl, $C_{3-6}$cycloalkyl, $C_{1-6}$alkyl-S (O)$_2$— and $C_{1-6}$-alkylcarbonyl; or $R^i$ and $R^j$ taken together with the nitrogen to which they are attached form a 4-7 membered heterocyclic ring, which may have an additional heteroatom selected from O, S, or N; wherein the 4-7 membered heterocyclic ring may be optionally substituted on carbon by one or more substituents selected from the group consisting of fluorine, hydroxyl, oxo, cyano, $C_{1-6}$alkyl, $C_{1-6}$alkoxy, $R^aR^bN$—, $R^aR^bN$—SO$_2$— and $R^aR^bN$-carbonyl-; wherein said $C_{1-6}$alkyl or $C_{1-6}$alkoxy may optionally be substituted by fluorine, hydroxyl or cyano; and wherein the 4-7 membered heterocyclic ring may be optionally substituted on nitrogen by one or more substituents selected from the group consisting of $C_{1-6}$alkyl and $R^aR^bN$-carbonyl-; and wherein said $C_{1-6}$alkyl may be optionally substituted by one or more substituents selected from the group consisting of fluorine, hydroxyl, cyano;

$R^P$ is independently selected, for each occurrence, from the group consisting of halogen, hydroxyl, cyano, $C_{1-6}$alkoxy, $R^iR^jN$—, $R^iR^jN$-carbonyl-, $R^iR^jN$—SO$_2$— and $R^iR^jN$-carbonyl-N($R^a$)—; and pharmaceutically acceptable salts, stereoisomers, esters and prodrugs thereof.

2. The method of claim 1, wherein the patient is a human.
3. The method of claim 1, wherein the compound is administered orally.
4. A method of treating fatty liver disease wherein the fatty liver disease is selected from the group consisting of non-alcoholic steatohepatitis, liver cirrhosis, focal fatty liver, and hepatocellular carcinoma, comprising administering to a patient in need thereof a therapeutically effective amount of the compound represented by

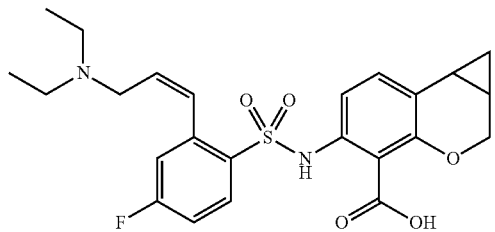 [SMILES: CCN(CC)C/C=C\c1cc(F)ccc1S(=O)(=O)Nc1ccc2c(c1C(=O)O)OCC1CC21]

or a pharmaceutically acceptable salt thereof.

5. A method of treating liver fibrosis comprising administering to a patient in need thereof a therapeutically effective amount of the compound represented by

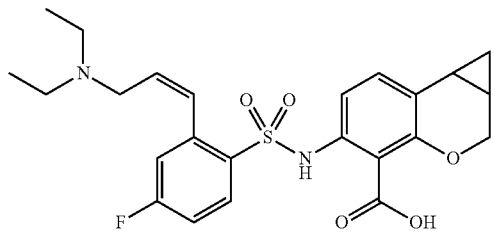 [SMILES: CCN(CC)C/C=C\c1cc(F)ccc1S(=O)(=O)Nc1ccc2c(c1C(=O)O)OCC1CC21]

or a pharmaceutically acceptable salt thereof.

6. The method of claim 4, wherein the the compound is administered orally.
7. The method of claim 1, wherein the compound is administered in a once daily or twice daily dosage.
8. The method of claim 1, wherein the dose of the compound is less than about 10 mg/kg.
9. A method of reducing total plasma cholesterol in a patient in need thereof comprising administering to a patient in a therapeutically effective amount of compound represented by:

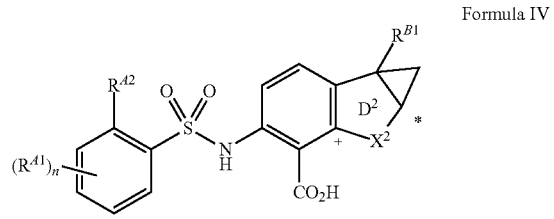

Formula IV wherein:

$X^2$ is $^+$—$W^2$—C($R^{D5}R^{D6}$)—*; wherein the $^+$ and * indicate the attachment points of $X^2$ as indicated in Formula IV;

$W^2$ is O;

$R^{B1}$ is selected from the group consisting of H, F, OH, CN, $C_{1-2}$alkoxy or $C_{1-3}$alkyl; wherein $C_{1-3}$alkyl and $C_{1-2}$alkoxy are optionally substituted by a group selected from OH, $C_{1-2}$alkoxy, CN or one or more fluorine atoms;

$R^{A1}$ is selected, independently for each occurrence, from the group consisting of hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;

n is 0, 1, or 2;

$R^{A2}$ is selected from the group consisting of hydrogen, $R^iR^jN$—, heterocyclyl, heterocyclyloxy and heterocyclyl-$(NR^a)$—; wherein said heterocyclyl may optionally be substituted by one or more substituents selected from $R^g$ and wherein if said heterocyclyl contains a —NH moiety that nitrogen may optionally be substituted by one or more groups $R^h$; or $R^{A2}$ is selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$— (wherein w is 0, 1 or 2), $C_{1-6}$alkyl-$N(R^a)$—, $C_{1-6}$alkyl-$N(R^a)$-carbonyl-, $C_{1-6}$alkylcarbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-$N(R^a)$—, $C_{1-6}$alkylcarbonyl-N$(R^a)$—$C_{1-6}$alkyl-, $C_{1-6}$alkyl-$N(R^a)$-carbonyl-$C_{1-6}$alkyl-, $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$—, $C_{1-6}$alkyl-$N(R^a)$—, $C_{1-6}$alkyl-N$(R^a)$-carbonyl-, $C_{1-6}$alkylcarbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-N$(R^a)$—, $C_{1-6}$alkylcarbonyl-$N(R^a)C_{1-6}$alkyl-, $C_{1-6}$alkyl-$N(R^a)$-carbonyl-$C_{1-6}$alkyl-, $C_{1-6}$alkoxy-$C_{1-6}$alkyl may optionally be substituted by $R^P$, phenyl, phenoxy, heteroaryl, heteroaryloxy, heteroaryl-$(NR^a)$—, heterocyclyl, heterocyclyloxy or heterocyclyl-$N(R^a)$—; and wherein said heteroaryl or phenyl may optionally be substituted with one or more substituents selected from $R^f$; and wherein said heterocyclyl may optionally be substituted by one or more substituents selected from $R^g$; and wherein if said heterocyclyl contains a —NH moiety that nitrogen may optionally be substituted by one or more groups $R^h$;

$R^{D5}$ and $R^{D6}$ are each independently selected from the group consisting of hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by a substituent or substituents selected from the group consisting of: one or more fluorine atoms, cyano, hydroxyl or $N(R^aR^b)$;

$R^a$ and $R^b$ are independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;

or $R^a$ and $R^b$, together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;

$R^f$ is independently selected, for each occurrence, from the group consisting of $R^P$, hydrogen, $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-$S(O)_w$—, (wherein w is 0, 1 or 2), $C_{1-6}$alkylcarbonyl-$N(R^a)$— and $C_{1-6}$alkoxycarbonyl-$N(R^a)$—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-$S(O)_w$—, $C_{1-6}$alkylcarbonyl-$N(R^a)$—, $C_{1-6}$alkoxycarbonyl-$N(R^a)$— may be optionally substituted by one or more substituents selected from $R^P$;

$R^g$ is independently selected for each occurrence from the group consisting of $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-$S(O)_w$—, (wherein w is 0, 1 or 2), $C_{1-6}$alkylcarbonyl-$N(R^a)$— and $C_{1-6}$alkoxycarbonyl-$N(R^a)$—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-$S(O)_w$—, $C_{1-6}$alkylcarbonyl-$N(R^a)$—, $C_{1-6}$alkoxycarbonyl-$N(R^a)$— may be optionally substituted by one or more substituents selected from $R^P$;

$R^h$ is independently selected for each occurrence from the group consisting of hydrogen, $C_{1-6}$ alkyl, $C_{3-6}$alkenyl, $C_{3-6}$alkynyl, $C_{3-6}$cycloalkyl, $C_{1-6}$ alkyl-$S(O)_2$—, $C_{1-6}$ alkoxycarbonyl-, $R^iR^jN$-carbonyl- and $R^iR^jN$—$SO_2$—; wherein $C_{1-6}$alkyl, $C_{3-6}$alkenyl, $C_{3-6}$alkynyl $C_{3-6}$cycloalkyl and $C_{1-6}$alkyl-$S(O)_2$—, $C_{1-6}$alkylcarbonyl- may optionally be substituted by one or more substituents selected from $R^P$;

$R^i$ and $R^j$ are selected independently for each occurrence from the group consisting of hydrogen, $C_{1-4}$alkyl, $C_{3-6}$cycloalkyl, heterocyclyl and heterocyclylcarbonyl; wherein $C_{1-4}$alkyl and $C_{3-6}$cycloalkyl may be optionally substituted by one or more substituents selected from fluorine, hydroxyl, cyano, $R^aR^bN$—, $R^aR^bN$-carbonyl- and $C_{1-3}$alkoxy and wherein heterocyclyl and heterocyclylcarbonyl may be optionally substituted by one or more substituents selected from $C_{1-6}$alkyl, $C_{2-6}$alkenyl, $C_{2-6}$alkynyl, $C_{3-6}$cycloalkyl, $C_{1-6}$alkoxy, halo-$C_{1-6}$-alkyl, hydroxyl-$C_{1-6}$-alkyl, $R^aR^bN$—$C_{1-6}$alkyl- and $C_{1-6}$-alkoxy-$C_{1-6}$-alkyl group; and wherein if said heterocyclyl or heterocyclylcarbonyl contains a —NH moiety that nitrogen may optionally be substituted by one or more groups $C_{1-6}$alkyl, $C_{3-6}$alkenyl, $C_{3-6}$alkynyl, $C_{3-6}$cycloalkyl, $C_{1-6}$alkyl-S$(O)_2$— and $C_{1-6}$-alkylcarbonyl; or $R^i$ and $R^j$ taken together with the nitrogen to which they are attached form a 4-7 membered heterocyclic ring, which may have an additional heteroatom selected from O, S, or N; wherein the 4-7 membered heterocyclic ring may be optionally substituted on carbon by one or more substituents selected from the group consisting of fluorine, hydroxyl, oxo, cyano, $C_{1-6}$alkyl, $C_{1-6}$alkoxy, $R^aR^bN$—, $R^aR^bN$—$SO_2$— and $R^aR^bN$-carbonyl-; wherein said $C_{1-6}$alkyl or $C_{1-6}$alkoxy may optionally be substituted by fluorine, hydroxyl or cyano; and wherein the 4-7 membered heterocyclic ring may be optionally substituted on nitrogen by one or more substituents selected from the group consisting of $C_{1-6}$alkyl and $R^aR^bN$-carbonyl-; and wherein said $C_{1-6}$alkyl may be optionally substituted by one or more substituents selected from the group consisting of fluorine, hydroxyl, cyano;

$R^P$ is independently selected, for each occurrence, from the group consisting of halogen, hydroxyl, cyano, $C_{1-6}$alkoxy, $R^iR^jN$—, $R^iR^jN$-carbonyl-, $R^iR^jN$—$SO_2$— and $R^iR^jN$-carbonyl-$N(R^a)$—; and pharmaceutically acceptable salts, stereoisomers, esters and prodrugs thereof.

10. The method of claim 9, wherein the compound is represented by

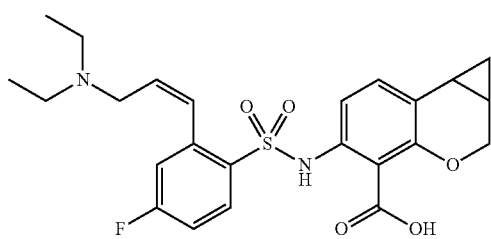 [SMILES: CCN(CC)C/C=C\c1cc(F)ccc1S(=O)(=O)Nc1ccc2c(c1C(=O)O)OCC1CC21]

or a pharmaceutically acceptable salt thereof.

11. A method of decreasing whole blood $HbA_{1c}$ or lowering the plasma level of $HbA_{1c}$ in a patient in need thereof, comprising administering to the patient a therapeutically effective amount of compound represented by:

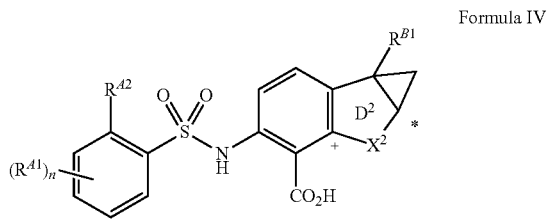

Formula IV wherein:
$X^2$ is $^+$—$W^2$—$C(R^{D5}R^{D6})$—*; wherein the $^+$ and * indicate the attachment points of $X^2$ as indicated in Formula IV;
$W^2$ is O;
$R^{B1}$ is selected from the group consisting of H, F, OH, CN, $C_{1-2}$alkoxy or $C_{1-3}$alkyl; wherein $C_{1-3}$alkyl and $C_{1-2}$alkoxy are optionally substituted by a group selected from OH, $C_{1-2}$alkoxy, CN or one or more fluorine atoms;
$R^{A1}$ is selected, independently for each occurrence, from the group consisting of hydrogen, hydroxyl, cyano, halogen, $C_{1-4}$alkyl or $C_{1-3}$alkoxy; wherein $C_{1-4}$alkyl, or $C_{1-3}$alkoxy may be optionally substituted by one or more fluorines;
n is 0, 1, or 2;
$R^{A2}$ is selected from the group consisting of hydrogen, $R^iR^jN$—, heterocyclyl, heterocyclyloxy and heterocyclyl-$(NR^a)$—; wherein said heterocyclyl may optionally be substituted by one or more substituents selected from $R^g$ and wherein if said heterocyclyl contains a —NH moiety that nitrogen may optionally be substituted by one or more groups $R^h$; or
$R^{A2}$ is selected from the group consisting of: $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$— (wherein w is 0, 1 or 2), $C_{1-6}$alkyl-$N(R^a)$—, $C_{1-6}$alkyl-$N(R^a)$-carbonyl-, $C_{1-6}$alkylcarbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-$N(R^a)$—, $C_{1-6}$ alkylcarbonyl-N$(R^a)$—$C_{1-6}$alkyl-, $C_{1-6}$alkyl-$N(R^a)$-carbonyl-$C_{1-6}$alkyl-, $C_{1-6}$alkoxy$C_{1-6}$alkyl-; wherein $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$—, $C_{1-6}$alkyl-$N(R^a)$—, $C_{1-6}$alkyl-$N(R^a)$-carbonyl-, $C_{1-6}$alkylcarbonyl-$N(R^a)$—, $C_{1-6}$alkyl-$N(R^a)$-carbonyl-$N(R^a)$—, $C_{1-6}$alkyl-$N(R^a)$—$SO_2$—, $C_{1-6}$alkyl-$SO_2$—$N(R^a)$—, $C_{1-6}$alkoxycarbonyl-N$(R^a)$—, $C_{1-6}$alkylcarbonyl-$N(R^a)C_{1-6}$alkyl-, $C_{1-6}$alkyl-$N(R^a)$-carbonyl-$C_{1-6}$alkyl-, $C_{1-6}$alkoxy-$C_{1-6}$alkyl may optionally be substituted by $R^P$, phenyl, phenoxy, heteroaryl, heteroaryloxy, heteroaryl-$(NR^a)$—, heterocyclyl, heterocyclyloxy or heterocyclyl-$N(R^a)$—; and wherein said heteroaryl or phenyl may optionally be substituted with one or more substituents selected from $R^f$; and wherein said heterocyclyl may optionally be substituted by one or more substituents selected from $R^g$; and wherein if said heterocyclyl contains a —NH moiety that nitrogen may optionally be substituted by one or more groups $R^h$;
$R^{D5}$ and $R^{D6}$ are each independently selected from the group consisting of hydrogen, fluorine, hydroxyl, cyano, $C_{1-2}$alkyl or $C_{1-2}$alkoxy; wherein the $C_{1-2}$alkyl and $C_{1-2}$alkoxy may optionally be substituted by a substituent or substituents selected from the group consisting of: one or more fluorine atoms, cyano, hydroxyl or $N(R^aR^b)$;
$R^a$ and $R^b$ are independently selected, for each occurrence, from the group consisting of hydrogen and $C_{1-3}$alkyl; wherein $C_{1-3}$alkyl may optionally be substituted by one or more substituents selected from fluorine, cyano, oxo and hydroxyl;
or $R^a$ and $R^b$, together with the nitrogen to which they are attached, may form a 4-6 membered heterocyclic ring, which may have an additional heteroatom selected from O, S, or N; wherein the 4-6 membered heterocyclic ring may optionally be substituted by one or more substituents selected from the group consisting of fluorine, cyano, oxo or hydroxyl;
$R^f$ is independently selected, for each occurrence, from the group consisting of $R^P$, hydrogen, $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-$S(O)_w$—, (wherein w is 0, 1 or 2), $C_{1-6}$alkylcarbonyl-$N(R^a)$— and $C_{1-6}$alkoxycarbonyl-$N(R^a)$—; wherein $C_{1-6}$alkyl, $C_{3-6}$cycloalkyl, $C_{2-6}$alkenyl, $C_{2-6}$alkynyl, $C_{1-6}$alkoxy, $C_{1-6}$alkyl-$S(O)_w$—, $C_{1-6}$alkylcarbonyl-$N(R^a)$—, $C_{1-6}$alkoxycarbonyl-$N(R^a)$— may be optionally substituted by one or more substituents selected from $R^P$;
$R^g$ is independently selected for each occurrence from the group consisting of $R^P$, hydrogen, oxo, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-$S(O)_w$—, (wherein w is 0, 1 or 2), $C_{1-6}$alkylcarbonyl-$N(R^a)$— and $C_{1-6}$alkoxycarbonyl-$N(R^a)$—; wherein $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-$S(O)_w$—, $C_{1-6}$alkylcarbonyl-$N(R^a)$—, $C_{1-6}$alkoxycarbonyl-$N(R^a)$— may be optionally substituted by one or more substituents selected from $R^P$;
$R^h$ is independently selected for each occurrence from the group consisting of hydrogen, $C_{1-6}$alkyl, $C_{3-6}$alkenyl, $C_{3-6}$alkynyl, $C_{3-6}$cycloalkyl, $C_{1-6}$alkoxycarbonyl-, $R^iR^jN$-carbonyl- and $R^iR^jN$—$SO_2$—; wherein $C_{1-6}$alkyl, $C_{3-6}$alkenyl, $C_{3-6}$alkynyl $C_{3-6}$cycloalkyl and $C_{1-6}$alkyl-$S(O)_2$—, $C_{1-6}$alkylcarbonyl- may optionally be substituted by one or more substituents selected from $R^P$;
$R^i$ and $R^j$ are selected independently for each occurrence from the group consisting of hydrogen, $C_{1-4}$alkyl, $C_{3-6}$cycloalkyl, heterocyclyl and heterocyclylcarbonyl; wherein $C_{1-4}$alkyl and $C_{3-6}$cycloalkyl may be optionally substituted by one or more substituents selected from fluorine, hydroxyl, cyano, $R^aR^bN$—, $R^aR^bN$-carbonyl- and $C_{1-3}$alkoxy and wherein heterocyclyl and heterocyclylcarbonyl may be optionally substituted by one or more substituents selected from $C_{1-6}$alkyl, $C_{2-6}$alkenyl, $C_{2-6}$alkynyl, $C_{3-6}$cycloalkyl, $C_{1-6}$alkoxy, halo-$C_{1-6}$-alkyl, hydroxyl-$C_{1-6}$-alkyl, $R^aR^bN$—$C_{1-6}$alkyl- and $C_{1-6}$-alkoxy-$C_{1-6}$-alkyl group; and wherein if said heterocyclyl or heterocyclylcarbonyl contains a —NH moiety that nitrogen may optionally be substituted by one or more groups $C_{1-6}$alkyl, $C_{3-6}$alkenyl, $C_{3-6}$alkynyl, $C_{3-6}$cycloalkyl, $C_{1-6}$alkyl-S$(O)_2$— and $C_{1-6}$-alkylcarbonyl; or $R^i$ and $R^j$ taken together with the nitrogen to which they are attached form a 4-7 membered heterocyclic ring, which may have an additional heteroatom selected from O, S, or N; wherein the 4-7 membered heterocyclic ring may be optionally substituted on carbon by one or more substituents selected from the group consisting of fluorine, hydroxyl, oxo, cyano, $C_{1-6}$alkyl, $C_{1-6}$alkoxy, $R^aR^bN$—, $R^aR^bN$—$SO_2$— and $R^aR^bN$-carbonyl-; wherein said $C_{1-6}$alkyl or $C_{1-6}$alkoxy may optionally be substituted by fluorine, hydroxyl or cyano; and wherein the 4-7 membered heterocyclic ring may be optionally substituted on nitrogen by one or more substituents selected from the group consisting of $C_{1-6}$alkyl and $R^aR^bN$-carbonyl-; and wherein said $C_{1-6}$alkyl may be optionally substituted by one or more substituents selected from the group consisting of fluorine, hydroxyl, cyano;

$R^p$ is independently selected, for each occurrence, from the group consisting of halogen, hydroxyl, cyano, $C_{1-6}$alkoxy, $R^iR^jN$—, $R^iR^jN$-carbonyl-, $R^iR^jN$—$SO_2$— and $R^iR^jN$-carbonyl-$N(R^a)$—; and pharmaceutically acceptable salts, stereoisomers, esters and prodrugs thereof.

12. The method of claim 11, wherein the patient has a diabetic condition.

13. The method of claim 1, wherein the patient is not obese.

* * * * *